US012735469B2

(12) United States Patent
Bowerman et al.

(10) Patent No.: US 12,735,469 B2
(45) Date of Patent: Sep. 15, 2026

(54) MAGE-A4 T CELL RECEPTORS AND METHODS OF USE THEREOF

(71) Applicant: Regeneron Pharmaceuticals, Inc., Tarrytown, NY (US)

(72) Inventors: Natalie Bowerman, Tarrytown, NY (US); Cagan Gurer, Tarrytown, NY (US); Johanna Hansen, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1078 days.

(21) Appl. No.: 17/618,973

(22) PCT Filed: Jun. 17, 2020

(86) PCT No.: PCT/US2020/038142

§ 371 (c)(1),
(2) Date: Dec. 14, 2021

(87) PCT Pub. No.: WO2020/257288

PCT Pub. Date: Dec. 24, 2020

(65) Prior Publication Data

US 2022/0324939 A1 Oct. 13, 2022

Related U.S. Application Data

(60) Provisional application No. 62/871,793, filed on Jul. 9, 2019, provisional application No. 62/862,726, filed on Jun. 18, 2019.

(51) Int. Cl.

| | |
|---|---|
| ***A61K 9/00*** | (2006.01) |
| ***A61K 35/00*** | (2006.01) |
| ***A61K 47/00*** | (2006.01) |
| ***C07K 14/705*** | (2006.01) |
| ***C07K 14/725*** | (2006.01) |

(52) U.S. Cl.

CPC ........ *C07K 14/7051* (2013.01); *A61K 9/0019* (2013.01); *A61K 9/0053* (2013.01); *A61K 35/00* (2013.01); *A61K 47/00* (2013.01)

(58) Field of Classification Search

CPC ............ C07K 14/7051; C07K 14/4748; A61K 40/11; A61K 40/32; A61K 40/4268; A61K 2121/00; A61K 40/42; A61P 35/00

See application file for complete search history.

(56) References Cited

U.S. PATENT DOCUMENTS

| | | | |
|---|---|---|---|
| 9,976,121 | B2 | 5/2018 | Laugel et al. |
| 2004/0033541 | A1 | 2/2004 | Zhang et al. |
| 2017/0267738 | A1 | 9/2017 | Maurer et al. |
| 2017/0296641 | A1 | 10/2017 | Weinschenk et al. |
| 2019/0092834 | A1 | 3/2019 | Hayes et al. |
| 2019/0127436 | A1 | 5/2019 | Tribble et al. |

FOREIGN PATENT DOCUMENTS

| | | | |
|---|---|---|---|
| EP | 1930433 | A1 | 6/2008 |
| WO | WO-2016199141 | A2 | 12/2016 |
| WO | WO-2017158103 | A1 | 9/2017 |
| WO | WO-2017/175006 | A1 | 10/2017 |
| WO | WO-2017174823 | A1 | 10/2017 |
| WO | WO-2017174824 | A1 | 10/2017 |
| WO | WO-2019/036688 | A1 | 2/2019 |
| WO | WO-2020/243134 | A1 | 12/2020 |

OTHER PUBLICATIONS

Weon et al. The MAGE protein family and cancer. Curr Opin Cell Biol. Dec. 2015;37:1-8. Epub Sep. 3, 2015. (Year: 2015).*

Schooten et al. MAGE-A antigens as targets for cancer immunotherapy. Cancer Treat Rev. Jun. 2018;67:54-62. Epub Apr. 26, 2018. (Year: 2018).*

Sang et al. MAGE-A family: attractive targets for cancer immunotherapy. Vaccine. Nov. 3, 2011;29(47):8496-500. Epub Sep. 18, 2011. (Year: 2011).*

Wu et al., "Identification of a Novel CD8+ T Cell Epitope Derived from Cancer-Testis Antigen MAGE-4 in Oesophageal Carcinoma", Scandinavian Journal of Immunology 74, 561-567, 2011.

Duffour et al., "A MAGE-A4 peptide presented by HLA-A2 is recognized by cytolytic T lymphocytes", Eur. J. Immunol. 1999. 29: 3329-3337.

Jia et al., "Identification of Two Novel HLA-A□0201-Restricted CTL Epitopes Derived from MAGE-A4", Clinical and Developmental Immunology, Article ID 567594, 7 pages.

Sun et al. "T-cell receptor gene therapy targeting melanoma-associated antigen-A4 by silencing of endogenous TCR inhibits tumor growth in mice and human," Cell Death & Disease, Jun. 17, 2019 (Jun. 18, 2019), vol. 10, No. 7, pp. 1-10.

International Search Report and Written Opinion from PCT/US2020/038142, mailed Feb. 12, 2021.

* cited by examiner

*Primary Examiner* — Jeffrey Stucker
*Assistant Examiner* — Sarah Cooper Patterson
(74) *Attorney, Agent, or Firm* — McCarter & English, LLP; Marcie B. Clarke; Deborah L. Nagle

(57) ABSTRACT

The present invention provides isolated T cell receptors (TCRs) that specifically bind to an HLA-displayed cancer testis antigen Melanoma-Associated Antigen A4 (MAGE-A4) peptide, as well as therapeutic and diagnostic methods of using those isolated TCRs. The present invention provides T cell receptors (TCRs) that were generated against a MAGE-A4 peptide antigen in the context of MHC (HLA-A2). The unique TCR sequences identified have shown specific binding to the small peptide MAGE-A4 presented in the groove of an HLA molecule and exhibited activation of T cells in a reporter assay.

15 Claims, 8 Drawing Sheets

Specification includes a Sequence Listing.

A.

B.

A.

B.

SEQUENCE LISTING

```
<160> NUMBER OF SEQ ID NOS: 871

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Ser Glu Ser Asp Tyr Tyr
1               5


<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

```
Gln Glu Ala Tyr Lys Gln Gln Asn
1               5


<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Tyr Arg Ser Ala Thr Gly Asn Gln Phe Tyr
1               5                   10


<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

accagtgaga gtgattatta t                                               21


<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

caagaagctt ataagcaaca gaat                                            24


<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

gcttatagga gcgcgaccgg taaccagttc tat                                  33


<210> SEQ ID NO 7
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Val Asn Arg Phe
    50                  55                  60
```

```
Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Thr Gly Asn Gln Phe Tyr Phe Gly Thr Gly Thr Ser Leu Thr Val
            100                 105                 110

Ile Pro


<210> SEQ ID NO 8
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

gctcagacag tcactcagtc tcaaccagag atgtctgtgc aggaggcaga gaccgtgacc     60

ctgagctgca catatgacac cagtgagagt gattattatt tattctggta caagcagcct    120

cccagcaggc agatgattct cgttattcgc caagaagctt ataagcaaca gaatgcaaca    180

gtgaatcgtt tctctgtgaa cttccagaaa gcagccaaat ccttcagtct caagatctca    240

gactcacagc tgggggatgc cgcgatgtat ttctgtgctt ataggagcgc gaccggtaac    300

cagttctatt ttgggacagg gacaagtttg acggtcattc ca                       342


<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Asp His Glu Asn
1               5


<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Tyr Asp Val Lys Met
1               5


<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ser Ser Leu Trp Gly Ser Asn Thr Glu Ala Phe
1               5                   10


<210> SEQ ID NO 12
```

<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
atggaccatg aaaat 15

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
tcatatgatg ttaaaatg 18

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14
gccagcagtt tatggggcag taacactgaa gctttc 36

<210> SEQ ID NO 15
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Gly Ser Asn Thr Glu Ala Phe Phe Gly Gln Gly Thr Arg Leu Thr Val
            100                 105                 110

Val
```

<210> SEQ ID NO 16
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgccagca gtttatgggg cagtaacact    300

gaagctttct ttggacaagg caccagactc acagttgta                           339
```

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

```
Thr Ser Glu Ser Asp Tyr Tyr
1               5
```

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

```
Gln Glu Ala Tyr Lys Gln Gln Asn
1               5
```

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

```
Ala Tyr Arg Ser Ala Thr Gly Asn Gln Phe Tyr
1               5                   10
```

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20

```
accagtgaga gtgattatta t                                               21
```

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
caagaagctt ataagcaaca gaat 24

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
gcttatagga gcgcgaccgg taaccagttc tat 33

<210> SEQ ID NO 23
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Thr Gly Asn Gln Phe Tyr Phe Gly Thr Gly Thr Ser Leu Thr Val
            100                 105                 110

Ile Pro
```

<210> SEQ ID NO 24
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
gctcagacag tcactcagtc tcaaccagag atgtctgtgc aggaggcaga gaccgtgacc     60

ctgagctgca catatgacac cagtgagagt gattattatt tattctggta caagcagcct    120

cccagcaggc agatgattct cgttattcgc caagaagctt ataagcaaca gaatgcaaca    180

gagaatcgtt tctctgtgaa cttccagaag gcagccaaat ccttcagtct caagatctca    240

gactcacagc tgggggatgc cgcgatgtat ttctgtgctt ataggagcgc gaccggtaac    300

cagttctatt ttgggacagg gacaagtttg acggtcattc ca                      342
```

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Met Asp His Glu Asn
1 5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Ser Tyr Asp Val Lys Met
1 5

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Ala Ser Ser Leu Trp Gly Trp Asn Ser Pro Leu His
1 5 10

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
atggaccatg aaaat 15

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
tcatatgatg ttaaaatg 18

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
gccagcagtt tatgggggtg gaattcaccc ctccac 36

<210> SEQ ID NO 31
<211> LENGTH: 113

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 31

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Gly Trp Asn Ser Pro Leu His Phe Gly Asn Gly Thr Arg Leu Thr Val
            100                 105                 110

Thr
```

<210> SEQ ID NO 32
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 32

```
gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgccagca gtttatgggg gtggaattca    300

cccctccact ttgggaacgg gaccaggctc actgtgaca                           339
```

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

```
Thr Ser Glu Ser Asp Tyr Tyr
1               5
```

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 34

```
Gln Glu Ala Tyr Lys Gln Gln Asn
1               5


<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Tyr Arg Ser Ala Pro Gly Asn Gln Phe Tyr
1               5                   10


<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

accagtgaga gtgattatta t                                                21


<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

caagaagctt ataagcaaca gaat                                             24


<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

gcttatagga gcgctcccgg taaccagttc tat                                   33


<210> SEQ ID NO 39
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60
```

-continued

```
Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Pro Gly Asn Gln Phe Tyr Phe Gly Thr Gly Thr Ser Leu Thr Val
            100                 105                 110

Ile Pro


<210> SEQ ID NO 40
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

gctcagacag tcactcagtc tcaaccagag atgtctgtgc aggaggcaga gaccgtgacc     60

ctgagctgca catatgacac cagtgagagt gattattatt tattctggta caagcagcct    120

cccagcaggc agatgattct cgttattcgc caagaagctt ataagcaaca gaatgcaaca    180

gagaatcgtt tctctgtgaa cttccagaaa gcagccaaat ccttcagtct caagatctca    240

gactcacagc tgggggatgc cgcgatgtat ttctgtgctt ataggagcgc tcccggtaac    300

cagttctatt ttgggacagg gacaagtttg acggtcattc ca                       342


<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Met Asp His Glu Asn
1               5


<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Tyr Asp Val Lys Met
1               5


<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Ser Ser Leu Phe Ala Thr Asn Glu Lys Leu Phe
1               5                   10


<210> SEQ ID NO 44
<211> LENGTH: 15
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
atggaccatg aaaat 15

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tcatatgatg ttaaaatg 18

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gccagcagtt tatttgcaac taatgaaaaa ctgttt 36

<210> SEQ ID NO 47
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Phe
                85                  90                  95

Ala Thr Asn Glu Lys Leu Phe Phe Gly Ser Gly Thr Gln Leu Ser Val
            100                 105                 110

Leu
```

<210> SEQ ID NO 48
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gatgtgaaag taacccagag ctcgagatat ctagtcaaaa ggacgggaga gaaagttttt 60
ctggaatgtg tccaggatat ggaccatgaa aatatgttct ggtatcgaca agacccaggt 120
ctggggctac ggctgatcta tttctcatat gatgttaaaa tgaaagaaaa aggagatatt 180
cctgaggggt acagtgtctc tagagagaag aaggagcgct tctccctgat tctggagtcc 240
gccagcacca accagacatc tatgtacctc tgtgccagca gtttatttgc aactaatgaa 300
aaactgtttt ttggcagtgg aacccagctc tctgtcttg 339

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Ser Val Phe Ser Ser
1 5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Val Val Thr Gly Gly Glu Val
1 5

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Ala Gly Glu Arg Asp Ser Trp Gly Lys Phe Gln
1 5 10

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 52
agtgtttttt ccagc 15

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 53
gtagttacgg gtggagaagt g 21

<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 54
gcaggagaga gggacagctg gggaaattc cag 33

<210> SEQ ID NO 55
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Glu Arg Asp Ser Trp
                85                  90                  95

Gly Lys Phe Gln Phe Gly Ala Gly Thr Gln Val Val Val Thr Pro
            100                 105                 110
```

<210> SEQ ID NO 56
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
acccagctgc tggagcagag ccctcagttt ctaagcatcc aagagggaga aaatctcact     60

gtgtactgca actcctcaag tgttttttcc agcttacaat ggtacagaca ggagcctggg    120

gaaggtcctg tcctcctggt gacagtagtt acgggtggag aagtgaagaa gctgaagaga    180

ctaacctttc agtttggtga tgcaagaaag gacagttctc tccacatcac tgcggcccag    240

cctggtgata caggcctcta cctctgtgca ggagagaggg acagctgggg gaaattccag    300

tttggagcag ggacccaggt tgtggtcacc cca                                 333
```

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Met Asn His Asn Tyr
1 5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Ser Val Gly Ala Gly Ile
1 5

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Ala Ser Ser Phe Trp Thr Gly Gly Asp Glu Lys Leu Phe
1 5 10

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60
atgaaccata actac 15

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61
tcagttggtg ctggtatc 18

<210> SEQ ID NO 62
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
gccagcagtt tttggacagg gggcgatgaa aaactgttt 39

<210> SEQ ID NO 63
<211> LENGTH: 114
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 63

```
Asn Ala Gly Val Thr Gln Thr Pro Lys Phe Arg Ile Leu Lys Ile Gly
1               5                   10                  15

Gln Ser Met Thr Leu Gln Cys Ala Gln Asp Met Asn His Asn Tyr Met
            20                  25                  30

Tyr Trp Tyr Arg Gln Asp Pro Gly Met Gly Leu Lys Leu Ile Tyr Tyr
        35                  40                  45

Ser Val Gly Ala Gly Ile Thr Asp Lys Gly Glu Val Pro Asn Gly Tyr
    50                  55                  60

Asn Val Ser Arg Ser Thr Thr Glu Tyr Phe Pro Leu Arg Leu Glu Leu
65                  70                  75                  80

Ala Ala Pro Ser Gln Thr Ser Val Tyr Phe Cys Ala Ser Ser Phe Trp
                85                  90                  95

Thr Gly Gly Asp Glu Lys Leu Phe Phe Gly Ser Gly Thr Gln Leu Ser
            100                 105                 110

Val Leu
```

<210> SEQ ID NO 64
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64

```
aatgctggtg tcactcagac cccaaaattc cgcatcctga agataggaca gagcatgaca      60

ctgcagtgtg cccaggatat gaaccataac tacatgtact ggtatcgaca agacccaggc     120

atggggctga agctgattta ttattcagtt ggtgctggta tcactgataa aggagaagtc     180

ccgaatggct acaacgtctc cagatcaacc acagagtatt tcccgctcag gctggagttg     240

gctgctccct cccagacatc tgtgtacttc tgtgccagca gtttttggac agggggcgat     300

gaaaaactgt tttttggcag tggaacccag ctctctgtct tg                        342
```

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

```
Thr Ser Glu Ser Asp Tyr Tyr
1               5
```

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

```
Gln Glu Ala Tyr Lys Gln Gln Asn
1               5
```

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Ala Tyr Arg Ser Ala Pro Gly Asn Gln Phe Tyr
1 5 10

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
accagtgaga gtgattatta t 21

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
caagaagctt ataagcaaca gaat 24

<210> SEQ ID NO 70
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
gcttatagga gcgcgcccgg taaccagttc tat 33

<210> SEQ ID NO 71
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Ser Asp Tyr
20 25 30

Tyr Leu Phe Trp Tyr Lys Gln Pro Pro Ser Arg Gln Met Ile Leu Val
35 40 45

Ile Arg Gln Glu Ala Tyr Lys Gln Gln Asn Ala Thr Glu Asn Arg Phe
50 55 60

Ser Val Asn Phe Gln Lys Ala Ala Lys Ser Phe Ser Leu Lys Ile Ser
65 70 75 80

```
Asp Ser Gln Leu Gly Asp Ala Ala Met Tyr Phe Cys Ala Tyr Arg Ser
                85                  90                  95

Ala Pro Gly Asn Gln Phe Tyr Phe Gly Thr Gly Thr Ser Leu Thr Val
            100                 105                 110

Ile Pro


<210> SEQ ID NO 72
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

gctcagacag tcactcagtc tcaaccagag atgtctgtgc aggaggcaga gaccgtgacc      60

ctgagctgca catatgacac cagtgagagt gattattatt tattctggta caagcagcct     120

cccagcaggc agatgattct cgttattcgc caagaagctt ataagcaaca gaatgcaaca     180

gagaatcgtt tctctgtgaa cttccagaaa gcagccaaat ccttcagtct caagatctca     240

gactcacagc tgggggatgc cgcgatgtat ttctgtgctt ataggagcgc gcccggtaac     300

cagttctatt ttgggacagg gacaagtttg acggtcattc ca                        342


<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Met Asp His Glu Asn
1               5


<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Tyr Asp Val Lys Met
1               5


<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Ser Ser Leu Trp Ala Thr Asn Glu Lys Leu Phe
1               5                   10


<210> SEQ ID NO 76
<211> LENGTH: 15
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 76
atggaccatg aaaat 15

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tcatatgatg ttaaaatg 18

<210> SEQ ID NO 78
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gccagcagtt tatgggcaac taatgaaaaa ctgttt 36

<210> SEQ ID NO 79
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Ala Thr Asn Glu Lys Leu Phe Phe Gly Ser Gly Thr Gln Leu Ser Val
            100                 105                 110

Leu
```

<210> SEQ ID NO 80
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
gatgtgaaag taacccagag ctcgagatat ctagtcaaaa ggacgggaga gaaagttttt 60

```
ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgccagca gtttatgggc aactaatgaa    300

aaactgtttt ttggcagtgg aacccagctc tctgtcttg                           339


<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Ser Glu Ser Asp Tyr Tyr
1               5


<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Glu Ala Tyr Lys Gln Gln Asn
1               5


<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Tyr Arg Ser Ala Arg Gly Asn Gln Phe Tyr
1               5                   10


<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84

accagtgaga gtgattatta t                                               21


<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85

caagaagctt ataagcaaca gaat                                            24
```

<210> SEQ ID NO 86
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
gcttatagga gcgctcgggg taaccagttc tat 33

<210> SEQ ID NO 87
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

```
Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Arg Gly Asn Gln Phe Tyr Phe Gly Thr Gly Thr Ser Leu Thr Val
            100                 105                 110

Ile Pro
```

<210> SEQ ID NO 88
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88

```
gctcagacag tcactcagtc tcaaccagag atgtctgtgc aggaggcaga gaccgtgacc     60

ctgagctgca catatgacac cagtgagagt gattattatt tattctggta caagcagcct    120

cccagcaggc agatgattct cgttattcgc caagaagctt ataagcaaca gaatgcaaca    180

gagaatcgtt tctctgtgaa cttccagaaa gcagccaaat ccttcagtct caagatctca    240

gactcacagc tgggggatgc cgcgatgtat ttctgtgctt ataggagcgc tcggggtaac    300

cagttctatt ttgggacagg gacaagtttg acggtcattc ca                       342
```

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

Met Asp His Glu Asn
1               5

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ser Tyr Asp Val Lys Met
1               5

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Ser Ser Leu Trp Gly Val Asn Ser Pro Leu His
1               5                   10

<210> SEQ ID NO 92
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
atggaccatg aaaa                                                    14

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tcatatgatg ttaaaatg                                                18

<210> SEQ ID NO 94
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gccagcagtt tatgggggt aaattcaccc ctccac                             36

<210> SEQ ID NO 95
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Gly Val Asn Ser Pro Leu His Phe Gly Asn Gly Thr Arg Leu Thr Val
            100                 105                 110

Thr

<210> SEQ ID NO 96
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
gatgtgaaag taacccagag ctcgagatat ctagtcaaaa ggacgggaga gaaagttttt     60
ctggaatgtg tccaggatat ggaccatgaa aatatgttct ggtatcgaca agacccaggt    120
ctggggctac ggctgatcta tttctcatat gatgttaaaa tgaaagaaaa aggagatatt    180
cctgaggggt acagtgtctc tagagagaag aaggagcgct tctccctgat tctggagtcc    240
gccagcacca accagacatc tatgtacctc tgtgccagca gtttatgggg ggtaaattca    300
cccctccact ttgggaacgg gaccaggctc actgtgaca                           339

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Ser Glu Ser Asp Tyr Tyr
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Glu Ala Tyr Lys Gln Gln Asn
1               5

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

```
Ala Tyr Arg Ser Ala Pro Gly Asn Gln Phe Tyr
1               5                   10
```

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 100

```
accagtgaga gtgattatta t                                                21
```

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 101

```
caagaagctt ataagcaaca gaat                                             24
```

<210> SEQ ID NO 102
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102

```
gcttatagga gcgcgcccgg taaccagttc tat                                   33
```

<210> SEQ ID NO 103
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

```
Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
```

```
                85                  90                  95

Ala Pro Gly Asn Gln Phe Tyr Phe Gly Thr Gly Thr Ser Leu Thr Val
            100                 105                 110

Ile Pro


<210> SEQ ID NO 104
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

gctcagacag tcactcagtc tcaaccagag atgtctgtgc aggaggcaga gaccgtgacc      60

ctgagctgca catatgacac cagtgagagt gattattatt tattctggta caagcagcct     120

cccagcaggc agatgattct cgttattcgc caagaagctt ataagcaaca gaatgcaaca     180

gagaatcgtt tctctgtgaa cttccagaaa gcagccaaat ccttcagtct caagatctca     240

gactcacagc tgggggatgc cgcgatgtat ttctgtgctt ataggagcgc gcccggtaac     300

cagttctatt ttgggacagg gacaagtttg acggtcattc ca                        342


<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Met Asp His Glu Asn
1               5


<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Tyr Asp Val Lys Met
1               5


<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Ser Ser Leu Trp Gly Leu Asn Thr Glu Ala Phe
1               5                   10


<210> SEQ ID NO 108
<211> LENGTH: 15
<212> TYPE: DNA
<213> ORGANISM: Artificial Sequence
<220> FEATURE:
<223> OTHER INFORMATION: Description of Artificial Sequence: Synthetic
```

oligonucleotide

<400> SEQUENCE: 108
atggaccatg aaaat 15

<210> SEQ ID NO 109
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 109
tcatatgatg ttaaaatg 18

<210> SEQ ID NO 110
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 110
gccagcagtt tatgggggtt gaacactgaa gctttc 36

<210> SEQ ID NO 111
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Gly Leu Asn Thr Glu Ala Phe Phe Gly Gln Gly Thr Arg Leu Thr Val
            100                 105                 110

Val
```

<210> SEQ ID NO 112
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112
gatgtgaaag taacccagag ctcgagatat ctagtcaaaa ggacgggaga gaaagttttt 60

```
ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgccagca gtttatgggg gttgaacact    300

gaagcttttct ttggacaagg caccagactc acagttgta                          339


<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Thr Ser Glu Ser Asp Tyr Tyr
1               5


<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gln Glu Ala Tyr Lys Gln Gln Asn
1               5


<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Tyr Arg Ser Ala Glu Gly Asn Gln Phe Tyr
1               5                   10


<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116

accagtgaga gtgattatta t                                               21


<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117

caagaagctt ataagcaaca gaat                                            24
```

```
<210> SEQ ID NO 118
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118

gcttatagga gcgcggaggg taaccagttc tat                                33


<210> SEQ ID NO 119
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Glu Gly Asn Gln Phe Tyr Phe Gly Thr Gly Thr Ser Leu Thr Val
            100                 105                 110

Ile Pro


<210> SEQ ID NO 120
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

gctcagacag tcactcagtc tcaaccagag atgtctgtgc aggaggcaga gaccgtgacc     60

ctgagctgca catatgacac cagtgagagt gattattatt tattctggta caagcagcct    120

cccagcaggc agatgattct cgttattcgc caagaagctt ataagcaaca gaatgcaaca    180

gagaatcgtt tctctgtgaa cttccagaaa gcagccaaat ccttcagtct caagatctca    240

gactcacagc tgggggatgc cgcgatgtat ttctgtgctt ataggagcgc ggagggtaac    300

cagttctatt ttgggacagg gacaagtttg acggtcattc ca                       342


<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121
```

Met Asp His Glu Asn
1 5

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 122

Ser Tyr Asp Val Lys Met
1 5

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 123

Ala Ser Ser Leu Trp Gly Leu Asn Thr Glu Ala Phe
1 5 10

<210> SEQ ID NO 124
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 124
atggaccatg aaaat 15

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 125
tcatatgatg ttaaaatg 18

<210> SEQ ID NO 126
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 126
gccagcagtt tatgggggtt gaacactgaa gctttc 36

<210> SEQ ID NO 127
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 127

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Gly Leu Asn Thr Glu Ala Phe Phe Gly Gln Gly Thr Arg Leu Thr Val
            100                 105                 110

Val

<210> SEQ ID NO 128
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128
gatgtgaaag taacccagag ctcgagatat ctagtcaaaa ggacgggaga gaaagttttt 60
ctggaatgtg tccaggatat ggaccatgaa aatatgttct ggtatcgaca agacccaggt 120
ctggggctac ggctgatcta tttctcatat gatgttaaaa tgaaagaaaa aggagatatt 180
cctgaggggt acagtgtctc tagagagaag aaggagcgct tctccctgat tctggagtcc 240
gccagcacca accagacatc tatgtacctc tgtgccagca gtttatgggg gttgaacact 300
gaagctttct ttggacaagg caccagactc acagttgta 339

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Thr Arg Asp Thr Thr Tyr Tyr
1               5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Arg Asn Ser Phe Asp Glu Gln Asn
1               5

<210> SEQ ID NO 131

<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

```
Ala Leu Ser Glu Gly Asp Thr Gly Gly Phe Lys Thr Ile
1               5                   10
```

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 132

```
acccgtgata ctacttatta c                                              21
```

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 133

```
cggaactctt ttgatgagca aaat                                           24
```

<210> SEQ ID NO 134
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 134

```
gctctgagtg agggggatac tggaggcttc aaaactatc                           39
```

<210> SEQ ID NO 135
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 135

```
Ala Gln Lys Val Thr Gln Ala Gln Thr Glu Ile Ser Val Val Glu Lys
1               5                   10                  15

Glu Asp Val Thr Leu Asp Cys Val Tyr Glu Thr Arg Asp Thr Thr Tyr
            20                  25                  30

Tyr Leu Phe Trp Tyr Lys Gln Pro Pro Ser Gly Glu Leu Val Phe Leu
        35                  40                  45

Ile Arg Arg Asn Ser Phe Asp Glu Gln Asn Glu Ile Ser Gly Arg Tyr
    50                  55                  60

Ser Trp Asn Phe Gln Lys Ser Thr Ser Ser Phe Asn Phe Thr Ile Thr
65                  70                  75                  80

Ala Ser Gln Val Val Asp Ser Ala Val Tyr Phe Cys Ala Leu Ser Glu
                85                  90                  95
```

```
Gly Asp Thr Gly Gly Phe Lys Thr Ile Phe Gly Ala Gly Thr Arg Leu
            100                 105                 110

Phe Val Lys Ala
        115


<210> SEQ ID NO 136
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136

gctcagaagg taactcaagc gcagactgaa atttctgtgg tggagaagga ggatgtgacc      60

ttggactgtg tgtatgaaac ccgtgatact acttattact tattctggta caagcaacca     120

ccaagtggag aattggtttt ccttattcgt cggaactctt ttgatgagca aaatgaaata     180

agtggtcggt attcttggaa cttccagaaa tccaccagtt ccttcaactt caccatcaca     240

gcctcacaag tcgtggactc agcagtatac ttctgtgctc tgagtgaggg ggatactgga     300

ggcttcaaaa ctatctttgg agcaggaaca agactatttg ttaaagca                  348


<210> SEQ ID NO 137
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Met Asn His Asn Tyr
1               5


<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ser Val Gly Ala Gly Ile
1               5


<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ala Ser Ser Tyr Phe Pro Asp Arg Gly Leu Gly Asn Thr Ile Tyr
1               5                   10                  15


<210> SEQ ID NO 140
<211> LENGTH: 15
<212> TYPE: DNA
<213> ORGANISM: Artificial Sequence
<220> FEATURE:
<223> OTHER INFORMATION: Description of Artificial Sequence: Synthetic
```

oligonucleotide

<400> SEQUENCE: 140
atgaaccata actac 15

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 141
tcagttggtg ctggtatc 18

<210> SEQ ID NO 142
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142
gccagcagtt acttcccgga cagggggctt ggaaacacca tatat 45

<210> SEQ ID NO 143
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 143

```
Asn Ala Gly Val Thr Gln Thr Pro Lys Phe Arg Ile Leu Lys Ile Gly
1               5                   10                  15

Gln Ser Met Thr Leu Gln Cys Ala Gln Asp Met Asn His Asn Tyr Met
            20                  25                  30

Tyr Trp Tyr Arg Gln Asp Pro Gly Met Gly Leu Lys Leu Ile Tyr Tyr
        35                  40                  45

Ser Val Gly Ala Gly Ile Thr Asp Lys Gly Glu Val Pro Asn Gly Tyr
    50                  55                  60

Asn Val Ser Arg Ser Thr Thr Glu Tyr Phe Pro Leu Arg Leu Glu Leu
65                  70                  75                  80

Ala Ala Pro Ser Gln Thr Ser Val Tyr Phe Cys Ala Ser Ser Tyr Phe
                85                  90                  95

Pro Asp Arg Gly Leu Gly Asn Thr Ile Tyr Phe Gly Glu Gly Ser Trp
            100                 105                 110

Leu Thr Val Val
        115
```

<210> SEQ ID NO 144
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 144
aatgctggtg tcactcagac cccaaaattc cgcatcctga agataggaca gagcatgaca 60

```
ctgcagtgtg cccaggatat gaaccataac tacatgtact ggtatcgaca agacccaggc    120

atggggctga agctgattta ttattcagtt ggtgctggta tcactgataa aggagaagtc    180

ccgaatggct acaacgtctc cagatcaacc acagagtatt tcccgctcag gctggagttg    240

gctgctccct cccagacatc tgtgtacttc tgtgccagca gttacttccc ggacaggggg    300

cttggaaaca ccatatattt tggagaggga agttggctca ctgttgta                 348
```

<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

```
Asp Arg Gly Ser Gln Ser
1               5
```

<210> SEQ ID NO 146
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

```
Ile Tyr Ser Asn Gly Asp
1               5
```

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

```
Ala Val Asn Leu Ser Trp Gly Lys Phe Gln
1               5                   10
```

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 148

```
gaccgaggtt cccagtcc                                                    18
```

<210> SEQ ID NO 149
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 149

```
atatactcca atggtgac                                                    18
```

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 150
gccgtgaact tgagctgggg gaaattccag 30

<210> SEQ ID NO 151
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 151

```
Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Leu Ser Trp Gly
                85                  90                  95

Lys Phe Gln Phe Gly Ala Gly Thr Gln Val Val Val Thr Pro
            100                 105                 110
```

<210> SEQ ID NO 152
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 152

```
cagaaggagg tggagcagaa ttctggaccc ctcagtgttc cagagggagc cattgcctct     60

ctcaactgca cttacagtga ccgaggttcc cagtccttct tctggtacag acaatattct    120

gggaaaagcc ctgagttgat aatgtccata tactccaatg gtgacaaaga agatggaagg    180

tttacagcac agctcaataa agccagccag tatgtttctc tgctcatcag agactcccag    240

cccagtgatt cagccaccta cctctgtgcc gtgaacttga gctgggggaa attccagttt    300

ggagcaggga cccaggttgt ggtcacccca                                     330
```

<210> SEQ ID NO 153
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 153

Ser Gly His Asp Thr
1 5

<210> SEQ ID NO 154
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Tyr Tyr Glu Glu Glu Glu
1 5

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 155

Ala Ser Ser Leu Asp Arg Ser Thr Glu Ala Phe
1 5 10

<210> SEQ ID NO 156
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 156
tctgggcatg acact 15

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 157
tattatgagg aggaagag 18

<210> SEQ ID NO 158
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 158
gccagcagct tggacaggag cactgaagct ttc 33

<210> SEQ ID NO 159
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 159

```
Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Leu Asp
                85                  90                  95

Arg Ser Thr Glu Ala Phe Phe Gly Gln Gly Thr Arg Leu Thr Val Val
            100                 105                 110
```

<210> SEQ ID NO 160
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 160

```
gacgctggag tcacccaaag tcccacacac ctgatcaaaa cgagaggaca gcaagtgact     60

ctgagatgct ctcctaagtc tgggcatgac actgtgtcct ggtaccaaca ggccctgggt    120

caggggcccc agtttatctt tcagtattat gaggaggaag agagacagag aggcaacttc    180

cctgatcgat tctcaggtca ccagttccct aactatagct ctgagctgaa tgtgaacgcc    240

ttgttgctgg gggactcggc cctctatctc tgtgccagca gcttggacag gagcactgaa    300

gctttctttg gacaaggcac cagactcaca gttgta                              336
```

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

```
Val Ser Gly Leu Arg Gly
1               5
```

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 162

```
Leu Tyr Ser Ala Gly Glu Glu
1               5
```

<210> SEQ ID NO 163
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

```
Ala Val Gln Ala Val Thr Gly Gly Gly Asn Lys Leu Thr
1               5                   10
```

<210> SEQ ID NO 164
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164

```
gtcagcggtt taagaggg                                                    18
```

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165

```
ctgtattcag ctggggaaga a                                                21
```

<210> SEQ ID NO 166
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166

```
gctgtgcagg cggtcacggg aggaggaaac aaactcacc                             39
```

<210> SEQ ID NO 167
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

```
Glu Asp Gln Val Thr Gln Ser Pro Glu Ala Leu Arg Leu Gln Glu Gly
1               5                   10                  15

Glu Ser Ser Ser Leu Asn Cys Ser Tyr Thr Val Ser Gly Leu Arg Gly
            20                  25                  30

Leu Phe Trp Tyr Arg Gln Asp Pro Gly Lys Gly Pro Glu Phe Leu Phe
        35                  40                  45

Thr Leu Tyr Ser Ala Gly Glu Glu Lys Glu Lys Glu Arg Leu Lys Ala
    50                  55                  60

Thr Leu Thr Lys Lys Glu Ser Phe Leu His Ile Thr Ala Pro Lys Pro
65                  70                  75                  80

Glu Asp Ser Ala Thr Tyr Leu Cys Ala Val Gln Ala Val Thr Gly Gly
                85                  90                  95

Gly Asn Lys Leu Thr Phe Gly Thr Gly Thr Gln Leu Lys Val Glu Leu
            100                 105                 110
```

<210> SEQ ID NO 168
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 168
gaagaccagg tgacgcagag tcccgaggcc ctgagactcc aggagggaga gagtagcagt 60
ctcaactgca gttacacagt cagcggttta agagggctgt tctggtatag gcaagatcct 120
gggaaaggcc ctgaattcct cttcaccctg tattcagctg gggaagaaaa ggagaaagaa 180
aggctaaaag ccacattaac aaagaaggaa agctttctgc acatcacagc ccctaaacct 240
gaagactcag ccacttatct ctgtgctgtg caggcggtca cgggaggagg aaacaaactc 300
acctttggga caggcactca gctaaaagtg gaactc 336

<210> SEQ ID NO 169
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Asp Phe Gln Ala Thr Thr
1 5

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

Ser Asn Glu Gly Ser Lys Ala
1 5

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Ser Ala Ser Trp Asp Arg Asp Tyr Gly Tyr Thr
1 5 10

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 172
gactttcagg ccacaact 18

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 173
tccaatgagg gctccaaggc c 21

<210> SEQ ID NO 174
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 174
agtgctagtt gggacaggga ctatggctac acc 33

<210> SEQ ID NO 175
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 175

Gly Ala Val Val Ser Gln His Pro Ser Trp Val Ile Cys Lys Ser Gly
1 5 10 15

Thr Ser Val Lys Ile Glu Cys Arg Ser Leu Asp Phe Gln Ala Thr Thr
20 25 30

Met Phe Trp Tyr Arg Gln Phe Pro Lys Gln Ser Leu Met Leu Met Ala
35 40 45

Thr Ser Asn Glu Gly Ser Lys Ala Thr Tyr Glu Gln Gly Val Glu Lys
50 55 60

Asp Lys Phe Leu Ile Asn His Ala Ser Leu Thr Leu Ser Thr Leu Thr
65 70 75 80

Val Thr Ser Ala His Pro Glu Asp Ser Ser Phe Tyr Ile Cys Ser Ala
85 90 95

Ser Trp Asp Arg Asp Tyr Gly Tyr Thr Phe Gly Ser Gly Thr Arg Leu
100 105 110

Thr Val Val
115

<210> SEQ ID NO 176
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 176
ggtgctgtcg tctctcaaca tccgagctgg gttatctgta agagtggaac ctctgtgaag 60
atcgagtgcc gttccctgga ctttcaggcc acaactatgt tttggtatcg tcagttcccg 120
aaacagagtc tcatgctgat ggcaacttcc aatgagggct ccaaggccac atacgagcaa 180
ggcgtcgaga aggacaagtt tctcatcaac catgcaagcc tgaccttgtc cactctgaca 240
gtgaccagtg cccatcctga agacagcagc ttctacatct gcagtgctag ttgggacagg 300
gactatggct acaccttcgg ttcggggacc aggttaaccg ttgta 345

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 177

Thr Ser Glu Ser Asp Tyr Tyr
1 5

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

Gln Glu Ala Tyr Lys Gln Gln Asn
1 5

<210> SEQ ID NO 179
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 179

Ala Tyr Arg Ser Ala Thr Gly Asn Gln Phe Tyr
1 5 10

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 180
accagtgaga gtgattatta t 21

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 181
caagaagctt ataagcaaca gaat 24

<210> SEQ ID NO 182
<211> LENGTH: 33
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 182
gcttatagga gcgccaccgg taaccagttc tat 33

<210> SEQ ID NO 183
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

```
Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Thr Gly Asn Gln Phe Tyr Phe Gly Thr Gly Thr Ser Leu Thr Val
            100                 105                 110

Ile Pro
```

<210> SEQ ID NO 184
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 184

```
gctcagacag tcactcagtc tcaaccagag atgtctgtgc aggaggcaga gaccgtgacc     60

ctgagctgca catatgacac cagtgagagt gattattatt tattctggta caagcagcct    120

cccagcaggc agatgattct cgttattcgc caagaagctt ataagcaaca gaatgcaaca    180

gagaatcgtt tctctgtgaa cttccagaaa gcagccaaat ccttcagtct caagatctca    240

gactcacagc tgggggatgc cgcgatgtat ttctgtgctt ataggagcgc caccggtaac    300

cagttctatt ttgggacagg gacaagtttg acggtcattc ca                       342
```

<210> SEQ ID NO 185
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

```
Met Asp His Glu Asn
1               5
```

<210> SEQ ID NO 186
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 186

Ser Tyr Asp Val Lys Met
1 5

<210> SEQ ID NO 187
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 187

Ala Ser Ser Leu Trp Gly Trp Gly Thr Glu Ala Phe
1 5 10

<210> SEQ ID NO 188
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 188
atggaccatg aaaat 15

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 189
tcatatgatg ttaaaatg 18

<210> SEQ ID NO 190
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 190
gccagcagtt tatggggttg gggcactgaa gctttc 36

<210> SEQ ID NO 191
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 191

Asp Val Lys Val Thr Gln Ser Ser Arg Tyr Leu Val Lys Arg Thr Gly
1 5 10 15

```
Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Gly Trp Gly Thr Glu Ala Phe Phe Gly Gln Gly Thr Arg Leu Thr Val
            100                 105                 110

Val


<210> SEQ ID NO 192
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192

gatgtgaaag taacccagag ctcgagatat ctagtcaaaa ggacgggaga gaaagttttt      60

ctggaatgtg tccaggatat ggaccatgaa aatatgttct ggtatcgaca agacccaggt     120

ctggggctac ggctgatcta tttctcatat gatgttaaaa tgaaagaaaa aggagatatt     180

cctgaggggt acagtgtctc tagagagaag aaggagcgct tctccctgat tctggagtcc     240

gccagcacca accagacatc tatgtacctc tgtgccagca gtttatgggg ttggggcact     300

gaagctttct ttggacaagg caccagactc acagttgta                            339


<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Thr Ser Glu Ser Asp Tyr Tyr
1               5


<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gln Glu Ala Tyr Lys Gln Gln Asn
1               5


<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 195

Ala Tyr Arg Ser Pro Thr Gly Asn Gln Phe Tyr
1 5 10

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 196
accagtgaga gtgattatta t 21

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 197
caagaagctt ataagcaaca gaat 24

<210> SEQ ID NO 198
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 198
gcttatagga gccccaccgg taaccagttc tat 33

<210> SEQ ID NO 199
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 199

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Ser Asp Tyr
20 25 30

Tyr Leu Phe Trp Tyr Lys Gln Pro Pro Ser Arg Gln Met Ile Leu Val
35 40 45

Ile Arg Gln Glu Ala Tyr Lys Gln Gln Asn Ala Thr Glu Asn Arg Phe
50 55 60

Ser Val Asn Phe Gln Lys Ala Ala Lys Ser Phe Ser Leu Lys Ile Ser
65 70 75 80

Asp Ser Gln Leu Gly Asp Ala Ala Met Tyr Phe Cys Ala Tyr Arg Ser
85 90 95

Pro Thr Gly Asn Gln Phe Tyr Phe Gly Thr Gly Thr Ser Leu Thr Val
100 105 110

Ile Pro

<210> SEQ ID NO 200
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 200
gctcagacag tcactcagtc tcaaccagag atgtctgtgc aggaggcaga gaccgtgacc 60
ctgagctgca catatgacac cagtgagagt gattattatt tattctggta caagcagcct 120
cccagcaggc agatgattct cgttattcgc caagaagctt ataagcaaca gaatgcaaca 180
gagaatcgtt tctctgtgaa cttccagaaa gcagccaaat ccttcagtct caagatctca 240
gactcacagc tgggggatgc cgcgatgtat ttctgtgctt ataggagccc caccggtaac 300
cagttctatt ttgggacagg gacaagtttg acggtcattc ca 342

<210> SEQ ID NO 201
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 201

Met Asp His Glu Asn
1 5

<210> SEQ ID NO 202
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 202

Ser Tyr Asp Val Lys Met
1 5

<210> SEQ ID NO 203
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 203

Ala Ser Ser Leu Trp Ala Met Asn Thr Glu Ala Phe
1 5 10

<210> SEQ ID NO 204
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 204
atggaccatg aaaat 15

<210> SEQ ID NO 205
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 205
tcatatgatg ttaaaatg 18

<210> SEQ ID NO 206
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 206
gccagcagtt tatgggcaat gaacactgaa gctttc 36

<210> SEQ ID NO 207
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 207

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Ala Met Asn Thr Glu Ala Phe Phe Gly Gln Gly Thr Arg Leu Thr Val
            100                 105                 110

Val
```

<210> SEQ ID NO 208
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 208

```
gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240
```

gccagcacca accagacatc tatgtacctc tgtgccagca gtttatgggc aatgaacact 300
gaagctttct ttggacaagg caccagactc acagttgta 339

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 209

Thr Ser Glu Ser Asp Tyr Tyr
1 5

<210> SEQ ID NO 210
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 210

Gln Glu Ala Tyr Lys Gln Gln Asn
1 5

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 211

Ala Tyr Arg Ser Ala Arg Gly Asn Gln Phe Tyr
1 5 10

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 212
accagtgaga gtgattatta t 21

<210> SEQ ID NO 213
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 213
caagaagctt ataagcaaca gaat 24

<210> SEQ ID NO 214
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 214
gcttatagga gcgcgcgggg taaccagttc tat 33

<210> SEQ ID NO 215
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 215

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Ser Asp Tyr
20 25 30

Tyr Leu Phe Trp Tyr Lys Gln Pro Pro Ser Arg Gln Met Ile Leu Val
35 40 45

Ile Arg Gln Glu Ala Tyr Lys Gln Gln Asn Ala Thr Glu Asn Arg Phe
50 55 60

Ser Val Asn Phe Gln Lys Ala Ala Lys Ser Phe Ser Leu Lys Ile Ser
65 70 75 80

Asp Ser Gln Leu Gly Asp Ala Ala Met Tyr Phe Cys Ala Tyr Arg Ser
85 90 95

Ala Arg Gly Asn Gln Phe Tyr Phe Gly Thr Gly Thr Ser Leu Thr Val
100 105 110

Ile Pro

<210> SEQ ID NO 216
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 216
gctcagacag tcactcagtc tcaaccagag atgtctgtgc aggaggcaga gaccgtgacc 60
ctgagctgca catatgacac cagtgagagt gattattatt tattctggta caagcagcct 120
cccagcaggc agatgattct cgttattcgc caagaagctt ataagcaaca gaatgcaaca 180
gagaatcgtt tctctgtgaa cttccagaaa gcagccaaat ccttcagtct caagatctca 240
gactcacagc tgggggatgc cgcgatgtat ttctgtgctt ataggagcgc gcggggtaac 300
cagttctatt ttgggacagg gacaagtttg acggtcattc ca 342

<210> SEQ ID NO 217
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 217

Met Asp His Glu Asn
1 5

<210> SEQ ID NO 218

<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 218

Ser Tyr Asp Val Lys Met
1 5

<210> SEQ ID NO 219
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 219

Ala Ser Ser Leu Trp Gly Thr Asn Glu Lys Leu Phe
1 5 10

<210> SEQ ID NO 220
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 220
atggaccatg aaaat 15

<210> SEQ ID NO 221
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 221
tcatatgatg ttaaaatg 18

<210> SEQ ID NO 222
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 222
gccagcagtt tatgggggac taatgaaaaa ctgttt 36

<210> SEQ ID NO 223
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 223

Asp Val Lys Val Thr Gln Ser Ser Arg Tyr Leu Val Lys Arg Thr Gly
1 5 10 15

```
Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Gly Thr Asn Glu Lys Leu Phe Phe Gly Ser Gly Thr Gln Leu Ser Val
            100                 105                 110

Leu


<210> SEQ ID NO 224
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 224

gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgccagca gtttatgggg gactaatgaa    300

aaactgtttt ttggcagtgg aacccagctc tctgtcttg                           339


<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Thr Ser Glu Ser Asp Tyr Tyr
1               5


<210> SEQ ID NO 226
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gln Glu Ala Tyr Lys Gln Gln Asn
1               5


<210> SEQ ID NO 227
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 227

Ala Tyr Arg Ser Ala Thr Gly Asn Gln Phe Tyr
1 5 10

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 228
accagtgaga gtgattatta t 21

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 229
caagaagctt ataagcaaca gaat 24

<210> SEQ ID NO 230
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 230
gcttatagga gcgcaaccgg taaccagttc tat 33

<210> SEQ ID NO 231
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 231

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Ser Asp Tyr
20 25 30

Tyr Leu Phe Trp Tyr Lys Gln Pro Pro Ser Arg Gln Met Ile Leu Val
35 40 45

Ile Arg Gln Glu Ala Tyr Lys Gln Gln Asn Ala Thr Glu Asn Arg Phe
50 55 60

Ser Val Asn Phe Gln Lys Ala Ala Lys Ser Phe Ser Leu Lys Ile Ser
65 70 75 80

Asp Ser Gln Leu Gly Asp Ala Ala Met Tyr Phe Cys Ala Tyr Arg Ser
85 90 95

Ala Thr Gly Asn Gln Phe Tyr Phe Gly Thr Gly Thr Ser Leu Thr Val
100 105 110

Ile Pro

<210> SEQ ID NO 232
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 232
gctcagacag tcactcagtc tcaaccagag atgtctgtgc aggaggcaga gaccgtgacc 60
ctgagctgca catatgacac cagtgagagt gattattatt tattctggta caagcagcct 120
cccagcaggc agatgattct cgttattcgc caagaagctt ataagcaaca gaatgcaaca 180
gagaatcgtt tctctgtgaa cttccagaaa gcagccaaat ccttcagtct caagatctca 240
gactcacagc tgggggatgc cgcgatgtat ttctgtgctt ataggagcgc aaccggtaac 300
cagttctatt ttgggacagg gacaagtttg acggtcattc ca 342

<210> SEQ ID NO 233
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 233

Met Asp His Glu Asn
1 5

<210> SEQ ID NO 234
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 234

Ser Tyr Asp Val Lys Met
1 5

<210> SEQ ID NO 235
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 235

Ala Ser Ser Leu Trp Gly Thr Asn Glu Lys Leu Phe
1 5 10

<210> SEQ ID NO 236
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 236
atggaccatg aaaat 15

<210> SEQ ID NO 237
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 237
tcatatgatg ttaaaatg 18

<210> SEQ ID NO 238
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 238
gccagcagtt tgtggggaac taatgaaaaa ctgttt 36

<210> SEQ ID NO 239
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 239

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Gly Thr Asn Glu Lys Leu Phe Phe Gly Ser Gly Thr Gln Leu Ser Val
            100                 105                 110

Leu
```

<210> SEQ ID NO 240
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 240

```
gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgccagca gtttgtgggg aactaatgaa    300
```

aaactgtttt ttggcagtgg aacccagctc tctgtcttg 339

<210> SEQ ID NO 241
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 241

Thr Ser Glu Ser Asp Tyr Tyr
1 5

<210> SEQ ID NO 242
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 242

Gln Glu Ala Tyr Lys Gln Gln Asn
1 5

<210> SEQ ID NO 243
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 243

Ala Tyr Arg Ser Ala Pro Gly Asn Gln Phe Tyr
1 5 10

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 244
accagtgaga gtgattatta t 21

<210> SEQ ID NO 245
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 245
caagaagctt ataagcaaca gaat 24

<210> SEQ ID NO 246
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 246
gcttatagga gcgcgcccgg taaccagttc tat 33

<210> SEQ ID NO 247
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 247

```
Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Pro Gly Asn Gln Phe Tyr Phe Gly Thr Gly Thr Ser Leu Thr Val
            100                 105                 110

Ile Pro
```

<210> SEQ ID NO 248
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 248

```
gctcagacag tcactcagtc tcaaccagag atgtctgtgc aggaggcaga gaccgtgacc     60

cttagctgca catatgacac cagtgagagt gattattatt tattctggta caagcagcct    120

cccagcaggc agatgattct cgttattcgc caagaagctt ataagcaaca gaatgcaaca    180

gagaatcgtt tctctgtgaa cttccagaaa gcagccaaat ccttcagtct caagatctca    240

gactcacagc tgggggatgc cgcgatgtat ttctgtgctt ataggagcgc gcccggtaac    300

cagttctatt ttgggacagg gacaagtttg acggtcattc ca                       342
```

<210> SEQ ID NO 249
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 249

```
Met Asp His Glu Asn
1               5
```

<210> SEQ ID NO 250
<211> LENGTH: 6

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 250

Ser Tyr Asp Val Lys Met
1 5

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 251

Ala Ser Ser Leu Trp Gly Thr Asn Glu Lys Leu Phe
1 5 10

<210> SEQ ID NO 252
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 252
atggaccatg aaaat 15

<210> SEQ ID NO 253
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 253
tcatatgatg ttaaaatg 18

<210> SEQ ID NO 254
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 254
gccagcagtt tatgggggac taatgaaaaa ctgttt 36

<210> SEQ ID NO 255
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 255

Asp Val Lys Val Thr Gln Ser Ser Arg Tyr Leu Val Lys Arg Thr Gly
1 5 10 15

Glu Lys Val Phe Leu Glu Cys Val Gln Asp Met Asp His Glu Asn Met

```
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Gly Thr Asn Glu Lys Leu Phe Phe Gly Ser Gly Thr Gln Leu Ser Val
            100                 105                 110

Leu


<210> SEQ ID NO 256
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 256

gatgtgaaag taacccagag ctcgagatat ctagtcaaaa ggacgggaga gaaagttttt      60

ctggaatgtg tccaggatat ggaccatgaa aatatgttct ggtatcgaca agacccaggt     120

ctggggctac ggctgatcta tttctcatat gatgttaaaa tgaaagaaaa aggagatatt     180

cctgaggggt acagtgtctc tagagagaag aaggagcgct tctccctgat tctggagtcc     240

gccagcacca accagacatc tatgtacctc tgtgccagca gtttatgggg gactaatgaa     300

aaactgtttt ttggcagtgg aacccagctc tctgtcttg                            339


<210> SEQ ID NO 257
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Thr Ser Glu Ser Asp Tyr Tyr
1               5


<210> SEQ ID NO 258
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gln Glu Ala Tyr Lys Gln Gln Asn
1               5


<210> SEQ ID NO 259
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 259

Ala Tyr Arg Ser Ala Ser Gly Asn Gln Phe Tyr
1 5 10

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 260
accagtgaga gtgattatta t 21

<210> SEQ ID NO 261
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 261
caagaagctt ataagcaaca gaat 24

<210> SEQ ID NO 262
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 262
gcttatagga gcgcgtccgg taaccagttc tat 33

<210> SEQ ID NO 263
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 263

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Ser Asp Tyr
20 25 30

Tyr Leu Phe Trp Tyr Lys Gln Pro Pro Ser Arg Gln Met Ile Leu Val
35 40 45

Ile Arg Gln Glu Ala Tyr Lys Gln Gln Asn Ala Thr Glu Asn Arg Phe
50 55 60

Ser Val Asn Phe Gln Lys Ala Ala Lys Ser Phe Ser Leu Lys Ile Ser
65 70 75 80

Asp Ser Gln Leu Gly Asp Ala Ala Met Tyr Phe Cys Ala Tyr Arg Ser
85 90 95

Ala Ser Gly Asn Gln Phe Tyr Phe Gly Thr Gly Thr Ser Leu Thr Val
100 105 110

Ile Pro

<210> SEQ ID NO 264
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 264
gctcagacag tcactcagtc tcaaccagag atgtctgtgc aggaggcaga gaccgtgacc      60
ctgagctgca catatgacac cagtgagagt gattattatt tattctggta caagcagcct     120
cccagcaggc agatgattct cgttattcgc caagaagctt ataagcaaca gaatgcaaca     180
gagaatcgtt tctctgtgaa cttccagaaa gcagccaaat ccttcagtct caagatctca     240
gactcacagc tgggggatgc cgcgatgtat ttctgtgctt ataggagcgc gtccggtaac     300
cagttctatt ttgggacagg gacaagtttg acggtcattc ca                        342

<210> SEQ ID NO 265
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Met Asp His Glu Asn
1               5

<210> SEQ ID NO 266
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ser Tyr Asp Val Lys Met
1               5

<210> SEQ ID NO 267
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ala Ser Ser Leu Trp Gly Thr Asn Glu Lys Leu Phe
1               5                   10

<210> SEQ ID NO 268
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
atggaccatg aaaat                                                       15

<210> SEQ ID NO 269

<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 269
tcatatgatg ttaaaatg 18

<210> SEQ ID NO 270
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 270
gccagcagtt tatggggcac taatgaaaaa ctgttt 36

<210> SEQ ID NO 271
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 271

Asp Val Lys Val Thr Gln Ser Ser Arg Tyr Leu Val Lys Arg Thr Gly
1 5 10 15

Glu Lys Val Phe Leu Glu Cys Val Gln Asp Met Asp His Glu Asn Met
20 25 30

Phe Trp Tyr Arg Gln Asp Pro Gly Leu Gly Leu Arg Leu Ile Tyr Phe
35 40 45

Ser Tyr Asp Val Lys Met Lys Glu Lys Gly Asp Ile Pro Glu Gly Tyr
50 55 60

Ser Val Ser Arg Glu Lys Lys Glu Arg Phe Ser Leu Ile Leu Glu Ser
65 70 75 80

Ala Ser Thr Asn Gln Thr Ser Met Tyr Leu Cys Ala Ser Ser Leu Trp
85 90 95

Gly Thr Asn Glu Lys Leu Phe Phe Gly Ser Gly Thr Gln Leu Ser Val
100 105 110

Leu

<210> SEQ ID NO 272
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 272
gatgtgaaag taacccagag ctcgagatat ctagtcaaaa ggacgggaga gaaagttttt 60
ctggaatgtg tccaggatat ggaccatgaa aatatgttct ggtatcgaca agacccaggt 120
ctggggctac ggctgatcta tttctcatat gatgttaaaa tgaaagaaaa aggagatatt 180
cctgaggggt acagtgtctc tagagagaag aaggagcgct tctccctgat tctggagtcc 240
gccagcacca accagacatc tatgtacctc tgtgccagca gtttatgggg cactaatgaa 300
aaactgtttt ttggcagtgg aacccagctc tctgtcttg 339

<210> SEQ ID NO 273
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 273

Thr Ser Glu Ser Asp Tyr Tyr
1 5

<210> SEQ ID NO 274
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 274

Gln Glu Ala Tyr Lys Gln Gln Asn
1 5

<210> SEQ ID NO 275
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 275

Ala Tyr Arg Ser Ala Pro Gly Asn Gln Phe Tyr
1 5 10

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 276
accagtgaga gtgattatta t 21

<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 277
caagaagctt ataagcaaca gaat 24

<210> SEQ ID NO 278
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 278
gcttatagga gcgcgcccgg taaccagttc tat 33

<210> SEQ ID NO 279
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 279

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Ser Asp Tyr
20 25 30

Tyr Leu Phe Trp Tyr Lys Gln Pro Pro Ser Arg Gln Met Ile Leu Val
35 40 45

Ile Arg Gln Glu Ala Tyr Lys Gln Gln Asn Ala Thr Glu Asn Arg Phe
50 55 60

Ser Val Asn Phe Gln Lys Ala Ala Lys Ser Phe Ser Leu Lys Ile Ser
65 70 75 80

Asp Ser Gln Leu Gly Asp Ala Ala Met Tyr Phe Cys Ala Tyr Arg Ser
85 90 95

Ala Pro Gly Asn Gln Phe Tyr Phe Gly Thr Gly Thr Ser Leu Thr Val
100 105 110

Ile Pro

<210> SEQ ID NO 280
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 280
gctcagacag tcactcagtc tcaaccagag atgtctgtgc aggaggcaga gaccgtgacc 60
ctgagctgca catatgacac cagtgagagt gattattatt tattctggta caagcagcct 120
cccagcaggc agatgattct cgttattcgc caagaagctt ataagcaaca gaatgcaaca 180
gagaatcgtt tctctgtgaa cttccagaaa gcagccaaat ccttcagtct caagatctca 240
gactcacagc tgggggatgc cgcgatgtat ttctgtgctt ataggagcgc gcccggtaac 300
cagttctatt ttgggacagg gacaagtttg acggtcattc ca 342

<210> SEQ ID NO 281
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 281

Met Asp His Glu Asn
1 5

<210> SEQ ID NO 282
<211> LENGTH: 6
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 282

Ser Tyr Asp Val Lys Met
1 5

<210> SEQ ID NO 283
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 283

Ala Ser Ser Phe Trp Gly Trp Asn Thr Glu Ala Phe
1 5 10

<210> SEQ ID NO 284
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 284
atggaccatg aaaat 15

<210> SEQ ID NO 285
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 285
tcatatgatg ttaaaatg 18

<210> SEQ ID NO 286
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 286
gccagcagtt tctggggatg gaacactgaa gctttc 36

<210> SEQ ID NO 287
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 287

Asp Val Lys Val Thr Gln Ser Ser Arg Tyr Leu Val Lys Arg Thr Gly
1 5 10 15

Glu Lys Val Phe Leu Glu Cys Val Gln Asp Met Asp His Glu Asn Met
20 25 30

```
Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Phe Trp
                85                  90                  95

Gly Trp Asn Thr Glu Ala Phe Phe Gly Gln Gly Thr Arg Leu Thr Val
            100                 105                 110

Val


<210> SEQ ID NO 288
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 288

gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgccagca gtttctgggg atggaacact    300

gaagctttct ttggacaagg caccagactc acagttgta                           339


<210> SEQ ID NO 289
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Thr Ser Glu Ser Asp Tyr Tyr
1               5


<210> SEQ ID NO 290
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gln Glu Ala Tyr Lys Gln Gln Asn
1               5


<210> SEQ ID NO 291
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291
```

Ala Tyr Arg Ser Ala Thr Gly Asn Gln Phe Tyr
1               5                   10

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 292
accagtgaga gtgattatta t 21

<210> SEQ ID NO 293
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 293
caagaagctt ataagcaaca gaat 24

<210> SEQ ID NO 294
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 294
gcttatagga gcgcgaccgg taaccagttc tat 33

<210> SEQ ID NO 295
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 295

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Thr Gly Asn Gln Phe Tyr Phe Gly Thr Gly Thr Ser Leu Thr Val
            100                 105                 110

Ile Pro

<210> SEQ ID NO 296

<211> LENGTH: 342
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 296
gctcagacag tcactcagtc tcaaccagag atgtctgtgc aggaggcaga gaccgtgacc 60
ctgagctgca catatgacac cagtgagagt gattattatt tattctggta caagcagcct 120
cccagcaggc agatgattct cgttattcgc caagaagctt ataagcaaca gaatgcaaca 180
gagaatcgtt tctctgtgaa cttccagaaa gcagccaaat ccttcagtct caagatctca 240
gactcacagc tgggggatgc cgcgatgtat ttctgtgctt ataggagcgc gaccggtaac 300
cagttctatt ttgggacagg gacaagtttg acggtcattc ca 342

<210> SEQ ID NO 297
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 297

Met Asn His Glu Tyr
1 5

<210> SEQ ID NO 298
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 298

Ser Met Asn Val Glu Val
1 5

<210> SEQ ID NO 299
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 299

Ala Ser Ser Leu Leu Tyr Ser Asn Gln Pro Gln His
1 5 10

<210> SEQ ID NO 300
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 300
atgaaccatg agtat 15

<210> SEQ ID NO 301
<211> LENGTH: 18

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 301
tcaatgaatg ttgaggtg 18

<210> SEQ ID NO 302
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 302
gccagcagtt tactgtatag caatcagccc cagcat 36

<210> SEQ ID NO 303
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 303

```
Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Leu Leu
                85                  90                  95

Tyr Ser Asn Gln Pro Gln His Phe Gly Asp Gly Thr Arg Leu Ser Ile
            100                 105                 110

Leu
```

<210> SEQ ID NO 304
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 304

```
gaagcccaag tgacccagaa cccaagatac ctcatcacag tgactggaaa gaagttaaca     60

gtgacttgtt ctcagaatat gaaccatgag tatatgtcct ggtatcgaca agacccaggg    120

ctgggcttaa ggcagatcta ctattcaatg aatgttgagg tgactgataa gggagatgtt    180

cctgaagggt acaaagtctc tcgaaaagag aagaggaatt tcccccctgat cctggagtcg    240

cccagcccca accagacctc tctgtacttc tgtgccagca gtttactgta tagcaatcag    300

ccccagcatt ttggtgatgg gactcgactc tccatccta                           339
```

<210> SEQ ID NO 305
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 305

Thr Ser Glu Ser Asp Tyr Tyr
1 5

<210> SEQ ID NO 306
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 306

Gln Glu Ala Tyr Lys Gln Gln Asn
1 5

<210> SEQ ID NO 307
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 307

Ala Tyr Arg Ser Ala Ser Gly Asn Gln Phe Tyr
1 5 10

<210> SEQ ID NO 308
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 308
accagtgaga gtgattatta t 21

<210> SEQ ID NO 309
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 309
caagaagctt ataagcaaca gaat 24

<210> SEQ ID NO 310
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 310
gcttatagga gcgcgtccgg taaccagttc tat 33

<210> SEQ ID NO 311
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 311

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Ser Asp Tyr
20 25 30

Tyr Leu Phe Trp Tyr Lys Gln Pro Pro Ser Arg Gln Met Ile Leu Val
35 40 45

Ile Arg Gln Glu Ala Tyr Lys Gln Gln Asn Ala Thr Glu Asn Arg Phe
50 55 60

Ser Val Asn Phe Gln Lys Ala Ala Lys Ser Phe Ser Leu Lys Ile Ser
65 70 75 80

Asp Ser Gln Leu Gly Asp Ala Ala Met Tyr Phe Cys Ala Tyr Arg Ser
85 90 95

Ala Ser Gly Asn Gln Phe Tyr Phe Gly Thr Gly Thr Ser Leu Thr Val
100 105 110

Ile Pro

<210> SEQ ID NO 312
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 312
gctcagacag tcactcagtc tcaaccagag atgtctgtgc aggaggcaga gaccgtgacc 60
ctgagctgca catatgacac cagtgagagt gattattatt tattctggta caagcagcct 120
cccagcaggc agatgattct cgttattcgc caagaagctt ataagcaaca gaatgcaaca 180
gagaatcgtt tctctgtgaa cttccagaaa gcagccaaat ccttcagtct caagatctca 240
gactcacagc tgggggatgc cgcgatgtat ttctgtgctt ataggagcgc gtccggtaac 300
cagttctatt ttgggacagg gacaagtttg acggtcattc ca 342

<210> SEQ ID NO 313
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 313

Met Asp His Glu Asn
1 5

<210> SEQ ID NO 314
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 314

Ser Tyr Asp Val Lys Met
1 5

<210> SEQ ID NO 315
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 315

Ala Ser Ser Leu Trp Gly Met Asn Thr Glu Ala Phe
1 5 10

<210> SEQ ID NO 316
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 316
atggaccatg aaaat 15

<210> SEQ ID NO 317
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 317
tcatatgatg ttaaaatg 18

<210> SEQ ID NO 318
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 318
gccagcagtt tatgggggat gaacactgaa gctttc 36

<210> SEQ ID NO 319
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 319

Asp Val Lys Val Thr Gln Ser Ser Arg Tyr Leu Val Lys Arg Thr Gly
1 5 10 15

Glu Lys Val Phe Leu Glu Cys Val Gln Asp Met Asp His Glu Asn Met
20 25 30

```
Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Gly Met Asn Thr Glu Ala Phe Phe Gly Gln Gly Thr Arg Leu Thr Val
            100                 105                 110

Val


<210> SEQ ID NO 320
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 320

gatgtgaaag taacccagag ctcgagatat ctagtcaaaa ggacgggaga gaaagttttt      60

ctggaatgtg tccaggatat ggaccatgaa aatatgttct ggtatcgaca agacccaggt     120

ctggggctac ggctgatcta tttctcatat gatgttaaaa tgaaagaaaa aggagatatt     180

cctgaggggt acagtgtctc tagagagaag aaggagcgct tctccctgat tctggagtcc     240

gccagcacca accagacatc tatgtacctc tgtgccagca gtttatgggg gatgaacact     300

gaagctttct ttggacaagg caccagactc acagttgta                            339


<210> SEQ ID NO 321
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Ser Ser Asn Phe Tyr Ala
1               5


<210> SEQ ID NO 322
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Met Thr Leu Asn Gly Asp Glu
1               5


<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323
```

```
Ala Leu Asn Arg Asp Asp Lys Ile Ile
1               5


<210> SEQ ID NO 324
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324

tccagcaatt tttatgcc                                                   18


<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325

atgactttaa atggggatga a                                               21


<210> SEQ ID NO 326
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326

gccctgaaca gagatgacaa gatcatc                                         27


<210> SEQ ID NO 327
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Ile Leu Asn Val Glu Gln Ser Pro Gln Ser Leu His Val Gln Glu Gly
1               5                   10                  15

Asp Ser Thr Asn Phe Thr Cys Ser Phe Pro Ser Ser Asn Phe Tyr Ala
            20                  25                  30

Leu His Trp Tyr Arg Trp Glu Thr Ala Lys Ser Pro Glu Ala Leu Phe
        35                  40                  45

Val Met Thr Leu Asn Gly Asp Glu Lys Lys Lys Gly Arg Ile Ser Ala
    50                  55                  60

Thr Leu Asn Thr Lys Glu Gly Tyr Ser Tyr Leu Tyr Ile Lys Gly Ser
65                  70                  75                  80

Gln Pro Glu Asp Ser Ala Thr Tyr Leu Cys Ala Leu Asn Arg Asp Asp
                85                  90                  95

Lys Ile Ile Phe Gly Lys Gly Thr Arg Leu His Ile Leu Pro
            100                 105                 110


<210> SEQ ID NO 328
<211> LENGTH: 330
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 328
atactgaacg tggaacaaag tcctcagtca ctgcatgttc aggagggaga cagcaccaat     60
ttcacctgca gcttcccttc cagcaatttt tatgccttac actggtacag atgggaaact    120
gcaaaaagcc ccgaggcctt gtttgtaatg actttaaatg ggatgaaaa gaagaaagga    180 cgaataagtg ccactcttaa taccaaggag ggttacagct atttgtacat caaaggatcc    240
cagcctgaag actcagccac atacctctgt gccctgaaca gagatgacaa gatcatcttt    300
ggaaaaggga cacgacttca tattctcccc                                     330

<210> SEQ ID NO 329
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Lys Gly His Asp Arg
1               5

<210> SEQ ID NO 330
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Ser Phe Asp Val Lys Asp
1               5

<210> SEQ ID NO 331
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Ala Thr Ser Asp Pro Gln Arg Asn Gln Pro Gln His
1               5                   10

<210> SEQ ID NO 332
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
aagggtcatg ataga                                                      15

<210> SEQ ID NO 333
<211> LENGTH: 18
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 333
tcctttgatg tcaaagat 18

<210> SEQ ID NO 334
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
gccaccagtg atcctcagag aaatcagccc cagcat 36

<210> SEQ ID NO 335
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

```
Asp Ala Asp Val Thr Gln Thr Pro Arg Asn Arg Ile Thr Lys Thr Gly
1               5                   10                  15

Lys Arg Ile Met Leu Glu Cys Ser Gln Thr Lys Gly His Asp Arg Met
            20                  25                  30

Tyr Trp Tyr Arg Gln Asp Pro Gly Leu Gly Leu Arg Leu Ile Tyr Tyr
        35                  40                  45

Ser Phe Asp Val Lys Asp Ile Asn Lys Gly Glu Ile Ser Asp Gly Tyr
    50                  55                  60

Ser Val Ser Arg Gln Ala Gln Ala Lys Phe Ser Leu Ser Leu Glu Ser
65                  70                  75                  80

Ala Ile Pro Asn Gln Thr Ala Leu Tyr Phe Cys Ala Thr Ser Asp Pro
                85                  90                  95

Gln Arg Asn Gln Pro Gln His Phe Gly Asp Gly Thr Arg Leu Ser Ile
            100                 105                 110

Leu
```

<210> SEQ ID NO 336
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 336

```
gatgctgatg ttacccagac cccaaggaat aggatcacaa agacaggaaa gaggattatg     60

ctggaatgtt ctcagactaa gggtcatgat agaatgtact ggtatcgaca agacccagga    120

ctgggcctac ggttgatcta ttactccttt gatgtcaaag atataaacaa aggagagatc    180

tctgatggat acagtgtctc tcgacaggca caggctaaat tctccctgtc cctagagtct    240

gccatcccca accagacagc tctttacttc tgtgccacca gtgatcctca gagaaatcag    300

ccccagcatt ttggtgatgg gactcgactc tccatccta                           339
```

<210> SEQ ID NO 337

<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 337

Asn Ser Ala Ser Asp Tyr
1 5

<210> SEQ ID NO 338
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 338

Ile Arg Ser Asn Met Asp Lys
1 5

<210> SEQ ID NO 339
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 339

Ala Glu Lys Arg Asp Asn Tyr Gly Gln Asn Phe Val
1 5 10

<210> SEQ ID NO 340
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 340
aacagcgcct cagactac 18

<210> SEQ ID NO 341
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 341
attcgttcaa atatggacaa a 21

<210> SEQ ID NO 342
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 342
gcagagaaga gggataacta tggtcagaat tttgtc 36

<210> SEQ ID NO 343
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 343

```
Gly Glu Ser Val Gly Leu His Leu Pro Thr Leu Ser Val Gln Glu Gly
1               5                   10                  15

Asp Asn Ser Ile Ile Asn Cys Ala Tyr Ser Asn Ser Ala Ser Asp Tyr
            20                  25                  30

Phe Ile Trp Tyr Lys Gln Glu Ser Gly Lys Gly Pro Gln Phe Ile Ile
        35                  40                  45

Asp Ile Arg Ser Asn Met Asp Lys Arg Gln Gly Gln Arg Val Thr Val
    50                  55                  60

Leu Leu Asn Lys Thr Val Lys His Leu Ser Leu Gln Ile Ala Ala Thr
65                  70                  75                  80

Gln Pro Gly Asp Ser Ala Val Tyr Phe Cys Ala Glu Lys Arg Asp Asn
                85                  90                  95

Tyr Gly Gln Asn Phe Val Phe Gly Pro Gly Thr Arg Leu Ser Val Leu
            100                 105                 110

Pro
```

<210> SEQ ID NO 344
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 344

```
ggagagagtg tggggctgca tcttcctacc ctgagtgtcc aggagggtga caactctatt     60

atcaactgtg cttattcaaa cagcgcctca gactacttca tttggtacaa gcaagaatct    120

ggaaaaggtc ctcaattcat tatagacatt cgttcaaata tggacaaaag gcaaggccaa    180

agagtcaccg ttttattgaa taagacagtg aaacatctct ctctgcaaat tgcagctact    240

caacctggag actcagctgt ctacttttgt gcagagaaga gggataacta tggtcagaat    300

tttgtctttg gtcccggaac cagattgtcc gtgctgccc                          339
```

<210> SEQ ID NO 345
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 345

```
Met Asp His Glu Asn
1               5
```

<210> SEQ ID NO 346
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 346

Ser Tyr Asp Val Lys Met
1               5

<210> SEQ ID NO 347
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 347

Ala Ser Ser Leu Tyr Ser Tyr Gly Tyr Thr
1               5                   10

<210> SEQ ID NO 348
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 348
atggaccatg aaaat 15

<210> SEQ ID NO 349
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 349
tcatatgatg ttaaaatg 18

<210> SEQ ID NO 350
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 350
gccagcagtt tatacagcta tggctacacc 30

<210> SEQ ID NO 351
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 351

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

```
Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Tyr
                85                  90                  95

Ser Tyr Gly Tyr Thr Phe Gly Ser Gly Thr Arg Leu Thr Val Val
            100                 105                 110
```

<210> SEQ ID NO 352
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 352

```
gatgtgaaag taacccagag ctcgagatat ctagtcaaaa ggacgggaga gaaagttttt      60

ctggaatgtg tccaggatat ggaccatgaa aatatgttct ggtatcgaca agacccaggt     120

ctggggctac ggctgatcta tttctcatat gatgttaaaa tgaaagaaaa aggagatatt     180

cctgaggggt acagtgtctc tagagagaag aaggagcgct tctccctgat tctggagtcc     240

gccagcacca accagacatc tatgtacctc tgtgccagca gtttatacag ctatggctac     300

accttcggtt cggggaccag gttaaccgtt gta                                  333
```

<210> SEQ ID NO 353
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 353

```
Thr Ser Asp Pro Ser Tyr Gly
1               5
```

<210> SEQ ID NO 354
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 354

```
Gln Gly Ser Tyr Asp Gln Gln Asn
1               5
```

<210> SEQ ID NO 355
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 355

```
Ala Met Arg Asp Leu Thr Thr Ser Gly Thr Tyr Lys Tyr Ile
1               5                   10
```

<210> SEQ ID NO 356

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 356
accagtgatc caagttatgg t 21

<210> SEQ ID NO 357
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 357
caggggtctt atgaccagca aaat 24

<210> SEQ ID NO 358
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 358
gcaatgagag accttactac ctcaggaacc tacaaataca tc 42

<210> SEQ ID NO 359
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 359

```
Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Pro Ser Tyr
            20                  25                  30

Gly Leu Phe Trp Tyr Lys Gln Pro Ser Ser Gly Glu Met Ile Phe Leu
        35                  40                  45

Ile Tyr Gln Gly Ser Tyr Asp Gln Gln Asn Ala Thr Glu Gly Arg Tyr
    50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Asp
                85                  90                  95

Leu Thr Thr Ser Gly Thr Tyr Lys Tyr Ile Phe Gly Thr Gly Thr Arg
            100                 105                 110

Leu Lys Val Leu Ala
        115
```

<210> SEQ ID NO 360
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 360
gcccagaaga taactcaaac ccaaccagga atgttcgtgc aggaaaagga ggctgtgact 60
ctggactgca catatgacac cagtgatcca agttatggtc tattctggta caagcagccc 120
agcagtgggg aaatgatttt tcttatttat caggggtctt atgaccagca aaatgcaaca 180
gaaggtcgct actcattgaa tttccagaag gcaagaaaat ccgccaacct tgtcatctcc 240
gcttcacaac tgggggactc agcaatgtac ttctgtgcaa tgagagacct tactacctca 300
ggaacctaca aatacatctt tggaacaggc accaggctga aggttttagc a 351

<210> SEQ ID NO 361
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 361

Met Asp His Glu Asn
1 5

<210> SEQ ID NO 362
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 362

Ser Tyr Asp Val Lys Met
1 5

<210> SEQ ID NO 363
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 363

Ala Ser Ser Phe Gly Gly Trp Gly Tyr Gly Tyr Thr
1 5 10

<210> SEQ ID NO 364
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 364
atggaccatg aaaat 15

<210> SEQ ID NO 365
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 365
tcatatgatg ttaaaatg 18

<210> SEQ ID NO 366
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 366
gccagcagtt tcgggggctg ggctatggc tacacc 36

<210> SEQ ID NO 367
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 367

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Phe Gly
                85                  90                  95

Gly Trp Gly Tyr Gly Tyr Thr Phe Gly Ser Gly Thr Arg Leu Thr Val
            100                 105                 110

Val

<210> SEQ ID NO 368
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 368
gatgtgaaag taacccagag ctcgagatat ctagtcaaaa ggacgggaga gaaagttttt 60
ctggaatgtg tccaggatat ggaccatgaa aatatgttct ggtatcgaca agacccaggt 120
ctggggctac ggctgatcta tttctcatat gatgttaaaa tgaaagaaaa aggagatatt 180
cctgaggggt acagtgtctc tagagagaag aaggagcgct tctccctgat tctggagtcc 240
gccagcacca accagacatc tatgtacctc tgtgccagca gtttcggggg ctggggctat 300
ggctacacct tcggttcggg gaccaggtta accgttgta 339

<210> SEQ ID NO 369
<211> LENGTH: 7
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 369

Thr Ser Glu Ser Asp Tyr Tyr
1 5

<210> SEQ ID NO 370
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 370

Gln Glu Ala Tyr Lys Gln Gln Asn
1 5

<210> SEQ ID NO 371
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 371

Ala Tyr Arg Ser Ala Ile Gly Asn Gln Phe Tyr
1 5 10

<210> SEQ ID NO 372
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 372
accagtgaga gtgattatta t 21

<210> SEQ ID NO 373
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 373
caagaagctt ataagcaaca gaat 24

<210> SEQ ID NO 374
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 374
gcttatagga gcgcgatcgg taaccagttc tat 33

<210> SEQ ID NO 375

<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 375

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Ser Asp Tyr
20 25 30

Tyr Leu Phe Trp Tyr Lys Gln Pro Pro Ser Arg Gln Met Ile Leu Val
35 40 45

Ile Arg Gln Glu Ala Tyr Lys Gln Gln Asn Ala Thr Glu Asn Arg Phe
50 55 60

Ser Val Asn Phe Gln Lys Ala Ala Lys Ser Phe Ser Leu Lys Ile Ser
65 70 75 80

Asp Ser Gln Leu Gly Asp Ala Ala Met Tyr Phe Cys Ala Tyr Arg Ser
85 90 95

Ala Ile Gly Asn Gln Phe Tyr Phe Gly Thr Gly Thr Ser Leu Thr Val
100 105 110

Ile Pro

<210> SEQ ID NO 376
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 376
gctcagacag tcactcagtc tcaaccagag atgtctgtgc aggaggcaga gaccgtgacc 60
ctgagctgca catatgacac cagtgagagt gattattatt tattctggta caagcagcct 120
cccagcaggc agatgattct cgttattcgc caagaagctt ataagcaaca gaatgcaaca 180
gagaatcgtt tctctgtgaa cttccagaaa gcagccaaat ccttcagtct caagatctca 240
gactcacagc tgggggatgc cgcgatgtat ttctgtgctt ataggagcgc gatcggtaac 300
cagttctatt ttgggacagg gacaagtttg acggtcattc ca 342

<210> SEQ ID NO 377
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 377

Met Asp His Glu Asn
1 5

<210> SEQ ID NO 378
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 378

Ser Tyr Asp Val Lys Met
1 5

<210> SEQ ID NO 379
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 379

Ala Ser Ser Leu Trp Gly Val Asn Thr Glu Ala Phe
1 5 10

<210> SEQ ID NO 380
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 380
atggaccatg aaaat 15

<210> SEQ ID NO 381
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 381
tcatatgatg ttaaaatg 18

<210> SEQ ID NO 382
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 382
gccagcagtt tatggggtgt gaacactgaa gctttc 36

<210> SEQ ID NO 383
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 383

Asp Val Lys Val Thr Gln Ser Ser Arg Tyr Leu Val Lys Arg Thr Gly
1 5 10 15

Glu Lys Val Phe Leu Glu Cys Val Gln Asp Met Asp His Glu Asn Met
20 25 30

Phe Trp Tyr Arg Gln Asp Pro Gly Leu Gly Leu Arg Leu Ile Tyr Phe
35 40 45

Ser Tyr Asp Val Lys Met Lys Glu Lys Gly Asp Ile Pro Glu Gly Tyr
50 55 60

```
Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Gly Val Asn Thr Glu Ala Phe Phe Gly Gln Gly Thr Arg Leu Thr Val
            100                 105                 110

Val


<210> SEQ ID NO 384
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 384

gatgtgaaag taacccagag ctcgagatat ctagtcaaaa ggacgggaga gaaagttttt      60

ctggaatgtg tccaggatat ggaccatgaa aatatgttct ggtatcgaca agacccaggt     120

ctggggctac ggctgatcta tttctcatat gatgttaaaa tgaaagaaaa aggagatatt     180

cctgaggggt acagtgtctc tagagagaag aaggagcgct tctccctgat tctggagtcc     240

gccagcacca accagacatc tatgtacctc tgtgccagca gtttatgggg tgtgaacact     300

gaagctttct ttggacaagg caccagactc acagttgta                            339


<210> SEQ ID NO 385
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Thr Ser Glu Ser Asp Tyr Tyr
1               5


<210> SEQ ID NO 386
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Gln Glu Ala Tyr Lys Gln Gln Asn
1               5


<210> SEQ ID NO 387
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Ala Tyr Arg Ser Ala Thr Gly Asn Gln Phe Tyr
1               5                   10


<210> SEQ ID NO 388
```

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 388
accagtgaga gtgattatta t 21

<210> SEQ ID NO 389
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 389
caagaagctt ataagcaaca gaat 24

<210> SEQ ID NO 390
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 390
gcttatagga gcgcgaccgg taaccagttc tat 33

<210> SEQ ID NO 391
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 391

```
Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Thr Gly Asn Gln Phe Tyr Phe Gly Thr Gly Thr Ser Leu Thr Val
            100                 105                 110

Ile Pro
```

<210> SEQ ID NO 392
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 392

```
gctcagacag tcactcagtc tcaaccagag atgtctgtgc aggaggcaga gaccgtgacc     60
ctgagctgca catatgacac cagtgagagt gattattatt tattctggta caagcagcct    120
cccagcaggc agatgattct cgttattcgc caagaagctt ataagcaaca gaatgcaaca    180
gagaatcgtt tctctgtgaa cttccagaaa gcagccaaat ccttcagtct caagatctca    240
gactcacagc tgggggatgc cgcgatgtat ttctgtgctt ataggagcgc gaccggtaac    300
cagttctatt ttgggacagg gacaagtttg acggtcattc ca                       342
```

<210> SEQ ID NO 393
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 393

```
Met Asp His Glu Asn
1               5
```

<210> SEQ ID NO 394
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 394

```
Ser Tyr Asp Val Lys Met
1               5
```

<210> SEQ ID NO 395
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 395

```
Ala Ser Ser Leu Trp Ala Val Asn Glu Lys Leu Phe
1               5                   10
```

<210> SEQ ID NO 396
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 396

```
atggaccatg aaaat                                                      15
```

<210> SEQ ID NO 397
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 397
tcatatgatg ttaaaatg 18

<210> SEQ ID NO 398
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 398
gccagcagtt tatgggccgt taatgaaaaa ctgttt 36

<210> SEQ ID NO 399
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 399

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Ala Val Asn Glu Lys Leu Phe Phe Gly Ser Gly Thr Gln Leu Ser Val
            100                 105                 110

Leu
```

<210> SEQ ID NO 400
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 400

```
gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgccagca gtttatgggc cgttaatgaa    300

aaactgtttt ttggcagtgg aacccagctc tctgtcttg                           339
```

<210> SEQ ID NO 401
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 401

Thr Ile Ser Gly Asn Glu Tyr
1 5

<210> SEQ ID NO 402
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 402

Gly Leu Lys Asn Asn
1 5

<210> SEQ ID NO 403
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 403

Ile Val Arg Pro Gly Gly Thr Tyr Lys Tyr Ile
1 5 10

<210> SEQ ID NO 404
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 404
accatcagtg gaaatgagta t 21

<210> SEQ ID NO 405
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 405
ggtctaaaaa acaat 15

<210> SEQ ID NO 406
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 406
atcgtcagac cgggggaac ctacaaatac atc 33

<210> SEQ ID NO 407
<211> LENGTH: 110

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 407

```
Asp Ala Lys Thr Thr Gln Pro Pro Ser Met Asp Cys Ala Glu Gly Arg
1               5                   10                  15

Ala Ala Asn Leu Pro Cys Asn His Ser Thr Ile Ser Gly Asn Glu Tyr
            20                  25                  30

Val Tyr Trp Tyr Arg Gln Ile His Ser Gln Gly Pro Gln Tyr Ile Ile
        35                  40                  45

His Gly Leu Lys Asn Asn Glu Thr Asn Glu Met Ala Ser Leu Ile Ile
    50                  55                  60

Thr Glu Asp Arg Lys Ser Ser Thr Leu Ile Leu Pro His Ala Thr Leu
65                  70                  75                  80

Arg Asp Thr Ala Val Tyr Tyr Cys Ile Val Arg Pro Gly Gly Thr Tyr
                85                  90                  95

Lys Tyr Ile Phe Gly Thr Gly Thr Arg Leu Lys Val Leu Ala
            100                 105                 110
```

<210> SEQ ID NO 408
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 408

```
gatgctaaga ccacccagcc accctccatg gattgcgctg aaggaagagc tgcaaacctg     60

ccttgtaatc actctaccat cagtggaaat gagtatgtgt attggtatcg acagattcac    120

tcccaggggc cacagtatat cattcatggt ctaaaaaaca atgaaaccaa tgaaatggcc    180

tctctgatca tcacagaaga cagaaagtcc agcaccttga tcctgcccca cgctacgctg    240

agagacactg ctgtgtacta ttgcatcgtc agaccggggg gaacctacaa atacatcttt    300

ggaacaggca ccaggctgaa ggttttagca                                     330
```

<210> SEQ ID NO 409
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 409

```
Met Asp His Glu Asn
1               5
```

<210> SEQ ID NO 410
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 410

```
Ser Tyr Asp Val Lys Met
1               5
```

<210> SEQ ID NO 411
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

```
Ala Thr Gly Gly Asp Asn Gln Pro Gln His
1               5                   10
```

<210> SEQ ID NO 412
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412

```
atggaccatg aaaat                                                     15
```

<210> SEQ ID NO 413
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413

```
tcatatgatg ttaaaatg                                                  18
```

<210> SEQ ID NO 414
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414

```
gcgaccgggg gtgacaatca gccccagcat                                     30
```

<210> SEQ ID NO 415
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80
```

```
Ala Ser Thr Asn Gln Thr Ser Met Tyr Leu Cys Ala Thr Gly Gly Asp
                85                  90                  95

Asn Gln Pro Gln His Phe Gly Asp Gly Thr Arg Leu Ser Ile Leu
            100                 105                 110
```

<210> SEQ ID NO 416
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 416

```
gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgcgaccg ggggtgacaa tcagccccag    300

cattttggtg atgggactcg actctccatc cta                                  333
```

<210> SEQ ID NO 417
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 417

```
Thr Ser Glu Asn Asn Tyr Tyr
1               5
```

<210> SEQ ID NO 418
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 418

```
Gln Glu Ala Tyr Lys Gln Gln Asn
1               5
```

<210> SEQ ID NO 419
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 419

```
Ala Leu Asn Thr Gly Asn Gln Phe Tyr
1               5
```

<210> SEQ ID NO 420
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 420
accagtgaga ataattatta t 21

<210> SEQ ID NO 421
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 421
caagaagctt ataagcaaca gaat 24

<210> SEQ ID NO 422
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 422
gccctcaaca ccggtaacca gttctat 27

<210> SEQ ID NO 423
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 423

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Asn Asn Tyr
20 25 30

Tyr Leu Phe Trp Tyr Lys Gln Pro Pro Ser Arg Gln Met Ile Leu Val
35 40 45

Ile Arg Gln Glu Ala Tyr Lys Gln Gln Asn Ala Thr Glu Asn Arg Phe
50 55 60

Ser Val Asn Phe Gln Lys Ala Ala Lys Ser Phe Ser Leu Lys Ile Ser
65 70 75 80

Asp Ser Gln Leu Gly Asp Thr Ala Met Tyr Phe Cys Ala Leu Asn Thr
85 90 95

Gly Asn Gln Phe Tyr Phe Gly Thr Gly Thr Ser Leu Thr Val Ile Pro
100 105 110

<210> SEQ ID NO 424
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 424
gcccagacag tcactcagtc tcaaccagag atgtctgtgc aggaggcaga gactgtgacc 60
ctgagttgca catatgacac cagtgagaat aattattatt tgttctggta caagcagcct 120
cccagcaggc agatgattct cgttattcgc caagaagctt ataagcaaca gaatgcaacg 180
gagaatcgtt tctctgtgaa cttccagaaa gcagccaaat ccttcagtct caagatctca 240
gactcacagc tgggggacac tgcgatgtat ttctgtgccc tcaacaccgg taaccagttc 300
tattttggga cagggacaag tttgacggtc attcca 336

<210> SEQ ID NO 425
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 425

Asp Phe Gln Ala Thr Thr
1 5

<210> SEQ ID NO 426
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 426

Ser Asn Glu Gly Ser Lys Ala
1 5

<210> SEQ ID NO 427
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 427

Ser Ala Trp Asp Gly Phe Tyr Gly Tyr Thr
1 5 10

<210> SEQ ID NO 428
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 428
gactttcagg ccacaact 18

<210> SEQ ID NO 429
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 429
tccaatgagg gctccaaggc c 21

<210> SEQ ID NO 430
<211> LENGTH: 30

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430

agtgcctggg acggattcta tggctacacc                                        30


<210> SEQ ID NO 431
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 431

Gly Ala Val Val Ser Gln His Pro Ser Trp Val Ile Cys Lys Ser Gly
1               5                   10                  15

Thr Ser Val Lys Ile Glu Cys Arg Ser Leu Asp Phe Gln Ala Thr Thr
            20                  25                  30

Met Phe Trp Tyr Arg Gln Phe Pro Lys Gln Ser Leu Met Leu Met Ala
        35                  40                  45

Thr Ser Asn Glu Gly Ser Lys Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Trp Asp Gly Phe Tyr Gly Tyr Thr Phe Gly Ser Gly Thr Arg Leu Thr
            100                 105                 110

Val Val


<210> SEQ ID NO 432
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 432

ggtgctgtcg tctctcaaca tccgagctgg gttatctgta agagtggaac ctctgtgaag      60

atcgagtgcc gttccctgga ctttcaggcc acaactatgt tttggtatcg tcagttcccg     120

aaacagagtc tcatgctgat ggcaacttcc aatgagggct ccaaggccac atacgagcaa     180

ggcgtcgaga aggacaagtt tctcatcaac catgcaagcc tgaccttgtc cactctgaca     240

gtgaccagtg cccatcctga agacagcagc ttctacatct gcagtgcctg ggacggattc     300

tatggctaca ccttcggttc ggggaccagg ttaaccgttg ta                        342


<210> SEQ ID NO 433
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Thr Ser Glu Ser Asp Tyr Tyr
```

1 5

<210> SEQ ID NO 434
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 434

Gln Glu Ala Tyr Lys Gln Gln Asn
1 5

<210> SEQ ID NO 435
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 435

Ala Tyr Arg Ser Ala Thr Gly Asn Gln Phe Tyr
1 5 10

<210> SEQ ID NO 436
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 436
accagtgaga gtgattatta t 21

<210> SEQ ID NO 437
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 437
caagaagctt ataagcaaca gaat 24

<210> SEQ ID NO 438
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 438
gcttatagga gcgcgaccgg taaccagttc tat 33

<210> SEQ ID NO 439
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 439

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Thr Gly Asn Gln Phe Tyr Phe Gly Thr Gly Thr Ser Leu Thr Val
            100                 105                 110

Ile Pro

<210> SEQ ID NO 440
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 440
gctcagacag tcactcagtc tcaaccagag atgtctgtgc aggaggcaga gaccgtgacc 60
ctgagctgca catatgacac cagtgagagt gattattatt tattctggta caagcagcct 120
cccagcaggc agatgattct cgttattcgc caagaagctt ataagcaaca gaatgcaaca 180
gagaatcgtt tctctgtgaa cttccagaaa gcagccaaat ccttcagtct caagatctca 240
gactcacagc tgggggatgc cgcgatgtat ttctgtgctt ataggagcgc gaccggtaac 300
cagttctatt ttgggacagg gacaagtttg acggtcattc ca 342

<210> SEQ ID NO 441
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 441

Met Asp His Glu Asn
1               5

<210> SEQ ID NO 442
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 442

Ser Tyr Asp Val Lys Met
1               5

<210> SEQ ID NO 443
<211> LENGTH: 12
<212> TYPE: PRT

<213> ORGANISM: Artificial Sequence
<220> FEATURE:
<223> OTHER INFORMATION: Description of Artificial Sequence: Synthetic peptide

<400> SEQUENCE: 443

Ala Ser Ser Leu Trp Gly Leu Asn Thr Glu Ala Phe
1 5 10

<210> SEQ ID NO 444
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 444
atggaccatg aaaat 15

<210> SEQ ID NO 445
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 445
tcatatgatg ttaaaatg 18

<210> SEQ ID NO 446
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 446
gccagcagtt tatggggctt aaacactgaa gctttc 36

<210> SEQ ID NO 447
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 447

Asp Val Lys Val Thr Gln Ser Ser Arg Tyr Leu Val Lys Arg Thr Gly
1 5 10 15

Glu Lys Val Phe Leu Glu Cys Val Gln Asp Met Asp His Glu Asn Met
20 25 30

Phe Trp Tyr Arg Gln Asp Pro Gly Leu Gly Leu Arg Leu Ile Tyr Phe
35 40 45

Ser Tyr Asp Val Lys Met Lys Glu Lys Gly Asp Ile Pro Glu Gly Tyr
50 55 60

Ser Val Ser Arg Glu Lys Lys Glu Arg Phe Ser Leu Ile Leu Glu Ser
65 70 75 80

Ala Ser Thr Asn Gln Thr Ser Met Tyr Leu Cys Ala Ser Ser Leu Trp
85 90 95

Gly Leu Asn Thr Glu Ala Phe Phe Gly Gln Gly Thr Arg Leu Thr Val

```
        100                 105                 110

Val


<210> SEQ ID NO 448
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 448

gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgccagca gtttatgggg cttaaacact    300

gaagctttct ttggacaagg caccagactc acagttgta                          339


<210> SEQ ID NO 449
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Lys Thr Leu Tyr Gly
1               5


<210> SEQ ID NO 450
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Leu Gln Lys Gly Gly Glu Glu
1               5


<210> SEQ ID NO 451
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Gly Ala Asp Met Tyr Ser Gly Gly Gly Ala Asp Gly Leu Thr
1               5                   10


<210> SEQ ID NO 452
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
```

```
aagacgttat atggc                                                   15


<210> SEQ ID NO 453
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453

ctacagaaag gtggggaaga g                                            21


<210> SEQ ID NO 454
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454

ggagcagaca tgtattcagg aggaggtgct gacggactca cc                     42


<210> SEQ ID NO 455
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Ser Gln Glu Leu Glu Gln Ser Gln Gln Ser Leu Ile Val Gln Glu Gly
1               5                   10                  15

Lys Asn Leu Thr Ile Asn Cys Thr Ser Ser Lys Thr Leu Tyr Gly Leu
            20                  25                  30

Tyr Trp Tyr Lys Gln Lys Tyr Gly Glu Gly Leu Ile Phe Leu Met Met
        35                  40                  45

Leu Gln Lys Gly Gly Glu Glu Lys Ser His Glu Lys Ile Thr Ala Lys
    50                  55                  60

Leu Asp Glu Lys Lys Gln Gln Ser Ser Leu His Ile Thr Ala Ser Gln
65                  70                  75                  80

Pro Ser His Ala Gly Ile Tyr Leu Cys Gly Ala Asp Met Tyr Ser Gly
                85                  90                  95

Gly Gly Ala Asp Gly Leu Thr Phe Gly Lys Gly Thr His Leu Ile Ile
            100                 105                 110

Gln Pro


<210> SEQ ID NO 456
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 456

agccaagaac tggagcagag tcaacagtcc ttgatcgtcc aagagggaaa gaatctcacc     60

ataaactgca cgtcatcaaa gacgttatat ggcttatact ggtataagca aaagtatggt    120

gaaggtctta tcttcttgat gatgctacag aaaggtgggg aagagaaaag tcatgaaaag    180
```

ataactgcca agttggatga gaaaaagcag caaagttccc tgcatatcac agcctcccag 240
cccagccatg caggcatcta cctctgtgga gcagacatgt attcaggagg aggtgctgac 300
ggactcacct ttggcaaagg gactcatcta atcatccagc cc 342

<210> SEQ ID NO 457
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 457

Asp Phe Gln Ala Thr Thr
1 5

<210> SEQ ID NO 458
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 458

Ser Asn Glu Gly Ser Lys Ala
1 5

<210> SEQ ID NO 459
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 459

Ser Ala Trp Asp Gly Phe Tyr Gly Tyr Thr
1 5 10

<210> SEQ ID NO 460
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 460
gactttcagg ccacaact 18

<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 461
tccaatgagg gctccaaggc c 21

<210> SEQ ID NO 462
<211> LENGTH: 30
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 462
agtgcctggg acggattcta tggctacacc 30

<210> SEQ ID NO 463
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 463

Gly Ala Val Val Ser Gln His Pro Ser Trp Val Ile Cys Lys Ser Gly
1 5 10 15

Thr Ser Val Lys Ile Glu Cys Arg Ser Leu Asp Phe Gln Ala Thr Thr
20 25 30

Met Phe Trp Tyr Arg Gln Phe Pro Lys Gln Ser Leu Met Leu Met Ala
35 40 45

Thr Ser Asn Glu Gly Ser Lys Ala Thr Tyr Glu Gln Gly Val Glu Lys
50 55 60

Asp Lys Phe Leu Ile Asn His Ala Ser Leu Thr Leu Ser Thr Leu Thr
65 70 75 80

Val Thr Ser Ala His Pro Glu Asp Ser Ser Phe Tyr Ile Cys Ser Ala
85 90 95

Trp Asp Gly Phe Tyr Gly Tyr Thr Phe Gly Ser Gly Thr Arg Leu Thr
100 105 110

Val Val

<210> SEQ ID NO 464
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 464
ggtgctgtcg tctctcaaca tccgagctgg gttatctgta agagtggaac ctctgtgaag 60
atcgagtgcc gttccctgga ctttcaggcc acaactatgt tttggtatcg tcagttcccg 120
aaacagagtc tcatgctgat ggcaacttcc aatgagggct ccaaggccac atacgagcaa 180
ggcgtcgaga aggacaagtt tctcatcaac catgcaagcc tgaccttgtc cactctgaca 240
gtgaccagtg cccatcctga agacagcagc ttctacatct gcagtgcctg ggacggattc 300
tatggctaca ccttcggttc ggggaccagg ttaaccgttg ta 342

<210> SEQ ID NO 465
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 465

Thr Ser Glu Asn Asn Tyr Tyr
1 5

<210> SEQ ID NO 466
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 466

Gln Glu Ala Tyr Lys Gln Gln Asn
1 5

<210> SEQ ID NO 467
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 467

Ala Phe Gly Met Tyr Ser Gly Gly Gly Ala Asp Gly Leu Thr
1 5 10

<210> SEQ ID NO 468
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 468
accagtgaga ataattatta t 21

<210> SEQ ID NO 469
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 469
caagaagctt ataagcaaca gaat 24

<210> SEQ ID NO 470
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 470
gctttcggta tgtattcagg aggaggtgct gacggactca cc 42

<210> SEQ ID NO 471
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 471

```
Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Asn Asn Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Thr Ala Met Tyr Phe Cys Ala Phe Gly Met
                85                  90                  95

Tyr Ser Gly Gly Gly Ala Asp Gly Leu Thr Phe Gly Lys Gly Thr His
            100                 105                 110

Leu Ile Ile Gln Pro
        115
```

<210> SEQ ID NO 472
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 472

```
gcccagacag tcactcagtc tcaaccagag atgtctgtgc aggaggcaga gactgtgacc     60

ctgagttgca catatgacac cagtgagaat aattattatt tgttctggta caagcagcct    120

cccagcaggc agatgattct cgttattcgc caagaagctt ataagcaaca gaatgcaacg    180

gagaatcgtt tctctgtgaa cttccagaaa gcagccaaat ccttcagtct caagatctca    240

gactcacagc tgggggacac tgcgatgtat ttctgtgctt tcggtatgta ttcaggagga    300

ggtgctgacg gactcacctt tggcaaaggg actcatctaa tcatccagcc c             351
```

<210> SEQ ID NO 473
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 473

```
Pro Arg His Asp Thr
1               5
```

<210> SEQ ID NO 474
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 474

```
Phe Tyr Glu Lys Met Gln
1               5
```

<210> SEQ ID NO 475
<211> LENGTH: 12
<212> TYPE: PRT

<213> ORGANISM: Artificial Sequence
<220> FEATURE:
<223> OTHER INFORMATION: Description of Artificial Sequence: Synthetic peptide

<400> SEQUENCE: 475

```
Ala Ser Ser Pro Thr Gly Thr Gly Asp Gly Tyr Thr
1               5                   10
```

<210> SEQ ID NO 476
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 476

```
cctagacacg acact                                                    15
```

<210> SEQ ID NO 477
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 477

```
ttttatgaaa agatgcag                                                 18
```

<210> SEQ ID NO 478
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 478

```
gccagcagcc ctaccgggac aggggatggc tacacc                             36
```

<210> SEQ ID NO 479
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 479

```
Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Pro Thr
                85                  90                  95

Gly Thr Gly Asp Gly Tyr Thr Phe Gly Ser Gly Thr Arg Leu Thr Val
```

```
            100                 105                 110

Val


<210> SEQ ID NO 480
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 480

gctgctggag tcatccagtc cccaagacat ctgatcaaag aaaagaggga aacagccact     60

ctgaaatgct atcctatccc tagacacgac actgtctact ggtaccagca gggtccaggt    120

caggaccccc agttcctcat ttcgttttat gaaaagatgc agagcgataa aggaagcatc    180

cctgatcgat tctcagctca acagttcagt gactatcatt ctgaactgaa catgagctcc    240

ttggagctgg gggactcagc cctgtacttc tgtgccagca gccctaccgg gacaggggat    300

ggctacacct tcggttcggg gaccaggtta accgttgta                           339


<210> SEQ ID NO 481
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Ser Ser Val Pro Pro Tyr
1               5


<210> SEQ ID NO 482
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Tyr Thr Thr Gly Ala Thr Leu Val
1               5


<210> SEQ ID NO 483
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Ala Val Ser Ser Gly Ser Ala Arg Gln Leu Thr
1               5                   10


<210> SEQ ID NO 484
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
```

tcgtctgttc caccatat 18

<210> SEQ ID NO 485
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 485
tacacaacag gggccaccct ggtt 24

<210> SEQ ID NO 486
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 486
gctgtgagtt ctggttctgc aaggcaactg acc 33

<210> SEQ ID NO 487
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 487

Ala Gln Ser Val Thr Gln Pro Gly Ser His Val Ser Val Ser Glu Gly
1 5 10 15

Ala Leu Val Leu Leu Arg Cys Asn Tyr Ser Ser Ser Val Pro Pro Tyr
20 25 30

Leu Phe Trp Tyr Val Gln Tyr Pro Asn Gln Gly Leu Gln Leu Leu Leu
35 40 45

Lys Tyr Thr Thr Gly Ala Thr Leu Val Lys Gly Ile Asn Gly Phe Glu
50 55 60

Ala Glu Phe Lys Lys Ser Glu Thr Ser Phe His Leu Thr Lys Pro Ser
65 70 75 80

Ala His Met Ser Asp Ala Ala Glu Tyr Phe Cys Ala Val Ser Ser Gly
85 90 95

Ser Ala Arg Gln Leu Thr Phe Gly Ser Gly Thr Gln Leu Thr Val Leu
100 105 110

Pro

<210> SEQ ID NO 488
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 488
gcccagtcgg tgacccagcc tggcagccac gtctctgtct ctgagggagc cctggttctg 60
ctgaggtgca actactcatc gtctgttcca ccatatctct tctggtatgt gcaatacccc 120
aaccaaggac tccagcttct cctgaagtac acaacagggg ccaccctggt taaaggcatc 180
aacggttttg aggctgaatt taagaagagt gaaacctcct tccacctgac gaaaccctca 240
gcccatatga gcgacgcggc tgagtacttc tgtgctgtga gttctggttc tgcaaggcaa 300
ctgacctttg gatctgggac acaattgact gttttacct 339

<210> SEQ ID NO 489
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 489

Met Asp His Glu Asn
1 5

<210> SEQ ID NO 490
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 490

Ser Tyr Asp Val Lys Met
1 5

<210> SEQ ID NO 491
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 491

Ala Ser Ser His Asp Arg Trp Asp Tyr Gly Tyr Thr
1 5 10

<210> SEQ ID NO 492
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 492
atggaccatg aaaat 15

<210> SEQ ID NO 493
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 493
tcatatgatg ttaaaatg 18

<210> SEQ ID NO 494
<211> LENGTH: 36
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 494
gccagcagtc atgacaggtg ggactatggc tacacc 36

<210> SEQ ID NO 495
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 495

Asp Val Lys Val Thr Gln Ser Ser Arg Tyr Leu Val Lys Arg Thr Gly
1 5 10 15

Glu Lys Val Phe Leu Glu Cys Val Gln Asp Met Asp His Glu Asn Met
20 25 30

Phe Trp Tyr Arg Gln Asp Pro Gly Leu Gly Leu Arg Leu Ile Tyr Phe
35 40 45

Ser Tyr Asp Val Lys Met Lys Glu Lys Gly Asp Ile Pro Glu Gly Tyr
50 55 60

Ser Val Ser Arg Glu Lys Lys Glu Arg Phe Ser Leu Ile Leu Glu Ser
65 70 75 80

Ala Ser Thr Asn Gln Thr Ser Met Tyr Leu Cys Ala Ser Ser His Asp
85 90 95

Arg Trp Asp Tyr Gly Tyr Thr Phe Gly Ser Gly Thr Arg Leu Thr Val
100 105 110

Val

<210> SEQ ID NO 496
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 496
gatgtgaaag taacccagag ctcgagatat ctagtcaaaa ggacgggaga gaaagttttt 60
ctggaatgtg tccaggatat ggaccatgaa aatatgttct ggtatcgaca agacccaggt 120
ctggggctac ggctgatcta tttctcatat gatgttaaaa tgaaagaaaa aggagatatt 180
cctgaggggt acagtgtctc tagagagaag aaggagcgct tctccctgat tctggagtcc 240
gccagcacca accagacatc tatgtacctc tgtgccagca gtcatgacag gtgggactat 300
ggctacacct tcggttcggg gaccaggtta accgttgta 339

<210> SEQ ID NO 497
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 497

Thr Ser Glu Ser Asp Tyr Tyr
1 5

<210> SEQ ID NO 498
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 498

```
Gln Glu Ala Tyr Lys Gln Gln Asn
1               5
```

<210> SEQ ID NO 499
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 499

```
Ala Tyr Arg Ser Ala Thr Gly Asn Gln Phe Tyr
1               5                   10
```

<210> SEQ ID NO 500
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 500

```
accagtgaga gtgattatta t                                               21
```

<210> SEQ ID NO 501
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 501

```
caagaagctt ataagcaaca gaat                                            24
```

<210> SEQ ID NO 502
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 502

```
gcttatagga gcgccaccgg taaccagttc tat                                  33
```

<210> SEQ ID NO 503
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 503

```
Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Thr Gly Asn Gln Phe Tyr Phe Gly Thr Gly Thr Ser Leu Thr Val
            100                 105                 110

Ile Pro
```

<210> SEQ ID NO 504
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 504

```
gctcagacag tcactcagtc tcaaccagag atgtctgtgc aggaggcaga gaccgtgacc     60

ctgagctgca catatgacac cagtgagagt gattattatt tattctggta caagcagcct    120

cccagcaggc agatgattct cgttattcgc caagaagctt ataagcaaca gaatgcaaca    180

gagaatcgtt tctctgtgaa cttccagaaa gcagccaaat ccttcagtct caagatctca    240

gactcacagc tgggggatgc cgcgatgtat ttctgtgctt ataggagcgc caccggtaac    300

cagttctatt ttgggacagg gacaagtttg acggtcattc ca                       342
```

<210> SEQ ID NO 505
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 505

```
Met Asp His Glu Asn
1               5
```

<210> SEQ ID NO 506
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 506

```
Ser Tyr Asp Val Lys Met
1               5
```

<210> SEQ ID NO 507
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 507

Ala Ser Ser Leu Trp Ala Leu Asn Thr Glu Ala Phe
1               5                   10


<210> SEQ ID NO 508
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508

atggaccatg aaaat                                                    15


<210> SEQ ID NO 509
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509

tcatatgatg ttaaaatg                                                 18


<210> SEQ ID NO 510
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510

gccagcagtt tgtgggcatt gaacactgaa gctttc                             36


<210> SEQ ID NO 511
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 511

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Ala Leu Asn Thr Glu Ala Phe Phe Gly Gln Gly Thr Arg Leu Thr Val
            100                 105                 110
```

Val

<210> SEQ ID NO 512
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 512
gatgtgaaag taacccagag ctcgagatat ctagtcaaaa ggacgggaga gaaagttttt 60
ctggaatgtg tccaggatat ggaccatgaa aatatgttct ggtatcgaca agacccaggt 120
ctggggctac ggctgatcta tttctcatat gatgttaaaa tgaaagaaaa aggagatatt 180
cctgaggggt acagtgtctc tagagagaag aaggagcgct tctccctgat tctggagtcc 240
gccagcacca accagacatc tatgtacctc tgtgccagca gtttgtgggc attgaacact 300
gaagctttct ttggacaagg caccagactc acagttgta 339

<210> SEQ ID NO 513
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 513

Thr Ser Glu Ser Asp Tyr Tyr
1 5

<210> SEQ ID NO 514
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 514

Gln Glu Ala Tyr Lys Gln Gln Asn
1 5

<210> SEQ ID NO 515
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 515

Ala Tyr Arg Ser Ala Thr Gly Asn Gln Phe Tyr
1 5 10

<210> SEQ ID NO 516
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 516
accagtgaga gtgattatta t 21

<210> SEQ ID NO 517
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 517
caagaagctt ataagcaaca gaat 24

<210> SEQ ID NO 518
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 518
gcttatagga gcgcgaccgg taaccagttc tat 33

<210> SEQ ID NO 519
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 519

```
Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Thr Gly Asn Gln Phe Tyr Phe Gly Thr Gly Thr Ser Leu Thr Val
            100                 105                 110

Ile Pro
```

<210> SEQ ID NO 520
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 520
gctcagacag tcactcagtc tcaaccagag atgtctgtgc aggaggcaga gaccgtgacc 60
ctgagctgca catatgacac cagtgagagt gattattatt tattctggta caagcagcct 120
cccagcaggc agatgattct cgttattcgc caagaagctt ataagcaaca gaatgcaaca 180
gagaatcgtt tctctgtgaa cttccagaaa gcagccaaat ccttcagtct caagatctca 240
gactcacagc tgggggatgc cgcgatgtat ttctgtgctt ataggagcgc gaccggtaac 300
cagttctatt ttgggacagg gacaagtttg acggtcattc ca 342

<210> SEQ ID NO 521
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 521

Met Asp His Glu Asn
1 5

<210> SEQ ID NO 522
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 522

Ser Tyr Asp Val Lys Met
1 5

<210> SEQ ID NO 523
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 523

Ala Ser Ser Leu Phe Ala Leu Asn Thr Glu Ala Phe
1 5 10

<210> SEQ ID NO 524
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 524
atggaccatg aaaat 15

<210> SEQ ID NO 525
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 525
tcatatgatg ttaaaatg 18

<210> SEQ ID NO 526
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 526
gccagcagtt tattcgcatt gaacactgaa gctttc 36

<210> SEQ ID NO 527
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 527

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Phe
                85                  90                  95

Ala Leu Asn Thr Glu Ala Phe Phe Gly Gln Gly Thr Arg Leu Thr Val
            100                 105                 110

Val
```

<210> SEQ ID NO 528
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 528

```
gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgccagca gtttattcgc attgaacact    300

gaagctttct ttggacaagg caccagactc acagttgta                           339
```

<210> SEQ ID NO 529
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 529

```
Thr Ile Ser Gly Asn Glu Tyr
1               5
```

<210> SEQ ID NO 530
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 530

Gly Leu Lys Asn Asn
1               5

<210> SEQ ID NO 531
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 531

Ile Val Tyr Gly Gly Ser Gln Gly Asn Leu Ile
1               5                   10

<210> SEQ ID NO 532
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 532
accatcagtg gaaatgagta t                                              21

<210> SEQ ID NO 533
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 533
ggtctaaaaa acaat                                                     15

<210> SEQ ID NO 534
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 534
atcgtttatg gaggaagcca aggaaatctc atc                                 33

<210> SEQ ID NO 535
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 535

Asp Ala Lys Thr Thr Gln Pro Pro Ser Met Asp Cys Ala Glu Gly Arg

```
1               5                   10                  15

Ala Ala Asn Leu Pro Cys Asn His Ser Thr Ile Ser Gly Asn Glu Tyr
            20                  25                  30

Val Tyr Trp Tyr Arg Gln Ile His Ser Gln Gly Pro Gln Tyr Ile Ile
        35                  40                  45

His Gly Leu Lys Asn Asn Glu Thr Asn Glu Met Ala Ser Leu Ile Ile
    50                  55                  60

Thr Glu Asp Arg Lys Ser Ser Thr Leu Ile Leu Pro His Ala Thr Leu
65                  70                  75                  80

Arg Asp Thr Ala Val Tyr Tyr Cys Ile Val Tyr Gly Gly Ser Gln Gly
                85                  90                  95

Asn Leu Ile Phe Gly Lys Gly Thr Lys Leu Ser Val Lys Pro
            100                 105                 110


<210> SEQ ID NO 536
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 536

gatgctaaga ccacccagcc cccctccatg gattgcgctg aaggaagagc tgcaaacctg      60

ccttgtaatc actctaccat cagtggaaat gagtatgtgt attggtatcg acagattcac     120

tcccaggggc cacagtatat cattcatggt ctaaaaaaca atgaaaccaa tgaaatggcc     180

tctctgatca tcacagaaga cagaaagtcc agcaccttga tcctgcccca cgctacgctg     240

agagacactg ctgtgtacta ttgcatcgtt tatggaggaa gccaaggaaa tctcatcttt     300

ggaaaaggca ctaaactctc tgttaaacca                                      330


<210> SEQ ID NO 537
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Ser Gly His Asp Thr
1               5


<210> SEQ ID NO 538
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Tyr Tyr Glu Glu Glu Glu
1               5


<210> SEQ ID NO 539
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 539

Ala Ser Ser Phe Ser Arg Val Gln Pro Gln His
1 5 10

<210> SEQ ID NO 540
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 540
tctgggcatg acact 15

<210> SEQ ID NO 541
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 541
tattatgagg aggaagag 18

<210> SEQ ID NO 542
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 542
gccagcagct tcagcagggt ccagccccag cat 33

<210> SEQ ID NO 543
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 543

Asp Ala Gly Val Thr Gln Ser Pro Thr His Leu Ile Lys Thr Arg Gly
1 5 10 15

Gln Gln Val Thr Leu Arg Cys Ser Pro Lys Ser Gly His Asp Thr Val
20 25 30

Ser Trp Tyr Gln Gln Ala Leu Gly Gln Gly Pro Gln Phe Ile Phe Gln
35 40 45

Tyr Tyr Glu Glu Glu Glu Arg Gln Arg Gly Asn Phe Pro Asp Arg Phe
50 55 60

Ser Gly His Gln Phe Pro Asn Tyr Ser Ser Glu Leu Asn Val Asn Ala
65 70 75 80

Leu Leu Leu Gly Asp Ser Ala Leu Tyr Leu Cys Ala Ser Ser Phe Ser
85 90 95

Arg Val Gln Pro Gln His Phe Gly Asp Gly Thr Arg Leu Ser Ile Leu
100 105 110

<210> SEQ ID NO 544

<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 544
gacgctggag tcacccaaag tcccacacac ctgatcaaaa cgagaggaca gcaagtgact 60
ctgagatgct ctcctaagtc tgggcatgac actgtgtcct ggtaccaaca ggccctgggt 120
caggggcccc agtttatctt tcagtattat gaggaggaag agagacagag aggcaacttc 180
cctgatcgat tctcaggtca ccagttccct aactatagct ctgagctgaa tgtgaacgcc 240
ttgttgctgg gggactcggc cctctatctc tgtgccagca gcttcagcag ggtccagccc 300
cagcattttg gtgatgggac tcgactctcc atccta 336

<210> SEQ ID NO 545
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 545

Thr Ser Glu Ser Asp Tyr Tyr
1 5

<210> SEQ ID NO 546
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 546

Gln Glu Ala Tyr Lys Gln Gln Asn
1 5

<210> SEQ ID NO 547
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 547

Ala Tyr Arg Ser Ala Leu Gly Asn Asp Met Arg
1 5 10

<210> SEQ ID NO 548
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 548
accagtgaga gtgattatta t 21

<210> SEQ ID NO 549
<211> LENGTH: 24

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
caagaagctt ataagcaaca gaat 24

<210> SEQ ID NO 550
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
gcttatagga gcgcgttggg caatgacatg cgc 33

<210> SEQ ID NO 551
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 551

```
Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Leu Gly Asn Asp Met Arg Phe Gly Ala Gly Thr Arg Leu Thr Val
            100                 105                 110

Lys Pro
```

<210> SEQ ID NO 552
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 552

```
gctcagacag tcactcagtc tcaaccagag atgtctgtgc aggaggcaga gaccgtgacc     60

ctgagctgca catatgacac cagtgagagt gattattatt tattctggta caagcagcct    120

cccagcaggc agatgattct cgttattcgc caagaagctt ataagcaaca gaatgcaaca    180

gagaatcgtt tctctgtgaa cttccagaaa gcagccaaat ccttcagtct caagatctca    240

gactcacagc tgggggatgc cgcgatgtat ttctgtgctt ataggagcgc gttgggcaat    300

gacatgcgct ttggagcagg gaccagactg acagtaaaac ca                       342
```

<210> SEQ ID NO 553
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 553

Met Asp His Glu Asn
1 5

<210> SEQ ID NO 554
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 554

Ser Tyr Asp Val Lys Met
1 5

<210> SEQ ID NO 555
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 555

Ala Ser Ser Leu Trp Ala Leu Asn Thr Glu Ala Phe
1 5 10

<210> SEQ ID NO 556
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 556
atggaccatg aaaat 15

<210> SEQ ID NO 557
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 557
tcatatgatg ttaaaatg 18

<210> SEQ ID NO 558
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 558
gccagcagtt tatgggcact gaacactgaa gctttc 36

<210> SEQ ID NO 559
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 559

Asp Val Lys Val Thr Gln Ser Ser Arg Tyr Leu Val Lys Arg Thr Gly
1 5 10 15

Glu Lys Val Phe Leu Glu Cys Val Gln Asp Met Asp His Glu Asn Met
20 25 30

Phe Trp Tyr Arg Gln Asp Pro Gly Leu Gly Leu Arg Leu Ile Tyr Phe
35 40 45

Ser Tyr Asp Val Lys Met Lys Glu Lys Gly Asp Ile Pro Glu Gly Tyr
50 55 60

Ser Val Ser Arg Glu Lys Lys Glu Arg Phe Ser Leu Ile Leu Glu Ser
65 70 75 80

Ala Ser Thr Asn Gln Thr Ser Met Tyr Leu Cys Ala Ser Ser Leu Trp
85 90 95

Ala Leu Asn Thr Glu Ala Phe Phe Gly Gln Gly Thr Arg Leu Thr Val
100 105 110

Val

<210> SEQ ID NO 560
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 560
gatgtgaaag taacccagag ctcgagatat ctagtcaaaa ggacgggaga gaaagttttt 60
ctggaatgtg tccaggatat ggaccatgaa aatatgttct ggtatcgaca agacccaggt 120
ctggggctac ggctgatcta tttctcatat gatgttaaaa tgaaagaaaa aggagatatt 180
cctgaggggt acagtgtctc tagagagaag aaggagcgct tctccctgat tctggagtcc 240
gccagcacca accagacatc tatgtacctc tgtgccagca gtttatgggc actgaacact 300
gaagctttct ttggacaagg caccagactc acagttgta 339

<210> SEQ ID NO 561
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 561

Thr Ser Glu Asn Asn Tyr Tyr
1 5

<210> SEQ ID NO 562
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 562

Gln Glu Ala Tyr Lys Gln Gln Asn
1 5

<210> SEQ ID NO 563
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 563

Ala Phe Met Lys Thr Gln Gly Gly Ser Glu Lys Leu Val
1 5 10

<210> SEQ ID NO 564
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 564
accagtgaga ataattatta t 21

<210> SEQ ID NO 565
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 565
caagaagctt ataagcaaca gaat 24

<210> SEQ ID NO 566
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 566
gctttcatga aaactcaggg cggatctgaa aagctggtc 39

<210> SEQ ID NO 567
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 567

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Asn Asn Tyr
20 25 30

```
Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Thr Ala Met Tyr Phe Cys Ala Phe Met Lys
                85                  90                  95

Thr Gln Gly Gly Ser Glu Lys Leu Val Phe Gly Lys Gly Thr Lys Leu
            100                 105                 110

Thr Val Asn Pro
        115


<210> SEQ ID NO 568
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 568

gcccagacag tcactcagtc tcaaccagag atgtctgtgc aggaggcaga gactgtgacc     60

ctgagttgca catatgacac cagtgagaat aattattatt tgttctggta caagcagcct    120

cccagcaggc agatgattct cgttattcgc caagaagctt ataagcaaca gaatgcaacg    180

gagaatcgtt tctctgtgaa cttccagaaa gcagccaaat ccttcagtct caagatctca    240

gactcacagc tgggggacac tgcgatgtat ttctgtgctt tcatgaaaac tcagggcgga    300

tctgaaaagc tggtctttgg aaagggaacg aaactgacag taaaccca                348


<210> SEQ ID NO 569
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Pro Arg His Asp Thr
1               5


<210> SEQ ID NO 570
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Phe Tyr Glu Lys Met Gln
1               5


<210> SEQ ID NO 571
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571
```

```
Ala Ser Ser Leu Val Gly Tyr Gly Tyr Thr
1               5                   10


<210> SEQ ID NO 572
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572

cctagacacg acact                                                       15


<210> SEQ ID NO 573
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573

ttttatgaaa agatgcag                                                    18


<210> SEQ ID NO 574
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574

gccagcagct tagttgggta tggctacacc                                       30


<210> SEQ ID NO 575
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 575

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
            20                  25                  30

Tyr Trp Tyr Gln Gln Gly Pro Gly Gln Asp Pro Gln Phe Leu Ile Ser
        35                  40                  45

Phe Tyr Glu Lys Met Gln Ser Asp Lys Gly Ser Ile Pro Asp Arg Phe
    50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Leu Val
                85                  90                  95

Gly Tyr Gly Tyr Thr Phe Gly Ser Gly Thr Arg Leu Thr Val Val
            100                 105                 110


<210> SEQ ID NO 576
<211> LENGTH: 333
<212> TYPE: DNA
```

<213> ORGANISM: Artificial Sequence
<220> FEATURE:
<223> OTHER INFORMATION: Description of Artificial Sequence: Synthetic
polynucleotide

<400> SEQUENCE: 576
gctgctggag tcatccagtc cccaagacat ctgatcaaag aaaagaggga aacagccact 60
ctgaaatgct atcctatccc tagacacgac actgtctact ggtaccagca gggtccaggt 120
caggaccccc agttcctcat ttcgttttat gaaaagatgc agagcgataa aggaagcatc 180
cctgatcgat tctcagctca acagttcagt gactatcatt ctgaactgaa catgagctcc 240
ttggagctgg gggactcagc cctgtacttc tgtgccagca gcttagttgg gtatggctac 300
accttcggtt cggggaccag gttaaccgtt gta 333

<210> SEQ ID NO 577
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 577

Thr Ser Glu Ser Asp Tyr Tyr
1 5

<210> SEQ ID NO 578
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 578

Gln Glu Ala Tyr Lys Gln Gln Asn
1 5

<210> SEQ ID NO 579
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 579

Ala Tyr Arg Ser Ala Thr Gly Asn Gln Phe Tyr
1 5 10

<210> SEQ ID NO 580
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 580
accagtgaga gtgattatta t 21

<210> SEQ ID NO 581
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 581
caagaagctt ataagcaaca gaat 24

<210> SEQ ID NO 582
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
gcttatagga gcgcaaccgg taaccagttc tat 33

<210> SEQ ID NO 583
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 583

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Ala Thr Gly Asn Gln Phe Tyr Phe Gly Thr Gly Thr Ser Leu Thr Val
            100                 105                 110

Ile Pro

<210> SEQ ID NO 584
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 584
gctcagacag tcactcagtc tcaaccagag atgtctgtgc aggaggcaga gaccgtgacc 60
ctgagctgca catatgacac cagtgagagt gattattatt tattctggta caagcagcct 120
cccagcaggc agatgattct cgttattcgc caagaagctt ataagcaaca gaatgcaaca 180
gagaatcgtt tctctgtgaa cttccagaaa gcagccaaat ccttcagtct caagatctca 240
gactcacagc tgggggatgc cgcgatgtat ttctgtgctt ataggagcgc aaccggtaac 300
cagttctatt ttgggacagg gacaagtttg acggtcattc ca 342

<210> SEQ ID NO 585
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 585

Met Asp His Glu Asn
1               5

<210> SEQ ID NO 586
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 586

Ser Tyr Asp Val Lys Met
1               5

<210> SEQ ID NO 587
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 587

Ala Ser Ser Leu Trp Gly Thr His Glu Lys Leu Phe
1               5                   10

<210> SEQ ID NO 588
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 588
atggaccatg aaaat                                                   15

<210> SEQ ID NO 589
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 589
tcatatgatg ttaaaatg                                                18

<210> SEQ ID NO 590
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 590
gccagcagtt tatgggggac acatgaaaaa ctgttt                            36

<210> SEQ ID NO 591
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 591

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Gly Thr His Glu Lys Leu Phe Phe Gly Ser Gly Thr Gln Leu Ser Val
            100                 105                 110

Leu

<210> SEQ ID NO 592
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 592
gatgtgaaag taacccagag ctcgagatat ctagtcaaaa ggacgggaga gaaagttttt 60
ctggaatgtg tccaggatat ggaccatgaa aatatgttct ggtatcgaca agacccaggt 120
ctggggctac ggctgatcta tttctcatat gatgttaaaa tgaaagaaaa aggagatatt 180
cctgaggggt acagtgtctc tagagagaag aaggagcgct tctccctgat tctggagtcc 240
gccagcacca accagacatc tatgtacctc tgtgccagca gtttatgggg gacacatgaa 300
aaactgtttt ttggcagtgg aacccagctc tctgtcttg 339

<210> SEQ ID NO 593
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 593

Thr Ser Glu Ser Asp Tyr Tyr
1               5

<210> SEQ ID NO 594
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 594

Gln Glu Ala Tyr Lys Gln Gln Asn
1 5

<210> SEQ ID NO 595
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 595

Ala Tyr Arg Ser Ser Thr Gly Asn Gln Phe Tyr
1 5 10

<210> SEQ ID NO 596
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 596
accagtgaga gtgattatta t 21

<210> SEQ ID NO 597
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 597
caagaagctt ataagcaaca gaat 24

<210> SEQ ID NO 598
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 598
gcttatagga gctccaccgg taaccagttc tat 33

<210> SEQ ID NO 599
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 599

Ala Gln Thr Val Thr Gln Ser Gln Pro Glu Met Ser Val Gln Glu Ala
1 5 10 15

Glu Thr Val Thr Leu Ser Cys Thr Tyr Asp Thr Ser Glu Ser Asp Tyr
20 25 30

Tyr Leu Phe Trp Tyr Lys Gln Pro Pro Ser Arg Gln Met Ile Leu Val
35 40 45

Ile Arg Gln Glu Ala Tyr Lys Gln Gln Asn Ala Thr Glu Asn Arg Phe
50 55 60

Ser Val Asn Phe Gln Lys Ala Ala Lys Ser Phe Ser Leu Lys Ile Ser
65 70 75 80

Asp Ser Gln Leu Gly Asp Ala Ala Met Tyr Phe Cys Ala Tyr Arg Ser
85 90 95

Ser Thr Gly Asn Gln Phe Tyr Phe Gly Thr Gly Thr Ser Leu Thr Val
100 105 110

Ile Pro

<210> SEQ ID NO 600
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 600
gctcagacag tcactcagtc tcaaccagag atgtctgtgc aggaggcaga gaccgtgacc 60
ctgagctgca catatgacac cagtgagagt gattattatt tattctggta caagcagcct 120
cccagcaggc agatgattct cgttattcgc caagaagctt ataagcaaca gaatgcaaca 180
gagaatcgtt tctctgtgaa cttccagaaa gcagccaaat ccttcagtct caagatctca 240
gactcacagc tgggggatgc cgcgatgtat ttctgtgctt ataggagctc caccggtaac 300
cagttctatt ttgggacagg gacaagtttg acggtcattc ca 342

<210> SEQ ID NO 601
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 601

Met Asp His Glu Asn
1 5

<210> SEQ ID NO 602
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 602

Ser Tyr Asp Val Lys Met
1 5

<210> SEQ ID NO 603
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 603

Ala Ser Ser Leu Trp Gly Thr Asn Glu Lys Leu Phe
1 5 10

<210> SEQ ID NO 604
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 604
atggaccatg aaaat 15

<210> SEQ ID NO 605
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 605
tcatatgatg ttaaaatg 18

<210> SEQ ID NO 606
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 606
gccagcagtt tatggggaac taatgaaaaa ctgttt 36

<210> SEQ ID NO 607
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 607

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Trp
                85                  90                  95

Gly Thr Asn Glu Lys Leu Phe Phe Gly Ser Gly Thr Gln Leu Ser Val
            100                 105                 110

Leu
```

<210> SEQ ID NO 608
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 608

```
gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgccagca gtttatgggg aactaatgaa    300

aaactgtttt ttggcagtgg aacccagctc tctgtcttg                           339
```

<210> SEQ ID NO 609
<211> LENGTH: 9
<212> TYPE: PRT
<213> ORGANISM: Homo sapiens

<400> SEQUENCE: 609

```
Lys Val Leu Glu His Val Val Arg Val
1               5
```

<210> SEQ ID NO 610
<211> LENGTH: 1724
<212> TYPE: DNA
<213> ORGANISM: Homo sapiens

<400> SEQUENCE: 610

```
agagacaagc gagcttctgc gtctgactcg cagcttgaga ctggcggagg gaagcccgcc     60

caggctctat aaggagacaa ggttctgagc agacaggcca accggaggac aggattccct    120

ggaggccaca gaggagcacc aaggagaaga tctgcctgtg ggtccccatt gcccagcttt    180

tgcctgcact cttgcctgct gccctgacca gagtcatcat gtcttctgag cagaagagtc    240

agcactgcaa gcctgaggaa ggcgttgagg cccaagaaga ggccctgggc ctggtgggtg    300

cacaggctcc tactactgag gagcaggagg ctgctgtctc ctcctcctct cctctggtcc    360

ctggcaccct ggaggaagtg cctgctgctg agtcagcagg tcctccccag agtcctcagg    420

gagcctctgc cttacccact accatcagct tcacttgctg gaggcaaccc aatgagggtt    480

ccagcagcca agaagaggag gggccaagca cctcgcctga cgcagagtcc ttgttccgag    540

aagcactcag taacaaggtg gatgagttgg ctcattttct gctccgcaag tatcgagcca    600

aggagctggt cacaaaggca gaaatgctgg agagagtcat caaaaattac aagcgctgct    660

ttcctgtgat cttcggcaaa gcctccgagt ccctgaagat gatctttggc attgacgtga    720

aggaagtgga ccccgccagc aacacctaca cccttgtcac ctgcctgggc ctttcctatg    780

atggcctgct gggtaataat cagatctttc ccaagacagg ccttctgata atcgtcctgg    840

gcacaattgc aatggagggc gacagcgcct ctgaggagga aatctgggag gagctgggtg    900

tgatgggggt gtatgatggg agggagcaca ctgtctatgg ggagcccagg aaactgctca    960

cccaagattg ggtgcaggaa aactacctgg agtaccggca ggtacccggc agtaatcctg   1020

cgcgctatga gttcctgtgg ggtccaaggg ctctggctga aaccagctat gtgaaagtcc   1080

tggagcatgt ggtcagggtc aatgcaagag ttcgcattgc ctacccatcc ctgcgtgaag   1140

cagctttgtt agaggaggaa gagggagtct gagcatgagt tgcagccagg gctgtgggga   1200

aggggcaggg ctgggccagt gcatctaaca gccctgtgca gcagcttccc ttgcctcgtg   1260
```

```
taacatgagg cccattcttc actctgtttg aagaaaatag tcagtgttct tagtagtggg   1320

tttctatttt gttggatgac ttggagattt atctctgttt ccttttacaa ttgttgaaat   1380

gttcctttta atggatggtt gaattaactt cagcatccaa gtttatgaat cgtagttaac   1440

gtatattgct gttaatatag tttaggagta agagtcttgt tttttattca gattgggaaa   1500

tccgttctat tttgtgaatt tgggacataa taacagcagt ggagtaagta tttagaagtg   1560

tgaattcacc gtgaaatagg tgagataaat taaaagatac ttaattcccg ccttatgcct   1620

cagtctattc tgtaaaattt aaaaaatata tatgcatacc tggatttcct tggcttcgtg   1680

aatgtaagag aaattaaatc tgaataaata attctttctg ttaa                    1724


<210> SEQ ID NO 611
<211> LENGTH: 317
<212> TYPE: PRT
<213> ORGANISM: Homo sapiens

<400> SEQUENCE: 611

Met Ser Ser Glu Gln Lys Ser Gln His Cys Lys Pro Glu Glu Gly Val
1               5                   10                  15

Glu Ala Gln Glu Glu Ala Leu Gly Leu Val Gly Ala Gln Ala Pro Thr
            20                  25                  30

Thr Glu Glu Gln Glu Ala Ala Val Ser Ser Ser Ser Pro Leu Val Pro
        35                  40                  45

Gly Thr Leu Glu Glu Val Pro Ala Ala Glu Ser Ala Gly Pro Pro Gln
    50                  55                  60

Ser Pro Gln Gly Ala Ser Ala Leu Pro Thr Thr Ile Ser Phe Thr Cys
65                  70                  75                  80

Trp Arg Gln Pro Asn Glu Gly Ser Ser Ser Gln Glu Glu Glu Gly Pro
                85                  90                  95

Ser Thr Ser Pro Asp Ala Glu Ser Leu Phe Arg Glu Ala Leu Ser Asn
            100                 105                 110

Lys Val Asp Glu Leu Ala His Phe Leu Leu Arg Lys Tyr Arg Ala Lys
        115                 120                 125

Glu Leu Val Thr Lys Ala Glu Met Leu Glu Arg Val Ile Lys Asn Tyr
    130                 135                 140

Lys Arg Cys Phe Pro Val Ile Phe Gly Lys Ala Ser Glu Ser Leu Lys
145                 150                 155                 160

Met Ile Phe Gly Ile Asp Val Lys Glu Val Asp Pro Ala Ser Asn Thr
                165                 170                 175

Tyr Thr Leu Val Thr Cys Leu Gly Leu Ser Tyr Asp Gly Leu Leu Gly
            180                 185                 190

Asn Asn Gln Ile Phe Pro Lys Thr Gly Leu Leu Ile Ile Val Leu Gly
        195                 200                 205

Thr Ile Ala Met Glu Gly Asp Ser Ala Ser Glu Glu Glu Ile Trp Glu
    210                 215                 220

Glu Leu Gly Val Met Gly Val Tyr Asp Gly Arg Glu His Thr Val Tyr
225                 230                 235                 240

Gly Glu Pro Arg Lys Leu Leu Thr Gln Asp Trp Val Gln Glu Asn Tyr
                245                 250                 255

Leu Glu Tyr Arg Gln Val Pro Gly Ser Asn Pro Ala Arg Tyr Glu Phe
            260                 265                 270

Leu Trp Gly Pro Arg Ala Leu Ala Glu Thr Ser Tyr Val Lys Val Leu
        275                 280                 285

Glu His Val Val Arg Val Asn Ala Arg Val Arg Ile Ala Tyr Pro Ser
```

```
    290                 295                 300

Leu Arg Glu Ala Ala Leu Leu Glu Glu Glu Glu Gly Val
305                 310                 315


<210> SEQ ID NO 612
<211> LENGTH: 10
<212> TYPE: PRT
<213> ORGANISM: Homo sapiens

<400> SEQUENCE: 612

Gly Val Tyr Asp Gly Arg Glu His Thr Val
1               5                   10


<210> SEQ ID NO 613
<211> LENGTH: 10
<212> TYPE: PRT
<213> ORGANISM: Unknown
<220> FEATURE:
<223> OTHER INFORMATION: Description of Unknown:
      MAGE-A8 sequence

<400> SEQUENCE: 613

Gly Leu Tyr Asp Gly Arg Glu His Ser Val
1               5                   10


<210> SEQ ID NO 614
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Thr Ile Ser Gly Asn Glu Tyr
1               5


<210> SEQ ID NO 615
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Gly Leu Lys Asn Asn
1               5


<210> SEQ ID NO 616
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Ile Val Arg Pro Tyr Asn Ala Gly Asn Asn Arg Lys Leu
1               5                   10


<210> SEQ ID NO 617
<211> LENGTH: 21
<212> TYPE: DNA
<213> ORGANISM: Artificial Sequence
<220> FEATURE:
<223> OTHER INFORMATION: Description of Artificial Sequence: Synthetic
```

oligonucleotide

<400> SEQUENCE: 617
accatcagtg gaaatgagta t 21

<210> SEQ ID NO 618
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 618
ggtctaaaaa acaat 15

<210> SEQ ID NO 619
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 619
atcgtcagac cttataatgc tggcaacaac cgtaagctg 39

<210> SEQ ID NO 620
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 620

```
Asp Ala Lys Thr Thr Gln Pro Pro Ser Met Asp Cys Ala Glu Gly Arg
1               5                   10                  15

Ala Ala Asn Leu Pro Cys Asn His Ser Thr Ile Ser Gly Asn Glu Tyr
            20                  25                  30

Val Tyr Trp Tyr Arg Gln Ile His Ser Gln Gly Pro Gln Tyr Ile Ile
        35                  40                  45

His Gly Leu Lys Asn Asn Glu Thr Asn Glu Met Ala Ser Leu Ile Ile
    50                  55                  60

Thr Glu Asp Arg Lys Ser Ser Thr Leu Ile Leu Pro His Ala Thr Leu
65                  70                  75                  80

Arg Asp Thr Ala Val Tyr Tyr Cys Ile Val Arg Pro Tyr Asn Ala Gly
                85                  90                  95

Asn Asn Arg Lys Leu Ile Trp Gly Leu Gly Thr Ser Leu Ala Val Asn
            100                 105                 110

Pro
```

<210> SEQ ID NO 621
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 621
gatgctaaga ccacccagcc cccctccatg gattgcgctg aaggaagagc tgcaaacctg 60

```
ccttgtaatc actctaccat cagtggaaat gagtatgtgt attggtatcg acagattcac    120

tcccaggggc cacagtatat cattcatggt ctaaaaaaca atgaaaccaa tgaaatggcc    180

tctctgatca tcacagaaga cagaaagtcc agcaccttga tcctgcccca cgctacgctg    240

agagacactg ctgtgtacta ttgcatcgtc agaccttata atgctggcaa caaccgtaag    300

ctgatttggg gattgggaac aagcctggca gtaaatccg                           339


<210> SEQ ID NO 622
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 622

Met Asp His Glu Asn
1               5


<210> SEQ ID NO 623
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

Ser Tyr Asp Val Lys Met
1               5


<210> SEQ ID NO 624
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 624

Ala Ser Ser Phe Gly Gly Gly Tyr Tyr Gly Tyr Thr
1               5                   10


<210> SEQ ID NO 625
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 625

atggaccatg aaaat                                                      15


<210> SEQ ID NO 626
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626

tcatatgatg ttaaaatg                                                   18
```

<210> SEQ ID NO 627
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 627
gccagcagtt ttgggggggg atactatggc tacacc 36

<210> SEQ ID NO 628
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 628

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Phe Gly
                85                  90                  95

Gly Gly Tyr Tyr Gly Tyr Thr Phe Gly Ser Gly Thr Arg Leu Thr Val
            100                 105                 110

Val
```

<210> SEQ ID NO 629
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 629

```
gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat cctggagtcc    240

gccagcacca accagacatc tatgtacctc tgtgccagca gttttggggg gggatactat    300

ggctacacct tcggttcggg gaccaggcta accgttgta                           339
```

<210> SEQ ID NO 630
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 630

Thr Ser Asp Pro Ser Tyr Gly
1 5

<210> SEQ ID NO 631
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 631

Gln Gly Ser Tyr Asp Gln Gln
1 5

<210> SEQ ID NO 632
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 632

Ala Met Arg Glu Gly Pro Gly Asn Asn Ala Arg Leu
1 5 10

<210> SEQ ID NO 633
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 633
accagtgatc caagttatgg t 21

<210> SEQ ID NO 634
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 634
caggggtctt atgaccagca a 21

<210> SEQ ID NO 635
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 635
gcaatgagag agggccctgg taacaatgcc agactc 36

<210> SEQ ID NO 636
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 636

```
Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Pro Ser Tyr
            20                  25                  30

Gly Leu Phe Trp Tyr Lys Gln Pro Ser Ser Gly Glu Met Ile Phe Leu
        35                  40                  45

Ile Tyr Gln Gly Ser Tyr Asp Gln Gln Asn Ala Thr Glu Gly Arg Tyr
    50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Glu
                85                  90                  95

Gly Pro Gly Asn Asn Ala Arg Leu Met Phe Gly Asp Gly Thr Gln Leu
            100                 105                 110

Val Val Lys Pro
        115
```

<210> SEQ ID NO 637
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 637

```
gcccagaaga taactcaaac ccaaccagga atgttcgtgc aggaaaagga ggctgtgact     60

ctggactgca catatgacac cagtgatcca agttatggtc tattctggta caagcagccc    120

agcagtgggg aaatgatttt tcttatttat caggggtctt atgaccagca aaatgcaaca    180

gaaggtcgct actcattgaa tttccagaag gcaagaaaat ccgccaacct tgtcatctcc    240

gcttcacaac tgggggactc agcaatgtac ttctgtgcaa tgagagaggg ccctggtaac    300

aatgccagac tcatgtttgg agatggaact cagctggtgg tgaagccc                 348
```

<210> SEQ ID NO 638
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 638

```
Met Asn His Glu Tyr
1               5
```

<210> SEQ ID NO 639
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 639

```
Ser Val Gly Glu Gly Thr
1               5
```

<210> SEQ ID NO 640
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 640

```
Ala Ser Ser Tyr Trp Asp Arg Gly Ser Pro Leu His
1               5                   10
```

<210> SEQ ID NO 641
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 641

```
atgaaccatg aatac                                                    15
```

<210> SEQ ID NO 642
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 642

```
tcagttggtg agggtaca                                                 18
```

<210> SEQ ID NO 643
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 643

```
gccagcagtt actgggacag gggctcaccc ctccac                             36
```

<210> SEQ ID NO 644
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 644

```
Asn Ala Gly Val Thr Gln Thr Pro Lys Phe Arg Val Leu Lys Thr Gly
1               5                   10                  15

Gln Ser Met Thr Leu Leu Cys Ala Gln Asp Met Asn His Glu Tyr Met
            20                  25                  30

Tyr Trp Tyr Arg Gln Asp Pro Gly Met Gly Leu Arg Leu Ile His Tyr
        35                  40                  45

Ser Val Gly Glu Gly Thr Thr Ala Lys Gly Glu Val Pro Asp Gly Tyr
    50                  55                  60

Asn Val Ser Arg Leu Lys Lys Gln Asn Phe Leu Leu Gly Leu Glu Ser
65                  70                  75                  80

Ala Ala Pro Ser Gln Thr Ser Val Tyr Phe Cys Ala Ser Ser Tyr Trp
```

```
                85                  90                  95

Asp Arg Gly Ser Pro Leu His Phe Gly Asn Gly Thr Arg Leu Thr Val
            100                 105                 110

Thr
```

<210> SEQ ID NO 645
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 645

```
aatgctggtg tcactcagac cccaaaattc cgggtcctga agacaggaca gagcatgaca     60

ctgctgtgtg cccaggatat gaaccatgaa tacatgtact ggtatcgaca agacccaggc    120

atggggctga ggctgattca ttactcagtt ggtgagggta caactgccaa aggagaggtc    180

cctgatggct acaatgtctc cagattaaaa aaacagaatt tcctgctggg gttggagtcg    240

gctgctccct cccaaacatc tgtgtacttc tgtgccagca gttactggga caggggctca    300

cccctccact ttgggaacgg gaccaggctc actgtgaca                           339
```

<210> SEQ ID NO 646
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 646

```
Thr Ile Ser Gly Asn Glu Tyr
1               5
```

<210> SEQ ID NO 647
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 647

```
Gly Leu Lys Asn
1
```

<210> SEQ ID NO 648
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 648

```
Ile Val Arg Pro Tyr Asn Ala Gly Asn Asn Arg Lys Leu
1               5                   10
```

<210> SEQ ID NO 649
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 649
accatcagtg gaaatgagta t 21

<210> SEQ ID NO 650
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 650
ggtctaaaaa ac 12

<210> SEQ ID NO 651
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 651
atcgtcagac cttataatgc tggcaacaac cgtaagctg 39

<210> SEQ ID NO 652
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 652

```
Asp Ala Lys Thr Thr Gln Pro Pro Ser Met Asp Cys Ala Glu Gly Arg
1               5                   10                  15

Ala Ala Asn Leu Pro Cys Asn His Ser Thr Ile Ser Gly Asn Glu Tyr
            20                  25                  30

Val Tyr Trp Tyr Arg Gln Ile His Ser Gln Gly Pro Gln Tyr Ile Ile
        35                  40                  45

His Gly Leu Lys Asn Asn Glu Thr Asn Glu Met Ala Ser Leu Ile Ile
    50                  55                  60

Thr Glu Asp Arg Lys Ser Ser Thr Leu Ile Leu Pro His Ala Thr Leu
65                  70                  75                  80

Arg Asp Thr Ala Val Tyr Tyr Cys Ile Val Arg Pro Tyr Asn Ala Gly
                85                  90                  95

Asn Asn Arg Lys Leu Ile Trp Gly Leu Gly Thr Ser Leu Ala Val Asn
            100                 105                 110

Pro
```

<210> SEQ ID NO 653
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 653
gatgctaaga ccacccagcc cccctccatg gattgcgctg aaggaagagc tgcaaacctg 60

```
ccttgtaatc actctaccat cagtggaaat gagtatgtgt attggtatcg acagattcac    120

tcccaggggc cacagtatat cattcatggt ctaaaaaaca atgaaaccaa tgaaatggcc    180

tctctgatca tcacagaaga cagaaagtcc agcaccttga tcctgcccca cgctacgctg    240

agagacactg ctgtgtacta ttgcatcgtc agaccttata atgctggcaa caaccgtaag    300

ctgatttggg gattgggaac aagcctggca gtaaatccg                           339
```

<210> SEQ ID NO 654
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 654

```
Met Asp His Glu Asn
1               5
```

<210> SEQ ID NO 655
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 655

```
Ser Tyr Asp Val Lys Met
1               5
```

<210> SEQ ID NO 656
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 656

```
Ala Ser Ser Phe Glu Gly Gly Tyr Tyr Gly Tyr Thr
1               5                   10
```

<210> SEQ ID NO 657
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 657

```
atggaccatg aaaat                                                      15
```

<210> SEQ ID NO 658
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 658

```
tcatatgatg ttaaaatg                                                   18
```

<210> SEQ ID NO 659
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 659
gccagcagtt ttgagggggg atactatggc tacacc 36

<210> SEQ ID NO 660
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 660

Asp Val Lys Val Thr Gln Ser Ser Arg Tyr Leu Val Lys Arg Thr Gly
1 5 10 15

Glu Lys Val Phe Leu Glu Cys Val Gln Asp Met Asp His Glu Asn Met
20 25 30

Phe Trp Tyr Arg Gln Asp Pro Gly Leu Gly Leu Arg Leu Ile Tyr Phe
35 40 45

Ser Tyr Asp Val Lys Met Lys Glu Lys Gly Asp Ile Pro Glu Gly Tyr
50 55 60

Ser Val Ser Arg Glu Lys Lys Glu Arg Phe Ser Leu Ile Leu Glu Ser
65 70 75 80

Ala Ser Thr Asn Gln Thr Ser Met Tyr Leu Cys Ala Ser Ser Phe Glu
85 90 95

Gly Gly Tyr Tyr Gly Tyr Thr Phe Gly Ser Gly Thr Arg Leu Thr Val
100 105 110

Val

<210> SEQ ID NO 661
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 661
gatgtgaaag taacccagag ctcgagatat ctagtcaaaa ggacgggaga gaaagttttt 60
ctggaatgtg tccaggatat ggaccatgaa aatatgttct ggtatcgaca agacccaggt 120
ctggggctac ggctgatcta tttctcatat gatgttaaaa tgaaagaaaa aggagatatt 180
cctgaggggt acagtgtctc tagagagaag aaggagcgct tctccctgat tctggagtcc 240
gccagcacca accagacatc tatgtacctc tgtgccagca gttttgaggg gggatactat 300
ggctacacct tcggttcggg gaccaggtta accgttgta 339

<210> SEQ ID NO 662
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 662

Thr Ser Asp Pro Ser Tyr Gly
1 5

<210> SEQ ID NO 663
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 663

Gln Gly Ser Tyr Asp Gln Gln
1 5

<210> SEQ ID NO 664
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 664

Ala Met Arg Gly Gly Gly Ser Gly Gly Ser Tyr Ile Pro Thr
1 5 10

<210> SEQ ID NO 665
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 665
accagtgatc caagttatgg t 21

<210> SEQ ID NO 666
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 666
caggggtctt atgaccagca a 21

<210> SEQ ID NO 667
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 667
gcaatgagag ggggggggatc aggaggaagc tacataccta ca 42

<210> SEQ ID NO 668
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 668

```
Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Pro Ser Tyr
            20                  25                  30

Gly Leu Phe Trp Tyr Lys Gln Pro Ser Ser Gly Glu Met Ile Phe Leu
        35                  40                  45

Ile Tyr Gln Gly Ser Tyr Asp Gln Gln Asn Ala Thr Glu Gly Arg Tyr
    50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Gly
                85                  90                  95

Gly Gly Ser Gly Gly Ser Tyr Ile Pro Thr Phe Gly Arg Gly Thr Ser
            100                 105                 110

Leu Ile Val His Pro
        115
```

<210> SEQ ID NO 669
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 669

```
gcccagaaga taactcaaac ccaaccagga atgttcgtgc aggaaaagga ggctgtgact      60

ctggactgca catatgacac cagtgatcca agttatggtc tattctggta caagcagccc     120

agcagtgggg aaatgatttt tcttatttat caggggtctt atgaccagca aaatgcaaca     180

gaaggtcgct actcattgaa tttccagaag gcaagaaaat ccgccaacct tgtcatctcc     240

gcttcacaac tgggggactc agcaatgtac ttctgtgcaa tgagaggggg gggatcagga     300

ggaagctaca tacctacatt tggaagagga accagcctta ttgttcatcc g              351
```

<210> SEQ ID NO 670
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 670

```
Met Asp His Glu Asn
1               5
```

<210> SEQ ID NO 671
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 671

```
Ser Tyr Asp Val Lys Met
1               5
```

<210> SEQ ID NO 672
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 672

Ala Ser Ser Phe Thr Gly Pro Tyr Asn Ser Pro Leu His
1 5 10

<210> SEQ ID NO 673
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 673
atggaccatg aaaat 15

<210> SEQ ID NO 674
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 674
tcatatgatg ttaaaatg 18

<210> SEQ ID NO 675
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 675
gccagcagtt tcacagggcc ctataattca cccctccac 39

<210> SEQ ID NO 676
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 676

Asp Val Lys Val Thr Gln Ser Ser Arg Tyr Leu Val Lys Arg Thr Gly
1 5 10 15

Glu Lys Val Phe Leu Glu Cys Val Gln Asp Met Asp His Glu Asn Met
20 25 30

Phe Trp Tyr Arg Gln Asp Pro Gly Leu Gly Leu Arg Leu Ile Tyr Phe
35 40 45

Ser Tyr Asp Val Lys Met Lys Glu Lys Gly Asp Ile Pro Glu Gly Tyr
50 55 60

Ser Val Ser Arg Glu Lys Lys Glu Arg Phe Ser Leu Ile Leu Glu Ser
65 70 75 80

Ala Ser Thr Asn Gln Thr Ser Met Tyr Leu Cys Ala Ser Ser Phe Thr

```
                85                  90                  95

Gly Pro Tyr Asn Ser Pro Leu His Phe Gly Asn Gly Thr Arg Leu Thr
            100                 105                 110

Val Thr


<210> SEQ ID NO 677
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 677

gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgccagca gtttcacagg gccctataat    300

tcacccctcc actttgggaa cgggaccagg ctcactgtga ca                       342


<210> SEQ ID NO 678
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 678

Thr Ser Asp Pro Ser Tyr Gly
1               5


<210> SEQ ID NO 679
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 679

Gln Gly Ser Tyr Asp Glu Gln
1               5


<210> SEQ ID NO 680
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 680

Ala Met Arg Glu Gly Pro Gly Ser Gly Asn Thr Gly Lys Leu Ile
1               5                   10                  15


<210> SEQ ID NO 681
<211> LENGTH: 21
<212> TYPE: DNA
<213> ORGANISM: Artificial Sequence
<220> FEATURE:
<223> OTHER INFORMATION: Description of Artificial Sequence: Synthetic
```

oligonucleotide

<400> SEQUENCE: 681
accagtgatc caagttatgg t 21

<210> SEQ ID NO 682
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 682
caggggtctt atgacgagca a 21

<210> SEQ ID NO 683
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 683
gcaatgagag agggcccggg ctctggcaac acaggcaaac taatc 45

<210> SEQ ID NO 684
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 684

```
Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Pro Ser Tyr
            20                  25                  30

Gly Leu Phe Trp Tyr Lys Gln Pro Ser Ser Gly Glu Met Ile Phe Leu
        35                  40                  45

Ile Tyr Gln Gly Ser Tyr Asp Glu Gln Asn Ala Thr Glu Gly Arg Tyr
    50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Glu
                85                  90                  95

Gly Pro Gly Ser Gly Asn Thr Gly Lys Leu Ile Phe Gly Gln Gly Thr
            100                 105                 110

Thr Leu Gln Val Lys Pro
        115
```

<210> SEQ ID NO 685
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 685
gcccagaaga taactcaaac ccaaccagga atgttcgtgc aggaaaagga ggctgtgact 60
ctggactgca catatgacac cagtgatcca agttatggtc tattctggta caagcagccc 120
agcagtgggg aaatgatttt tcttatttat caggggtctt atgacgagca aaatgcaaca 180
gaaggtcgct actcattgaa tttccagaag gcaagaaaat ccgccaacct tgtcatctcc 240
gcttcacaac tgggggactc agcaatgtac ttctgtgcaa tgagagaggg cccgggctct 300
ggcaacacag gcaaactaat ctttgggcaa gggacaactt tacaagtaaa acca 354

<210> SEQ ID NO 686
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 686

Met Asn His Asn Tyr
1 5

<210> SEQ ID NO 687
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 687

Ser Val Gly Ala Gly Ile
1 5

<210> SEQ ID NO 688
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 688

Ala Ser Ser Tyr Ser Glu Trp Gln Asn Tyr Gly Tyr Thr
1 5 10

<210> SEQ ID NO 689
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 689
atgaaccata actac 15

<210> SEQ ID NO 690
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 690
tcagttggtg ctggtatc 18

<210> SEQ ID NO 691
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 691
gccagcagtt actcggagtg gcagaactat ggctacacc 39

<210> SEQ ID NO 692
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 692

Asn Ala Gly Val Thr Gln Thr Pro Lys Phe Arg Ile Leu Lys Ile Gly
1 5 10 15

Gln Ser Met Thr Leu Gln Cys Ala Gln Asp Met Asn His Asn Tyr Met
20 25 30

Tyr Trp Tyr Arg Gln Asp Pro Gly Met Gly Leu Lys Leu Ile Tyr Tyr
35 40 45

Ser Val Gly Ala Gly Ile Thr Asp Lys Gly Glu Val Pro Asn Gly Tyr
50 55 60

Asn Val Ser Arg Ser Thr Thr Glu Tyr Phe Pro Leu Arg Leu Glu Leu
65 70 75 80

Ala Ala Pro Ser Gln Thr Ser Val Tyr Phe Cys Ala Ser Ser Tyr Ser
85 90 95

Glu Trp Gln Asn Tyr Gly Tyr Thr Phe Gly Ser Gly Thr Arg Leu Thr
100 105 110

Val Val

<210> SEQ ID NO 693
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 693
aatgctggtg tcactcagac cccaaaattc cgcatcctga agataggaca gagcatgaca 60
ctgcagtgtg cccaggatat gaaccataac tacatgtact ggtatcgaca agacccaggc 120
atggggctga agctgattta ttattcagtt ggtgctggta tcactgataa aggagaagtc 180
ccgaatggct acaacgtctc cagatcaacc acagagtatt tcccgctcag gctggagttg 240
gctgctccct cccagacatc tgtgtacttc tgtgccagca gttactcgga gtggcagaac 300
tatggctaca ccttcggttc ggggaccagg ttaaccgttg ta 342

<210> SEQ ID NO 694
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 694

Thr Ser Asp Pro Ser Tyr Gly
1 5

<210> SEQ ID NO 695
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 695

Gln Gly Ser Tyr Asp Gln Gln
1 5

<210> SEQ ID NO 696
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 696

Ala Met Arg Glu Gly Pro Gly Asn Asn Ala Arg Leu
1 5 10

<210> SEQ ID NO 697
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 697
accagtgatc caagttatgg t 21

<210> SEQ ID NO 698
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 698
caggggtctt atgaccagca a 21

<210> SEQ ID NO 699
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 699
gcaatgagag agggccctgg taacaatgcc agactc 36

<210> SEQ ID NO 700
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 700

Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Pro Ser Tyr
            20                  25                  30

Gly Leu Phe Trp Tyr Lys Gln Pro Ser Ser Gly Glu Met Ile Phe Leu
        35                  40                  45

Ile Tyr Gln Gly Ser Tyr Asp Gln Gln Asn Ala Thr Glu Gly Arg Tyr
    50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Glu
                85                  90                  95

Gly Pro Gly Asn Asn Ala Arg Leu Met Phe Gly Asp Gly Thr Gln Leu
            100                 105                 110

Val Val Lys Pro
        115

<210> SEQ ID NO 701
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 701
gcccagaaga taactcaaac ccaaccagga atgttcgtgc aggaaaagga ggctgtgact     60
ctggactgca catatgacac cagtgatcca agttatggtc tattctggta caagcagccc    120
agcagtgggg aaatgatttt tcttatttat caggggtctt atgaccagca aaatgcaaca    180
gaaggtcgct actcattgaa tttccagaag gcaagaaaat ccgccaacct tgtcatctcc    240
gcttcacaac tgggggactc agcaatgtac ttctgtgcaa tgagagaggg ccctggtaac    300
aatgccagac tcatgtttgg agatggaact cagctggtgg tgaagccc                 348

<210> SEQ ID NO 702
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 702

Met Asn His Glu Tyr
1               5

<210> SEQ ID NO 703
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 703

Ser Met Asn Val Glu Val
1               5

<210> SEQ ID NO 704
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 704

Ala Ser Ser Leu Trp Thr Gly Gly Gly Tyr Thr
1 5 10

<210> SEQ ID NO 705
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 705
atgaaccatg agtat 15

<210> SEQ ID NO 706
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 706
tcaatgaatg ttgaggtg 18

<210> SEQ ID NO 707
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 707
gccagcagtt tatggacagg gggaggctac acc 33

<210> SEQ ID NO 708
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 708

Glu Ala Gln Val Thr Gln Thr Pro Arg Tyr Leu Ile Thr Val Thr Gly
1 5 10 15

Lys Lys Leu Thr Val Thr Cys Ser Gln Asn Met Asn His Glu Tyr Met
20 25 30

Ser Trp Tyr Arg Gln Asp Pro Gly Leu Gly Leu Arg Gln Ile Tyr Tyr
35 40 45

Ser Met Asn Val Glu Val Thr Asp Lys Gly Asp Val Pro Glu Gly Tyr
50 55 60

Lys Val Ser Arg Lys Glu Lys Arg Asn Phe Pro Leu Ile Leu Glu Ser
65 70 75 80

```
Pro Ser Pro Asn Gln Thr Ser Leu Tyr Phe Cys Ala Ser Ser Leu Trp
                85                  90                  95

Thr Gly Gly Gly Tyr Thr Phe Gly Ser Gly Thr Arg Leu Thr Val Val
            100                 105                 110


<210> SEQ ID NO 709
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 709

gaagcccaag tgacccagac cccaagatac ctcatcacag tgactggaaa gaagttaaca     60

gtgacttgtt ctcagaatat gaaccatgag tatatgtcct ggtatcgaca agacccaggg    120

ctgggcttaa ggcagatcta ctattcaatg aatgttgagg tgactgataa gggagatgtt    180

cctgaagggt acaaagtctc tcgaaaagag aagaggaatt tccccctgat cctggagtcg    240

cccagcccca accagacctc tctgtacttc tgtgccagca gtttatggac agggggaggc    300

tacaccttcg gttcggggac caggttaacc gttgta                              336


<210> SEQ ID NO 710
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 710

Val Ser Gly Leu Arg Gly
1               5


<210> SEQ ID NO 711
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 711

Leu Tyr Ser Ala Gly Glu Glu
1               5


<210> SEQ ID NO 712
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 712

Ala Val Gln Pro Leu Asn Ala Gly Asn Asn Arg Lys Leu
1               5                   10


<210> SEQ ID NO 713
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 713
gtcagcggtt taagaggg 18

<210> SEQ ID NO 714
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 714
ctgtattcag ctggggaa 18

<210> SEQ ID NO 715
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 715
gctgtgcagc cccttaatgc tggcaacaac cgtaagctg 39

<210> SEQ ID NO 716
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 716

```
Glu Asp Gln Val Thr Gln Ser Pro Glu Ala Leu Arg Leu Gln Glu Gly
1               5                   10                  15

Glu Ser Ser Ser Leu Asn Cys Ser Tyr Thr Val Ser Gly Leu Arg Gly
            20                  25                  30

Leu Phe Trp Tyr Arg Gln Asp Pro Gly Lys Gly Pro Glu Phe Leu Phe
        35                  40                  45

Thr Leu Tyr Ser Ala Gly Glu Glu Lys Glu Lys Glu Arg Leu Lys Ala
    50                  55                  60

Thr Leu Thr Lys Lys Glu Ser Phe Leu His Ile Thr Ala Pro Lys Pro
65                  70                  75                  80

Glu Asp Ser Ala Thr Tyr Leu Cys Ala Val Gln Pro Leu Asn Ala Gly
                85                  90                  95

Asn Asn Arg Lys Leu Ile Trp Gly Leu Gly Thr Ser Leu Ala Val Asn
            100                 105                 110

Pro
```

<210> SEQ ID NO 717
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 717
gaagaccagg tgacgcagag tcccgaggcc ctgagactcc aggagggaga gagtagcagt 60
ctcaactgca gttacacagt cagcggttta agagggctgt tctggtatag gcaagatcct 120
gggaaaggcc ctgaattcct cttcaccctg tattcagctg gggaagaaaa ggagaaagaa 180
aggctaaaag ccacattaac aaagaaggaa agctttctgc acatcacagc ccctaaacct 240
gaagactcag ccacttatct ctgtgctgtg cagcccctta atgctggcaa caaccgtaag 300
ctgatttggg gattgggaac aagcctggca gtaaatccg 339

<210> SEQ ID NO 718
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 718

Asp Phe Gln Ala Thr Thr
1 5

<210> SEQ ID NO 719
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 719

Ser Asn Glu Gly Ser Lys Ala
1 5

<210> SEQ ID NO 720
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 720

Ser Ala Arg Glu Trp Gly Gly Thr Glu Ala Phe
1 5 10

<210> SEQ ID NO 721
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 721
gactttcagg ccacaact 18

<210> SEQ ID NO 722
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 722
tccaatgagg gctccaaggc c 21

<210> SEQ ID NO 723

<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 723
agtgctagag aatggggtgg cactgaagct ttc 33

<210> SEQ ID NO 724
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 724

Gly Ala Val Val Ser Gln His Pro Ser Trp Val Ile Cys Lys Ser Gly
1 5 10 15

Thr Ser Val Lys Ile Glu Cys Arg Ser Leu Asp Phe Gln Ala Thr Thr
20 25 30

Met Phe Trp Tyr Arg Gln Phe Pro Lys Gln Ser Leu Met Leu Met Ala
35 40 45

Thr Ser Asn Glu Gly Ser Lys Ala Thr Tyr Glu Gln Gly Val Glu Lys
50 55 60

Asp Lys Phe Leu Ile Asn His Ala Ser Leu Thr Leu Ser Thr Leu Thr
65 70 75 80

Val Thr Ser Ala His Pro Glu Asp Ser Ser Phe Tyr Ile Cys Ser Ala
85 90 95

Arg Glu Trp Gly Gly Thr Glu Ala Phe Phe Gly Gln Gly Thr Arg Leu
100 105 110

Thr Val Val
115

<210> SEQ ID NO 725
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 725
ggtgctgtcg tctctcaaca tccgagctgg gttatctgta agagtggaac ctctgtgaag 60
atcgagtgcc gttccctgga ctttcaggcc acaactatgt tttggtatcg tcagttcccg 120
aaacagagtc tcatgctgat ggcaacttcc aatgagggct ccaaggccac atacgagcaa 180
ggcgtcgaga aggacaagtt tctcatcaac catgcaagcc tgaccttgtc cactctgaca 240
gtgaccagtg cccatcctga agacagcagc ttctacatct gcagtgctag agaatggggt 300
ggcactgaag ctttctttgg acaaggcacc agactcacag ttgta 345

<210> SEQ ID NO 726
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 726

Val Ser Gly Leu Arg Gly
1 5

<210> SEQ ID NO 727
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 727

Leu Tyr Ser Ala Gly Glu
1 5

<210> SEQ ID NO 728
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 728

Ala Val Gln Pro Ser Tyr Ser Gly Ala Gly Ser Tyr Gln Leu Thr
1 5 10 15

<210> SEQ ID NO 729
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 729
gtcagcggtt taagaggg 18

<210> SEQ ID NO 730
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 730
ctgtattcag ctggggaa 18

<210> SEQ ID NO 731
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 731
gctgtgcagc cctcatactc tggggctggg agttaccaac tcact 45

<210> SEQ ID NO 732
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 732

Glu Asp Gln Val Thr Gln Ser Pro Glu Ala Leu Arg Leu Gln Glu Gly
1 5 10 15

Glu Ser Ser Ser Leu Asn Cys Ser Tyr Thr Val Ser Gly Leu Arg Gly
20 25 30

Leu Phe Trp Tyr Arg Gln Asp Pro Gly Lys Gly Pro Glu Phe Leu Phe
35 40 45

Thr Leu Tyr Ser Ala Gly Glu Glu Lys Glu Lys Glu Arg Leu Lys Ala
50 55 60

Thr Leu Thr Lys Lys Glu Ser Phe Leu His Ile Thr Ala Pro Lys Pro
65 70 75 80

Glu Asp Ser Ala Thr Tyr Leu Cys Ala Val Gln Pro Ser Tyr Ser Gly
85 90 95

Ala Gly Ser Tyr Gln Leu Thr Phe Gly Lys Gly Thr Lys Leu Ser Val
100 105 110

Ile Pro

<210> SEQ ID NO 733
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 733
gaagaccagg tgacgcagag tcccgaggcc ctgagactcc aggagggaga gagtagcagt 60
ctcaactgca gttacacagt cagcggttta agagggctgt tctggtatag gcaagatcct 120
gggaaaggcc ctgaattcct cttcaccctg tattcagctg gggaagaaaa ggagaaagaa 180
aggctaaaag ccacattaac aaagaaggaa agctttctgc acatcacagc ccctaaacct 240
gaagactcag ccacttatct ctgtgctgtg cagccctcat actctggggc tgggagttac 300
caactcactt tcgggaaggg gaccaaactc tcggtcatac ca 342

<210> SEQ ID NO 734
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 734

Met Asn His Glu Tyr
1 5

<210> SEQ ID NO 735
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 735

Ser Met Asn Val Glu Val
1 5

<210> SEQ ID NO 736

<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 736

Ala Ser Ser Pro Gly Thr Gly Gly Phe Ser Pro Leu His
1 5 10

<210> SEQ ID NO 737
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 737
atgaaccatg agtat 15

<210> SEQ ID NO 738
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 738
tcaatgaatg ttgaggtg 18

<210> SEQ ID NO 739
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 739
gccagcagtc ccgggacagg gggattttca cccctccac 39

<210> SEQ ID NO 740
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 740

Glu Ala Gln Val Thr Gln Asn Pro Arg Tyr Leu Ile Thr Val Thr Gly
1 5 10 15

Lys Lys Leu Thr Val Thr Cys Ser Gln Asn Met Asn His Glu Tyr Met
20 25 30

Ser Trp Tyr Arg Gln Asp Pro Gly Leu Gly Leu Arg Gln Ile Tyr Tyr
35 40 45

Ser Met Asn Val Glu Val Thr Asp Lys Gly Asp Val Pro Glu Gly Tyr
50 55 60

Lys Val Ser Arg Lys Glu Lys Arg Asn Phe Pro Leu Ile Leu Glu Ser
65 70 75 80

Pro Ser Pro Asn Gln Thr Ser Leu Tyr Phe Cys Ala Ser Ser Pro Gly
85 90 95

```
Thr Gly Gly Phe Ser Pro Leu His Phe Gly Asn Gly Thr Arg Leu Thr
            100                 105                 110

Val Thr


<210> SEQ ID NO 741
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 741

gaagcccaag tgacccagaa cccaagatac ctcatcacag tgactggaaa gaagttaaca      60

gtgacttgtt ctcagaatat gaaccatgag tatatgtcct ggtatcgaca agacccaggg     120

ctgggcttaa ggcagatcta ctattcaatg aatgttgagg tgactgataa gggagatgtt     180

cctgaagggt acaaagtctc tcgaaaagag aagaggaatt tccccctgat cctggagtcg     240

cccagcccca accagacctc tctgtacttc tgtgccagca gtcccgggac agggggattt     300

tcacccctcc actttgggaa cgggaccagg ctcactgtga ca                        342


<210> SEQ ID NO 742
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 742

Val Ser Gly Leu Arg Gly
1               5


<210> SEQ ID NO 743
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 743

Leu Tyr Ser Ala Gly Glu Glu
1               5


<210> SEQ ID NO 744
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 744

Ala Val Gln Pro Ser Tyr Ser Gly Ala Gly Ser Tyr Gln Leu Thr
1               5                   10                  15


<210> SEQ ID NO 745
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 745
gtcagcggtt taagaggg 18

<210> SEQ ID NO 746
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 746
ctgtattcag ctggggaa 18

<210> SEQ ID NO 747
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 747
gctgtgcagc cctcatactc tggggctggg agttaccaac tcact 45

<210> SEQ ID NO 748
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 748

Glu Asp Gln Val Thr Gln Ser Pro Glu Ala Leu Arg Leu Gln Glu Gly
1 5 10 15

Glu Ser Ser Ser Leu Asn Cys Ser Tyr Thr Val Ser Gly Leu Arg Gly
20 25 30

Leu Phe Trp Tyr Arg Gln Asp Pro Gly Lys Gly Pro Glu Phe Leu Phe
35 40 45

Thr Leu Tyr Ser Ala Gly Glu Glu Lys Glu Lys Glu Arg Leu Lys Ala
50 55 60

Thr Leu Thr Lys Lys Glu Ser Phe Leu His Ile Thr Ala Pro Lys Pro
65 70 75 80

Glu Asp Ser Ala Thr Tyr Leu Cys Ala Val Gln Pro Ser Tyr Ser Gly
85 90 95

Ala Gly Ser Tyr Gln Leu Thr Phe Gly Lys Gly Thr Lys Leu Ser Val
100 105 110

Ile Pro

<210> SEQ ID NO 749
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 749
gaagaccagg tgacgcagag tcccgaggcc ctgagactcc aggagggaga gagtagcagt 60
ctcaactgca gttacacagt cagcggttta agagggctgt tctggtatag gcaagatcct 120

```
gggaaaggcc ctgaattcct cttcaccctg tattcagctg gggaagaaaa ggagaaagaa    180

aggctaaaag ccacattaac aaagaaggaa agctttctgc acatcacagc ccctaaacct    240

gaagactcag ccacttatct ctgtgctgtg cagccctcat actctggggc tgggagttac    300

caactcactt tcgggaaggg gaccaaactc tcggtcatac ca                      342
```

```
<210> SEQ ID NO 750
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 750

Asp Phe Gln Ala Thr Thr
1               5


<210> SEQ ID NO 751
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 751

Ser Asn Glu Gly Ser Lys Ala
1               5


<210> SEQ ID NO 752
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 752

Ser Ala Arg Glu Trp Arg Gly Thr Glu Ala Phe
1               5                   10


<210> SEQ ID NO 753
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 753

gactttcagg ccacaact                                                   18


<210> SEQ ID NO 754
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 754

tccaatgagg gctccaaggc c                                               21


<210> SEQ ID NO 755
```

<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 755
agtgctagag agtggagggg cactgaagct ttc 33

<210> SEQ ID NO 756
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 756

Gly Ala Val Val Ser Gln His Pro Ser Trp Val Ile Cys Lys Ser Gly
1 5 10 15

Thr Ser Val Lys Ile Glu Cys Arg Ser Leu Asp Phe Gln Ala Thr Thr
20 25 30

Met Phe Trp Tyr Arg Gln Phe Pro Lys Gln Ser Leu Met Leu Met Ala
35 40 45

Thr Ser Asn Glu Gly Ser Lys Ala Thr Tyr Glu Gln Gly Val Glu Lys
50 55 60

Asp Lys Phe Leu Ile Asn His Ala Ser Leu Thr Leu Ser Thr Leu Thr
65 70 75 80

Val Thr Ser Ala His Pro Glu Asp Ser Ser Phe Tyr Ile Cys Ser Ala
85 90 95

Arg Glu Trp Arg Gly Thr Glu Ala Phe Phe Gly Gln Gly Thr Arg Leu
100 105 110

Thr Val Val
115

<210> SEQ ID NO 757
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 757
ggtgctgtcg tctctcaaca tccgagctgg gttatctgta agagtggaac ctctgtgaag 60
atcgagtgcc gttccctgga ctttcaggcc acaactatgt tttggtatcg tcagttcccg 120
aaacagagtc tcatgctgat ggcaacttcc aatgagggct ccaaggccac atacgagcaa 180
ggcgtcgaga aggacaagtt tctcatcaac catgcaagcc tgaccttgtc cactctgaca 240
gtgaccagtg cccatcctga agacagcagc ttctacatct gcagtgctag agagtggagg 300
ggcactgaag ctttctttgg acaaggcacc agactcacag ttgta 345

<210> SEQ ID NO 758
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 758

Ser Val Phe Ser Ser
1 5

<210> SEQ ID NO 759
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 759

Val Val Thr Gly Gly Glu
1 5

<210> SEQ ID NO 760
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 760

Ala Glu Asp Gly Gly Ser Gln Gly Asn Leu Ile
1 5 10

<210> SEQ ID NO 761
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 761
agtgtttttt ccagc 15

<210> SEQ ID NO 762
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 762
gtagttacgg gtggagaa 18

<210> SEQ ID NO 763
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 763
gcagaagatg gaggaagcca aggaaatctc atc 33

<210> SEQ ID NO 764
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 764

```
Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Glu Asp Gly Gly Ser Gln
                85                  90                  95

Gly Asn Leu Ile Phe Gly Lys Gly Thr Lys Leu Ser Val Lys Pro
            100                 105                 110
```

<210> SEQ ID NO 765
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 765

```
acccagctgc tggagcagag tcctcagttt ctaagcatcc aagagggaga aaatctcact     60

gtgtactgca actcctcaag tgtttttcc agcttacaat ggtacagaca ggagcctggg    120

gaaggtcctg tcctcctggt gacagtagtt acgggtggag aagtgaagaa gctgaagaga    180

ctaacctttc agtttggtga tgcaagaaag gacagttctc tccacatcac tgcggcccag    240

cctggtgata caggcctcta cctctgtgca gaagatggag gaagccaagg aaatctcatc    300

tttggaaaag gcactaaact ctctgttaaa cca                                333
```

<210> SEQ ID NO 766
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 766

```
Met Asp His Glu Asn
1               5
```

<210> SEQ ID NO 767
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 767

```
Ser Tyr Asp Val Lys Met
1               5
```

<210> SEQ ID NO 768
<211> LENGTH: 12
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 768

```
Ala Ser Ser Leu Gln Gly Arg Tyr Tyr Gly Tyr Thr
1               5                   10
```

<210> SEQ ID NO 769
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 769

```
atggaccatg aaaat                                                   15
```

<210> SEQ ID NO 770
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 770

```
tcatatgatg ttaaaatg                                                18
```

<210> SEQ ID NO 771
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 771

```
gccagcagtt tacaggggag gtactatggc tacacc                            36
```

<210> SEQ ID NO 772
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 772

```
Asp Val Lys Val Thr Gln Thr Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Gln
                85                  90                  95

Gly Arg Tyr Tyr Gly Tyr Thr Phe Gly Ser Gly Thr Arg Leu Thr Val
```

100 105 110

Val

<210> SEQ ID NO 773
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 773
gatgtgaaag taacccagac ctcgagatat ctagtcaaaa ggacgggaga gaaagttttt 60
ctggaatgtg tccaggatat ggaccatgaa aatatgttct ggtatcgaca agacccaggt 120
ctggggctac ggctgatcta tttctcatat gatgttaaaa tgaaagaaaa aggagatatt 180
cctgaggggt acagtgtctc tagagagaag aaggagcgct tctccctgat tctggagtcc 240
gccagcacca accagacatc tatgtacctc tgtgccagca gtttacaggg gaggtactat 300
ggctacacct tcggttcggg gaccaggtta accgttgta 339

<210> SEQ ID NO 774
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 774

Ala Thr Gly Tyr Pro Ser
1 5

<210> SEQ ID NO 775
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 775

Ala Thr Lys Ala Asp Asp
1 5

<210> SEQ ID NO 776
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 776

Ala Leu Ser Asp Thr Arg Asp Asp Lys Ile Ile
1 5 10

<210> SEQ ID NO 777
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 777
gccacaggat acccttcc 18

<210> SEQ ID NO 778
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 778
gccacgaagg ctgatgac 18

<210> SEQ ID NO 779
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 779
gctctgagtg ataccagaga tgacaagatc atc 33

<210> SEQ ID NO 780
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 780

Gly Asn Ser Val Thr Gln Met Glu Gly Pro Val Thr Leu Ser Glu Glu
1 5 10 15

Ala Phe Leu Thr Ile Asn Cys Thr Tyr Thr Ala Thr Gly Tyr Pro Ser
20 25 30

Leu Phe Trp Tyr Val Gln Tyr Pro Gly Glu Gly Leu Gln Leu Leu Leu
35 40 45

Lys Ala Thr Lys Ala Asp Asp Lys Gly Ser Asn Lys Gly Phe Glu Ala
50 55 60

Thr Tyr Arg Lys Glu Thr Thr Ser Phe His Leu Glu Lys Gly Ser Val
65 70 75 80

Gln Val Ser Asp Ser Ala Val Tyr Phe Cys Ala Leu Ser Asp Thr Arg
85 90 95

Asp Asp Lys Ile Ile Phe Gly Lys Gly Thr Arg Leu His Ile Leu Pro
100 105 110

<210> SEQ ID NO 781
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 781

Glu Ala Gln Val Thr Gln Ser Pro Arg Tyr Leu Ile Thr Val Thr Gly
1 5 10 15

Lys Lys Leu Thr Val Thr Cys Ser Gln Asn Met Asn His Glu Tyr Met
20 25 30

Ser Trp Tyr Arg Gln Asp Pro Gly Leu Gly Leu Arg Gln Ile Tyr Tyr

```
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Pro Gly
                85                  90                  95

Thr Gly Gly Phe Ser Pro Leu His Phe Gly Asn Gly Thr Arg Leu Thr
            100                 105                 110

Val Thr


<210> SEQ ID NO 782
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 782

Met Asn His Glu Tyr
1               5


<210> SEQ ID NO 783
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 783

Ser Met Asn Val Glu Val
1               5


<210> SEQ ID NO 784
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 784

Ala Ser Ser Pro Gly Thr Gly Gly Phe Ser Pro Leu His
1               5                   10


<210> SEQ ID NO 785
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 785

atgaaccatg agtat                                                       15


<210> SEQ ID NO 786
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 786
tcaatgaatg ttgaggtg 18

<210> SEQ ID NO 787
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 787
gccagcagtc ccgggacagg gggattttca cccctccac 39

<210> SEQ ID NO 788
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 788
ggaaattcag tgacccagat ggaagggcca gtgactctct cagaagaggc cttcctgact 60
ataaactgca cgtacacagc cacaggatac ccttcccttt tctggtatgt ccaatatcct 120
ggagaaggtc tacagctcct cctgaaagcc acgaaggctg atgacaaggg aagcaacaaa 180
ggttttgaag ccacataccg taaagaaacc acttctttcc acttggagaa aggctcagtt 240
caagtgtcag actcagcggt gtacttctgt gctctgagtg ataccagaga tgacaagatc 300
atctttggaa aagggacacg acttcatatt ctcccc 336

<210> SEQ ID NO 789
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 789
gaagcccaag tgacccagag cccaagatac ctcatcacag tgactggaaa gaagttaaca 60
gtgacttgtt ctcagaatat gaaccatgag tatatgtcct ggtatcgaca agacccaggg 120
ctgggcttaa ggcagatcta ctattcaatg aatgttgagg tgactgataa gggagatgtt 180
cctgaagggt acaaagtctc tcgaaaagag aagaggaatt tccccctgat cctggagtcg 240
cccagcccca accagacctc tctgtacttc tgtgccagca gtcccgggac agggggattt 300
tcacccctcc actttgggaa cgggaccagg ctcactgtga ca 342

<210> SEQ ID NO 790
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 790

Ala Thr Gly Tyr Pro Ser
1 5

<210> SEQ ID NO 791
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 791

Ala Thr Lys Ala Asp Asp
1 5

<210> SEQ ID NO 792
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 792

Ala Leu Ser Asp Thr Arg Asp Asp Lys Thr Ile
1 5 10

<210> SEQ ID NO 793
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 793
gccacaggat acccttcc 18

<210> SEQ ID NO 794
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 794
gccacgaagg ctgatgac 18

<210> SEQ ID NO 795
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 795
gctctgagtg ataccagaga tgacaagacc atc 33

<210> SEQ ID NO 796
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 796

Gly Asn Ser Val Thr Gln Ile Glu Gly Pro Val Thr Leu Ser Glu Glu
1 5 10 15

```
Ala Phe Leu Thr Ile Asn Cys Thr Tyr Thr Ala Thr Gly Tyr Pro Ser
            20                  25                  30

Leu Phe Trp Tyr Val Gln Tyr Pro Gly Glu Gly Leu Gln Leu Leu Leu
        35                  40                  45

Lys Ala Thr Lys Ala Asp Asp Lys Gly Ser Asn Lys Gly Phe Glu Ala
    50                  55                  60

Thr Tyr Arg Lys Glu Thr Thr Ser Phe His Leu Glu Lys Gly Ser Val
65                  70                  75                  80

Gln Val Ser Asp Ser Ala Val Tyr Phe Cys Ala Leu Ser Asp Thr Arg
                85                  90                  95

Asp Asp Lys Thr Ile Phe Gly Lys Gly Thr Arg Leu His Ile Leu Pro
            100                 105                 110
```

<210> SEQ ID NO 797
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 797

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Gln
                85                  90                  95

Gly Arg Tyr Tyr Gly Tyr Thr Phe Gly Ser Gly Thr Arg Leu Thr Val
            100                 105                 110

Val
```

<210> SEQ ID NO 798
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 798

```
Met Asp His Glu Asn
1               5
```

<210> SEQ ID NO 799
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 799

```
Ser Tyr Asp Val Lys Met
```

1 5

<210> SEQ ID NO 800
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 800

Ala Ser Ser Leu Gln Gly Arg Tyr Tyr Gly Tyr Thr
1 5 10

<210> SEQ ID NO 801
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 801
atggaccatg aaaat 15

<210> SEQ ID NO 802
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 802
tcatatgatg ttaaaatg 18

<210> SEQ ID NO 803
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 803
gccagcagtt tacaggggag gtactatggc tacacc 36

<210> SEQ ID NO 804
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 804
ggaaattcag tgacccagat tgaagggcca gtgactctct cagaagaggc cttcctgact 60
ataaactgca cgtacacagc cacaggatac ccttcccttt tctggtatgt ccaatatcct 120
ggagaaggtc tacagctcct cctgaaagcc acgaaggctg atgacaaggg aagcaacaaa 180
ggttttgaag ccacataccg taaagaaacc acttctttcc acttggagaa aggctcagtt 240
caagtgtcag actcagcggt gtacttctgt gctctgagtg ataccagaga tgacaagacc 300
atctttggaa aagggacacg acttcatatt ctcccc 336

<210> SEQ ID NO 805
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 805
gatgtgaaag taacccagag ttcgagatat ctagtcaaaa ggacgggaga gaaagttttt 60
ctggaatgtg tccaggatat ggaccatgaa aatatgttct ggtatcgaca agacccaggt 120
ctggggctac ggctgatcta tttctcatat gatgttaaaa tgaaagaaaa aggagatatt 180
cctgaggggt acagtgtctc tagagagaag aaggagcgct tctccctgat tctggagtcc 240
gccagcacca accagacatc tatgtacctc tgtgccagca gtttacaggg gaggtactat 300
ggctacacct tcggttcggg gaccaggtta accgttgta 339

<210> SEQ ID NO 806
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 806

Tyr Gly Ala Thr Pro Tyr
1               5

<210> SEQ ID NO 807
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 807

Tyr Phe Ser Gly Asp Thr Leu
1               5

<210> SEQ ID NO 808
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 808

Ala Val Gly Ala Gly Ser Ala Arg Gln Leu Thr
1               5                   10

<210> SEQ ID NO 809
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 809
tatggggcaa caccttat 18

<210> SEQ ID NO 810

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 810
tacttttcag gagacactct g 21

<210> SEQ ID NO 811
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 811
gctgtgggtg ctggttctgc aaggcaactg acc 33

<210> SEQ ID NO 812
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 812

```
Ala Gln Ser Val Thr Gln Pro Asp Ile His Ile Thr Val Ser Glu Gly
1               5                   10                  15

Ala Ser Leu Glu Leu Arg Cys Asn Tyr Ser Tyr Gly Ala Thr Pro Tyr
            20                  25                  30

Leu Phe Trp Tyr Val Gln Ser Pro Gly Gln Gly Leu Gln Leu Leu Leu
        35                  40                  45

Lys Tyr Phe Ser Gly Asp Thr Leu Val Gln Gly Ile Lys Gly Phe Glu
    50                  55                  60

Ala Glu Phe Lys Arg Ser Gln Ser Ser Phe Asn Leu Arg Lys Pro Ser
65                  70                  75                  80

Val His Trp Ser Asp Ala Ala Glu Tyr Phe Cys Ala Val Gly Ala Gly
                85                  90                  95

Ser Ala Arg Gln Leu Thr Phe Gly Ser Gly Thr Gln Leu Thr Val Leu
            100                 105                 110

Pro
```

<210> SEQ ID NO 813
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 813

```
Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
```

```
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Phe Asp
                85                  90                  95

Thr Glu Ala Phe Phe Gly Gln Gly Thr Arg Leu Thr Val Val
            100                 105                 110


<210> SEQ ID NO 814
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 814

Ser Gly His Asp Thr
1               5


<210> SEQ ID NO 815
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 815

Tyr Tyr Glu Glu Glu Glu
1               5


<210> SEQ ID NO 816
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 816

Ala Ser Ser Phe Asp Thr Glu Ala Phe
1               5


<210> SEQ ID NO 817
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 817

tctgggcatg acact                                                        15


<210> SEQ ID NO 818
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 818

tattatgagg aggaagag                                                     18
```

<210> SEQ ID NO 819
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 819
gccagcagct ttgacactga agctttc 27

<210> SEQ ID NO 820
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 820
gcccagtcag tgacccagcc tgacatccac atcactgtct ctgaaggagc ctcactggag 60
ttgagatgta actattccta tggggcaaca ccttatctct tctggtatgt ccagtccccc 120
ggccaaggcc tccagctgct cctgaagtac ttttcaggag acactctggt tcaaggcatt 180
aaaggctttg aggctgaatt taagaggagt caatcttcct tcaatctgag gaaaccctct 240
gtgcattgga gtgatgctgc tgagtacttc tgtgctgtgg gtgctggttc tgcaaggcaa 300
ctgacctttg gatctgggac acaattgact gttttacct 339

<210> SEQ ID NO 821
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 821
gacgctggag tcacccaaag tcccacacac ctgatcaaaa cgagaggaca gcaagtgact 60
ctgagatgct ctcctaagtc tgggcatgac actgtgtcct ggtaccaaca ggccctgggt 120
caggggcccc agtttatctt tcagtattat gaggaggaag agagacagag aggcaacttc 180
cctgatcgat tctcaggtca ccagttccct aactatagct ctgagctgaa tgtgaacgcc 240
ttgttgctgg gggactcggc cctctatctc tgtgccagca gctttgacac tgaagctttc 300
tttggacaag gcaccagact cacagttgta 330

<210> SEQ ID NO 822
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 822

Thr Ser Asp Pro Ser Tyr Gly
1 5

<210> SEQ ID NO 823
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 823

Gln Gly Ser Tyr Asp Gln Gln
1               5

<210> SEQ ID NO 824
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 824

Ala Met Arg Glu Gly Pro Gly Ser Gly Asn Thr Gly Lys Leu Ile
1               5                   10                  15

<210> SEQ ID NO 825
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 825
accagtgatc caagttatgg t                                               21

<210> SEQ ID NO 826
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 826
caggggtctt atgaccagca a                                               21

<210> SEQ ID NO 827
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 827
gcaatgagag agggcccggg ctctggcaac acaggcaaac taatc                     45

<210> SEQ ID NO 828
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 828

Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Pro Ser Tyr
            20                  25                  30

Gly Leu Phe Trp Tyr Lys Gln Pro Ser Ser Gly Glu Met Ile Phe Leu

```
        35                  40                  45

Ile Tyr Gln Gly Ser Tyr Asp Gln Gln Asn Ala Thr Glu Gly Arg Tyr
    50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Glu
                85                  90                  95

Gly Pro Gly Ser Gly Asn Thr Gly Lys Leu Ile Phe Gly Gln Gly Thr
            100                 105                 110

Thr Leu Gln Val Lys Pro
        115


<210> SEQ ID NO 829
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 829

Asn Ala Gly Val Thr Gln Thr Pro Lys Phe Arg Ile Leu Lys Ile Gly
1               5                   10                  15

Gln Ser Met Thr Leu Gln Cys Ala Gln Asp Met Asn His Asn Tyr Met
            20                  25                  30

Tyr Trp Tyr Arg Gln Asp Pro Gly Met Gly Leu Lys Leu Ile Tyr Tyr
        35                  40                  45

Ser Val Gly Ala Gly Ile Thr Asp Lys Gly Glu Val Pro Asn Gly Tyr
    50                  55                  60

Asn Val Ser Arg Ser Thr Thr Glu Tyr Phe Pro Leu Arg Leu Glu Leu
65                  70                  75                  80

Ala Ala Pro Ser Gln Thr Ser Val Tyr Phe Cys Ala Ser Ser Tyr Ser
                85                  90                  95

Glu Trp Gln Asn Tyr Gly Tyr Thr Phe Gly Ser Gly Thr Arg Leu Thr
            100                 105                 110

Val Val


<210> SEQ ID NO 830
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 830

Met Asn His Asn Tyr
1               5


<210> SEQ ID NO 831
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 831

Ser Val Gly Ala Gly Ile
1               5
```

<210> SEQ ID NO 832
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 832

Ala Ser Ser Tyr Ser Glu Trp Gln Asn Tyr Gly Tyr Thr
1 5 10

<210> SEQ ID NO 833
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 833
atgaaccata actac 15

<210> SEQ ID NO 834
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 834
tcagttggtg ctggtatc 18

<210> SEQ ID NO 835
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 835
gccagcagtt actcggagtg gcagaactat ggctacacc 39

<210> SEQ ID NO 836
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 836
gcccagaaga taactcaaac ccaaccagga atgttcgtgc aggaaaagga ggctgtgact 60
ctggactgca catatgacac cagtgatcca agttatggtc tattctggta caagcagccc 120
agcagtgggg aaatgatttt tcttatttat caggggtctt atgaccagca aaatgcaaca 180
gaaggtcgct actcattgaa tttccagaag gcaagaaaat ccgccaacct tgtcatctcc 240
gcttcacaac tgggggactc agcaatgtac ttctgtgcaa tgagagaggg cccgggctct 300
ggcaacacag gcaaactaat ctttgggcaa gggacaactt tacaagtaaa acca 354

<210> SEQ ID NO 837
<211> LENGTH: 342

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 837
aatgctggtg tcactcagac cccaaaattc cgcatcctga agataggaca gagcatgaca 60
ctgcagtgtg cccaggatat gaaccataac tacatgtact ggtatcgaca agacccaggc 120
atggggctga agctgattta ttattcagtt ggtgctggta tcactgataa aggagaagtc 180
ccgaatggct acaacgtctc cagatcaacc acagagtatt tcccgctcag gctggagttg 240
gctgctccct cccagacatc tgtgtacttc tgtgccagca gttactcgga gtggcagaac 300
tatggctaca ccttcggttc ggggaccagg ttaaccgttg ta 342

<210> SEQ ID NO 838
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 838

Thr Ser Glu Ser Asp Tyr Tyr
1 5

<210> SEQ ID NO 839
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 839

Gln Glu Ala Tyr Lys Gln Gln
1 5

<210> SEQ ID NO 840
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 840

Ala Tyr Arg Ser Gly Ala Gly Gly Thr Ser Tyr Gly Lys Leu Thr
1 5 10 15

<210> SEQ ID NO 841
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 841
accagtgaga gtgattatta t 21

<210> SEQ ID NO 842
<211> LENGTH: 21
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 842
caagaagctt ataagcaaca g 21

<210> SEQ ID NO 843
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 843
gcttatagga gcggtgctgg tggtactagc tatggaaagc tgaca 45

<210> SEQ ID NO 844
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 844

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Tyr Arg Ser
                85                  90                  95

Gly Ala Gly Gly Thr Ser Tyr Gly Lys Leu Thr Phe Gly Gln Gly Thr
            100                 105                 110

Ile Leu Thr Val His Pro
        115

<210> SEQ ID NO 845
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 845

Asp Ala Gly Val Thr Gln Ser Pro Thr His Leu Ile Lys Thr Arg Gly
1               5                   10                  15

Gln Gln Val Thr Leu Arg Cys Ser Pro Ile Ser Gly His Lys Ser Val
            20                  25                  30

Ser Trp Tyr Gln Gln Val Leu Gly Gln Gly Pro Gln Phe Ile Phe Gln
        35                  40                  45

Tyr Tyr Glu Lys Glu Glu Arg Gly Arg Gly Asn Phe Pro Asp Arg Phe
    50                  55                  60

```
Ser Ala Arg Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Ile Arg
                85                  90                  95

Asp Thr Tyr Gly Tyr Thr Phe Gly Ser Gly Thr Arg Leu Thr Val Val
            100                 105                 110


<210> SEQ ID NO 846
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 846

Ser Gly His Lys Ser
1               5


<210> SEQ ID NO 847
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 847

Tyr Tyr Glu Lys Glu Glu
1               5


<210> SEQ ID NO 848
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 848

Ala Ser Ser Ile Arg Asp Thr Tyr Gly Tyr Thr
1               5                   10


<210> SEQ ID NO 849
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 849

tctgggcaca agagt                                                       15


<210> SEQ ID NO 850
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 850

tattatgaga aagaagag                                                    18
```

<210> SEQ ID NO 851
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 851
gccagcagca tccgggacac ctatggctac acc 33

<210> SEQ ID NO 852
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 852
gctcagacag tcactcagtc tcaaccagag atgtctgtgc aggaggcaga gaccgtgacc 60
ctgagctgca catatgacac cagtgagagt gattattatt tattctggta caagcagcct 120
cccagcaggc agatgattct cgttattcgc caagaagctt ataagcaaca gaatgcaaca 180
gagaatcgtt tctctgtgaa cttccagaaa gcagccaaat ccttcagtct caagatctca 240
gactcacagc tgggggatgc cgcgatgtat ttctgtgctt ataggagcgg tgctggtggt 300
actagctatg gaaagctgac atttggacaa gggaccatct tgactgtcca tcca 354

<210> SEQ ID NO 853
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 853
gacgctggag tcacccaaag tcccacacac ctgatcaaaa cgagaggaca gcaagtgact 60
ctgagatgct ctcctatctc tgggcacaag agtgtgtcct ggtaccaaca ggtcctgggt 120
caggggcccc agtttatctt tcagtattat gagaaagaag agagaggaag aggaaacttc 180
cctgatcgat tctcagctcg ccagttccct aactatagct ctgagctgaa tgtgaacgcc 240
ttgttgctgg gggactcggc cctgtatctc tgtgccagca gcatccggga cacctatggc 300
tacaccttcg gttcggggac caggttaacc gttgta 336

<210> SEQ ID NO 854
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 854

Ala Thr Gly Tyr Pro Ser
1 5

<210> SEQ ID NO 855
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 855

Ala Thr Lys Ala Asp Asp
1 5

<210> SEQ ID NO 856
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 856

Ala Leu Ser Asp Thr Arg Asp Asp Lys Ile Ile
1 5 10

<210> SEQ ID NO 857
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 857
gccacaggat acccttcc 18

<210> SEQ ID NO 858
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 858
gccacgaagg ctgatgac 18

<210> SEQ ID NO 859
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 859
gctctgagtg ataccagaga tgacaagatc atc 33

<210> SEQ ID NO 860
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 860

Gly Asn Ser Val Thr Gln Met Glu Gly Pro Val Thr Leu Ser Glu Glu
1 5 10 15

Ala Phe Leu Thr Ile Asn Cys Thr Tyr Thr Ala Thr Gly Tyr Pro Ser
20 25 30

Leu Phe Trp Tyr Val Gln Tyr Pro Gly Glu Gly Leu Gln Leu Leu Leu
35 40 45

```
Lys Ala Thr Lys Ala Asp Asp Lys Gly Ser Asn Lys Gly Phe Glu Ala
    50                  55                  60

Thr Tyr Arg Lys Glu Thr Thr Ser Phe His Leu Glu Lys Gly Ser Val
65                  70                  75                  80

Gln Val Ser Asp Ser Ala Val Tyr Phe Cys Ala Leu Ser Asp Thr Arg
                85                  90                  95

Asp Asp Lys Ile Ile Phe Gly Lys Gly Thr Arg Leu His Ile Leu Pro
            100                 105                 110
```

<210> SEQ ID NO 861
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 861

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Gln
                85                  90                  95

Gly Arg Tyr Tyr Gly Tyr Thr Phe Gly Ser Gly Thr Arg Leu Thr Val
            100                 105                 110

Val
```

<210> SEQ ID NO 862
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 862

```
Met Asp His Glu Asn
1               5
```

<210> SEQ ID NO 863
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 863

```
Ser Tyr Asp Val Lys Met
1               5
```

<210> SEQ ID NO 864
<211> LENGTH: 12
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 864

Ala Ser Ser Leu Gln Gly Arg Tyr Tyr Gly Tyr Thr
1 5 10

<210> SEQ ID NO 865
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 865
atggaccatg aaaat 15

<210> SEQ ID NO 866
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 866
tcatatgatg ttaaaatg 18

<210> SEQ ID NO 867
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 867
gccagcagtt tacaggggag gtactatggc tacacc 36

<210> SEQ ID NO 868
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 868
ggaaattcag tgacccagat ggaagggcca gtgactctct cagaagaggc cttcctgact 60
ataaactgca cgtacacagc cacaggatac ccttcccttt tctggtatgt ccaatatcct 120
ggagaaggtc tacagctcct cctgaaagcc acgaaggctg atgacaaggg aagcaacaaa 180
ggttttgaag ccacataccg taaagaaacc acttctttcc acttggagaa aggctcagtt 240
caagtgtcag actcagcggt gtacttctgt gctctgagtg ataccagaga tgacaagatc 300
atctttggaa aagggacacg acttcatatt ctcccc 336

<210> SEQ ID NO 869
<211> LENGTH: 339
<212> TYPE: DNA
<213> ORGANISM: Artificial Sequence -continued

```
<220> FEATURE:
<223> OTHER INFORMATION: Description of Artificial Sequence: Synthetic
      polynucleotide

<400> SEQUENCE: 869

gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgccagca gtttacaggg gaggtactat    300

ggctacacct tcggttcggg gaccaggtta accgttgta                           339


<210> SEQ ID NO 870
<211> LENGTH: 954
<212> TYPE: DNA
<213> ORGANISM: Homo sapiens

<400> SEQUENCE: 870

atgtcttctg agcagaagag tcagcactgc aagcctgagg aaggcgttga ggcccaagaa     60

gaggccctgg gcctggtggg tgcacaggct cctactactg aggagcagga ggctgctgtc    120

tcctcctcct ctcctctggt ccctggcacc ctggaggaag tgcctgctgc tgagtcagca    180

ggtcctcccc agagtcctca gggagcctct gccttaccca ctaccatcag cttcacttgc    240

tggaggcaac ccaatgaggg ttccagcagc caagaagagg aggggccaag cacctcgcct    300

gacgcagagt ccttgttccg agaagcactc agtaacaagg tggatgagtt ggctcatttt    360

ctgctccgca agtatcgagc caaggagctg gtcacaaagg cagaaatgct ggagagagtc    420

atcaaaaatt acaagcgctg ctttcctgtg atcttcggca aagcctccga gtccctgaag    480

atgatctttg gcattgacgt gaaggaagtg gaccccgcca gcaacaccta caccctgtc    540

acctgcctgg gcctttccta tgatggcctg ctgggtaata atcagatctt tcccaagaca    600

ggccttctga taatcgtcct gggcacaatt gcaatggagg gcgacagcgc ctctgaggag    660

gaaatctggg aggagctggg tgtgatgggg gtgtatgatg ggagggagca cactgtctat    720

ggggagccca ggaaactgct cacccaagat tgggtgcagg aaaactacct ggagtaccgg    780

caggtacccg gcagtaatcc tgcgcgctat gagttcctgt ggggtccaag ggctctggct    840

gaaaccagct atgtgaaagt cctggagcat gtggtcaggg tcaatgcaag agttcgcatt    900

gcctacccat ccctgcgtga agcagctttg ttagaggagg aagagggagt ctga          954


<210> SEQ ID NO 871
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 871

His His His His His His
1               5
```

MAGE-A4 T CELL RECEPTORS AND METHODS OF USE THEREOF

RELATED APPLICATIONS

This application is a 35 U.S.C. § 371 national stage filing of International Application No. PCT/US2020/038142, filed on Jun. 17, 2020, which in turn claims the benefit of priority to U.S. Provisional Application No. 62/862,726, filed on Jun. 18, 2019, and U.S. Provisional Patent Application No. 62/871,793, filed on Jul. 9, 2019. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Jun. 15, 2020, is named 118003_00320_SL.txt and is 344,832 bytes in size.

BACKGROUND

T cell receptors (TCRs) are membrane bound heterodimers comprising an α and β chain resembling an immunoglobulin variable (V) and constant (C) region. The TCR α chain includes a V-α chain covalently linked to a C-α chain, whereas the β chain includes a V-β chain covalently linked to a C-β chain. The V-α and V-β chains form a pocket or cleft that can bind an antigen in the context of a major histocompatibility complex (MHC) (known in humans as an HLA complex). (Davis *Ann. Rev. of Immunology* 3: 537 (1985); *Fundamental Immunology* 3rd Ed., W. Paul Ed. New York (1993)).

TCRs are primary effectors of the immune system that have unique advantages as a platform for developing therapeutics. While antibody therapeutics are limited to recognition of pathogens in the blood and extracellular spaces, or to protein targets on the cell surface, T cell receptors can recognize antigens displayed with MHC molecules on the surface of cells, including antigens derived from intracellular proteins. Depending on the subtype of T cells that recognize displayed antigen and become activated, TCRs can participate in controlling various immune responses. For instance, T cells are involved in regulation of the humoral immune response through induction of differentiation of B cells into antibody producing cells. In addition, activated T cells act to initiate cell-mediated immune responses. In addition, TCRs have been reported to mediate cell killing, increase B cell proliferation, and impact the development and severity of various disorders including cancer, allergies, viral infections and autoimmune disorders.

In view of the function of TCRs, antigen-specific TCRs have been evaluated for use in immunotherapy for their ability to redirect T cells to tumors expressing the antigen. TCRs will bind to a small peptide, only 8-12 amino acids in length, which are bound on the surface of a target cell by the Major Histocompatibility Complex (MHC). TCRs can therefore recognize intracellular antigens derived from cancer or viral proteins because these antigens are processed and displayed as peptides in the context of the surface MHC. Hence, TCRs can recognize additional internal cell targets not available to antibodies or therapies that cannot penetrate the cell.

However, the challenge of the industry is to engineer TCRs that lack immunogenicity when administered to a patient and have fine specificity to the particular peptide antigen of interest, without cross-reacting to other peptides on MHC or similar epitopes found in the natural protein repertoire.

MAGE-A4, or Melanoma-Associated Antigen A4, is a well-known cancer-testis antigen (CTAs) on the X chromosome. The function of MAGE-A4 is unknown, but it may be involved in cell cycle progression/regulation, transcriptional control, cell survival and/or apoptosis. For example, overexpression of MAGE-A4 has been shown to promote growth of spontaneously transformed oral keratinocytes; and inhibit growth arrest of cells in G1 (Bhan, et al. (2012) *Oncol Rep* 28(4):1496).

MAGE-A4 is abundantly expressed by many tumors of different histological types, such as head and neck squamous cell carcinoma, lung carcinoma, such as non-small cell lung carcinoma, esophageal squamous cell carcinoma, colon carcinoma, bladder cancer, mucosal and cutaneous melanomas, ovarian carcinoma, e.g., serous carcinoma, and uterine carcinoma but, in normal healthy adult tissues, MAGE-A4 expression is restricted to the testes.

The ability of MAGE-A4 antigens to elicit immune responses together with its restricted expression pattern have rendered MAGE-A4 a good candidate for cancer immunotherapy.

There is an unmet need in the art for new targeting agents based on T cell receptors that specifically bind to MAGE-A4 antigens, as well as methods for producing and using such agents in therapeutic and diagnostic settings.

SUMMARY

The present invention provides T cell receptors (TCRs) that were generated against a MAGE-A4 peptide antigen in the context of MHC (HLA-A2). The unique TCR sequences identified have shown specific binding to the small peptide MAGE-A4 presented in the groove of an HLA molecule and exhibited activation of T cells in a reporter assay. Furthermore, the TCRs of the invention do not cross-react with other "like" peptides.

Accordingly, in one aspect, the present invention provides a T cell receptor (TCR) (e.g., an isolated TCR or a TCR expressed on an isolated cell) that binds specifically to an HLA-A2 presented cancer testis antigen melanoma-associated antigen 4 (MAGE-A4) peptide comprising the amino acid sequence of KVLEHVVRV (SEQ ID NO:609) (MAGE-A4 286-294), wherein the TCR comprises an alpha chain variable domain comprising a complementary determining region (CDR)3, wherein the CDR3 comprises the amino acid sequence of Formula I:

$$N_1\text{-}N_2\text{-}N_3\text{-}N_4\text{-}N_5\text{-}N_6\text{-}N_7\text{-}N_8\text{-}N_9\text{-}N_{10}\text{-}N_{11}\text{-}N_{12}\text{-}N_{13}\text{-}N_{14}\text{-}N_{15} \quad \text{(Formula I)}$$

wherein $N_1$ is a non-polar amino acid;

$N_2$, which may or may not be present, is Val;

$N_3$ is Tyr, Gly, Leu, Val, Glu, Met, Ala, or Phe;

$N_4$, which may or may not be present, is Arg, Glu, Ser, Asn, Gln, Lys, Asp, Gly, or Met;

$N_5$, which may or may not be present, is Ser, Arg, Glu, Leu, Ala, Asp, Pro, Met, Gly or Lys;

$N_6$, which may or may not be present, is Ala, Asp, Gly, Ser, Val, Pro, Leu, Tyr, or Thr;

$N_7$ is Thr, Pro, Ser, Glu, Asp, Trp, Arg, Asn, Ile, Gln, or Leu;

$N_8$ is His, Trp, Thr, Lys, Tyr, or Ala;

$N_9$ is Asn, Gly, Lys, Ile, Ser, or Arg;

$N_{10}$, which may or may not be present, is Gln, Lys, Gly, Thr, Leu, Asp, or Ser;

$N_{11}$, which may or may not be present, is Phe, Asn, Thr, Tyr, Ala, Leu, Met or Glu;

$N_{12}$, which may or may not be present, is Lys, Phe, Tyr, or Asp;

$N_{13}$, which may or may not be present, is Lys or Gly;

$N_{14}$, which may or may not be present, is Thr, Leu, or Tyr; and $N_{15}$ is Tyr, Gln, Ile, Thr, Val, or Arg.

In one embodiment, $N_1$ is Ala, Ile, or Gly.

In another aspect, the present invention provides isolated T cell receptor (TCR) that binds specifically to an HLA-A2 presented cancer testis antigen melanoma-associated antigen 4 (MAGE-A4) peptide comprising the amino acid sequence of KVLEHVVRV (SEQ ID NO:609) (MAGE-A4 286-294), wherein the TCR comprises a beta chain variable domain comprising complementary determining region (CDR)3, wherein the CDR3 comprises the amino acid sequence of Formula II:

$$N_1\text{-}N_2\text{-}N_3\text{-}N_4\text{-}N_5\text{-}N_6\text{-}N_7\text{-}N_8\text{-}N_9\text{-}N_{10}\text{-}N_{11}\text{-}N_{12}\text{-}N_{13}\text{-}N_{14}\text{-}N_{15}\text{-}N_{16}\text{-}N_{17}\text{-}N_{18} \quad \text{(Formula II)},$$

wherein $N_1$ is Ala or Ser;

$N_2$ is Ala, Ser, or Thr;

$N_3$ is Ser, Gly, or Trp;

$N_4$ is Leu, Tyr, Trp, Asp, Phe, Gly, Pro, or His;

$N_5$, which may or may not be present, is Gly or Asp;

$N_6$, which may or may not be present, is Phe or Arg;

$N_7$, which may or may not be present, is Trp, Phe, Asp, Pro, Tyr, Gly, Thr, Ser, or Val;

$N_8$, which may or may not be present, is Pro, Arg, Asp, Tyr, Gln, Asn, or Gly;

$N_9$, which may or may not be present, is Asp;

$N_{10}$, which may or may not be present, is Arg;

$N_{11}$, which may or may not be present, is Gly, Ala, or Thr;

$N_{12}$ is Ser, Trp, Thr, Gly, Val, Leu, Arg, Met, Tyr, or Gln;

$N_{13}$, which may or may not be present, is Gly;

$N_{14}$, which may or may not be present, is Asn, Asp, Gly, Thr, Pro, Gln, or His;

$N_{15}$, which may or may not be present, is Thr, Ser, Glu, Asn, Tyr, Gln, Asp, or Pro;

$N_{16}$, which may or may not be present, is Glu, Pro, Lys, Thr, Ala, Gly, or Gln;

$N_{17}$, which may or may not be present, is Ala, Leu, Be, Tyr, or Gln; and $N_{18}$ is Phe, His, Tyr, or Thr.

In one embodiment, the alpha chain variable domain further comprises a CDR1 and a CDR2, wherein the CDR1 comprises any one of the alpha chain variable domain CDR1 amino acid sequences set forth in Table 2 and the CDR2 independently comprises any one of the alpha chain variable domain CDR2 amino acid sequences set forth in Table 2.

In another embodiment, the beta chain variable domain further comprises a CDR1 and a CDR2, wherein the CDR1 comprises any one of the beta chain variable CDR1 amino acid sequences set forth in Table 2 and the CDR2 independently comprises any one of the beta chain variable domain CDR2 amino acid sequences set forth in Table 2.

The TCR may include at least one TCR alpha chain variable domain and/or at least one beta chain variable domain; or the TCR may include a TCR alpha chain variable domain and a TCR beta chain variable domain.

In one embodiment, the TCR comprises alpha chain variable domain CDR1, CDR2 and CDR3 contained within any one of the alpha chain variable domain sequences listed in Table 4; and beta chain variable domain CDR1, CDR2 and CDR3 contained within any one of the beta chain variable domain sequences listed in Table 4.

In another embodiment, the TCR comprises an alpha chain variable domain having an amino acid sequence that has at least 85% amino acid identity to the entire amino acid sequence of any one of the amino acid sequences of the alpha chain variable domain amino acid sequences listed in Table 4.

In yet another embodiment, the TCR comprises a beta chain variable domain having an amino acid sequence that has at least 85% amino acid identity to the entire amino acid sequence of any one of the amino acid sequences of the beta chain variable domain amino acid sequences listed in Table 4.

In one embodiment, the TCR comprises (a) an alpha chain variable domain having an amino acid sequence that has at least 85% amino acid identity to the entire amino acid sequence of any one of the amino acid sequences of the alpha chain variable domain amino acid sequences listed in Table 4; and (b) a beta chain variable domain having an amino acid sequence that has at least 85% amino acid identity to the entire amino acid sequence of any one of the amino acid sequences of the beta chain variable domain amino acid sequences listed in Table 4.

In one embodiment, the TCR comprises (a) an alpha chain variable domain CDR1 domain having an amino acid sequence selected from the group consisting of SEQ ID NOs: 1, 17, 33, 49, 65, 81, 97, 113, 129, 145, 161, 177, 193, 209, 225, 241, 257, 273, 289, 305, 321, 337, 353, 369, 385, 401, 417, 433, 449, 465, 481, 497, 513, 529, 545, 561, 577, and 593; (b) an alpha chain variable domain CDR2 domain having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370, 386, 402, 418, 434, 450, 466, 482, 498 514, 530, 546, 562, 578, and 594; (c) an alpha chain variable domain CDR3 domain having an amino acid sequence selected from the group consisting of SEQ ID NOs: 3, 19, 35, 51, 67, 83, 99, 115, 131, 147, 163, 179, 195, 211, 227, 243, 259, 275, 291, 307, 323, 339, 355, 371, 387, 403, 419, 435, 451, 467, 483, 499, 515, 531, 547, 563, 579, and 595; (d) a beta chain variable domain CDR1 having an amino acid sequence selected from the group consisting of SEQ ID NOs: 9, 25, 41, 57, 73, 89, 105, 121, 137, 153, 169, 185, 201, 217, 233, 249, 265, 281, 297, 313, 329, 345, 361, 377, 393, 409, 425, 441, 457, 473, 489, 505, 521, 537, 553, 569, 585, and 601; (e) a beta chain variable domain CDR2 having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378, 394, 410, 426, 442, 458, 474, 490, 506, 522, 538, 554, 570, 586, and 602; and (f) a beta chain variable domain CDR3 having an amino acid sequence selected from the group consisting of SEQ ID NOs: 11, 27, 43, 59, 75, 91, 107, 123, 139, 155, 171, 187, 203, 219, 235, 251, 267, 283, 299, 315, 331, 347, 363, 379, 395, 411, 427, 443, 459, 475, 491, 507, 523, 539, 555, 571, 587, and 603.

In one embodiment, the TCR comprises an alpha chain variable domain/beta chain variable domain amino acid sequence pair selected from the group consisting of SEQ ID NOs:7/15, 23/31, 39/47, 55/63, 71/79, 87/95, 103/111, 119/127, 135/143, 151/159, 167/175, 183/191, 199/207, 215/223, 231/239, 247/255, 263/271, 279/287, 295/303, 311/319, 327/335, 343/351, 359/367, 375/383, 391/399, 407/

415, 423/431, 439/447, 455/463, 471/479, 487/495, 503/511, 519/527, 535/543, 551/559, 567/575, 583/591, and 599/607.

In one embodiment, the TCR comprises CDR sequences contained within an alpha chain variable domain/beta chain variable domain amino acid sequence pair selected from the group consisting of SEQ ID NOs:7/15, 23/31, 39/47, 55/63, 71/79, 87/95, 103/111, 119/127, 135/143, 151/159, 167/175, 183/191, 199/207, 215/223, 231/239, 247/255, 263/271, 279/287, 295/303, 311/319, 327/335, 343/351, 359/367, 375/383, 391/399, 407/415, 423/431, 439/447, 455/463, 471/479, 487/495, 503/511, 519/527, 535/543, 551/559, 567/575, 583/591, and 599/607.

In another embodiment, the TCR comprises an alpha chain variable domain/beta chain variable domain amino acid sequence pair selected from the group consisting of SEQ ID NOs: 87/31, 23/95, 231/607, 231/223, 231/591, 231/255, 231/271, 231/79, 231/47, 231/399, 599/239, 599/223, 599/591, 599/255, 599/271, 599/79, 599/47, 599/399, 215/239, 215/607, 215/591, 215/255, 215/271, 215/79, 215/47, 215/399, 583/239, 583/607, 583/223, 583/255, 583/271, 583/79, 583/47, 583/399, 247/239, 247/607, 247/223, 247/591, 247/271, 247/79, 247/47, 247/399, 263/239, 263/607, 263/223, 263/591, 263/255, 263/79, 263/47, 263/399, 71/239, 71/607, 71/223, 71/591, 71/255, 71/271, 71/47, 71/399, 39/239, 39/607, 39/223, 39/591, 39/255, 39/271, 39/79, 39/399, 391/239, 391/607, 391/223, 391/591, 391/255, 391/271, 391/79, 391/47, 439/127, 439/319, 439/287, 439/15, 439/111, 439/383, 439/191, 439/511, 439/527, 439/559, 439/207, 119/447, 119/319, 119/287, 119/15, 119/111, 119/383, 119/191, 119/511, 119/527, 119/559, 119/207, 311/447, 311/127, 311/287, 311/15, 311/111, 311/383, 311/191, 311/511, 311/527, 311/559, 311/207, 279/447, 279/127, 279/319, 279/15, 279/111, 279/383, 279/191, 279/511, 279/527, 279/559, 279/207, 7/447, 7/127, 7/319, 7/287, 7/111, 7/383, 7/191, 7/511, 7/527, 7/559, 7/207, 103/447, 103/127, 103/319, 103/287, 103/15, 103/383, 103/191, 103/511, 103/527, 103/559, 103/207, 375/447, 375/127, 375/319, 375/287, 375/15, 375/111, 375/191, 375/511, 375/527, 375/559, 375/207, 183/447, 183/127, 183/319, 183/287, 183/15, 183/111, 183/383, 183/511, 183/527, 183/559, 183/207, 503/447, 503/127, 503/319, 503/287, 503/15, 503/111, 503/383, 503/191, 503/527, 503/559, 503/207, 519/447, 519/127, 519/319, 519/287, 519/15, 519/111, 519/383, 519/191, 519/511, 519/559, 519/207, 551/447, 551/127, 551/319, 551/287, 551/15, 551/111, 551/383, 551/191, 551/511, 551/527, 551/207, 199/447, 199/127, 199/319, 199/287, 199/15, 199/111, 199/383, 199/191, 199/511, 199/527, and 199/559.

In another embodiment, the TCR comprises the CDR sequences contained within an alpha chain variable domain/beta chain variable domain amino acid sequence pair selected from the group consisting of SEQ ID NOs: 87/31, 23/95, 231/607, 231/223, 231/591, 231/255, 231/271, 231/79, 231/47, 231/399, 599/239, 599/223, 599/591, 599/255, 599/271, 599/79, 599/47, 599/399, 215/239, 215/607, 215/591, 215/255, 215/271, 215/79, 215/47, 215/399, 583/239, 583/607, 583/223, 583/255, 583/271, 583/79, 583/47, 583/399, 247/239, 247/607, 247/223, 247/591, 247/271, 247/79, 247/47, 247/399, 263/239, 263/607, 263/223, 263/591, 263/255, 263/79, 263/47, 263/399, 71/239, 71/607, 71/223, 71/591, 71/255, 71/271, 71/47, 71/399, 39/239, 39/607, 39/223, 39/591, 39/255, 39/271, 39/79, 39/399, 391/239, 391/607, 391/223, 391/591, 391/255, 391/271, 391/79, 391/47, 439/127, 439/319, 439/287, 439/15, 439/111, 439/383, 439/191, 439/511, 439/527, 439/559, 439/207, 119/447, 119/319, 119/287, 119/15, 119/111, 119/383, 119/191, 119/511, 119/527, 119/559, 119/207, 311/447, 311/127, 311/287, 311/15, 311/111, 311/383, 311/191, 311/511, 311/527, 311/559, 311/207, 279/447, 279/127, 279/319, 279/15, 279/111, 279/383, 279/191, 279/511, 279/527, 279/559, 279/207, 7/447, 7/127, 7/319, 7/287, 7/111, 7/383, 7/191, 7/511, 7/527, 7/559, 7/207, 103/447, 103/127, 103/319, 103/287, 103/15, 103/383, 103/191, 103/511, 103/527, 103/559, 103/207, 375/447, 375/127, 375/319, 375/287, 375/15, 375/111, 375/191, 375/511, 375/527, 375/559, 375/207, 183/447, 183/127, 183/319, 183/287, 183/15, 183/111, 183/383, 183/511, 183/527, 183/559, 183/207, 503/447, 503/127, 503/319, 503/287, 503/15, 503/111, 503/383, 503/191, 503/527, 503/559, 503/207, 519/447, 519/127, 519/319, 519/287, 519/15, 519/111, 519/383, 519/191, 519/511, 519/559, 519/207, 551/447, 551/127, 551/319, 551/287, 551/15, 551/111, 551/383, 551/191, 551/511, 551/527, 551/207, 199/447, 199/127, 199/319, 199/287, 199/15, 199/111, 199/383, 199/191, 199/511, 199/527, and 199/559.

In some embodiments, the present invention provides a TCR comprising the CDRs contained within an alpha chain variable domain/beta chain variable domain amino acid sequence pair selected from the group consisting of SEQ ID NOs: 668/676, 103/111, 439/447, and 503/511. In some embodiments, a TCR of the present disclosure comprises alpha chain variable domain complementarity determining regions (CDRs) CDR1, CDR2, and CDR3, and beta chain variable domain CDRs CDR1, CDR2, and CDR3 comprising the respective amino acid sequences of: a) SEQ ID NOs: 662, 663, 664, 670, 671, and 672; b) SEQ ID NOs: 97, 98, 99, 105, 106, and 107; c) SEQ ID NOs: 433, 434, 435, 441, 442, and 443; and d) SEQ ID NOs: 497, 498, 499, 505, 506, and 507.

The present invention also provides a TCR (e.g., an isolated TCR or a TCR expressed on an isolated cell) that compete for binding to any one or more of the TCRs of the invention.

In some embodiment, the TCRs of the invention further comprise a detectable moiety.

The present invention further provides pharmaceutical compositions comprising any of the TCRs of the invention, and a pharmaceutically acceptable carrier or diluent; as well as isolated cells presenting any of the TCRs of the invention.

In one aspect, the present invention provides isolated polynucleotide molecules comprising a polynucleotide sequence that encodes an alpha chain variable domain of any of the TCRs of the invention.

In another aspect, the present invention provides isolated polynucleotide molecules comprising a polynucleotide sequence that encodes a beta chain variable domain of any of the TCRs of the invention.

The present invention also provides vectors comprising the polynucleotide molecule of the invention; cells expressing the vectors of the invention.

In one aspect, the present invention provides a method of treating a subject having a MAGE-A4-associated disease or disorder. The methods include administering to the subject a therapeutically effective amount of a TCR (e.g., an isolated TCR or a TCR expressed on an isolated cell), pharmaceutical composition, or a plurality of the cells of the invention, thereby treating the subject.

In one embodiment, the MAGE-A4-associated disease or disorder is MAGE-A4-associated cancer.

In one embodiment, the MAGE-A4-associated cancer is a liposarcoma, a neuroblastoma, a myeloma, a melanoma, a metastatic melanoma, a synovial sarcoma, a bladder cancer, an esophageal cancer, an esophageal squamous cell carcinoma, a hepatocellular cancer, a head and neck cancer, a non-small cell lung cancer, an ovarian cancer, an ovarian epithelial cancer, a prostate cancer, a breast cancer, an astrocytic tumor, a glioblastoma multiforme, an anaplastic astrocytoma, a brain tumor, a fallopian tube cancer, primary peritoneal cavity cancer, advanced solid tumors, soft tissue sarcoma, a sarcoma, a myelodysplastic syndrome, an acute myeloid leukemia, a Hodgkin lymphoma, a non-Hodgkin lymphoma, a Hodgkin disease, a multiple myeloma, a metastatic solid tumors, a colorectal carcinoma, a stomach cancer, a gastric cancer, a rhabdomyosarcoma, a myxoid round cell liposarcoma, or a recurrent non-small cell lung cancer.

In some embodiments of the invention, a TCR (e.g., an isolated TCR or a TCR expressed on an isolated cell), pharmaceutical composition, or a plurality of the cells of the invention is administered to the subject in combination with a second therapeutic agent.

The TCR, the pharmaceutical composition, or the plurality of cells may be administered subcutaneously, intravenously, intradermally, intraperitoneally, orally, intramuscularly or intracranially to the subject.

In one aspect, the present invention provides an isolated nucleic acid molecule encoding a T cell receptor (TCR), wherein the TCR binds specifically to an HLA-A2 presented cancer testis antigen melanoma-associated antigen 4 (MAGE-A4) peptide comprising the amino acid sequence of KVLEHVVRV (SEQ ID NO:609) (MAGE-A4 286-294), wherein the TCR has a property selected from the group consisting of: (a) does not bind to cells expressing predicted off-target peptides as determined by luminescence assay; (b) activates a T cell response about two times greater than a patient-derived MAGE-A4-specific TCR as determined by a TCR-mediated T cell signaling luminescent bioassay; and (c) activates a T cell response about two times greater than an affinity-matured (e.g., by phage display) MAGE-A4-specific TCR as determined by a TCR-mediated T cell signaling luminescent bioassay.

In one embodiment, the isolated nucleic acid molecule encodes at least one TCR alpha chain variable domain and/or at least one beta chain variable domain.

In one embodiment, the TCR comprises alpha chain variable domain complementary determining regions (CDR) 1, CDR2, and CDR3 contained within any one of the alpha chain variable domain sequences listed in Table 4; and beta chain variable domain CDR1, CDR2 and CDR3 contained within any one of the beta chain variable domain sequences listed in Table 4.

In another embodiment, the TCR (e.g., isolated TCR or TCR expressed on an isolated cell) comprises alpha chain variable domain having an amino acid sequence that has at least 85% amino acid identity to the entire amino acid sequence of any one of the amino acid sequences of the alpha chain variable domain amino acid sequences listed in Table 4.

In yet another embodiment, the TCR comprises beta chain variable domain having an amino acid sequence that has at least 85% amino acid identity to the entire amino acid sequence of any one of the amino acid sequences of the beta chain variable domain amino acid sequences listed in Table 4.

In one embodiment, the TCR comprises (a) an alpha chain variable domain having an amino acid sequence that has at least 85% amino acid identity to the entire amino acid sequence of any one of the amino acid sequences of the alpha chain variable domain amino acid sequences listed in Table 4; and (b) a beta chain variable domain having an amino acid sequence that has at least 85% amino acid identity to the entire amino acid sequence of any one of the amino acid sequences of the beta chain variable domain amino acid sequences listed in Table 4.

In one embodiment, the isolated antigen-binding protein comprises (a) an alpha chain variable domain CDR1 domain having an amino acid sequence selected from the group consisting of SEQ ID NOs: 1, 17, 33, 49, 65, 81, 97, 113, 129, 145, 161, 177, 193, 209, 225, 241, 257, 273, 289, 305, 321, 337, 353, 369, 385, 401, 417, 433, 449, 465, 481, 497, 513, 529, 545, 561, 577, and 593; (b) an alpha chain variable domain CDR2 domain having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370, 386, 402, 418, 434, 450, 466, 482, 498 514, 530, 546, 562, 578, and 594; (c) an alpha chain variable domain CDR3 domain having an amino acid sequence selected from the group consisting of SEQ ID NOs: 3, 19, 35, 51, 67, 83, 99, 115, 131, 147, 163, 179, 195, 211, 227, 243, 259, 275, 291, 307, 323, 339, 355, 371, 387, 403, 419, 435, 451, 467, 483, 499, 515, 531, 547, 563, 579, and 595; (d) a beta chain variable domain CDR1 having an amino acid sequence selected from the group consisting of SEQ ID NOs: 9, 25, 41, 57, 73, 89, 105, 121, 137, 153, 169, 185, 201, 217, 233, 249, 265, 281, 297, 313, 329, 345, 361, 377, 393, 409, 425, 441, 457, 473, 489, 505, 521, 537, 553, 569, 585, and 601; (e) a beta chain variable domain CDR2 having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378, 394, 410, 426, 442, 458, 474, 490, 506, 522, 538, 554, 570, 586, and 602; and (f) a beta chain variable domain CDR3 having an amino acid sequence selected from the group consisting of SEQ ID NOs: 11, 27, 43, 59, 75, 91, 107, 123, 139, 155, 171, 187, 203, 219, 235, 251, 267, 283, 299, 315, 331, 347, 363, 379, 395, 411, 427, 443, 459, 475, 491, 507, 523, 539, 555, 571, 587, and 603.

In one embodiment, the TCR comprises an alpha chain variable domain/beta chain variable domain amino acid sequence pair selected from the group consisting of SEQ ID NOs: 7/15, 23/31, 39/47, 55/63, 71/79, 87/95, 103/111, 119/127, 135/143, 151/159, 167/175, 183/191, 199/207, 215/223, 231/239, 247/255, 263/271, 279/287, 295/303, 311/319, 327/335, 343/351, 359/367, 375/383, 391/399, 407/415, 423/431, 439/447, 455/463, 471/479, 487/495, 503/511, 519/527, 535/543, 551/559, 567/575, 583/591, and 599/607.

In another embodiment, the TCR comprises an alpha chain variable domain/beta chain variable domain amino acid sequence pair selected from the group consisting of SEQ ID NOs: 87/31, 23/95, 231/607, 231/223, 231/591, 231/255, 231/271, 231/79, 231/47, 231/399, 599/239, 599/223, 599/591, 599/255, 599/271, 599/79, 599/47, 599/399, 215/239, 215/607, 215/591, 215/255, 215/271, 215/79, 215/47, 215/399, 583/239, 583/607, 583/223, 583/255, 583/271, 583/79, 583/47, 583/399, 247/239, 247/607, 247/223, 247/591, 247/271, 247/79, 247/47, 247/399, 263/239, 263/607, 263/223, 263/591, 263/255, 263/79, 263/47, 263/399, 71/239, 71/607, 71/223, 71/591, 71/255, 71/271, 71/47, 71/399, 39/239, 39/607, 39/223, 39/591, 39/255, 39/271, 39/79, 39/399, 391/239, 391/607, 391/223, 391/591, 391/255, 391/271, 391/79, 391/47, 439/127, 439/319, 439/287, 439/15, 439/111, 439/383, 439/191, 439/511, 439/527, 439/559, 439/207, 119/447, 119/319, 119/287, 119/15, 119/111, 119/383, 119/191, 119/511, 119/527, 119/559, 119/207, 311/447, 311/127, 311/287, 311/15, 311/111, 311/383, 311/191, 311/511, 311/527, 311/559, 311/207, 279/447, 279/127, 279/319, 279/15, 279/111, 279/383, 279/191, 279/511, 279/527, 279/559, 279/207, 7/447, 7/127, 7/319, 7/287, 7/111, 7/383, 7/191, 7/511, 7/527, 7/559, 7/207, 103/447, 103/127, 103/319, 103/287, 103/15, 103/383, 103/191, 103/511, 103/527, 103/559, 103/207, 375/447, 375/127, 375/319, 375/287, 375/15, 375/111, 375/191, 375/511, 375/527, 375/559, 375/207, 183/447, 183/127, 183/319, 183/287, 183/15, 183/111, 183/383, 183/511, 183/527, 183/559, 183/207, 503/447, 503/127, 503/319, 503/287, 503/15, 503/111, 503/383, 503/191, 503/527, 503/559, 503/207, 519/447, 519/127, 519/319, 519/287, 519/15, 519/111, 519/383, 519/191, 519/511, 510/559, 519/207, 551/447, 551/127, 551/319, 551/287, 551/15, 551/111, 551/383, 551/191, 551/511, 551/527, 551/207, 199/447, 199/127, 199/319, 199/287, 199/15, 199/111, 199/383, 199/191, 199/511, 199/527, and 199/559.

In one embodiment, the isolated antigen-binding protein comprises (a) an alpha chain variable domain CDR1 encoded by a nucleic acid sequence selected from the group consisting of SEQ ID NOs: 4, 20, 36, 52, 68, 84, 100, 116, 132, 148, 164, 180, 196, 212, 228, 244, 260, 276, 292, 308, 324, 340, 356, 372, 388, 404, 420, 436, 452, 468, 484, 500, 516, 532, 548, 564, 580, and 596; (b) an alpha chain variable domain CDR2 encoded by a nucleic acid sequence selected from the group consisting of SEQ ID NOs: 5, 21, 37, 53, 69, 85, 101, 117, 133, 149, 165, 181, 197, 213, 229, 245, 261, 277, 293, 309, 325, 341, 357, 373, 389, 405, 421, 437, 453, 469, 485, 501, 517, 533, 549, 565, 581, and 597; (c) an alpha chain variable domain CDR3 encoded by a nucleic acid sequence selected from the group consisting of SEQ ID NOs: 6, 22, 38, 54, 70, 86 102, 118, 134, 150, 166, 182, 198, 214, 230, 246, 262, 278, 294, 310, 326, 342, 358, 374, 390, 406, 422, 438, 454, 470, 486, 502, 518, 534, 550, 566, 582, and 598; (d) a beta chain variable domain CDR1 encoded by a nucleic acid sequence selected from the group consisting of SEQ ID NOs: 12, 28, 44, 60, 76, 92, 108, 124, 140, 156, 172, 188, 204, 220, 236, 252, 268, 284, 300, 316, 332, 348, 364, 380, 396, 412, 428, 444, 460, 476, 492, 508, 524, 540, 556, 572, 588, and 604; (e) a beta chain variable domain CDR2 encoded by a nucleic acid sequence selected from the group consisting of SEQ ID NOs: 13, 29, 45, 61, 77, 93, 109, 125, 141, 157, 173, 189, 205, 221, 237, 253, 269, 285, 301, 317, 333, 349, 365, 381, 397, 413, 429 445 461 477, 493, 509, 525, 541, 557, 573, 589, and 605; and (f) a beta chain variable domain CDR3 encoded by a nucleic acid sequence selected from the group consisting of SEQ ID NOs: 14, 30, 46, 62, 78, 94, 110, 126, 142, 158, 174, 190, 206, 222, 238, 254, 270, 286, 302, 318, 334, 350, 366, 382, 398, 414, 430, 446, 462, 478, 494, 510, 526, 542, 558, 574, 590, and 606.

In one embodiment, the TCR comprises an alpha chain variable domain/beta chain variable domain nucleic acid sequence pair selected from the group consisting of SEQ ID NOs: 8/16, 24/32, 40/48, 56/64, 72/80, 88/96, 104/112, 120/128, 136/144, 152/160, 168/176, 184/192, 200/208, 216/224, 232/240, 248/256, 264/272, 280/288, 296/304, 312/320, 328/336, 344/352, 360/368, 376/384, 392/400, 408/416, 424/432, 440/448, 456/464, 472/480, 488/496, 504/512, 520/528, 536/544, 552/560, 568/576, 584/592, 600/608.

The present invention also provides vectors comprising an isolated nucleic acid molecule of the invention and isolated cells comprising a vector of the invention.

In one aspect, the present invention provides a method of treating a subject having a MAGE-A4-associated disease or disorder, comprising administering to the subject a plurality of the cells as described herein, thereby treating the subject.

In one embodiment, the MAGE-A4-associated disease or disorder is MAGE-A4-associated cancer.

In one embodiment, the MAGE-A4-associated cancer is a liposarcoma, a neuroblastoma, a myeloma, a melanoma, a metastatic melanoma, a synovial sarcoma, a bladder cancer, an esophageal cancer, an esophageal squamous cell carcinoma, a hepatocellular cancer, a head and neck cancer, a non-small cell lung cancer, an ovarian cancer, an ovarian epithelial cancer, a prostate cancer, a breast cancer, an astrocytic tumor, a glioblastoma multiforme, an anaplastic astrocytoma, a brain tumor, a fallopian tube cancer, primary peritoneal cavity cancer, advanced solid tumors, soft tissue sarcoma, a sarcoma, a myelodysplastic syndrome, an acute myeloid leukemia, a Hodgkin lymphoma, a non-Hodgkin lymphoma, a Hodgkin disease, a multiple myeloma, a metastatic solid tumors, a colorectal carcinoma, a stomach cancer, a gastric cancer, a rhabdomyosarcoma, a myxoid round cell liposarcoma, or a recurrent non-small cell lung cancer.

In one embodiment, a plurality of cells is administered to the subject in combination with a second therapeutic agent.

In one aspect, the present invention provides a T cell receptor (TCR) (e.g., an isolated TCR or a TCR expressed on an isolated cell) that binds specifically to an HLA-A2 presented cancer testis antigen melanoma-associated antigen 4 (MAGE-A4) peptide comprising the amino acid sequence of KVLEHVVRV (SEQ ID NO:609) (MAGE-A4 286-294), wherein the TCR has a property selected from the group consisting of (a) does not bind to cells expressing predicted off-target peptides as determined by luminescence assay; (b) activates a T cell response having a signal to noise ratio greater than or equal to a patient-derived MAGE-A4-specific TCR as determined by a TCR-mediated T cell signaling luminescent bioassay; and (c) activates a T cell response about two times greater than an affinity-matured (e.g., by phage display) MAGE-A4-specific TCR as determined by a TCR-mediated T cell signaling luminescent bioassay.

In some embodiments, the TCR activates a T cell response about two times greater, or about three times greater, or about four times greater than a patient-derived MAGE-A4-specific TCR as determined by a TCR-mediated T cell signaling luminescent bioassay. In some embodiments, the TCR activates a T cell response about two times greater, or about three times greater, or about four times greater than an affinity-matured (e.g., by phage display) MAGE-A4-specific TCR as determined by a TCR-mediated T cell signaling luminescent bioassay In one aspect, the present disclosure provides a T cell receptor (TCR) (e.g., an isolated TCR or a TCR expressed on an isolated cell) that binds specifically to an HLA-A2 presented cancer testis antigen melanoma-associated antigen 4 (MAGE-A4) peptide comprising the amino acid sequence of GVYDGREHTV (SEQ ID NO:612) (MAGE-A4 230-239), wherein the TCR comprises a complementary determining region 3 (CDR3) contained with an alpha chain variable domain of any one of SEQ ID NOs: 620, 636, 652, 668, 684, 700, 716, 732, 748, 764, 780, 796, 812, 828, 844, and 860.

In one aspect, the present disclosure provides a T cell receptor (TCR) (e.g., an isolated TCR or a TCR expressed on an isolated cell) that binds specifically to an HLA-A2 presented cancer testis antigen melanoma-associated antigen 4 (MAGE-A4) peptide comprising the amino acid sequence of GVYDGREHTV (SEQ ID NO:612) (MAGE-A4 230-239), wherein the TCR comprises a complementary determining region 3 (CDR3) contained within a beta chain variable domain of any one of SEQ ID NOs: 628, 644, 660, 676, 692, 708, 724, 740, 756, 772, 788, 804, 820, 836, 852, and 868.

In some embodiments, the alpha chain variable domain further comprises a CDR1 and a CDR2, wherein the CDR1 comprises any one of the alpha chain variable domain CDR1 amino acid sequences set forth in Table 6 and the CDR2 independently comprises any one of the alpha chain variable domain CDR2 amino acid sequences set forth in Table 6. In some embodiments, the beta chain variable domain further comprises a CDR1 and a CDR2, wherein the CDR1 comprises any one of the beta chain variable CDR1 amino acid sequences set forth in Table 6 and the CDR2 independently comprises any one of the beta chain variable domain CDR2 amino acid sequences set forth in Table 6. In some embodiments, the TCR comprises at least one TCR alpha chain variable domain and/or at least one beta chain variable domain. In some embodiments, the TCR comprises a TCR alpha chain variable domain and a TCR beta chain variable domain.

In some embodiments, the TCR comprises alpha chain variable domain CDR1, CDR2 and CDR3 contained within any one of the alpha chain variable domain sequences listed in Table 8; and beta chain variable domain CDR1, CDR2 and CDR3 contained within any one of the beta chain variable domain sequences listed in Table 8. In some embodiments, the TCR comprises an alpha chain variable domain having an amino acid sequence that has at least 85% amino acid identity to the entire amino acid sequence of any one of the amino acid sequences of the alpha chain variable domain amino acid sequences listed in Table 8. In some embodiments, the TCR comprises a beta chain variable domain having an amino acid sequence that has at least 85% amino acid identity to the entire amino acid sequence of any one of the amino acid sequences of the beta chain variable domain amino acid sequences listed in Table 8. In some embodiments, the TCR comprises: (a) an alpha chain variable domain having an amino acid sequence that has at least 85% amino acid identity to the entire amino acid sequence of any one of the amino acid sequences of the alpha chain variable domain amino acid sequences listed in Table 8; and (b) a beta chain variable domain having an amino acid sequence that has at least 85% amino acid identity to the entire amino acid sequence of any one of the amino acid sequences of the beta chain variable domain amino acid sequences listed in Table 8.

In some embodiments, the TCR comprises: (a) an alpha chain variable domain CDR1 domain having an amino acid sequence selected from the group consisting of SEQ ID NOs: 614, 630, 646, 662, 678, 694, 710, 726, 742, 758, 774, 790, 806, 822, 838, and 854; (b) an alpha chain variable domain CDR2 domain having an amino acid sequence selected from the group consisting of SEQ ID NOs: 615, 631, 647, 663, 679, 695, 711, 727, 743, 759, 775, 791, 807, 823, 839, and 855; (c) an alpha chain variable domain CDR3 domain having an amino acid sequence selected from the group consisting of SEQ ID NOs: 616, 632, 648, 664, 680, 696, 712, 728, 744, 760, 776, 792, 808, 824, 840, and 856; (d) a beta chain variable domain CDR1 having an amino acid sequence selected from the group consisting of SEQ ID NOs: 622, 638, 654, 670, 686, 702, 718, 734, 750, 766, 782, 798, 814, 830, 846, and 862; (e) a beta chain variable domain CDR2 having an amino acid sequence selected from the group consisting of SEQ ID NOs: 623, 639, 655, 671, 687, 703, 719, 735, 751, 767, 783, 799, 815, 831, 847, and 863; and (f) a beta chain variable domain CDR3 having an amino acid sequence selected from the group consisting of SEQ ID NOs: 624, 640, 656, 672, 688, 704, 720, 736, 752, 768, 784, 800, 816, 832, 848, and 864.

In some embodiments, the TCR comprises an alpha chain variable domain/beta chain variable domain amino acid sequence pair selected from the group consisting of SEQ ID NOs: 620/628, 636/644, 652/660, 668/676, 684/692, 700/708, 716/724, 732/740, 748/756, 764/772, 780/788, 796/804, 812/820, 828/836, 844/852, and 860/868. In some embodiments, the TCR comprises an alpha chain variable domain/beta chain variable domain amino acid sequence pair selected from the group consisting of SEQ ID NOs: 620/628, 620/644, 620/660, 620/676, 620/692, 620/708, 620/724, 620/740, 620/756, 620/772, 620/788, 620/804, 620/820, 620/836, 620/852, 620/868, 636/628, 636/644, 636/660, 636/676, 636/692, 636/708, 636/724, 636/740, 636/756, 636/772, 636/788, 636/804, 636/820, 636/836, 636/852, 636/868, 652/628, 652/644, 652/660, 652/676, 652/692, 652/708, 652/724, 652/740, 652/756, 652/772, 652/788, 652/804, 652/820, 652/836 652/852, 652/868, 668/628, 668/644, 668/660, 668/676, 668/692, 668/708, 668/724, 668/740, 668/756, 668/772, 668/788, 668/804, 668/820, 668/836, 668/852, 668/868, 684/628, 684/644, 684/660, 684/676, 684/692, 684/708, 684/724, 684/740, 684/756, 684/772, 684/788, 684/804, 684/820, 684/836, 684/852, 684/868, 700/628, 700/644, 700/660, 700/676, 700/692, 700/708, 700/724, 700/740, 700/756, 700/772, 700/788, 700/804, 700/820, 700/836, 700/852, 700/868, 716/628, 716/644, 716/660, 716//676, 716/692, 716/708, 716/724, 716/740, 716/756, 716/772, 716/788, 716/804, 716/820, 716/836, 716/852, 716/868, 732/628, 732/644, 732/660, 732/676, 732/692, 732/708, 732/724, 732/740, 732/756, 732/772, 732/788, 732/804, 732/820, 732/836, 732/852, 732/868, 748/628, 748/644, 748/660, 748/676, 748/692, 748/708, 748/724, 748/740, 748/756, 748/772, 748/788, 748/804, 748/820, 748/836, 748/852, 748/868, 764/628, 764/644, 764/660, 764/676, 764/692, 764/708, 764/724, 764/740, 764/756, 764/772, 764/788, 764/804, 764/820, 764/836, 764/852, 764/868, 780/628, 780/644, 780/660, 780/676, 780/692, 780/708, 780/724, 780/740, 780/756, 780/772, 780/788, 780/804, 780/820, 780/836, 780/852, 780/868, 796/628, 796/644, 796/660, 796/676, 796/692, 796/708, 796/724, 796/740, 796/756, 796/772, 796/788, 796/804, 796/820, 796/836, 796/852, 796/868, 812/628, 812/644, 812/660, 812/676, 812/692, 812/708, 812/724, 812/740, 812/756, 812/772, 812/788, 812/804, 812/820, 812/836, 812/852, 812/868, 828/628, 828/644, 828/660, 828/676, 828/692, 828/708, 828/724, 828/740, 828/756, 828/772, 828/788, 828/804, 828/820, 828/836, 828/852, 828/868, 844/628, 844/644, 844/660, 844/676, 844/692, 844/708, 844/724, 844/740, 844/756, 844/772, 844/788, 844/804, 844/820, 844/836, 844/852, 844/868, 860/628, 860/644, 860/660, 860/676, 860/692, 860/708, 860/724, 860/740, 860/756, 860/772, 860/788, 860/804, 860/820, 860/836, 860/852, and 860/868.

In some embodiments, the TCR comprises a detectable moiety. In some embodiments, the TCR has an on-target binding/off-target binding value of greater than 2.5, greater than 3, greater than 3.5, greater than 4, greater than 4.5, greater than 5, greater than 10, greater than 15, greater than 20, greater than 50, greater than 100, greater than 200, greater than 300, greater than 400, greater than 500, greater than 600, greater than 700, greater than 800, greater than 900, or greater than 1000. In some embodiments, the TCR has an on-target binding/off-target binding value of greater than 10. In some embodiments, the TCR has an on-target binding/off-target binding value of greater than 500. In some embodiments, the TCR competes for binding to a TCR (e.g., an isolated TCR or a TCR expressed on an isolated cell) as described herein.

In one aspect, the present disclosure provides a pharmaceutical composition comprising a TCR (e.g., an isolated TCR or a TCR expressed on an isolated cell) as described herein and a pharmaceutically acceptable carrier or diluent. In one aspect, the present disclosure provides an isolated cell presenting a TCR as described herein. In one aspect, the present disclosure provides an isolated polynucleic acid comprising a polynucleotide sequence that encodes an alpha chain variable domain of a TCR (e.g., an isolated TCR or a TCR expressed on an isolated cell) as described herein. In one aspect, the present disclosure provides an isolated polynucleic acid comprising a polynucleotide sequence that encodes a beta chain variable domain of a TCR (e.g., an isolated TCR or a TCR expressed on an isolated cell) as described herein. In one aspect, the present disclosure provides a vector comprising a polynucleotide sequence as described herein. In one aspect, the present disclosure provides an isolated cell expressing that vector.

In one aspect, the present disclosure provides a method of treating a subject having a MAGE-A4-associated disease or disorder, comprising administering to the subject a therapeutically effective amount of a TCR (e.g., an isolated TCR or a TCR expressed on an isolated cell) as described herein, a pharmaceutical composition as described herein, or an isolated cell as described herein, thereby treating the subject. In some embodiments, the MAGE-A4-associated disease or disorder is MAGE-A4-associated cancer. In some embodiments, the MAGE-A4-associated cancer is a liposarcoma, a neuroblastoma, a myeloma, a melanoma, a metastatic melanoma, a synovial sarcoma, a bladder cancer, an esophageal cancer, an esophageal squamous cell carcinoma, a hepatocellular cancer, a head and neck cancer, a non-small cell lung cancer, an ovarian cancer, an ovarian epithelial cancer, a prostate cancer, a breast cancer, an astrocytic tumor, a glioblastoma multiforme, an anaplastic astrocytoma, a brain tumor, a fallopian tube cancer, primary peritoneal cavity cancer, advanced solid tumors, soft tissue sarcoma, a sarcoma, a myelodysplastic syndrome, an acute myeloid leukemia, a Hodgkin lymphoma, a non-Hodgkin lymphoma, a Hodgkin disease, a multiple myeloma, a metastatic solid tumors, a colorectal carcinoma, a stomach cancer, a gastric cancer, a rhabdomyosarcoma, a myxoid round cell liposarcoma, or a recurrent non-small cell lung cancer. In some embodiments, the TCR, the pharmaceutical composition, or the cell is administered to the subject in combination with a second therapeutic agent. In some embodiments, the administering is parenteral.

In one aspect, the present disclosure provides an isolated nucleic acid molecule encoding a T cell receptor (TCR), wherein the TCR binds specifically to an HLA-A2 presented cancer testis antigen melanoma-associated antigen 4 (MAGE-A4) peptide comprising the amino acid sequence of GVYDGREHTV (SEQ ID NO:612) (MAGE-A4 230-239), wherein the TCR has a property selected from the group consisting of: (a) does not bind to cells expressing predicted off-target peptides as determined by a luminescence assay; (b) does not bind to cells expressing predicted off-target peptides as determined by a flow cytometry assay; (c) activates a T cell response about two times greater than a patient-derived MAGE-A4-specific TCR as determined by a TCR-mediated T cell signaling luminescent bioassay; and (d) activates a T cell response about two times greater than an affinity-matured (e.g., by phage display) MAGE-A4-specific TCR as determined by a TCR-mediated T cell signaling luminescent bioassay. In some embodiments, the isolated nucleic acid molecule encodes at least one TCR alpha chain variable domain and/or at least one beta chain variable domain.

In some embodiments, the TCR comprises alpha chain variable domain complementary determining regions (CDR) 1, CDR2, and CDR3 contained within any one of the alpha chain variable domain sequences listed in Table 8; and beta chain variable domain CDR1, CDR2 and CDR3 contained within any one of the beta chain variable domain sequences listed in Table 8. In some embodiments, the TCR comprises alpha chain variable domain having an amino acid sequence that has at least 85% amino acid identity to the entire amino acid sequence of any one of the amino acid sequences of the alpha chain variable domain amino acid sequences listed in Table 8. In some embodiments, the TCR comprises a beta chain variable domain having an amino acid sequence that has at least 85% amino acid identity to the entire amino acid sequence of any one of the amino acid sequences of the beta chain variable domain amino acid sequences listed in Table 8.

In some embodiments, the TCR comprises (a) an alpha chain variable domain having an amino acid sequence that has at least 85% amino acid identity to the entire amino acid sequence of any one of the amino acid sequences of the alpha chain variable domain amino acid sequences listed in Table 8; and (b) a beta chain variable domain having an amino acid sequence that has at least 85% amino acid identity to the entire amino acid sequence of any one of the amino acid sequences of the beta chain variable domain amino acid sequences listed in Table 8. In some embodiments, the TCR comprises: (a) an alpha chain variable domain CDR1 domain having an amino acid sequence selected from the group consisting of SEQ ID NOs: 614, 630, 646, 662, 678, 694, 710, 726, 742, 758, 774, 790, 806, 822, 838, and 854; (b) an alpha chain variable domain CDR2 domain having an amino acid sequence selected from the group consisting of SEQ ID NOs: 615, 631, 647, 663, 679, 695, 711, 727, 743, 759, 775, 791, 807, 823, 839, and 855; (c) an alpha chain variable domain CDR3 domain having an amino acid sequence selected from the group consisting of SEQ ID NOs: 616, 632, 648, 664, 680, 696, 712, 728, 744, 760, 776, 792, 808, 824, 840, and 856; (d) a beta chain variable domain CDR1 having an amino acid sequence selected from the group consisting of SEQ ID NOs: 622, 638, 654, 670, 686, 702, 718, 734, 750, 766, 782, 798, 814, 830, 846, and 862; (e) a beta chain variable domain CDR2 having an amino acid sequence selected from the group consisting of SEQ ID NOs: 623, 639, 655, 671, 687, 703, 719, 735, 751, 767, 783, 799, 815, 831, 847, and 863; and (f) a beta chain variable domain CDR3 having an amino acid sequence selected from the group consisting of SEQ ID NOs: 624, 640, 656, 672, 688, 704, 720, 736, 752, 768, 784, 800, 816, 832, 848, and 864.

In some embodiments, the TCR comprises an alpha chain variable domain/beta chain variable domain amino acid sequence pair selected from the group consisting of SEQ ID NOs: 620/628, 636/644, 652/660, 668/676, 684/692, 700/708, 716/724, 732/740, 748/756, 764/772, 780/788, 796/804, 812/820, 828/836, 844/852, and 860/868. In some embodiments, the TCR comprises an alpha chain variable domain/beta chain variable domain amino acid sequence pair selected from the group consisting of SEQ ID NOs: 620/628, 620/644, 620/660, 620/676, 620/692, 620/708, 620/724, 620/740, 620/756, 620/772, 620/788, 620/804, 620/820, 620/836, 620/852, 620/868, 636/628, 636/644, 636/660, 636/676, 636/692, 636/708, 636/724, 636/740, 636/756, 636/772, 636/788, 636/804, 636/820, 636/836, 636/852, 636/868, 652/628, 652/644, 652/660, 652/676, 652/692, 652/708, 652/724, 652/740, 652/756, 652/772, 652/788, 652/804, 652/820, 652/836 652/852, 652/868, 668/628, 668/644, 668/660, 668/676, 668/692, 668/708, 668/724, 668/740, 668/756, 668/772, 668/788, 668/804, 668/820, 668/836, 668/852, 668/868, 684/628, 684/644, 684/660, 684/676, 684/692, 684/708, 684/724, 684/740, 684/756, 684/772, 684/788, 684/804, 684/820, 684/836, 684/852, 684/868, 700/628, 700/644, 700/660, 700/676, 700/692, 700/708, 700/724, 700/740, 700/756, 700/772, 700/788, 700/804, 700/820, 700/836, 700/852, 700/868, 716/628, 716/644, 716/660, 716//676, 716/692, 716/708, 716/724, 716/740, 716/756, 716/772, 716/788, 716/804, 716/820, 716/836, 716/852, 716/868, 732/628, 732/644, 732/660, 732/676, 732/692, 732/708, 732/724, 732/740, 732/756, 732/772, 732/788, 732/804, 732/820, 732/836, 732/852, 732/868, 748/628, 748/644, 748/660, 748/676, 748/692, 748/708, 748/724, 748/740, 748/756, 748/772, 748/788, 748/804, 748/820, 748/836, 748/852, 748/868, 764/628, 764/644, 764/660, 764/676, 764/692, 764/708, 764/724, 764/740, 764/756, 764/772, 764/788, 764/804, 764/820, 764/836, 764/852, 764/868, 780/628, 780/644, 780/660, 780/676, 780/692, 780/708, 780/724, 780/740, 780/756, 780/772, 780/788, 780/804, 780/820, 780/836, 780/852, 780/868, 796/628, 796/644, 796/660, 796/676, 796/692, 796/708, 796/724, 796/740, 796/756, 796/772, 796/788, 796/804, 796/820, 796/836, 796/852, 796/868, 812/628, 812/644, 812/660, 812/676, 812/692, 812/708, 812/724, 812/740, 812/756, 812/772, 812/788, 812/804, 812/820, 812/836, 812/852, 812/868, 828/628, 828/644, 828/660, 828/676, 828/692, 828/708, 828/724, 828/740, 828/756, 828/772, 828/788, 828/804, 828/820, 828/836, 828/852, 828/868, 844/628, 844/644, 844/660, 844/676, 844/692, 844/708, 844/724, 844/740, 844/756, 844/772, 844/788, 844/804, 844/820, 844/836, 844/852, 844/868, 860/628, 860/644, 860/660, 860/676, 860/692, 860/708, 860/724, 860/740, 860/756, 860/772, 860/788, 860/804, 860/820, 860/836, 860/852, and 860/868.

In some embodiments, the TCR comprises: (a) an alpha chain variable domain CDR1 encoded by a nucleic acid sequence selected from the group consisting of SEQ ID NOs: 617, 633, 649, 665, 681, 697, 713, 729, 745, 761, 777, 793, 809, 825, 841, and 857; (b) an alpha chain variable domain CDR2 encoded by a nucleic acid sequence selected from the group consisting of SEQ ID NOs: 618, 634, 650, 666, 682, 698, 714, 730, 746, 762, 778, 794, 810, 826, 842, and 858; (c) an alpha chain variable domain CDR3 encoded by a nucleic acid sequence selected from the group consisting of SEQ ID NOs: 619, 635, 651, 667, 683, 699, 715, 731, 747, 763, 779, 795, 811, 827, 843, and 859; (d) a beta chain variable domain CDR1 encoded by a nucleic acid sequence selected from the group consisting of SEQ ID NOs: 625, 641, 657, 673, 689, 705, 721, 737, 753, 769, 785, 801, 817, 833, 849, and 865; (e) a beta chain variable domain CDR2 encoded by a nucleic acid sequence selected from the group consisting of SEQ ID NOs: 626, 642, 658, 674, 690, 706, 722, 738, 754, 770, 786, 802, 818, 834, 850, and 866; and (f) a beta chain variable domain CDR3 encoded by a nucleic acid sequence selected from the group consisting of SEQ ID NOs: 627, 643, 659, 675, 691, 707, 723, 739, 755, 771, 787, 803, 819, 835, 851, and 867. In some embodiments, the TCR comprises an alpha chain variable domain/beta chain variable domain nucleic acid sequence pair selected from the group consisting of SEQ ID NOs: 621/629, 637/645, 653/661, 669/677, 685/693, 701/709, 717/725, 733/741, 749/757, 765/773, 781/789, 797/805, 813/821, 829/837, 845/853, and 861/869.

In one aspect, the present disclosure provides a vector comprising the polynucleotide sequence of an isolated nucleic acid molecule as described herein. In one aspect, the present disclosure provides an isolated cell comprising that vector. In one aspect, the present disclosure provides a method of treating a subject having a MAGE-A4-associated disease or disorder, comprising administering to the subject that cell, thereby treating the subject. In some embodiments, the MAGE-A4-associated disease or disorder is MAGE-A4-associated cancer. In some embodiments, the MAGE-A4-associated cancer is a liposarcoma, a neuroblastoma, a myeloma, a melanoma, a metastatic melanoma, a synovial sarcoma, a bladder cancer, an esophageal cancer, an esophageal squamous cell carcinoma, a hepatocellular cancer, a head and neck cancer, a non-small cell lung cancer, an ovarian cancer, an ovarian epithelial cancer, a prostate cancer, a breast cancer, an astrocytic tumor, a glioblastoma multiforme, an anaplastic astrocytoma, a brain tumor, a fallopian tube cancer, primary peritoneal cavity cancer, advanced solid tumors, soft tissue sarcoma, a sarcoma, a myelodysplastic syndrome, an acute myeloid leukemia, a Hodgkin lymphoma, a non-Hodgkin lymphoma, a Hodgkin disease, a multiple myeloma, a metastatic solid tumors, a colorectal carcinoma, a stomach cancer, a gastric cancer, a rhabdomyosarcoma, a myxoid round cell liposarcoma, or a recurrent non-small cell lung cancer. In some embodiments, the cell is administered to the subject in combination with a second therapeutic agent.

The present invention is further illustrated by the following detailed description and drawings.

DETAILED DESCRIPTION

Figure 1:
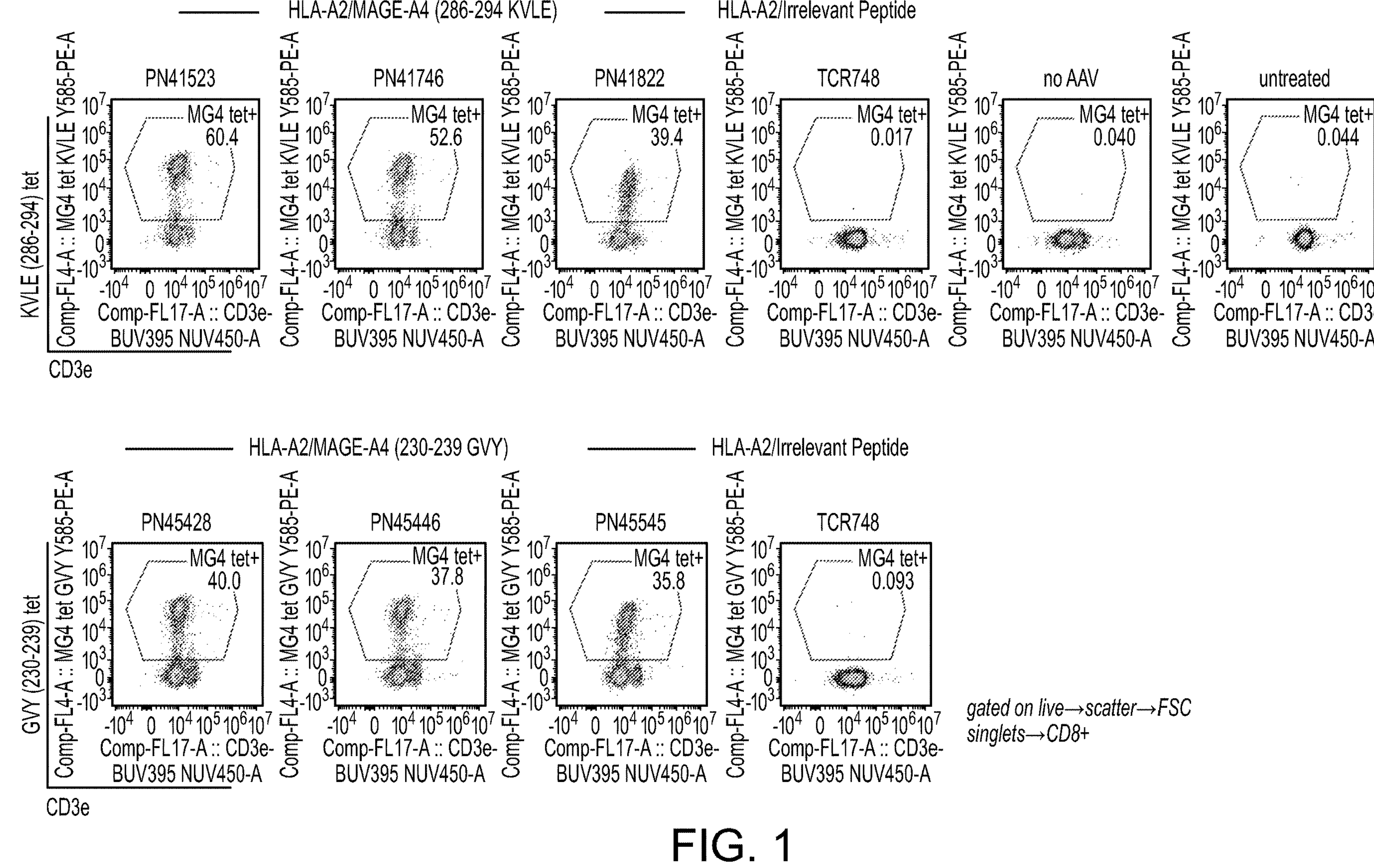
FIG. 1 depict FACS analysis showing the expression of TRACtargeted MAGE-A4 TCRs in primary human T cells, quantified by pMHC tetramer, analysis Day 14 post-activation. MAGE-A4 targets for these TCRs were either the MAGE-A4 (286-294) peptide (KVLEHVVRV, SEQ ID NO: 609; "KVLE") or the MAGE-A4 (230-239) peptide (GVYDGREHTV, SEQ ID NO: 612; "GVY") Transgenic TCR sequences were introduced to primary human T cells by site-directed targeting of adeno-associated virus (AAV) vector insertion at the human TRAC locus. Cells were stained with the indicated peptide MHC tetramer reagents (y axes) and antibodies for surface antigen markers, and analyzed by flow cytometry. Plots were gated on live, single CD8+ T cells.
Figure 2:
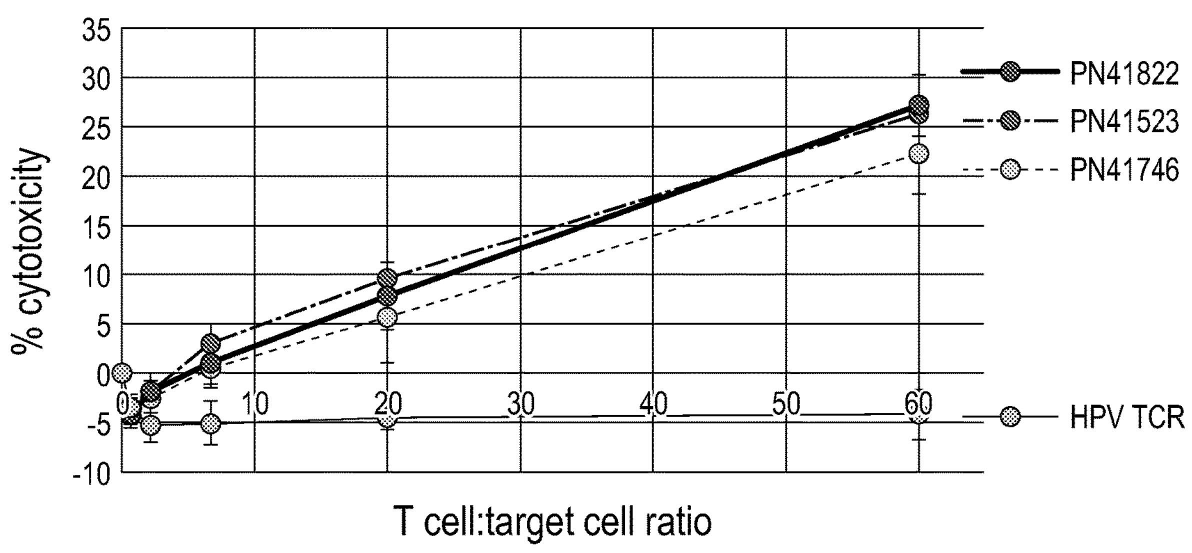
FIG. 2A and FIG. 2B depict the cytotoxic activity of MAGE-A4 TCRs against MAGE-A4 expressing A375 melanoma cells (Donor 1, 2 hour assay). Primary human T cells expressing TCRs against two different HLA-A2 restricted MAGE-A4 derived peptide antigens were tested for cytotoxic activity against HLA-A2*01 MAGE-A4 expressing A375 melanoma cells in a Calcein AM dye release assay. MAGE-A4 targets for these TCRs were either the MAGE-A4 (286-294) peptide (KVLEHVVRV, SEQ ID NO: 609; "KVLE") (FIG. 2A) or the MAGE-A4 (230-239) peptide (GVYDGREHTV, SEQ ID NO: 612; "GVY") (FIG. 2B). Control cells transduced with a TCR against an irrelevant antigen were included as a control for TCR target specificity.
Figure 2:
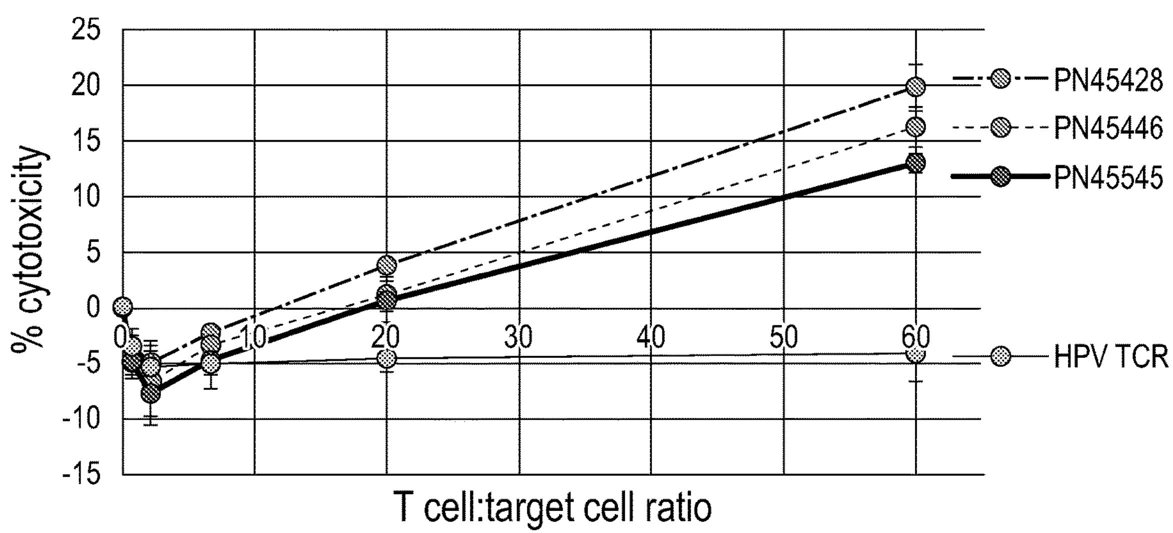
Figure 3:
FIG. 3A and FIG. 3B depicts the cytotoxic activity of MAGE-A4 TCRs against MAGE-A4 expressing A375 melanoma cells (Donor 2, 2.5 hour assay). MAGE-A4 targets for these TCRs were either the MAGE-A4 (286-294) peptide (KVLEHVVRV, SEQ ID NO: 609; "KVLE") (FIG. 3A) or the MAGE-A4 (230-239) peptide (GVYDGREHTV, SEQ ID NO: 612; "GVY") (FIG. 3B). Primary human T cells expressing TCRs against two different HLA-A2 restricted MAGE-A4 derived peptide antigens were tested for cytotoxic activity against HLA-A2*01 MAGE-A4 expressing A375 melanoma cells in a Calcein AM dye release assay. Untransduced (UTD) T cells were included as a control for TCR target specificity.
Figure 3:
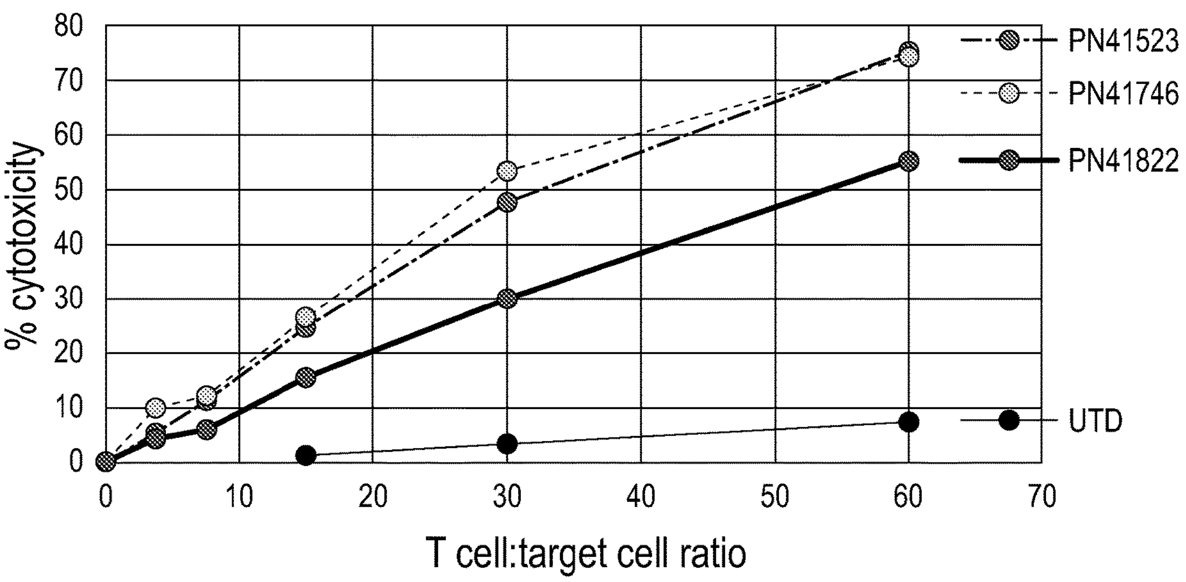
Figure 3:
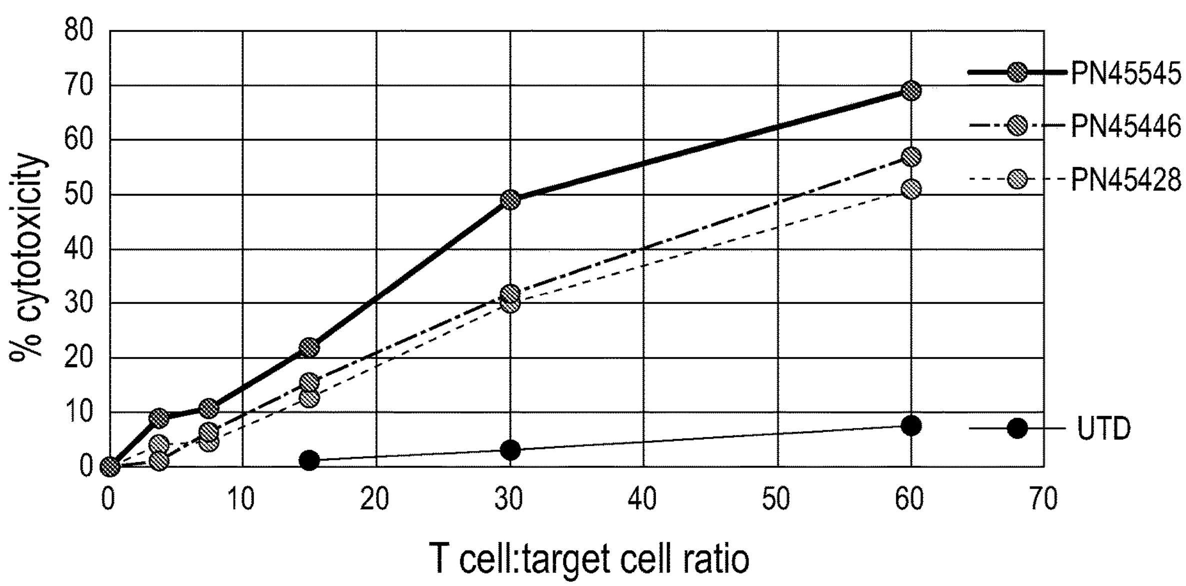

The present invention provides T cell receptors (TCRs) that were generated against a MAGE-A4 peptide antigen in the context of MHC (HLA-A2). The unique TCR sequences identified have shown specific binding to the small peptide MAGE-A4 presented in the groove of an HLA molecule and exhibited activation of T cells in a reporter assay. Furthermore, the TCRs of the invention do not cross-react with other "like" peptides.

I. Definitions

In order that the present invention may be more readily understood, certain terms are first defined. In addition, it should be noted that whenever a value or range of values of a parameter are recited, it is intended that values and ranges intermediate to the recited values are also part of this invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

The articles "a" and "an" are used herein to refer to one or to more than one (i.e., to at least one) of the grammatical object of the article. By way of example, "an element" means one element or more than one element.

The term "comprising" or "comprises" is used herein in reference to compositions, methods, and respective component(s) thereof, that are essential to the disclosure, yet open to the inclusion of unspecified elements, whether essential or not.

The term "consisting of" refers to compositions, methods, and respective components thereof as described herein, which are exclusive of any element not recited in that description of the embodiment.

The term "T cell receptor" (TCR), as used herein, refers to an immunoglobulin superfamily member having a variable binding domain, a constant domain, a transmembrane region, and a short cytoplasmic tail; see, e.g., Janeway et al., *Immunobiology: The Immune System in Health and Disease,* 3rd Ed., Current Biology Publications, p. 4:33, 1997) capable of specifically binding to an antigen peptide bound to a MHC receptor. A TCR can be found on the surface of a cell and generally is comprised of a heterodimer having $\alpha$ and $\beta$ chains (also known as TCR$\alpha$ and TCR$\beta$, respectively), or $\gamma$ and $\delta$ chains (also known as TCR$\gamma$ and TCR$\delta$, respectively). Like immunoglobulins, the extracellular portion of TCR chains (e.g., $\alpha$-chain, $\beta$-chain) contain two immunoglobulin regions, a variable region (e.g., TCR variable $\alpha$ region or V$\alpha$ and TCR variable $\beta$ region or V$\beta$; typically amino acids 1 to 116 based on Kabat numbering at the N-terminus), and one constant region (e.g., TCR constant domain $\alpha$ or C$\alpha$ and typically amino acids 117 to 259 based on Kabat, TCR constant domain $\beta$ or C$\beta$, typically amino acids 117 to 295 based on Kabat) adjacent to the cell membrane. Also, like immunoglobulins, the variable domains contain complementary determining regions (CDRs) separated by framework regions (FRs). In certain embodiments, a TCR is found on the surface of T cells (or T lymphocytes) and associates with the CD3 complex. The source of a TCR of the present disclosure may be from various animal species, such as a human, mouse, rat, rabbit or other mammal. In preferred embodiments, the source of a TCR of the present invention is a mouse genetically engineered to produce TCRs comprising human alpha and beta chains (see, e.g., PCT Publication No. WO 2016/164492, the entire contents of which are incorporated herein by reference).

The term "variable region" (variable region of an alpha chain (V$\alpha$), variable region of a beta chain (V$\beta$)) as used herein denotes each of the alpha and beta chains which is involved directly in binding the TCR to the antigen.

The "constant region" of the alpha chain and of the beta chain are not involved directly in binding of a TCR to an antigen, but exhibit various effector functions.

The term "antigen" as used herein is meant any substance that causes the immune system to produce antibodies or specific cell-mediated immune responses against it. A disease-associated antigen is any substance that is associated with any disease that causes the immune system to produce antibodies or a specific-cell mediated response against it.

The term "MAGE-A4," "MAGEA4" or "Melanoma-Associated Antigen A4" refers to the well-known cancer-testis antigen (CTAs) that is re-expressed in numerous cancer types.

The nucleotide and amino acid sequence of full-length MAGE-A4 is provided in GenBank as accession number NM_001011548 (DNA sequence: SEQ ID NO: 870; RNA sequence: SEQ ID NO: 610; amino acid sequence: SEQ ID NO: 611). The term "MAGE-A4" includes recombinant MAGE-A4 or a fragment thereof. The term also encompasses MAGE-A4 or a fragment thereof coupled to, for example, histidine tag, mouse or human Fc, or a signal sequence such as ROR1. In certain embodiments, the term comprises MAGE-A4 or a fragment thereof in the context of HLA-A2, linked to HLA-A2 or as displayed by HLA-A2. As used herein, the numbering of certain MAGE-A4 amino acid residues within the full-length MAGE-A4 sequence is with respect to SEQ ID NO: 611.

The term "HLA" refers to the human leukocyte antigen (HLA) system or complex, which is a gene complex encoding the major histocompatibility complex (MHC) proteins in humans. These cell-surface proteins are responsible for the regulation of the immune system in humans. HLAs corresponding to MHC class I (A, B, and C) present peptides from inside the cell.

The term "HLA-A" refers to the group of human leukocyte antigens (HLA) that are coded for by the HLA-A locus. HLA-A is one of three major types of human MHC class I cell surface receptors. The receptor is a heterodimer, and is composed of a heavy a chain and smaller β chain. The α chain is encoded by a variant HLA-A gene, and the β chain β2-microglobulin) is an invariant β2 microglobulin molecule.

The term "HLA-A2" (also referred to as "HLA-A2*01") is one particular class I major histocompatibility complex (MHC) allele group at the HLA-A locus; the α chain is encoded by the HLA-A*02 gene and the β chain is encoded by the β2-microglobulin or B2M locus.

The term "specifically binds," or "binds specifically to", or the like, means that TCR forms a complex with an antigen that is relatively stable under physiologic conditions. Specific binding can be characterized by an equilibrium dissociation constant of at least about $1\times10^{-8}$ M or less (e.g., a smaller KD denotes a tighter binding). Methods for determining whether two molecules specifically bind are well known in the art and include, for example, equilibrium dialysis, surface plasmon resonance, and the like. As described herein, the TCRs of the invention bind specifically to an HLA-A2 presented cancer testis antigen Melanoma-Associated Antigen A4 (MAGE-A4) peptide, e.g., a peptide comprising amino acid residues 230-239 or 286-294 of MAGE-A4 (e.g., of the full-length MAGE-A4 sequence of SEQ ID NO: 611).

The term "off-target peptide" refers to a peptide that differs by 1, 2, 3, 4, 5 or more amino acids from a target peptide (e.g., a MAGE-A4 230-239 peptide or a MAGE-A4 286-294 peptide). In certain embodiments, the term includes a peptide that differs by less than or equal to 3 amino acids than the target peptide. For example, for a 9-mer peptide, if 1, 2, or 3 amino acids are not identical to the target peptide, it is considered an "off-target" peptide. In certain embodiments, amino acid identity is expressed in terms of 'degree of similarity' (DoS). If 6 or more amino acids within a 9-mer peptide are identical, the DoS is 6. In certain embodiments, a peptide with DoS≤6 is considered an "off-target" peptide. The term "off-target" peptide also refers to a peptide that is similar to the target peptide based on sequence homology, is predicted to bind to HLA-A2 and is comprised in a protein that is expressed in essential, normal tissues.

The term "isolated" refers to a composition, compound, substance, or molecule altered by the hand of man from the natural state. For example, a composition or substance that occurs in nature is isolated if it has been changed or removed from its original environment, or both. For example, a polynucleotide or a polypeptide naturally present in a living animal is not isolated, but the same polynucleotide or polypeptide separated from the coexisting materials of its natural state is isolated, as the term is employed herein. More particularly, an isolated TCR can refer to a TCR that has been removed from a cell, for example, a TCR that has been purified. TCRs can also be expressed by an isolated cell, e.g., a cell that has been isolated from an animal or a cell from cell culture. In this context, the isolated cell can express the TCR on its surface (i.e., the cell can "present" the TCR).

The term "recombinant", as used herein, refers to TCRs of the invention created, expressed, isolated or obtained by technologies or methods known in the art as recombinant DNA technology which include, e.g., DNA splicing and transgenic expression. The term refers to TCRs expressed in a non-human mammal (including transgenic non-human mammals, e.g., transgenic mice), or a cell (e.g., CHO cells) expression system or isolated from a recombinant combinatorial human antibody library.

As used herein, the terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-, double-stranded and triple helical molecules, a gene or gene fragment, exons, introns, mRNA, tRNA, rRNA, ribozymes, antisense molecules, cDNA, recombinant polynucleotides, branched polynucleotides, aptamers, plasmids, vectors, isolated DNA of any sequence, isolated RNA of any sequence, nucleic acid probes, and primers. A nucleic acid molecule may also comprise modified nucleic acid molecules (e.g., comprising modified bases, sugars, and/or internucleotide linkers).

The term "polypeptide" is meant to refer to any polymer preferably consisting essentially of any of the 20 natural amino acids regardless of its size. Although the term "protein" is often used in reference to relatively large proteins, and "peptide" is often used in reference to small polypeptides, use of these terms in the field often overlaps. The term "polypeptide" refers generally to proteins, polypeptides, and peptides unless otherwise noted. Peptides useful in accordance with the present disclosure in general will be generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis.

The term "vector" is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g., promoter) for the expression of the inserted DNA. Common vectors include plasmid vectors and phage vectors.

In some embodiments, TCRs of the invention may be conjugated to a moiety such as a ligand, a detectable moiety, or a therapeutic moiety ("immunoconjugate"), such as a cytotoxin, an anti-cancer drug, or any other therapeutic moiety useful for treating a disease or condition including MAGE-A4-associated disease or disorder, such as a MAGE-A4-associated cancer.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "KD", also known as $K_D$ or $K_d$, is intended to refer to the equilibrium dissociation constant of a particular biomolecule and its binding partner. KD measurements are particularly useful for assessing protein-protein interactions, e.g. as in an antigen-binding protein-antigen interaction. The smaller the value of the KD, the greater (or e.g. stronger) the binding interaction or affinity between the antigen-binding protein and antigen (e.g. target). The larger the value of the KD, the weaker the binding interaction or affinity between the antigen-binding protein and antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

Sequence identity can be calculated using an algorithm, for example, the Needleman Wunsch algorithm (Needleman and Wunsch 1970, *J. Mol. Biol.* 48: 443-453) for global alignment, or the Smith Waterman algorithm (Smith and Waterman 1981, *J. Mol. Biol.* 147: 195-197) for local alignment. Another preferred algorithm is described by Dufresne et al in *Nature Biotechnology* in 2002 (vol. 20, pp. 1269-71) and is used in the software GenePAST (GQ Life Sciences, Inc. Boston, MA).

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 96%, 97%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) *Methods Mol. Biol.* 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) *Science* 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Sequences also can be compared using the Smith-Waterman homology search algorithm using an affine gap search with a gap open penalty of 12 and a gap extension penalty of 2, BLOSUM matrix of 62. Another preferred algorithm when comparing a sequence of the invention to a database containing a large number of sequences from different organisms is the computer program BLAST, especially BLASTP or TBLASTN, using default parameters. See, e.g., Altschul et al. (1990) *J. Mol. Biol.* 215: 403-410 and (1997) *Nucleic Acids Res.* 25:3389-3402, each of which is herein incorporated by reference.

A "patient-derived TCR" is a TCR that is produced by isolating the alpha and beta chains of a MAGE-A4 reactive TCR isolated from the T-lymphocytes that mediated in vivo regression of a tumor in a subject having a MAGE-A4-associated cancer.

An "affinity-matured TCR" is a TCR that is produced by mutagenesis and selection in vitro. For example, untargeted or targeted (e.g., oligonucleotide-directed) mutagenesis can be performed to introduce variation in TCR sequences, and the subsequent TCRs can then be screened for affinity against a target, e.g., by use of phage display.

The term "activates a T cell response having a signal to noise ratio stronger or equal to a patient-derived MAGE-A4-specific TCR" or "activates a T cell response having a signal to noise ratio stronger or equal to an affinity-matured MAGE-A4-specific TCR" is meant to refer to an increase, i.e., about 2-fold or more, an amplification, i.e., about 2-fold, an augmentation, i.e., about 2-fold, or a boost of a physiological activity, i.e., about 2-fold, i.e., T cell signaling, as measured by, for example, a luminescent bioassay. Reference to a greater T cell response, or a stronger T cell response or an activation signal, may be used interchangeably. Various measurements and assays of T cell response or T cell activation are well known to the skilled artisan.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) *The Art, Science and Technology of Pharmaceutical Compounding*). The term "effective amount" is intended to encompass contexts such as a pharmaceutically effective amount or therapeutically effective amount. For example, in certain embodiments, the effective amount is capable of achieving a beneficial state, beneficial outcome, functional activity in a screening assay, or improvement of a clinical condition.

As used herein, the term "subject" refers to an animal, preferably a mammal, in need of amelioration, prevention and/or treatment of a MAGE-A4-associated disease or disorder, such as a MAGE-A4-associated cancer (e.g., a MAGE-A4-positive cancer). The term includes human subjects who have or are at risk of having a MAGE-A4-associated disease or disorder, such as an n MAGE-A4-associated cancer.

As used herein, "anti-cancer drug" means any agent useful to treat or ameliorate or inhibit cancer including, but not limited to, cytotoxins and agents such as antimetabolites, alkylating agents, anthracyclines, antibiotics, antimitotic agents, procarbazine, hydroxyurea, asparaginase, corticosteroids, cyclophosphamide, mytotane (O,P'-(DDD)), biologics (e.g., antibodies and interferons) and radioactive agents. As used herein, "a cytotoxin or cytotoxic agent", also refers to a chemotherapeutic agent and means any agent that is detrimental to cells. Examples include Taxol® (paclitaxel), temozolamide, cytochalasin B, gramicidin D, ethidium bromide, emetine, cisplatin, mitomycin, etoposide, tenoposide, vincristine, vinbiastine, coichicin, doxorubicin, daunorubicin, dihydroxy anthracin dione, mitoxantrone, mithramycin, actinomycin D, l-dehydrotestosterone, glucocorticoids, procaine, tetracaine, lidocaine, propranolol, and puromycin and analogs or homologs thereof.

The terms "prevent", "preventing", "prevention", "prophylactic treatment" and the like are meant to refer to reducing the probability of developing a disorder or condition in a subject, who does not have, but is at risk of or susceptible to developing a disorder or condition. Prevention and the like do not mean preventing a subject from ever getting the specific disease or disorder. Prevention may require the administration of multiple doses. Prevention can include the prevention of a recurrence of a disease in a subject for whom all disease symptoms were eliminated, or prevention of recurrence in a relapsing-remitting disease.

II. MAGE-A4 T Cell (TCRs) and Compositions Comprising MAGE-A4 TCRS

T cells are a subgroup of cells which, together with other immune cell types (polymorphonuclear, eosinophils, basophils, mast cells, B-cells, NK cells), constitute the cellular component of the immune system. Under physiological conditions T cells function in immune surveillance and in the elimination of foreign antigen. However, under pathological conditions there is compelling evidence that T cells play a major role in the causation and propagation of disease. In these disorders, breakdown of T cell immunological tolerance, either central or peripheral is a fundamental process in the causation of autoimmune disease.

T cells bind epitopes on small antigenic determinants on the surface of antigen-presenting cells that are associated with a major histocompatibility complex (MHC; in mice) or human leukocyte antigen (HLA; in humans) complex. T cells bind these epitopes through a T cell receptor (TCR) complex on the surface of the T cell. T cell receptors are heterodimeric structures composed of two types of chains: an α (alpha) and β (beta) chain, or a γ (gamma) and δ (delta) chain. The α chain is encoded by the nucleic acid sequence located within the α locus (on human or mouse chromosome 14), which also encompasses the entire δ locus, and the β chain is encoded by the nucleic acid sequence located within the β locus (on mouse chromosome 6 or human chromosome 7). The majority of T cells have an αβ TCR; while a minority of T cells bears a γδ TCR.

T cell receptor α and β polypeptides (and similarly γ and δ polypeptides) are linked to each other via a disulfide bond. Each of the two polypeptides that make up the TCR contains an extracellular domain comprising constant and variable regions, a transmembrane domain, and a cytoplasmic tail (the transmembrane domain and the cytoplasmic tail also being a part of the constant region). The variable region of the TCR determines its antigen specificity, and similar to immunoglobulins, comprises three complementary determining regions (CDRs). The TCR is expressed on most T cells in the body and is known to be involved in the recognition of MHC-restricted antigens. The TCR α chain includes a covalently linked Vα and Cα region, whereas the β chain includes a Vβ region covalently linked to a Cβ region. The Vα and Vβ regions form a pocket or cleft that can bind an antigen in the context of a major histocompatibility complex (MHC) (or HLA in humans). TCRs are detection molecules with exquisite specificity, and exhibit, like antibodies, an enormous diversity.

The general structure of TCR molecules and methods of making and using, including binding to a peptide:Major Histocompatibility Complex have been disclosed. See, for example PCT/US98/04274; PCT/US98/20263; WO99/60120.

Non-human animals (e.g., rodents, e.g., mice or rats) can be genetically engineered to express a human or humanized T cell receptor (TCR) comprising a variable domain encoded by at least one human TCR variable region gene segment, as described in, for example, PCT Publication No. WO 2016/164492, the entire contents of which are hereby incorporated herein by reference. For example, the Veloci-T® mouse technology (Regeneron), a genetically modified mouse that allows for the production of fully human therapeutic TCRs against tumor and/or viral antigens, can be used to produce the TCRs of the invention. Those of skill in the art, through standard mutagenesis techniques, in conjunction with the assays described herein, can obtain altered TCR sequences and test them for particular binding affinity and/or specificity. Useful mutagenesis techniques known in the art include, without limitation, de novo gene synthesis, oligonucleotide-directed mutagenesis, region-specific mutagenesis, linker-scanning mutagenesis, and site-directed mutagenesis by PCR (see, e.g., Sambrook et al. (1989) and Ausubel et al. (1999)).

Briefly, in one embodiment, methods for generating a TCR to a MAGE-A4 230-239 peptide or a MAGE-A4 286-294 peptide may include immunizing a non-human animal (e.g., a rodent, e.g., a mouse or a rat), such as a genetically engineered non-human animal that comprises in its genome an un-rearranged human TCR variable gene locus, with a MAGE-A4 230-239 peptide or a MAGE-A4 286-294 peptide; allowing the animal to mount an immune response to the peptide; isolating from the animal a T cell reactive to the peptide; determining a nucleic acid sequence of a human TCR variable region expressed by the T cell; cloning the human TCR variable region into a nucleotide construct comprising a nucleic acid sequence of a human TCR constant region such that the human TCR variable region is operably linked to the human TCR constant region; and expressing from the construct a human T cell receptor specific for the MAGE-A4 230-239 peptide or the MAGE-A4 286-294 peptide, respectively. In one embodiment, the steps of isolating a T cell, determining a nucleic acid sequence of a human TCR variable region expressed by the T cell, cloning the human TCR variable region into a nucleotide construct comprising a nucleic acid sequence of a human TCR constant region, and expressing a human T cell receptor are performed using standard techniques known to those of skill the art.

In one embodiment, the nucleotide sequence encoding a T cell receptor specific for an antigen of interest is expressed in a cell. In one embodiment, the cell expressing the TCR is selected from a CHO, COS, 293, HeLa, PERC.6™ cell, etc.

In obtaining variant TCR coding sequences, those of ordinary skill in the art will recognize that TCR-derived proteins may be modified by certain amino acid substitutions, additions, deletions, and post-translational modifications, without loss or reduction of biological activity. In particular, it is well known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein.

In some embodiments, a TCR of the present disclosure can comprise a CDR sequence (e.g., a CDR3 sequence such as a Vα CDR3 or a Vβ CDR3) with 1 or more substitutions as compared to a CDR sequence (e.g., a CDR3 sequence such as a Vα CDR3 or a Vβ CDR3) of Table 6. For example, a TCR of the present disclosure can comprise a CDR sequence with 1, 2, 3, 4, 5, 6, 7, 8, 9, 10, or more substitutions as compared to a CDR sequence of Table 6. In general, the TCRs of the present invention function by binding to an HLA-A2 presented MAGE-A4 230-239 peptide or a HLA-A2 presented MAGE-A4 286-294 peptide. As used herein, an HLA presented peptide (such as an HLA-A2 presented peptide) can refer to a peptide that is bound to a human leukocyte antigen (HLA) protein, for example, an HLA protein expressed on the surface of a cell. Thus, a TCR that binds to an HLA presented peptide binds to the peptide that is bound by the HLA, and optionally also binds to the HLA itself. Interaction with the HLA can confer specificity for binding to a peptide presented by a particular HLA. In some embodiments, the TCR binds to an isolated HLA presented peptide. In some embodiments, the TCR binds to an HLA presented peptide on the surface of a cell.

The present invention includes MAGE-A4 TCRs that bind a MAGE-A4 230-239 peptide or a MAGE-A4 286-294 peptide in the context of HLA-A2 with high specificity. In some embodiments, the MAGE-A4 TCRs do not bind to the MAGE-A4 230-239 peptide or the MAGE-A4 286-294 peptide in the absence of HLA-A2, or such binding is minimal. Further, in some embodiments, the MAGE-A4 TCRs do not bind to an off-target peptide in the context of HLA-A2, or such binding is minimal. As used herein, an off-target peptide can refer to a peptide that differs from a target peptide by 1, 2, 3, 4, 5, or more amino acids. In some embodiments, binding specificity can be determined by a) measuring on-target binding (e.g., binding to the HLA-A2 presented MAGE-A4 (230-239) peptide or the HLA-A2 presented MAGE-A4 (230-239) peptide), b) measuring off-target binding, and c) quantifying the difference between the two, e.g., by calculating a ratio. This ratio can be calculated, for example, by dividing the values obtained in a) and b). Measurement of on-target and off-target binding can be achieved, for example, by measuring % binding to a peptide/HLA tetramer reagent (e.g., a MAGE-A4/HLA tetramer reagent or a MAGE-A8/HLA tetramer reagent), or by other techniques known in the art. In some embodiments, an on-target binding/off-target binding value (e.g., a value obtained by dividing the values obtained in a) and b) described above) of a TCR of the present disclosure can be greater than 5, greater than 6, greater than 7, greater than 8, greater than 9, greater than 10, greater than 11, greater than 12, greater than 13, greater than 14, greater than 15, greater than 16, greater than 17, greater than 18, greater than 19, greater than 20, greater than 21, greater than 22, greater than 23, greater than 24, greater than 25, greater than 26, greater than 27, greater than 28, greater than 29, greater than 30, greater than 35, greater than 40, greater than 45, greater than 50, greater than 55, greater than 60, greater than 65, greater than 70, greater than 75, greater than 80, greater than 85, greater than 90, greater than 95, greater than 100, greater than 110, greater than 120, greater than 130, greater than 140, greater than 150, greater than 160, greater than 170, greater than 180, greater than 190, greater than 200, greater than 225, greater than 250, greater than 275, greater than 300, greater than 325, greater than 350, greater than 375, greater than 400, greater than 425, greater than 450, greater than 475, greater than 500, greater than 550, greater than 600, greater than 650, greater than 700, greater than 750, greater than 800, greater than 850, greater than 900, greater than 950, greater than 1000, greater than 1100, greater than 1200, greater than 1300, greater than 1400, greater than 1500, greater than 1600, greater than 1700, greater than 1800, greater than 1900, or greater than 2000. In some embodiments, an on-target binding/off-target binding value (e.g., a value obtained by dividing the values obtained in a) and b) described above) can be about 5 to about 20, about 10 to about 30, about 20 to about 80, about 30 to about 70, about 40 to about 60, about 50 to about 250, about 100 to about 200, about 100 to about 1000, about 300 to about 700, about 500 to about 1500, about 800 to about 1200, about 900 to about 1100, about 800 to about 1500, about 1000 to about 1400, or about 1100 to about 1300.

In one embodiment, the invention provides a recombinant antigen-binding protein (e.g., an isolated antigen-binding protein) that binds specifically to a conformational epitope of an HLA-A2 presented human MAGE-A4 (286-294) peptide or to a conformational epitope of an HLA-A2 presented human MAGE-A4 (230-239) peptide, wherein the antigen-binding protein has a property selected from the group consisting of: (a) binds monomeric HLA-A2: MAGE-A4 (286-294) peptide or monomeric MAGE-A4 (230-239) peptide with a binding dissociation equilibrium constant ($K_D$) of less than about 20 nM as measured in a surface plasmon resonance assay at 25° C.; (b) binds monomeric HLA-A2: MAGE-A4 (286-294) peptide or monomeric MAGE-A4 (230-239) peptide with a binding dissociation equilibrium constant ($K_D$) of less than about 25 nM as measured in a surface plasmon resonance assay at 25° C.; (c) binds to HLA-A2: MAGE-A4 (286-294) peptide-expressing cells or MAGE-A4 (230-239) peptide-expressing cells with an $EC_{50}$ less than about 6 nM and does not bind to cells expressing predicted off-target peptides as determined by luminescence assay; (d) binds to HLA-A2: MAGE-A4 (286-294) peptide-expressing cells or MAGE-A4 (230-239) peptide-expressing cells with an $EC_{50}$ less than about 1 nM and do not substantially bind to cells expressing predicted off-target peptides as determined by luminescence assay; (e) binds to HLA-A2: MAGE-A4 (286-294) peptide-expressing cells or MAGE-A4 (230-239) peptide-expressing cells with an $EC_{50}$ less than about 30 nM as determined by flow cytometry assay; (f) binds to HLA-A2: MAGE-A4 (286-294) peptide-expressing cells or MAGE-A4 (230-239) peptide-expressing cells with an $EC_{50}$ less than about 75 nM as determined by flow cytometry assay; (g) mediates the killing of cancer cells (e.g., melanoma cells) in a dose dependent manner as determined by Calcein AM dye release assay, and (h) the conformational epitope comprises one or more amino acids of SEQ ID NO: 611 or of SEQ ID NO: 612.

In some embodiments, the MAGE-A4 TCRs of the present disclosure have specific activity or affinity for MAGE-A4 (230-239) or for MAGE-A4 (286-294) as measured by an in vitro assay. For example, cells (such as T2 cells) expressing an HLA can be pulsed with a MAGE-A4 (230-239) or a MAGE-A4 (286-294) polypeptide, or an off-target polypeptide thereby inducing the cells to present the polypeptide bound to the HLA. Alternatively or in addition to using an off-target polypeptide as a control, an off-target HLA (an HLA other than the HLA that is recognized by the TCR of interest) can be used. For example, an off-target HLA can be used to present the MAGE-A4 peptide to test for specificity of binding to the HLA-A2-presented MAGE-A4 peptide. In addition, a control can be a cell line that expresses neither MAGE-A4 nor the target HLA (e.g., HLA-A2). Cells can be co-cultured with a T-cell population expressing the TCR of interest, and activity measured as a function of the amount of a cytokine (such as interferon gamma) produced by the cells. In certain embodiments, the assay can comprise in vitro co-cultures of a TCR-expressing T cell population with $10^{-10}$ M peptide-loaded T2 cells at an effector cell:target cell ratio of 1:1 ($1\times10^5$ effector cells/96 well), and interferon gamma measurement 24 hours after co-culture (e.g., by a Meso Scale Discovery (MSD®) Sector Imager). In certain embodiments, the assay can comprise in vitro co-cultures of a TCR-expressing T cell population and effector cell at an effector cell:target cell ratio of 5:1 ($2.5\times10^5$ effector cells:$5\times10^4$ target cells), and interferon gamma measurement 24 hours after co-culture (e.g., by a Meso Scale Discovery (MSD®) Sector Imager). In certain embodiments, TCRs are expressed in primary T cells (e.g., cytotoxic T cells, regulatory T cells, helper T cells, or any combination thereof) by replacing an endogenous locus, e.g., an endogenous TRAC locus (KO/KI), and disrupting an endogenous locus, e.g., a TRBC locus (KO), using, e.g., CRISPR, TALEN, zinc finger, or other targeted disruption systems. In vitro assays comprising such cells can include cytotoxicity activity against HLA-A2*01 MAGE-A4 expressing A375 melanoma cells in a Calcein AM dye release assay.

Increasing amounts of cytokine detected can serve as an indicator of activity. The activity or specificity of a TCR of interest to its target peptide in comparison to a control (off-target) polypeptide, or the activity or specificity of a TCR of interest to its on-target HLA-bound target peptide in comparison to an off-target HLA-bound target peptide can be 2-fold or greater, 3-fold or greater, 4-fold or greater, 5-fold or greater, 6-fold or greater, 7-fold or greater, 8-fold or greater, 9-fold or greater, 10-fold or greater, 15-fold or greater, 20-fold or greater, 30-fold or greater, 40-fold or greater, 50-fold or greater, 100-fold or greater, 200-fold or greater, 300-fold or greater, 400-fold or greater, 500-fold or greater, 600-fold or greater, 700-fold or greater, 800-fold or greater, 900-fold or greater, 1.000-fold or greater, 1,500-fold or greater, 2,000-fold or greater, 2,500-fold or greater, 3,000-fold or greater, 4,000-fold or greater, 5,000-fold or greater, 10,000-fold or greater, 20,000-fold or greater, 30,000-fold or greater, 40,000-fold or greater, 50,000-fold or greater, 60,000-fold or greater, 70,000-fold or greater, 80.000-fold or greater, 90.000-fold or greater, or 100,000-fold or greater.

In certain embodiments, the MAGE-A4 TCRs of the present disclosure are useful in inhibiting the growth of a tumor or delaying the progression of cancer when administered prophylactically to a subject in need thereof and may increase survival of the subject. For example, the administration of a MAGE-A4 TCR of the present invention may lead to shrinking of a primary tumor and may prevent metastasis or development of secondary tumors. In certain embodiments, the MAGE-A4 TCRs of the present invention are useful in inhibiting the growth of a tumor when administered therapeutically to a subject in need thereof and may increase survival of the subject. For example, the administration of a therapeutically effective amount of a MAGE-A4 TCR of the invention to a subject may lead to shrinking and disappearance of an established tumor in the subject.

In one embodiment, the invention provides a TCR (e.g., an isolated TCR or a TCR expressed on an isolated cell) that specifically binds to an HLA-A2 presented MAGE-A4 286-294 peptide, wherein the antigen-binding protein exhibits one or more of the following characteristics: (i) comprises an alpha chain variable domain comprising complementary determining regions (CDR) 1, CDR2, and CDR3, wherein the CDR3 region comprises the amino acid sequence of Formula I: $N_1$-$N_2$-$N_3$-$N_4$-$N_5$-$N_6$-$N_7$-$N_8$-$N_9$-$N_{10}$-$N_{11}$-$N_{12}$-$N_{13}$-$N_{14}$-$N_{15}$ (Formula I), wherein $N_1$ is a Ala, Ile, or Gly; $N_2$, which may or may not be present, is Val; $N_3$ is Tyr, Gly, Leu, Val, Glu, Met, Ala, or Phe; $N_4$ is Arg, Glu, Ser, Asn, Gln, Lys, Asp, Gly, or Met; $N_5$, which may or may not be present, is Ser, Arg, Glu, Leu, Ala, Asp, Pro, Met, Gly or Lys; $N_6$, which may or may not be present, is Ala, Asp, Gly, Ser, Val, Pro, Leu, Tyr, or Thr; $N_7$ which may or may not be present, is Thr, Pro, Ser, Glu, Asp, Trp, Arg, Asn, Ile, Gln, or Leu; $N_8$ is Gly, Trp, Thr, Lys, Tyr, or Ala; $N_9$ is Asn, Gly, Lys, Ile, Ser, or Arg; $N_{10}$, which may or may not be present, is Gln, Lys, Gly, Thr, Leu, Asp, or Ser; $N_{11}$, which may or may not be present, is Phe, Asn, Thr, Tyr, Ala, Leu, Met or Glu; $N_{12}$, which may or may not be present, is Lys, Phe, Tyr, or Asp; $N_{13}$, which may or may not be present, is Lys or Gly; $N_{14}$, which may or may not be present, is Thr, Leu, or Tyr; and $N_{15}$ is Tyr, Gln, Ile, Thr, Val, or Arg; (ii) comprises a beta chain variable domain comprising beta chain variable domain comprises complementary determining regions (CDR) 1, CDR2, and CDR3, wherein the CDR3 region comprises amino acid sequence of Formula II: $N_1$-$N_2$-$N_3$-$N_4$-$N_5$-$N_6$-$N_7$-$N_8$-$N_9$-$N_{10}$-$N_{11}$-$N_{12}$-$N_{13}$-$N_{14}$-$N_{15}$-$N_{16}$-$N_{17}$-$N_{18}$ (Formula II), wherein $N_1$ is Ala or Ser; $N_2$ is Ala, Ser, or Thr; $N_3$ is Ser, Gly, or Trp; $N_4$ is Leu, Tyr, Trp, Asp, Phe, Gly, Pro, or His; $N_5$, which may or may not be present, is Gly or Asp; $N_6$, which may or may not be present, is Phe or Arg; $N_7$, which may or may not be present, is Trp, Phe, Asp, Pro, Tyr, Gly, Thr, Ser, or Val; $N_8$, which may or may not be present, is Pro, Arg, Asp, Tyr, Gln, Asn, or Gly; $N_9$, which may or may not be present, is Asp; $N_{10}$, which may or may not be present, is Arg; $N_{11}$, which may or may not be present, is Gly, Ala, or Thr; $N_{12}$ is Ser, Trp, Thr, Gly, Val, Leu, Arg, Met, Tyr, or Gln; $N_{13}$, which may or may not be present, is Gly; $N_{14}$, which may or may not be present, is Asn, Asp, Gly, Thr, Pro, Gln, or His; $N_{15}$, which may or may not be present, is Thr, Ser, Glu, Asn, Tyr, Gln, Asp, or Pro; $N_{16}$, which may or may not be present, is Glu, Pro, Lys, Thr, Ala, Gly, or Gln;

$N_{17}$, which may or may not be present, is Ala, Leu, Ile, Tyr, or Gln; and $N_{18}$ is Phe, His, Tyr, or Thr; and (iii) comprises a CDR1 of the alpha chain variable domain comprising any one of the CDR1 amino acid sequences set forth in Table 2, or a substantially similar sequence thereof having at least 90%, at least 95%, at least 96%, at least 97%, at least 98% or at least 99% sequence identity, and a CDR2 of the alpha chain variable domain independently comprising any one of the CDR2 amino acid sequences set forth in Table 2, or a substantially similar sequence thereof having at least 90%, at least 95%, at least 96%, at least 97%, at least 98% or at least 99% sequence identity; (iv) comprises a CDR1 of a beta chain variable domain comprising any one of the CDR1 amino acid sequences set forth in Table 2, or a substantially similar sequence thereof having at least 90%, at least 95%, at least 96%, at least 97%, at least 98% or at least 99% sequence identity, and a CDR2 of a beta chain variable domain independently comprising any one of the CDR2 amino acid sequences set forth in Table 2, or a substantially similar sequence thereof having at least 90%, at least 95%, at least 96%, at least 97%, at least 98% or at least 99% sequence identity; (v) comprises an alpha chain variable domain CDR1, CDR2 and CDR3 contained within any one of the alpha chain variable domain sequences listed in Table 4, or a substantially similar sequence thereof having at least 90%, at least 95%, at least 96%, at least 97%, at least 98% or at least 99% sequence identity; and beta chain variable domain CDR1, CDR2 and CDR3 contained within any one of the beta chain variable domain sequences listed in Table 4, or a substantially similar sequence thereof having at least 90%, at least 95%, at least 96%, at least 97%, at least 98% or at least 99% sequence identity; (vi) comprises an alpha chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the alpha chain variable domain amino acid sequences listed in Table 4; (vii) comprises a beta chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the beta chain variable domain amino acid sequences listed in Table 4; (viii) comprises (a) an alpha chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the alpha chain variable domain amino acid sequences listed in Table 4; and (b) a beta chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the beta chain variable domain amino acid sequences listed in Table 4; (ix) comprises (a) an alpha chain variable domain CDR1 domain having an amino acid sequence selected from the group consisting of SEQ ID NOs: 1, 17, 33, 49, 65, 81, 97, 113, 129, 145, 161, 177, 193, 209, 225, 241, 257, 273, 289, 305, 321, 337, 353, 369, 385, 401, 417, 433, 449, 465, 481, 497, 513, 529, 545, 561, 577, and 593, or a substantially similar sequence thereof having at least 90%, at least 95%, at least 96%, at least 97%, at least 98% or at least 99% sequence identity; (b) an alpha chain variable domain CDR2 domain having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370, 386, 402, 418, 434, 450, 466, 482, 498 514, 530, 546, 562, 578, and 594, or a substantially similar sequence thereof having at least 90%, at least 95%, at least 96%, at least 97%, at least 98% or at least 99% sequence identity; (c) an alpha chain variable domain CDR3 domain having an amino acid sequence selected from the group consisting of SEQ ID NOs: 3, 19, 35, 51, 67, 83, 99, 115, 131, 147, 163, 179, 195, 211, 227, 243, 259, 275, 291, 307, 323, 339, 355, 371, 387, 403, 419, 435, 451, 467, 483, 499, 515, 531, 547, 563, 579, and 595, or a substantially similar sequence thereof having at least 90%, at least 95%, at least 96%, at least 97%, at least 98% or at least 99% sequence identity; (d) a beta chain variable domain CDR1 having an amino acid sequence selected from the group consisting of SEQ ID NOs: 9, 25, 41, 57, 73, 89, 105, 121, 137, 153, 169, 185, 201, 217, 233, 249, 265, 281, 297, 313, 329, 345, 361, 377, 393, 409, 425, 441, 457, 473, 489, 505, 521, 537, 553, 569, 585, and 601, or a substantially similar sequence thereof having at least 90%, at least 95%, at least 96%, at least 97%, at least 98% or at least 99% sequence identity; (e) a beta chain variable domain CDR2 having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378, 394, 410, 426, 442, 458, 474, 490, 506, 522, 538, 554, 570, 586, and 602, or a substantially similar sequence thereof having at least 90%, at least 95%, at least 96%, at least 97%, at least 98% or at least 99% sequence identity; and (f) a beta chain variable domain CDR3 having an amino acid sequence selected from the group consisting of SEQ ID NOs: 11, 27, 43, 59, 75, 91, 107, 123, 139, 155, 171, 187, 203, 219, 235, 251, 267, 283, 299, 315, 331, 347, 363, 379, 395, 411, 427, 443, 459, 475, 491, 507, 523, 539, 555, 571, 587, and 603, or a substantially similar sequence thereof having at least 90%, at least 95%, at least 96%, at least 97%, at least 98% or at least 99% sequence identity; (x) comprises an alpha chain variable domain/beta chain variable domain amino acid sequence pair selected from the group consisting of SEQ ID NOs: 7/15, 23/31, 39/47, 55/63, 71/79, 87/95, 103/111, 119/127, 135/143, 151/159, 167/175, 183/191, 199/207, 215/223, 231/239, 247/255, 263/271, 279/287, 295/303, 311/319, 327/335, 343/351, 359/367, 375/383, 391/399, 407/415, 423/431, 439/447, 455/463, 471/479, 487/495, 503/511, 519/527, 535/543, 551/559, 567/575, 583/591, 599/607, or a substantially similar sequence thereof having at least 90%, at least 95%, at least 96%, at least 97%, at least 98% or at least 99% sequence identity; (xi) comprises an alpha chain variable domain/beta chain variable domain amino acid sequence pair selected from the group consisting of SEQ ID NOs: 87/31, 23/95, 231/607, 231/223, 231/591, 231/255, 231/271, 231/79, 231/47, 231/399, 599/239, 599/223, 599/591, 599/255, 599/271, 599/79, 599/47, 599/399, 215/239, 215/607, 215/591, 215/255, 215/271, 215/79, 215/47, 215/399, 583/239, 583/607, 583/223, 583/255, 583/271, 583/79, 583/47, 583/399, 247/239, 247/607, 247/223, 247/591, 247/271, 247/79, 247/47, 247/399, 263/239, 263/607, 263/223, 263/591, 263/255, 263/79, 263/47, 263/399, 71/239, 71/607, 71/223, 71/591, 71/255, 71/271, 71/47, 71/399, 39/239, 39/607, 39/223, 39/591, 39/255, 39/271, 39/79, 39/399, 391/239, 391/607, 391/223, 391/591, 391/255, 391/271, 391/79, 391/47, 439/127, 439/319, 439/287, 439/15, 439/111, 439/383, 439/191, 439/511, 439/527, 439/559, 439/207, 119/447, 119/319, 119/287, 119/15, 119/111, 119/383, 119/191, 119/511, 119/527, 119/559, 119/207, 311/447, 311/127, 311/287, 311/15, 311/111, 311/383, 311/191, 311/511, 311/527, 311/559, 311/

207, 279/447, 279/127, 279/319, 279/15, 279/111, 279/383, 279/191, 279/511, 279/527, 279/559, 279/207, 7/447, 7/127, 7/319, 7/287, 7/111, 7/383, 7/191, 7/511, 7/527, 7/559, 7/207, 103/447, 103/127, 103/319, 103/287, 103/15, 103/383, 103/191, 103/511, 103/527, 103/559, 103/207, 375/447, 375/127, 375/319, 375/287, 375/15, 375/111, 375/191, 375/511, 375/527, 375/559, 375/207, 183/447, 183/127, 183/319, 183/287, 183/15, 183/111, 183/383, 183/511, 183/527, 183/559, 183/207, 503/447, 503/127, 503/319, 503/287, 503/15, 503/111, 503/383, 503/191, 503/527, 503/559, 503/207, 519/447, 519/127, 519/319, 519/287, 519/15, 519/111, 519/383, 519/191, 519/511, 510/559, 519/207, 551/447, 551/127, 551/319, 551/287, 551/15, 551/111, 551/383, 551/191, 551/511, 551/527, 551/207, 199/447, 199/127, 199/319, 199/287, 199/15, 199/111, 199/383, 199/191, 199/511, 199/527, and 199/559, or a substantially similar sequence thereof having at least 90%, at least 95%, at least 96%, at least 97%, at least 98% or at least 99% sequence identity; and/or (xii) does not bind to cells expressing predicted off-target peptides.

In one embodiment, the invention provides a TCR (e.g., an isolated TCR or a TCR expressed on an isolated cell) that specifically binds to an HLA-A2 presented MAGE-A4 230-239 peptide, wherein the antigen-binding protein exhibits one or more of the following characteristics: (i) comprises a CDR1 of the alpha chain variable domain comprising any one of the CDR1 amino acid sequences set forth in Table 6, or a substantially similar sequence thereof having at least 90%, at least 95%, at least 96%, at least 97%, at least 98% or at least 99% sequence identity, and a CDR2 of the alpha chain variable domain independently comprising any one of the CDR2 amino acid sequences set forth in Table 6, or a substantially similar sequence thereof having at least 90%, at least 95%, at least 96%, at least 97%, at least 98% or at least 99% sequence identity; (iv) comprises a CDR1 of a beta chain variable domain comprising any one of the CDR1 amino acid sequences set forth in Table 6, or a substantially similar sequence thereof having at least 90%, at least 95%, at least 96%, at least 97%, at least 98% or at least 99% sequence identity, and a CDR2 of a beta chain variable domain independently comprising any one of the CDR2 amino acid sequences set forth in Table 6, or a substantially similar sequence thereof having at least 90%, at least 95%, at least 96%, at least 97%, at least 98% or at least 99% sequence identity; (v) comprises an alpha chain variable domain CDR1, CDR2 and CDR3 contained within any one of the alpha chain variable domain sequences listed in Table 8, or a substantially similar sequence thereof having at least 90%, at least 95%, at least 96%, at least 97%, at least 98% or at least 99% sequence identity; and beta chain variable domain CDR1, CDR2 and CDR3 contained within any one of the beta chain variable domain sequences listed in Table 8, or a substantially similar sequence thereof having at least 90%, at least 95%, at least 96%, at least 97%, at least 98% or at least 99% sequence identity; (vi) comprises an alpha chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the alpha chain variable domain amino acid sequences listed in Table 8; (vii) comprises a beta chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the beta chain variable domain amino acid sequences listed in Table 8; (viii) comprises (a) an alpha chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the alpha chain variable domain amino acid sequences listed in Table 8; and (b) a beta chain variable domain having an amino acid sequence that has at least 85%, 86%, 87%, 88%, 89%, 90%, 91%, 92%, 93%, 94%, 95%, 96%, 97%, 98%, 99% or about 100% amino acid identity to the entire amino acid sequence of any one of the amino acid sequences of the beta chain variable domain amino acid sequences listed in Table 8; (ix) comprises (a) an alpha chain variable domain CDR1 domain having an amino acid sequence selected from the group consisting of SEQ ID NOs: 614, 630, 646, 662, 678, 694, 710, 726, 742, 758, 774, 790, 806, 822, 838, and 854, or a substantially similar sequence thereof having at least 90%, at least 95%, at least 96%, at least 97%, at least 98% or at least 99% sequence identity; (b) an alpha chain variable domain CDR2 domain having an amino acid sequence selected from the group consisting of SEQ ID NOs: 615, 631, 647, 663, 679, 695, 711, 727, 743, 759, 775, 791, 807, 823, 839, and 855, or a substantially similar sequence thereof having at least 90%, at least 95%, at least 96%, at least 97%, at least 98% or at least 99% sequence identity; (c) an alpha chain variable domain CDR3 domain having an amino acid sequence selected from the group consisting of SEQ ID NOs: 616, 632, 648, 664, 680, 696, 712, 728, 744, 760, 776, 792, 808, 824, 840, and 856, or a substantially similar sequence thereof having at least 90%, at least 95%, at least 96%, at least 97%, at least 98% or at least 99% sequence identity; (d) a beta chain variable domain CDR1 having an amino acid sequence selected from the group consisting of SEQ ID NOs: 622, 638, 654, 670, 686, 702, 718, 734, 750, 766, 782, 798, 814, 830, 846, and 862, or a substantially similar sequence thereof having at least 90%, at least 95%, at least 96%, at least 97%, at least 98% or at least 99% sequence identity; (e) a beta chain variable domain CDR2 having an amino acid sequence selected from the group consisting of SEQ ID NOs: 623, 639, 655, 671, 687, 703, 719, 735, 751, 767, 783, 799, 815, 831, 847, and 863, or a substantially similar sequence thereof having at least 90%, at least 95%, at least 96%, at least 97%, at least 98% or at least 99% sequence identity; and (f) a beta chain variable domain CDR3 having an amino acid sequence selected from the group consisting of SEQ ID NOs: 624, 640, 656, 672, 688, 704, 720, 736, 752, 768, 784, 800, 816, 832, 848, and 864, or a substantially similar sequence thereof having at least 90%, at least 95%, at least 96%, at least 97%, at least 98% or at least 99% sequence identity; (x) comprises an alpha chain variable domain/beta chain variable domain amino acid sequence pair selected from the group consisting of SEQ ID NOs: 620/628, 636/644, 652/660, 668/676, 684/692, 700/708, 716/724, 732/740, 748/756, 764/772, 780/788, 796/804, 812/820, 828/836, 844/852, and 860/868, or a substantially similar sequence thereof having at least 90%, at least 95%, at least 96%, at least 97%, at least 98% or at least 99% sequence identity; (xi) comprises an alpha chain variable domain/beta chain variable domain amino acid sequence pair selected from the group consisting of SEQ ID NOs: 620/628, 620/644, 620/660, 620/676, 620/692, 620/708, 620/724, 620/740, 620/756, 620/772, 620/788, 620/804, 620/820, 620/836, 620/852, 620/868, 636/628, 636/644, 636/660, 636/676, 636/692, 636/708, 636/724, 636/740, 636/756, 636/772, 636/788, 636/804, 636/820, 636/836, 636/852, 636/868, 652/628, 652/644, 652/660, 652/676, 652/692, 652/

708, 652/724, 652/740, 652/756, 652/772, 652/788, 652/804, 652/820, 652/836 652/852, 652/868, 668/628, 668/644, 668/660, 668/676, 668/692, 668/708, 668/724, 668/740, 668/756, 668/772, 668/788, 668/804, 668/820, 668/836, 668/852, 668/868, 684/628, 684/644, 684/660, 684/676, 684/692, 684/708, 684/724, 684/740, 684/756, 684/772, 684/788, 684/804, 684/820, 684/836, 684/852, 684/868, 700/628, 700/644, 700/660, 700/676, 700/692, 700/708, 700/724, 700/740, 700/756, 700/772, 700/788, 700/804, 700/820, 700/836, 700/852, 700/868, 716/628, 716/644, 716/660, 716//676, 716/692, 716/708, 716/724, 716/740, 716/756, 716/772, 716/788, 716/804, 716/820, 716/836, 716/852, 716/868, 732/628, 732/644, 732/660, 732/676, 732/692, 732/708, 732/724, 732/740, 732/756, 732/772, 732/788, 732/804, 732/820, 732/836, 732/852, 732/868, 748/628, 748/644, 748/660, 748/676, 748/692, 748/708, 748/724, 748/740, 748/756, 748/772, 748/788, 748/804, 748/820, 748/836, 748/852, 748/868, 764/628, 764/644, 764/660, 764/676, 764/692, 764/708, 764/724, 764/740, 764/756, 764/772, 764/788, 764/804, 764/820, 764/836, 764/852, 764/868, 780/628, 780/644, 780/660, 780/676, 780/692, 780/708, 780/724, 780/740, 780/756, 780/772, 780/788, 780/804, 780/820, 780/836, 780/852, 780/868, 796/628, 796/644, 796/660, 796/676, 796/692, 796/708, 796/724, 796/740, 796/756, 796/772, 796/788, 796/804, 796/820, 796/836, 796/852, 796/868, 812/628, 812/644, 812/660, 812/676, 812/692, 812/708, 812/724, 812/740, 812/756, 812/772, 812/788, 812/804, 812/820, 812/836, 812/852, 812/868, 828/628, 828/644, 828/660, 828/676, 828/692, 828/708, 828/724, 828/740, 828/756, 828/772, 828/788, 828/804, 828/820, 828/836, 828/852, 828/868, 844/628, 844/644, 844/660, 844/676, 844/692, 844/708, 844/724, 844/740, 844/756, 844/772, 844/788, 844/804, 844/820, 844/836, 844/852, 844/868, 860/628, 860/644, 860/660, 860/676, 860/692, 860/708, 860/724, 860/740, 860/756, 860/772, 860/788, 860/804, 860/820, 860/836, 860/852, and 860/868, or a substantially similar sequence thereof having at least 90%, at least 95%, at least 96%, at least 97%, at least 98% or at least 99% sequence identity; and/or (xii) does not bind to cells expressing predicted off-target peptides.

The TCRs of the present invention may possess one or more of the aforementioned biological characteristics, or any combinations thereof. Other biological characteristics of the antigen-binding proteins of the present invention will be evident to a person of ordinary skill in the art from a review of the present disclosure including the working Examples herein.

In certain embodiments, a polynucleotide encoding a MAGE-A4 TCR described herein is inserted into a vector. The term "vector" as used herein refers to a vehicle into which a polynucleotide encoding a protein may be covalently inserted so as to bring about the expression of that protein and/or the cloning of the polynucleotide. Such vectors may also be referred to as "expression vectors". The isolated polynucleotide may be inserted into a vector using any suitable methods known in the art, for example, without limitation, the vector may be digested using appropriate restriction enzymes and then may be ligated with the isolated polynucleotide having matching restriction ends. Expression vectors have the ability to incorporate and express heterologous or modified nucleic acid sequences coding for at least part of a gene product capable of being transcribed in a cell. In most cases, RNA molecules are then translated into a protein. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are discussed infra. An expression vector may comprise additional elements, for example, the expression vector may have two replication systems, thus allowing it to be maintained in two organisms, for example in human cells for expression and in a prokaryotic host for cloning and amplification.

The expression vector may have the necessary 5' upstream and 3' downstream regulatory elements such as promoter sequences such as CMV, PGK and EF1α promoters, ribosome recognition and binding TATA box, and 3' UTR AAUAAA transcription termination sequence for the efficient gene transcription and translation in its respective host cell. Other suitable promoters include the constitutive promoter of simian virus 40 (SV40) early promoter, mouse mammary tumor virus (MMTV), HIV LTR promoter, MoMuLV promoter, avian leukemia virus promoter, EBV immediate early promoter, and rous sarcoma virus promoter. Human gene promoters may also be used, including, but not limited to the actin promoter, the myosin promoter, the hemoglobin promoter, and the creatine kinase promoter. In certain embodiments inducible promoters are also contemplated as part of the vectors expressing chimeric antigen receptor. This provides a molecular switch capable of turning on expression of the polynucleotide sequence of interest or turning off expression. Examples of inducible promoters include, but are not limited to a metallothionine promoter, a glucocorticoid promoter, a progesterone promoter, or a tetracycline promoter.

The expression vector may have additional sequence such as 6×-histidine (SEQ ID NO: 871), c-Myc, and FLAG tags which are incorporated into the expressed TCRs. Thus, the expression vector may be engineered to contain 5' and 3' untranslated regulatory sequences that sometimes can function as enhancer sequences, promoter regions and/or terminator sequences that can facilitate or enhance efficient transcription of the nucleic acid(s) of interest carried on the expression vector. An expression vector may also be engineered for replication and/or expression functionality (e.g., transcription and translation) in a particular cell type, cell location, or tissue type. Expression vectors may include a selectable marker for maintenance of the vector in the host or recipient cell.

Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are Lenti-X™ Bicistronic Expression System (Neo) vectors (Clontrch), pClneo vectors (Promega) for expression in mammalian cells; pLenti4/V5-DEST™, pLenti6/V5-DEST™, and pLenti6.2N$_5$-GW/lacZ (Invitrogen) for lentivirus-mediated gene transfer and expression in mammalian cells. The coding sequences of the TCRs disclosed herein can be ligated into such expression vectors for the expression of the chimeric protein in mammalian cells.

In certain embodiments, the nucleic acids encoding the TCR of the present invention are provided in a viral vector. A viral vector can be those derived from retrovirus, lentivirus, or foamy virus. As used herein, the term, "viral vector," refers to a nucleic acid vector construct that includes at least one element of viral origin and has the capacity to be packaged into a viral vector particle. The viral vector can contain the coding sequence for the various proteins described herein in place of nonessential viral genes. The vector and/or particle can be utilized for the purpose of transferring DNA, RNA or other nucleic acids into cells either in vitro or in vivo. Numerous forms of viral vectors are known in the art.

In certain embodiments, the viral vector containing the coding sequence for a TCR described herein is a retroviral vector or a lentiviral vector. The term "retroviral vector" refers to a vector containing structural and functional genetic elements that are primarily derived from a retrovirus. The term "lentiviral vector" refers to a vector containing structural and functional genetic elements outside the LTRs that are primarily derived from a lentivirus.

The retroviral vectors for use herein can be derived from any known retrovirus (e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend, Murine Stem Cell Virus (MSCV) and Rous Sarcoma Virus (RSV)). Retroviruses" of the invention also include human T cell leukemia viruses, HTLV-1 and HTLV-2, and the lentiviral family of retroviruses, such as Human Immunodeficiency Viruses, HIV-1, HIV-2, simian immunodeficiency virus (SIV), feline immunodeficiency virus (FIV), equine immnodeficiency virus (EIV), and other classes of retroviruses.

A lentiviral vector for use herein refers to a vector derived from a lentivirus, a group (or genus) of retroviruses that give rise to slowly developing disease. Viruses included within this group include HIV (human immunodeficiency virus; including HIV type 1, and HIV type 2); visna-maedi; a caprine arthritis-encephalitis virus; equine infectious anemia virus; feline immunodeficiency virus (FIV); bovine immune deficiency virus (BIV); and simian immunodeficiency virus (SIV). Preparation of the recombinant lentivirus can be achieved using the methods according to Dull et al. and Zufferey et al. (Dull et al., *J. Virol.,* 1998; 72: 8463-8471 and Zufferey et al., *J. Virol.* 1998; 72:9873-9880).

Retroviral vectors (i.e., both lentiviral and non-lentiviral) for use in the present invention can be formed using standard cloning techniques by combining the desired DNA sequences in the order and orientation described herein (*Current Protocols in Molecular Biology*, Ausubel, F. M. et al. (eds.) Greene Publishing Associates, (1989), Sections 9.10-9.14 and other standard laboratory manuals; Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol* 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Suitable sources for obtaining retroviral (i.e., both lentiviral and non-lentiviral) sequences for use in forming the vectors include, for example, genomic RNA and cDNAs available from commercially available sources, including the Type Culture Collection (ATCC), Rockville, Md. The sequences also can be synthesized chemically.

For expression of a MAGE-A4 TCR, the vector may be introduced into a host cell to allow expression of the polypeptide within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art, as described above. For example, the promoter sequences may be selected to promote the transcription of the polynucleotide in the vector. Suitable promoter sequences include, without limitation, T7 promoter, T3 promoter, SP6 promoter, beta-actin promoter, EF1a promoter, CMV promoter, and SV40 promoter. Enhancer sequences may be selected to enhance the transcription of the polynucleotide. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell.

For cloning of the polynucleotide, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vectors provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces.*

The TCRs of the present invention are introduced into a host cell using transfection and/or transduction techniques known in the art. As used herein, the terms, "transfection," and, "transduction," refer to the processes by which an exogenous nucleic acid sequence is introduced into a host cell. The nucleic acid may be integrated into the host cell DNA or may be maintained extrachromosomally. The nucleic acid may be maintained transiently or a may be a stable introduction. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Transduction refers to the delivery of a gene(s) using a viral or retroviral vector by means of viral infection rather than by transfection. In certain embodiments, retroviral vectors are transduced by packaging the vectors into virions prior to contact with a cell. For example, a nucleic acid encoding a MAGE-A4 TCR of the invention carried by a retroviral vector can be transduced into a cell through infection and pro virus integration.

As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably.

In particular, the TCRs of the present invention are introduced and expressed in immune effector cells so as to redirect their specificity to a target antigen of interest, e.g., an HLA-A2 displayed MAGE-A4 peptide, e.g., amino acid residues 230-239 or 286-294 of MAGE-A4.

The present invention provides methods for making the immune effector cells which express the TCRs as described herein. In one embodiment, the method comprises transfecting or transducing immune effector cells, e.g., immune effector cells isolated from a subject, such as a subject having a MAGE-A4-associated disease or disorder, such that the immune effector cells express one or more TCR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a TCR. In this regard, the immune effector cells may be cultured before or after being genetically modified (i.e., transduced or transfected to express a TCR as described herein).

Prior to in vitro manipulation or genetic modification of the immune effector cells described herein, the source of cells may be obtained from a subject. In particular, the immune effector cells for use with the TCRs as described herein comprise T cells.

T cells can be obtained from a number of sources, including peripheral blood mononuclear cells, bone marrow, lymph nodes tissue, cord blood, thymus issue, tissue from a site of infection, ascites, pleural effusion, spleen tissue, and tumors. In certain embodiments, T cell can be obtained from a unit of blood collected from the subject using any number of techniques known to the skilled person, such as FICOLL separation. In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. In one embodiment of the invention, the cells are washed with PBS. In an alternative embodiment, the washed solution lacks calcium and may lack magnesium or may lack many if not all divalent cations. As would be appreciated by those of ordinary skill in the art, a washing step may be accomplished by methods known to those in the art, such as by using a semiautomated flowthrough centrifuge. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells, such as CD28+, CD4+, CD8+, CD45RA+, and CD45RO+ T cells, can be further isolated by positive or negative selection techniques. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Flow cytometry and cell sorting may also be used to isolate cell populations of interest for use in the present invention.

PBMC may be used directly for genetic modification with the TCRs using methods as described herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion.

The immune effector cells, such as T cells, can be genetically modified following isolation using known methods, or the immune effector cells can be activated and expanded (or differentiated in the case of progenitors) in vitro prior to being genetically modified. In another embodiment, the immune effector cells, such as T cells, are genetically modified with the chimeric antigen receptors described herein (e.g., transduced with a viral vector comprising a nucleic acid encoding a TCR) and then are activated and expanded in vitro. Methods for activating and expanding T cells are known in the art and are described, for example, in U.S. Pat. Nos. 6,905,874; 6,867,041; 6,797,514; WO2012079000, US 2016/0175358.

The invention provides a population of modified immune effector cells for the treatment of a MAGE-A4-associated disease or disorder, e.g., cancer, the modified immune effector cells comprising a MAGE-A4 TCR as disclosed herein.

TCR-expressing immune effector cells prepared as described herein can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg.

III. Pharmaceutical Compositions

The invention provides therapeutic compositions comprising the MAGE-A4 TCRs of the invention or immune effector cells comprising the MAGE-A4 TCRs of the invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J Pharm Sci Technol* 52:238-311.

Depending on the severity of the condition, the frequency and the duration of the treatment can be adjusted.

In certain embodiments, the initial dose may be followed by administration of a second or a plurality of subsequent doses of MAGE-A4 TCRs of the invention or immune effector cells comprising the MAGE-A4 TCRs of the invention in an amount that can be approximately the same or less than that of the initial dose, In certain situations, the pharmaceutical composition can be delivered in a controlled release system. In one embodiment, a pump may be used.

Injectable preparations may include dosage forms for intravenous, subcutaneous, intracutaneous, intracranial, intraperitoneal and intramuscular injections, drip infusions, etc. The TCRs, pharmaceutical compositions, and cells described herein can be administered via parenteral administration. The preparations of the present disclosure may be prepared by methods publicly known. For example, the preparations may be prepared, e.g., by dissolving, suspending or emulsifying the antigen-binding protein or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

In some embodiments, TCR-expressing immune effector cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

A treatment-effective number of cells in the composition is typically greater than $10^2$ cells, and up to $10^6$ up to and including $10^8$ or $10^9$ cells and can be more than $10^{10}$ cells. The number of cells will depend upon the ultimate use for which the composition is intended as will the type of cells included therein.

The cells may be autologous or heterologous to the patient undergoing therapy. If desired, the treatment may also include administration of mitogens (e.g., PHA) or lymphokines, cytokines, and/or chemokines (e.g., IFN-γ, IL-2, IL-12, TNF-α, IL-18, and TNF-β, GM-CSF, IL-4, IL-13, Flt3-L, RANTES, MIP1α, etc.) as described herein to enhance induction of the immune response.

The TCR expressing immune effector cell populations of the present invention may be administered either alone, or as a pharmaceutical composition in combination with diluents and/or with other components such as IL-2 or other cytokines or cell populations. Briefly, pharmaceutical compositions of the present invention may comprise a TCR-expressing immune effector cell population, such as T cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

IV. Therapeutic Uses of MAGE-A4 TCRs or Immune Effector Cells Comprising MAGE-A4 TCRs The anti-tumor immune response induced in a subject by administering TCR expressing T cells described herein using the methods described herein, or other methods known in the art, may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present invention, which are well described in the art; e.g., *Current Protocols in Immunology*, Edited by: John E. Coligan, Ada M. Kruisbeek, David H. Margulies, Ethan M. Shevach, Warren Strober (2001) John Wiley & Sons, NY, N.Y.

Thus, the MAGE-A4 TCRs of the invention are useful, inter alia, for the treatment, prevention and/or amelioration of any disease or disorder associated with or mediated by MAGE-A4. For example, the present invention provides methods for treating a MAGE-A4-associated disease or disorder, such as a MAGE-A4-associated cancer (e.g., a MAGE-A4-positive cancer) (tumor growth inhibition) by administering a MAGE-A4 TCR (or pharmaceutical composition comprising a MAGE-A4 TCR or a plurality of cells comprising a MAGE-A4 TCR) as described herein to a patient in need of such treatment, and MAGE-A4 TCRs (or pharmaceutical composition comprising a MAGE-A4 TCR) for use in the treatment of a MAGE-A4-associated cancer. The antigen-binding proteins of the present invention are useful for the treatment, prevention, and/or amelioration of disease or disorder or condition such as a MAGE-A4-associated cancer and/or for ameliorating at least one symptom associated with such disease, disorder or condition. In the context of the methods of treatment described herein, the MAGE-A4 TCR (or pharmaceutical composition or plurality of cells) may be administered as a monotherapy (i.e., as the only therapeutic agent) or in combination with one or more additional therapeutic agents (examples of which are described elsewhere herein).

Accordingly, the present invention provides for methods of treating an individual diagnosed with or suspected of having, or at risk of developing, a MAGE-A4-associated disease or disorder, e.g., a MAGE-A4-associated cancer, comprising administering the individual a therapeutically effective amount of the TCR-expressing immune effector cells as described herein.

In one embodiment, the invention provides a method of treating a subject diagnosed with a MAGE-A4-positive cancer comprising removing immune effector cells from a subject diagnosed with a MAGE-A4-positive cancer, genetically modifying said immune effector cells with a vector comprising a nucleic acid encoding a TCR of the instant invention, thereby producing a population of modified immune effector cells, and administering the population of modified immune effector cells to the same subject. In one embodiment, the immune effector cells comprise T cells.

The methods for administering the cell compositions described herein includes any method which is effective to result in reintroduction of ex vivo genetically modified immune effector cells that either directly express a TCR of the invention in the subject or on reintroduction of the genetically modified progenitors of immune effector cells that on introduction into a subject differentiate into mature immune effector cells that express the TCR. One method comprises transducing peripheral blood T cells ex vivo with a nucleic acid construct in accordance with the invention and returning the transduced cells into the subject.

In some embodiments of the invention, the compositions described herein are useful for treating subjects suffering from primary or recurrent cancer, including, but not limited to, MAGE-A4-associated cancer, e.g., MAGE-A4-associated cancer is a liposarcoma, a neuroblastoma, a myeloma, a melanoma, a metastatic melanoma, a synovial sarcoma, a bladder cancer, an esophageal cancer, an esophageal squamous cell carcinoma, a hepatocellular cancer, a head and neck cancer, a non-small cell lung cancer, an ovarian cancer, an ovarian epithelial cancer, a prostate cancer, a breast cancer, an astrocytic tumor, a glioblastoma multiforme, an anaplastic astrocytoma, a brain tumor, a fallopian tube cancer, primary peritoneal cavity cancer, advanced solid tumors, soft tissue sarcoma, a sarcoma, a myelodysplastic syndrome, an acute myeloid leukemia, a Hodgkin lymphoma, a non-Hodgkin lymphoma, a Hodgkin disease, a multiple myeloma, a metastatic solid tumors, a colorectal carcinoma, a stomach cancer, a gastric cancer, a rhabdomyosarcoma, a myxoid round cell liposarcoma, or a recurrent non-small cell lung cancer. In one embodiment, the MAGE-A4-associated cancer is an ovarian cancer, a melanoma, a non-small cell lung carcinoma, a hepatocellular carcinoma, a colorectal carcinoma, an esophageal squamous cell carcinoma, an esophageal adenocarcinoma, a stomach cancer, a bladder cancer, a head and neck cancer, a gastric cancer, a synovial sarcoma, or a myxoid round cell liposarcoma.

The TCRs may be used to treat early stage or late-stage symptoms of the MAGE-A4-associated cancer. In one embodiment, a TCR of the invention may be used to treat advanced or metastatic cancer. The TCRs are useful in reducing or inhibiting or shrinking tumor growth. In certain embodiments, treatment with a TCR of the invention leads to more than 40% regression, more than 50% regression, more than 60% regression, more than 70% regression, more than 80% regression or more than 90% regression of a tumor in a subject. In certain embodiments, the TCRs may be used to prevent relapse of a tumor. In certain embodiments, the TCRs are useful in extending progression-free survival or overall survival in a subject with MAGE-A4-associated cancer. In some embodiments, the TCRs are useful in reducing toxicity due to chemotherapy or radiotherapy while maintaining long-term survival in a patient suffering from MAGE-A4-associated cancer.

One or more TCRs of the present invention may be administered to relieve or prevent or decrease the severity of one or more of the symptoms or conditions of the disease or disorder.

It is also contemplated herein to use one or more TCRs of the present invention prophylactically to patients at risk for developing a disease or disorder such as MAGE-A4-associated disease or disorder, such as a MAGE-A4-associated cancer.

In a further embodiment of the invention, the present TCRs are used for the preparation of a pharmaceutical composition for treating patients suffering from MAGE-A4-associated disease or disorder, such as a MAGE-A4-associated cancer. In another embodiment of the invention, the present TCRs are used as adjunct therapy with any other agent or any other therapy known to those skilled in the art useful for treating MAGE-A4-associated cancer.

Combination therapies may include a MAGE-A4 TCR of the invention, such as immune effector cell comprising a TCR of the invention, or a pharmaceutical composition of the invention, and any additional therapeutic agent that may be advantageously combined with a TCR of the invention. The TCRs of the present invention may be combined synergistically with one or more anti-cancer drugs or therapy used to treat or inhibit a MAGE-A4-associated disease or disorder, such as MAGE-A4-positive cancer, e.g., a liposarcoma, a neuroblastoma, a myeloma, a melanoma, a metastatic melanoma, a synovial sarcoma, a bladder cancer, an esophageal cancer, an esophageal squamous cell carcinoma, a hepatocellular cancer, a head and neck cancer, a non-small cell lung cancer, an ovarian cancer, an ovarian epithelial cancer, a prostate cancer, a breast cancer, an astrocytic tumor, a glioblastoma multiforme, an anaplastic astrocytoma, a brain tumor, a fallopian tube cancer, primary peritoneal cavity cancer, advanced solid tumors, soft tissue sarcoma, a sarcoma, a myelodysplastic syndrome, an acute myeloid leukemia, a Hodgkin lymphoma, a non-Hodgkin lymphoma, a Hodgkin disease, a multiple myeloma, a metastatic solid tumors, a colorectal carcinoma, a stomach cancer, a gastric cancer, a rhabdomyosarcoma, a myxoid round cell liposarcoma, or a recurrent non-small cell lung cancer.

It is contemplated herein to use the TCRs of the invention in combination with immunostimulatory and/or immunosupportive therapies to inhibit tumor growth, and/or enhance survival of cancer patients. The immunostimulatory therapies include direct immunostimulatory therapies to augment immune cell activity by either "releasing the brake" on suppressed immune cells or "stepping on the gas" to activate an immune response. Examples include targeting other checkpoint receptors, vaccination and adjuvants. The immunosupportive modalities may increase antigenicity of the tumor by promoting immunogenic cell death, inflammation or have other indirect effects that promote an anti-tumor immune response. Examples include radiation, chemotherapy, anti-angiogenic agents, and surgery.

In various embodiments, one or more TCRs of the present invention may be used in combination with a PD-1 inhibitor (e.g., an anti-PD-1 antibody such as nivolumab, pembrolizumab, pidilizumab, BGB-A317 or REGN2810), a PD-L1 inhibitor (e.g., an anti-PD-L1 antibody such as avelumab, atezolizumab, durvalumab, MDX-1105, or REGN3504), a CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen-binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA×CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, surgery, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as anti-oxidants or any other therapy care to treat cancer. In certain embodiments, the TCRs of the present invention may be used in combination with cancer vaccines including dendritic cell vaccines, oncolytic viruses, tumor cell vaccines, etc. to augment the anti-tumor response.

Examples of cancer vaccines that can be used in combination with TCRs of the present invention include MAGES vaccine for melanoma and bladder cancer, MUC1 vaccine for breast cancer, EGFRv3 (e.g., Rindopepimut) for brain cancer (including glioblastoma multiforme), or ALVAC-CEA (for CEA+ cancers).

In certain embodiments, the MAGE-A4 TCRs of the invention may be administered in combination with radiation therapy in methods to generate long-term durable anti-tumor responses and/or enhance survival of patients with cancer. In some embodiments, the MAGE-A4 TCRs of the invention may be administered prior to, concomitantly or after administering radiation therapy to a cancer patient. For example, radiation therapy may be administered in one or more doses to tumor lesions followed by administration of one or more doses of MAGE-A4 TCRs of the invention. In some embodiments, radiation therapy may be administered locally to a tumor lesion to enhance the local immunogenicity of a patient's tumor (adjuvinating radiation) and/or to kill tumor cells (ablative radiation) followed by systemic administration of a MAGE-A4 TCRs of the invention.

The additional therapeutically active agent(s)/component(s) may be administered prior to, concurrent with, or after the administration of the MAGE-A4 TCRs of the present invention. For purposes of the present disclosure, such administration regimens are considered the administration of a MAGE-A4 TCR "in combination with" a second therapeutically active component.

The additional therapeutically active component(s) may be administered to a subject prior to administration of a MAGE-A4 TCR of the present invention. In other embodiments, the additional therapeutically active component(s) may be administered to a subject after administration of a MAGE-A4 TCR of the present invention. In yet other embodiments, the additional therapeutically active component(s) may be administered to a subject concurrent with administration of a MAGE-A4 TCR of the present invention. "Concurrent" administration, for purposes of the present invention, includes, e.g., administration of a MAGE-A4 TCR and an additional therapeutically active component to a subject in a single dosage form (e.g., co-formulated), or in separate dosage forms administered to the subject within about 30 minutes or less of each other. If administered in separate dosage forms, each dosage form may be administered via the same route; alternatively, each dosage form may be administered via a different route. In any event, administering the components in a single dosage from, in separate dosage forms by the same route, or in separate dosage forms by different routes are all considered "concurrent administration," for purposes of the present disclosure. For purposes of the present disclosure, administration of a MAGE-A4 TCR "prior to", "concurrent with," or "after" (as those terms are defined herein above) administration of an additional therapeutically active component is considered administration of a MAGE-A4 TCR "in combination with" an additional therapeutically active component).

The present invention is further illustrated by the following Examples, which are not intended to be limiting in any way. The entire contents of all references, patents and published patent applications cited throughout this application, as well as the Figures, are hereby incorporated herein by reference.

EXAMPLES

Example 1. Identification of MAGE-A4 Specific T Cell Receptors

Mice humanized for cellular immune system components, Veloci-T® mice (see, e.g., PCT Publication No. WO 2016/164492, the entire contents of which are incorporated herein by reference), were immunized with MAGE-A4 (286-294) peptide (KVLEHVVRV, SEQ ID NO: 609) presented specifically by human HLA-A2, diluted in PBS and mixed with adjuvant, e.g. in equal volume with Complete Freund's Adjuvant (CFA; Chondrex, Inc.). Spleen suspensions from immunized mice were obtained and dissociated. Red blood cells were lysed in ACK lysis buffer (Life Technologies), and splenocytes were suspended in RPMI complete media. Isolated splenocytes were sorted and single T cells that bind MAGE-A4 (286-294) peptide in the context of MHC were isolated by fluorescent-activated cell sorting (FACS). Isolated T cells were single well plated and mixed with TCR alpha and beta variable region-specific PCR primers. cDNAs for each single T cell were synthesized via a reverse transcriptase (RT) reaction. Each resulting RT product was then split and transferred into two corresponding wells for subsequent TCR beta and alpha PCRs. One set of the resulting RT products was first amplified by PCR using a 5' degenerate primer specific for TCR beta variable region leader sequence or a 5' degenerate primer specific for TCR alpha chain variable region leader sequence and a 3' primer specific for TCR constant region, to form an amplicon. The amplicons were then amplified again by PCR using a 5' degenerate primer specific for TCR beta variable region framework 1 or a 5' degenerate primer specific for TCR alpha chain variable region framework 1 and a 3' primer specific for TCR constant region, to generate amplicons for cloning. The TCR beta and alpha derived PCR products were cloned into expression vectors containing beta constant region and alpha constant region, respectively. Expression vectors expressing full-length beta and alpha chain pairs were transfected into CHO cells and tested for binding to commercial MAGE-A4/HLA tetramer reagent (HLA-A02:01 MAGE-A4 tetramer; MBL International Corporation). CHO cells were incubated with soluble HLA-A2 (KVLEHVVRV) (SEQ ID NO:609) tetramer and an antibody specific for mouse TCR constant region (clone H57-597) (Biolegend, San Diego, CA). Samples were then analyzed on an LSRFortessa X-20 (BD Biosciences, San Jose, CA). To calculate percentage of tetramer positive cells, antigen positive (Ag+) gates were set based on a negative control TCR that does not bind to the HLA-A2 (KVLEHVVRV) (SEQ ID NO:609) tetramer using FlowJo (LLC, Ashland, OR). All Ag+ TCRs had a FlowJo criteria of ≥1% of cells in Ag+ gate with the mean fluorescence intensity (MFI)>250. Ag+ TCRs were determined by Next Generation Sequencing and the total number of TCRs that express identical TCR alpha and beta nucleotide sequences are shown in Table 1 below.

TABLE 1

| TCR ID | Total Ag + TCRs (CHOt) | % in Ag + gate > 250 MFI, > 1% |
|---|---|---|
| PN41520 | 2 | 16.90 |
| PN41494 | 1 | 9.24 |
| PN41703 | 24 | 42.50 |
| PN41573 | 2 | 85.70 |
| PN41869 | 1 | 76.50 |
| PN41568 | 8 | 82.90 |
| PN41868 | 1 | 67.10 |
| PN41577 | 45 | 80.00 |
| PN41607 | 18 | 81.00 |
| PN41518 | 19 | 34.90 |
| PN41513 | 36 | 29.60 |
| PN41702 | 42 | 8.13 |
| PN41654 | 2 | 36.20 |

TABLE 1-continued

| TCR ID | Total Ag + TCRs (CHOt) | % in Ag + gate > 250 MFI, > 1% |
|---|---|---|
| PN41656 | 5 | 13.80 |
| PN41820 | 3 | 8.32 |
| PN41746 | 1 | 90.20 |
| PN41532 | 7 | 85.40 |
| PN41617 | 11 | 90.60 |
| PN41608 | 6 | 77.00 |
| PN41475 | 1 | 65.50 |
| PN41523 | 6 | 90.50 |
| PN41690 | 3 | 75.30 |
| PN41559 | 2 | 74.30 |
| PN41822 | 32 | 63.50 |
| PN41829 | 1 | 19.50 |
| PN41852 | 1 | 18.00 |
| PN41565 | 1 | 4.02 |
| PN41805 | 61 | 30.40 |
| PN41867 | 2 | 73.00 |
| PN41712 | 16 | 20.70 |
| PN41748 | 3 | 9.56 |
| PN41557 | 2 | 8.76 |
| PN41636 | 1 | 78.30 |
| PN41613 | 1 | 58.70 |
| PN41550 | 17 | 92.20 |
| PN41839 | 1 | 85.40 |
| PN41539 | 1 | 10.90 |
| PN41516 | 1 | 7.83 |

A detailed list of the beta chain variable domain CDR1, CDR2, and CDR3 amino acid sequences, and the alpha chain variable domain CDR1, CDR2, and CDR3 amino acid sequences of the TCRs that were determined as described above are provided in Table 2. A detailed list of the beta chain variable domain CDR1, CDR2, and CDR3 polynucleic acid sequences, and the alpha chain variable domain CDR1, CDR2, and CDR3 polynucleic acid sequences of the TCRs that were determined as described above are provided in Table 3. Table 4 provides the amino acid and nucleotide sequences of the beta chain variable and alpha chain variable regions of the TCRs.

TABLE 2

Amino acid CDR sequences for Veloci-T ® TCRs specific for MAGE-A4 (286-294)/HLA-A2

| TCR No. | TCR ID | Vα CDR1 | SEQ ID NO | Vα CDR2 | SEQ ID NO | Vα CDR3 | SEQ ID NO: | Vβ CDR1 | SEQ ID NO | Vβ CDR2 | SEQ ID NO | Vβ CDR3 | SEQ ID NO: |
|---|---|---|---|---|---|---|---|---|---|---|---|---|---|
| 1 | PN41475 | TSESDYY | 1 | QEAYKQQN | 2 | AYRSATGNQFY | 3 | MDHEN | 9 | SYDVKM | 10 | ASSLWGSNTEAF | 11 |
| 2 | PN41494 | TSESDYY | 17 | QEAYKQQN | 18 | AYRSATGNQFY | 19 | MDHEN | 25 | SYDVKM | 26 | ASSLWGWNSPLH | 27 |
| 3 | PN41513 | TSESDYY | 33 | QEAYKQQN | 34 | AYRSAPGNQFY | 35 | MDHEN | 41 | SYDVKM | 42 | ASSLFATNEKLF | 43 |
| 4 | PN41516 | SVFSS | 49 | VVTGGEV | 50 | AGERDSWGKFQ | 51 | MNHNY | 57 | SVGAGI | 58 | ASSFWTGGDEKLF | 59 |
| 5 | PN41518 | TSESDYY | 65 | QEAYKQQN | 66 | AYRSAPGNQFY | 67 | MDHEN | 73 | SYDVKM | 74 | ASSLWATNEKLF | 75 |
| 6 | PN41520 | TSESDYY | 81 | QEAYKQQN | 82 | AYRSARGNQFY | 83 | MDHEN | 89 | SYDVKM | 90 | ASSLWGVNSPLH | 91 |
| 7 | PN41523 | TSESDYY | 97 | QEAYKQQN | 98 | AYRSAPGNQFY | 99 | MDHEN | 105 | SYDVKM | 106 | ASSLWGLNTEAF | 107 |
| 8 | PN41532 | TSESDYY | 113 | QEAYKQQN | 114 | AYRSAEGNQFY | 115 | MDHEN | 121 | SYDVKM | 122 | ASSLWGLNTEAF | 123 |
| 9 | PN41539 | TRDTTYY | 129 | RNSFDEQN | 130 | ALSEGDTGGFKTI | 131 | MNHNY | 137 | SVGAGI | 138 | ASSYFPDRGLGNTIY | 139 |
| 10 | PN41550 | DRGSQS | 145 | IYSNGD | 146 | AVNLSWGKFQ | 147 | SGHDT | 153 | YYEEEE | 154 | ASSLDRSTEAF | 155 |
| 11 | PN41557 | VSGLRG | 161 | LYSAGEE | 162 | AVQAVTGGGNKLT | 163 | DFQATT | 169 | SNEGSKA | 170 | SASWDRDYGYT | 171 |
| 12 | PN41559 | TSESDYY | 177 | QEAYKQQN | 178 | AYRSATGNQFY | 179 | MDHEN | 185 | SYDVKM | 186 | ASSLWGWGTEAF | 187 |
| 13 | PN41565 | TSESDYY | 193 | QEAYKQQN | 194 | AYRSPTGNQFY | 195 | MDHEN | 201 | SYDVKM | 202 | ASSLWAMNTEAF | 203 |
| 14 | PN41568 | TSESDYY | 209 | QEAYKQQN | 210 | AYRSARGNQFY | 211 | MDHEN | 217 | SYDVKM | 218 | ASSLWGTNEKLF | 219 |
| 15 | PN41573 | TSESDYY | 225 | QEAYKQQN | 226 | AYRSATGNQFY | 227 | MDHEN | 233 | SYDVKM | 234 | ASSLWGTNEKLF | 235 |
| 16 | PN41577 | TSESDYY | 241 | QEAYKQQN | 242 | AYRSAPGNQFY | 243 | MDHEN | 249 | SYDVKM | 250 | ASSLWGTNEKLF | 251 |
| 17 | PN41607 | TSESDYY | 257 | QEAYKQQN | 258 | AYRSASGNQFY | 259 | MDHEN | 265 | SYDVKM | 266 | ASSLWGTNEKLF | 267 |
| 18 | PN41608 | TSESDYY | 273 | QEAYKQQN | 274 | AYRSAPGNQFY | 275 | MDHEN | 281 | SYDVKM | 282 | ASSFWGWNTEAF | 283 |
| 19 | PN41613 | TSESDYY | 289 | QEAYKQQN | 290 | AYRSATGNQFY | 291 | MNHEY | 297 | SMNVEV | 298 | ASSLLYSNQPQH | 299 |
| 20 | PN41617 | TSESDYY | 305 | QEAYKQQN | 306 | AYRSASGNQFY | 307 | MDHEN | 313 | SYDVKM | 314 | ASSLWGMNTEAF | 315 |
| 21 | PN41636 | SSNFYA | 321 | MTLNGDE | 322 | ALNRDDKII | 323 | KGHDR | 329 | SFDVKD | 330 | ATSDPQRNQPQH | 331 |
| 22 | PN41654 | NSASDY | 337 | IRSNMDK | 338 | AEKRDNYGQNFV | 339 | MDHEN | 345 | SYDVKM | 346 | ASSLYSYGYT | 347 |
| 23 | PN41656 | TSDPSYG | 353 | QGSYDQQN | 354 | AMRDLTTSGTYKYI | 355 | MDHEN | 361 | SYDVKM | 362 | ASSFGGWGYGYT | 363 |

TABLE 2-continued

| Amino acid CDR sequences for Veloci-T ® TCRs specific for MAGE-A4 (286-294)/HLA-A2 | | | | | | | | | | | | | | |
|---|---|---|---|---|---|---|---|---|---|---|---|---|---|---|
| TCR No. | TCR ID | Vα CDR1 | SEQ ID NO | Vα CDR2 | SEQ ID NO | Vα CDR3 | SEQ ID NO: | Vβ CDR1 | SEQ ID NO | Vβ CDR2 | SEQ ID NO | Vβ CDR3 | SEQ ID NO: |
| 24 | PN41690 | TSESDYY | 369 | QEAYKQQN | 370 | AYRSAIGNQFY | 371 | MDHEN | 377 | SYDVKM | 378 | ASSLWGVNTEAF | 379 |
| 25 | PN41702 | TSESDYY | 385 | QEAYKQQN | 386 | AYRSATGNQFY | 387 | MDHEN | 393 | SYDVKM | 394 | ASSLWAVNEKLF | 395 |
| 26 | PN41703 | TISGNEY | 401 | GLKNN | 402 | IVRPGGTYKYI | 403 | MDHEN | 409 | SYDVKM | 410 | ATGGDNQPQH | 411 |
| 27 | PN41712 | TSENNYY | 417 | QEAYKQQN | 418 | ALNTGNQFY | 419 | DFQATT | 425 | SNEGSKA | 426 | SAWDGFYGYT | 427 |
| 28 | PN41746 | TSESDYY | 433 | QEAYKQQN | 434 | AYRSATGNQFY | 435 | MDHEN | 441 | SYDVKM | 442 | ASSLWGLNTEAF | 443 |
| 29 | PN41748 | KTLYG | 449 | LQKGGEE | 450 | GADMYSGGGADGLT | 451 | DFQATT | 457 | SNEGSKA | 458 | SAWDGFYGYT | 459 |
| 30 | PN41805 | TSENNYY | 465 | QEAYKQQN | 466 | AFGMYSGGGADGLT | 467 | PRHDT | 473 | FYEKMQ | 474 | ASSPTGTGDGYT | 475 |
| 31 | PN41820 | SSVPPY | 481 | YTTGATLV | 482 | AVSSGSARQLT | 483 | MDHEN | 489 | SYDVKM | 490 | ASSHDRWDYGYT | 491 |
| 32 | PN41822 | TSESDYY | 497 | QEAYKQQN | 498 | AYRSATGNQFY | 499 | MDHEN | 505 | SYDVKM | 506 | ASSLWALNTEAF | 507 |
| 33 | PN41829 | TSESDYY | 513 | QEAYKQQN | 514 | AYRSATGNQFY | 515 | MDHEN | 521 | SYDVKM | 522 | ASSLFALNTEAF | 523 |
| 34 | PN41839 | TISGNEY | 529 | GLKNN | 530 | IVYGGSQGNLI | 531 | SGHDT | 537 | YYEEEE | 538 | ASSFSRVQPQH | 539 |
| 35 | PN41852 | TSESDYY | 545 | QEAYKQQN | 546 | AYRSALGNDMR | 547 | MDHEN | 553 | SYDVKM | 554 | ASSLWALNTEAF | 555 |
| 36 | PN41867 | TSENNYY | 561 | QEAYKQQN | 562 | AFMKTQGGSEKLV | 563 | PRHDT | 569 | FYEKMQ | 570 | ASSLVGYGYT | 571 |
| 37 | PN41868 | TSESDYY | 577 | QEAYKQQN | 578 | AYRSATGNQFY | 579 | MDHEN | 585 | SYDVKM | 586 | ASSLWGTHEKLF | 587 |
| 38 | PN41869 | TSESDYY | 593 | QEAYKQQN | 594 | AYRSSTGNQFY | 595 | MDHEN | 601 | SYDVKM | 602 | ASSLWGTNEKLF | 603 |

TABLE 3

Nucleic acid CDR sequences for Veloci-T ® TCRs specific for MAGE-A4 (286-294)/HLA-A2

| TCR No. | TCR ID | Vα CDR1 | SEQ ID NO | Vα CDR2 | SEQ ID NO | Vα CDR3 | SEQ ID NO: | Vβ CDR1 | SEQ ID NO | Vβ CDR2 | SEQ ID NO | Vβ CDR3 | SEQ ID NO: |
|---|---|---|---|---|---|---|---|---|---|---|---|---|---|
| 1 | PN41475 | ACCAGTGAGAGTGATTATTAT | 4 | CAAGAAGCTTATAAGCAACAGAAT | 5 | GCTTATAGGAGCGCGACCGGTAACCAGTTCTAT | 6 | ATGGACCATGAAAAT | 12 | TCATATGATGTTAAAATG | 13 | GCCAGCAGTTTATGGGGCAGTAACACTGAAGCTTTC | 14 |
| 2 | PN41494 | ACCAGTGAGAGTGATTATTAT | 20 | CAAGAAGCTTATAAGCAACAGAAT | 21 | GCTTATAGGAGCGCGACCGGTAACCAGTTCTAT | 22 | ATGGACCATGAAAAT | 28 | TCATATGATGTTAAAATG | 29 | GCCAGCAGTTTATGGGGGTGGAATTCACCCCTCCAC | 30 |
| 3 | PN41513 | ACCAGTGAGAGTGATTATTAT | 36 | CAAGAAGCTTATAAGCAACAGAAT | 37 | GCTTATAGGAGCGCTCCCGGTAACCAGTTCTAT | 38 | ATGGACCATGAAAAT | 44 | TCATATGATGTTAAAATG | 45 | GCCAGCAGTTTATTTGCAACTAATGAAAAACTGTTT | 46 |
| 4 | PN41516 | AGTGTTTTTTCCAGC | 52 | GTAGTTACGGGTGGAGAAGTG | 53 | GCAGGAGAGAGGGACAGCTGGGGGAAATTCCAG | 54 | ATGAACCATAACTAC | 60 | TCAGTTGGTGCTGGTATC | 61 | GCCAGCAGTTTTTGGACAGGGGGCGATGAAAAACTGTTT | 62 |
| 5 | PN41518 | ACCAGTGAGAGTGATTATTAT | 68 | CAAGAAGCTTATAAGCAACAGAAT | 69 | GCTTATAGGAGCGCGCCCGGTAACCAGTTCTAT | 70 | ATGGACCATGAAAAT | 76 | TCATATGATGTTAAAATG | 77 | GCCAGCAGTTTATGGGCAACTAATGAAAAACTGTTT | 78 |
| 6 | PN41520 | ACCAGTGAGAGTGATTATTAT | 84 | CAAGAAGCTTATAAGCAACAGAAT | 85 | GCTTATAGGAGCGCTCGGGGTAACCAGTTCTAT | 86 | ATGGACCATGAAAA | 92 | TCATATGATGTTAAAATG | 93 | GCCAGCAGTTTATGGGGGGTAAATTCACCCCTCCAC | 94 |
| 7 | PN41523 | ACCAGTGAGAGTGATTATTAT | 100 | CAAGAAGCTTATAAGCAACAGAAT | 101 | GCTTATAGGAGCGCGCCCGGTAACCAGTTCTAT | 102 | ATGGACCATGAAAAT | 108 | TCATATGATGTTAAAATG | 109 | GCCAGCAGTTTATGGGGGTTGAACACTGAAGCTTTC | 110 |
| 8 | PN41532 | ACCAGTGAGAGTGATTATTAT | 116 | CAAGAAGCTTATAAGCAACAGAAT | 117 | GCTTATAGGAGCGCGGAGGGTAACCAGTTCTAT | 118 | ATGGACCATGAAAAT | 124 | TCATATGATGTTAAAATG | 125 | GCCAGCAGTTTATGGGGGTTGAACACTGAAGCTTTC | 126 |
| 9 | PN41539 | ACCCGTGATACTACTTATTAC | 132 | CGGAACTCTTTTGATGAGCAAAAT | 133 | GCTCTGAGTGAGGGGGATACTGGAGGCTTCAAAACTATC | 134 | ATGAACCATAACTAC | 140 | TCAGTTGGTGCTGGTATC | 141 | GCCAGCAGTTACTTCCCGGACAGGGGGCTTGGAAACACCATATAT | 142 |

TABLE 3-continued

Nucleic acid CDR sequences for Veloci-T ® TCRs specific for MAGE-A4 (286-294)/HLA-A2

| TCR No. | TCR ID | Vα CDR1 | SEQ ID NO | Vα CDR2 | SEQ ID NO | Vα CDR3 | SEQ ID NO: | Vβ CDR1 | SEQ ID NO | Vβ CDR2 | SEQ ID NO | Vβ CDR3 | SEQ ID NO: |
|---|---|---|---|---|---|---|---|---|---|---|---|---|---|
| 10 | PN41550 | GACCGAGGTTCCCAGTCC | 148 | ATATACTCCAATGGTGAC | 149 | GCCGTGAACTTGAGCTGGGGGAAATTCCAG | 150 | TCTGGGCATGACACT | 156 | TATTATGAGGAGGAAGAG | 157 | GCCAGCAGCTTGGACAGGAGCACTGAAGCTTTC | 158 |
| 11 | PN41557 | GTCAGCGGTTTAAGAGGG | 164 | CTGTATTCAGCTGGGGAAGAA | 165 | GCTGTGCAGGCGGTCACGGGAGGAGGAAACAAACTCACC | 166 | GACTTTCAGGCCACAACT | 172 | TCCAATGAGGGCTCCAAGGCC | 173 | AGTGCTAGTTGGGACAGGGACTATGGCTACACC | 174 |
| 12 | PN41559 | ACCAGTGAGAGTGATTATTAT | 180 | CAAGAAGCTTATAAGCAACAGAAT | 181 | GCTTATAGGAGCGCCACCGGTAACCAGTTCTAT | 182 | ATGGACCATGAAAAT | 188 | TCATATGATGTTAAAATG | 189 | GCCAGCAGTTTATGGGGTTGGGGCACTGAAGCTTTC | 190 |
| 13 | PN41565 | ACCAGTGAGAGTGATTATTAT | 196 | CAAGAAGCTTATAAGCAACAGAAT | 197 | GCTTATAGGAGCCCCACCGGTAACCAGTTCTAT | 198 | ATGGACCATGAAAAT | 204 | TCATATGATGTTAAAATG | 205 | GCCAGCAGTTTATGGGCAATGAACACTGAAGCTTTC | 206 |
| 14 | PN41568 | ACCAGTGAGAGTGATTATTAT | 212 | CAAGAAGCTTATAAGCAACAGAAT | 213 | GCTTATAGGAGCGCGCGGGGTAACCAGTTCTAT | 214 | ATGGACCATGAAAAT | 220 | TCATATGATGTTAAAATG | 221 | GCCAGCAGTTTATGGGGGACTAATGAAAAACTGTTT | 222 |
| 15 | PN41573 | ACCAGTGAGAGTGATTATTAT | 228 | CAAGAAGCTTATAAGCAACAGAAT | 229 | GCTTATAGGAGCGCAACCGGTAACCAGTTCTAT | 230 | ATGGACCATGAAAAT | 236 | TCATATGATGTTAAAATG | 237 | GCCAGCAGTTTGTGGGGAACTAATGAAAAACTGTTT | 238 |
| 16 | PN41577 | ACCAGTGAGAGTGATTATTAT | 244 | CAAGAAGCTTATAAGCAACAGAAT | 245 | GCTTATAGGAGCGCGCCCGGTAACCAGTTCTAT | 246 | ATGGACCATGAAAAT | 252 | TCATATGATGTTAAAATG | 253 | GCCAGCAGTTTATGGGGGACTAATGAAAAACTGTTT | 254 |
| 17 | PN41607 | ACCAGTGAGAGTGATTATTAT | 260 | CAAGAAGCTTATAAGCAACAGAAT | 261 | GCTTATAGGAGCGCGTCCGGTAACCAGTTCTAT | 262 | ATGGACCATGAAAAT | 268 | TCATATGATGTTAAAATG | 269 | GCCAGCAGTTTATGGGGCACTAATGAAAAACTGTTT | 270 |
| 18 | PN41608 | ACCAGTGAGAGTGATTATTAT | 276 | CAAGAAGCTTATAAGCAACAGAAT | 277 | GCTTATAGGAGCGCGCCCGGTAACCAGTTCTAT | 278 | ATGGACCATGAAAAT | 284 | TCATATGATGTTAAAATG | 285 | GCCAGCAGTTTCTGGGGATGGAACACTGAAGCTTTC | 286 |
| 19 | PN41613 | ACCAGTGAGAGTGATTATTAT | 292 | CAAGAAGCTTATAAGCAACAGAAT | 293 | GCTTATAGGAGCGCGACCGGTAACCAGTTCTAT | 294 | ATGAACCATGAGTAT | 300 | TCAATGAATGTTGAGGTG | 301 | GCCAGCAGTTTACTGTATAGCAATCAGCCCCAGCAT | 302 |

TABLE 3-continued

| Nucleic acid CDR sequences for Veloci-T ® TCRs specific for MAGE-A4 (286-294)/HLA-A2 | | | | | | | | | | | | | | |
|---|---|---|---|---|---|---|---|---|---|---|---|---|---|---|
| TCR No. | TCR ID | Vα CDR1 | SEQ ID NO | Vα CDR2 | SEQ ID NO | Vα CDR3 | SEQ ID NO: | Vβ CDR1 | SEQ ID NO | Vβ CDR2 | SEQ ID NO | Vβ CDR3 | SEQ ID NO: |
| 20 | PN41617 | ACCAGTGAGAGTGATTATTAT | 308 | CAAGAAGCTTATAAGCAACAGAAT | 309 | GCTTATAGGAGCGCGTCCGGTAACCAGTTCTAT | 310 | ATGGACCATGAAAAT | 316 | TCATATGATGTTAAAATG | 317 | GCCAGCAGTTTATGGGGGATGAACACTGAAGCTTTC | 318 |
| 21 | PN41636 | TCCAGCAATTTTTATGCC | 324 | ATGACTTTAAATGGGGATGAA | 325 | GCCCTGAACAGAGATGACAAGATCATC | 326 | AAGGGTCATGATAGA | 332 | TCCTTTGATGTCAAAGAT | 333 | GCCACCAGTGATCCTCAGAGAAATCAGCCCCAGCAT | 334 |
| 22 | PN41654 | AACAGCGCCTCAGACTAC | 340 | ATTCGTTCAAATATGGACAAA | 341 | GCAGAGAAGAGGGATAACTATGGTCAGAATTTTGTC | 342 | ATGGACCATGAAAAT | 348 | TCATATGATGTTAAAATG | 349 | GCCAGCAGTTTATACAGCTATGGCTACACC | 350 |
| 23 | PN41656 | ACCAGTGATCCAAGTTATGGT | 356 | CAGGGGTCTTATGACCAGCAAAAT | 357 | GCAATGAGAGACCTTACTACCTCAGGAACCTACAAATACATC | 358 | ATGGACCATGAAAAT | 364 | TCATATGATGTTAAAATG | 365 | GCCAGCAGTTTCGGGGGCTGGGGCTATGGCTACACC | 366 |
| 24 | PN41690 | ACCAGTGAGAGTGATTATTAT | 372 | CAAGAAGCTTATAAGCAACAGAAT | 373 | GCTTATAGGAGCGCGATCGGTAACCAGTTCTAT | 374 | ATGGACCATGAAAAT | 380 | TCATATGATGTTAAAATG | 381 | GCCAGCAGTTTATGGGGTGTGAACACTGAAGCTTTC | 382 |
| 25 | PN41702 | ACCAGTGAGAGTGATTATTAT | 388 | CAAGAAGCTTATAAGCAACAGAAT | 389 | GCTTATAGGAGCGCGACCGGTAACCAGTTCTAT | 390 | ATGGACCATGAAAAT | 396 | TCATATGATGTTAAAATG | 397 | GCCAGCAGTTTATGGGCCGTTAATGAAAAACTGTTT | 398 |
| 26 | PN41703 | ACCATCAGTGGAAATGAGTAT | 404 | GGTCTAAAAAACAAT | 405 | ATCGTCAGACCGGGGGGAACCTACAAATACATC | 406 | ATGGACCATGAAAAT | 412 | TCATATGATGTTAAAATG | 413 | GCGACCGGGGGTGACAATCAGCCCCAGCAT | 414 |
| 27 | PN41712 | ACCAGTGAGAATAATTATTAT | 420 | CAAGAAGCTTATAAGCAACAGAAT | 421 | GCCCTCAACACCGGTAACCAGTTCTAT | 422 | GACTTTCAGGCCACAACT | 428 | TCCAATGAGGGCTCCAAGGCC | 429 | AGTGCCTGGGACGGATTCTATGGCTACACC | 430 |
| 28 | PN41746 | ACCAGTGAGAGTGATTATTAT | 436 | CAAGAAGCTTATAAGCAACAGAAT | 437 | GCTTATAGGAGCGCGACCGGTAACCAGTTCTAT | 438 | ATGGACCATGAAAAT | 444 | TCATATGATGTTAAAATG | 445 | GCCAGCAGTTTATGGGGCTTAAACACTGAAGCTTTC | 446 |
| 29 | PN41748 | AAGACGTTATATGGC | 452 | CTACAGAAAGGTGGGGAAGAG | 453 | GGAGCAGACATGTATTCAGGAGGAGGTGCTGACGGACTCACC | 454 | GACTTTCAGGCCACAACT | 460 | TCCAATGAGGGCTCCAAGGCC | 461 | AGTGCCTGGGACGGATTCTATGGCTACACC | 462 |

TABLE 3-continued

| TCR No. | TCR ID | Vα CDR1 | SEQ ID NO | Vα CDR2 | SEQ ID NO | Vα CDR3 | SEQ ID NO: | Vβ CDR1 | SEQ ID NO | Vβ CDR2 | SEQ ID NO | Vβ CDR3 | SEQ ID NO: |
|---|---|---|---|---|---|---|---|---|---|---|---|---|---|
| Nucleic acid CDR sequences for Veloci-T ® TCRs specific for MAGE-A4 (286-294)/HLA-A2 | | | | | | | | | | | | | |
| 30 | PN41805 | ACCAGTGAGAATAATTATTAT | 468 | CAAGAAGCTTATAAGCAACAGAAT | 469 | GCTTTCGGTATGTATTCAGGAGGAGGTGCTGACGGACTCACC | 470 | CCTAGACACGACACT | 476 | TTTTATGAAAAGATGCAG | 477 | GCCAGCAGCCCTACCGGGACAGGGGATGGCTACACC | 478 |
| 31 | PN41820 | TCGTCTGTTCCACCATAT | 484 | TACACAACAGGGGCCACCCTGGTT | 485 | GCTGTGAGTTCTGGTTCTGCAAGGCAACTGACC | 486 | ATGGACCATGAAAAT | 492 | TCATATGATGTTAAAATG | 493 | GCCAGCAGTCATGACAGGTGGGACTATGGCTACACC | 494 |
| 32 | PN41822 | ACCAGTGAGAGTGATTATTAT | 500 | CAAGAAGCTTATAAGCAACAGAAT | 501 | GCTTATAGGAGCGCCACCGGTAACCAGTTCTAT | 502 | ATGGACCATGAAAAT | 508 | TCATATGATGTTAAAATG | 509 | GCCAGCAGTTTGTGGGCATTGAACACTGAAGCTTTC | 510 |
| 33 | PN41829 | ACCAGTGAGAGTGATTATTAT | 516 | CAAGAAGCTTATAAGCAACAGAAT | 517 | GCTTATAGGAGCGCGACCGGTAACCAGTTCTAT | 518 | ATGGACCATGAAAAT | 524 | TCATATGATGTTAAAATG | 525 | GCCAGCAGTTTATTCGCATTGAACACTGAAGCTTTC | 526 |
| 34 | PN41839 | ACCATCAGTGGAAATGAGTAT | 532 | GGTCTAAAAAACAAT | 533 | ATCGTTTATGGAGGAAGCCAAGGAAATCTCATC | 534 | TCTGGGCATGACACT | 540 | TATTATGAGGAGGAAGAG | 541 | GCCAGCAGCTTCAGCAGGGTCCAGCCCCAGCAT | 542 |
| 35 | PN41852 | ACCAGTGAGAGTGATTATTAT | 548 | CAAGAAGCTTATAAGCAACAGAAT | 549 | GCTTATAGGAGCGCGTTGGGCAATGACATGCGC | 550 | ATGGACCATGAAAAT | 556 | TCATATGATGTTAAAATG | 557 | GCCAGCAGTTTATGGGCACTGAACACTGAAGCTTTC | 558 |
| 36 | PN41867 | ACCAGTGAGAATAATTATTAT | 564 | CAAGAAGCTTATAAGCAACAGAAT | 565 | GCTTTCATGAAAACTCAGGGCGGATCTGAAAAGCTGGTC | 566 | CCTAGACACGACACT | 572 | TTTTATGAAAAGATGCAG | 573 | GCCAGCAGCTTAGTTGGGTATGGCTACACC | 574 |
| 37 | PN41868 | ACCAGTGAGAGTGATTATTAT | 580 | CAAGAAGCTTATAAGCAACAGAAT | 581 | GCTTATAGGAGCGCAACCGGTAACCAGTTCTAT | 582 | ATGGACCATGAAAAT | 588 | TCATATGATGTTAAAATG | 589 | GCCAGCAGTTTATGGGGGACACATGAAAAACTGTTT | 590 |
| 38 | PN41869 | ACCAGTGAGAGTGATTATTAT | 596 | CAAGAAGCTTATAAGCAACAGAAT | 597 | GCTTATAGGAGCTCCACCGGTAACCAGTTCTAT | 598 | ATGGACCATGAAAAT | 604 | TCATATGATGTTAAAATG | 605 | GCCAGCAGTTTATGGGGAACTAATGAAAAACTGTTT | 606 |

TABLE 4

Amino acid and nucleic acid sequences for Veloci ® TCRs specific for MAGE-A4 (286-294)/HLA-A2

| TCR name<br>Domain<br>name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
| PN41475<br>Vα | AQTVTQSQPEMSVQEAETVTLSCTYDTSESDYYLFWYKQPPSRQMILVIR<br>QEAYKQQNATVNRFSVNFQKAAKSFSLKISDSQLGDAAMYFCAYRSATG<br>NQFYFGTGTSLTVIP (SEQ ID NO: 7)<br>GCTCAGACAGTCACTCAGTCTCAACCAGAGATGTCTGTGCAGGAGGCA<br>GAGACCGTGACCCTGAGCTGCACATATGACACCAGTGAGAGTGATTAT<br>TATTTATTCTGGTACAAGCAGCCTCCCAGCAGGCAGATGATTCTCGTT<br>ATTCGCCAAGAAGCTTATAAGCAACAGAATGCAACAGTGAATCGTTTC<br>TCTGTGAACTTCCAGAAAGCAGCCAAATCCTTCAGTCTCAAGATCTCA<br>GACTCACAGCTGGGGGATGCCGCGATGTATTTCTGTGCTTATAGGAGC<br>GCGACCGGTAACCAGTTCTATTTTGGGACAGGGACAAGTTTGACGGTC<br>ATTCCA (SEQ ID NO: 8) |
| PN41475<br>Vβ | DVKVTQSSRYLVKRTGEKVFLECVQDMDHENMFWYRQDPGLGLRLIYF<br>SYDVKMKEKGDIPEGYSVSREKKERFSLILESASTNQTSMYLCASSLWGS<br>NTEAFFGQGTRLTVV (SEQ ID NO: 15)<br>GATGTGAAAGTAACCCAGAGCTCGAGATATCTAGTCAAAAGGACGGG<br>AGAGAAAGTTTTTCTGGAATGTGTCCAGGATATGGACCATGAAAATAT<br>GTTCTGGTATCGACAAGACCCAGGTCTGGGGCTACGGCTGATCTATTT<br>CTCATATGATGTTAAAATGAAAGAAAAAGGAGATATTCCTGAGGGGT<br>ACAGTGTCTCTAGAGAGAAGAAGGAGCGCTTCTCCCTGATTCTGGAGT<br>CCGCCAGCACCAACCAGACATCTATGTACCTCTGTGCCAGCAGTTTAT<br>GGGGCAGTAACACTGAAGCTTTCTTTGGACAAGGCACCAGACTCACA<br>GTTGTA (SEQ ID NO: 16) |
| PN41494<br>Vα | AQTVTQSQPEMSVQEAETVTLSCTYDTSESDYYLFWYKQPPSRQMILVIR<br>QEAYKQQNATENRFSVNFQKAAKSFSLKISDSQLGDAAMYFCAYRSATG<br>NQFYFGTGTSLTVIP (SEQ ID NO: 23)<br>GCTCAGACAGTCACTCAGTCTCAACCAGAGATGTCTGTGCAGGAGGCA<br>GAGACCGTGACCCTGAGCTGCACATATGACACCAGTGAGAGTGATTAT<br>TATTTATTCTGGTACAAGCAGCCTCCCAGCAGGCAGATGATTCTCGTT<br>ATTCGCCAAGAAGCTTATAAGCAACAGAATGCAACAGAGAATCGTTT<br>CTCTGTGAACTTCCAGAAGGCAGCCAAATCCTTCAGTCTCAAGATCTC<br>AGACTCACAGCTGGGGGATGCCGCGATGTATTTCTGTGCTTATAGGAG<br>CGCGACCGGTAACCAGTTCTATTTTGGGACAGGGACAAGTTTGACGGT<br>CATTCCA (SEQ ID NO: 24) |
| PN41494<br>Vβ | DVKVTQSSRYLVKRTGEKVFLECVQDMDHENMFWYRQDPGLGLRLIYF<br>SYDVKMKEKGDIPEGYSVSREKKERFSLILESASTNQTSMYLCASSLWGW<br>NSPLHFGNGTRLTVT (SEQ ID NO: 31)<br>GATGTGAAAGTAACCCAGAGCTCGAGATATCTAGTCAAAAGGACGGG<br>AGAGAAAGTTTTTCTGGAATGTGTCCAGGATATGGACCATGAAAATAT<br>GTTCTGGTATCGACAAGACCCAGGTCTGGGGCTACGGCTGATCTATTT<br>CTCATATGATGTTAAAATGAAAGAAAAAGGAGATATTCCTGAGGGGT<br>ACAGTGTCTCTAGAGAGAAGAAGGAGCGCTTCTCCCTGATTCTGGAGT<br>CCGCCAGCACCAACCAGACATCTATGTACCTCTGTGCCAGCAGTTTAT<br>GGGGGTGGAATTCACCCCTCCACTTTGGGAACGGGACCAGGCTCACTG<br>TGACA (SEQ ID NO: 32) |
| PN41513<br>Vα | AQTVTQSQPEMSVQEAETVTLSCTYDTSESDYYLFWYKQPPSRQMILVIR<br>QEAYKQQNATENRFSVNFQKAAKSFSLKISDSQLGDAAMYFCAYRSAPG<br>NQFYFGTGTSLTVIP (SEQ ID NO: 39)<br>GCTCAGACAGTCACTCAGTCTCAACCAGAGATGTCTGTGCAGGAGGCA<br>GAGACCGTGACCCTGAGCTGCACATATGACACCAGTGAGAGTGATTAT<br>TATTTATTCTGGTACAAGCAGCCTCCCAGCAGGCAGATGATTCTCGTT<br>ATTCGCCAAGAAGCTTATAAGCAACAGAATGCAACAGAGAATCGTTT<br>CTCTGTGAACTTCCAGAAAGCAGCCAAATCCTTCAGTCTCAAGATCTC<br>AGACTCACAGCTGGGGGATGCCGCGATGTATTTCTGTGCTTATAGGAG<br>CGCTCCCGGTAACCAGTTCTATTTTGGGACAGGGACAAGTTTGACGGT<br>CATTCCA (SEQ ID NO: 40) |
| PN41513<br>Vβ | DVKVTQSSRYLVKRTGEKVFLECVQDMDHENMFWYRQDPGLGLRLIYF<br>SYDVKMKEKGDIPEGYSVSREKKERFSLILESASTNQTSMYLCASSLFATN<br>EKLFFGSGTQLSVL (SEQ ID NO: 47)<br>GATGTGAAAGTAACCCAGAGCTCGAGATATCTAGTCAAAAGGACGGG<br>AGAGAAAGTTTTTCTGGAATGTGTCCAGGATATGGACCATGAAAATAT<br>GTTCTGGTATCGACAAGACCCAGGTCTGGGGCTACGGCTGATCTATTT<br>CTCATATGATGTTAAAATGAAAGAAAAAGGAGATATTCCTGAGGGGT<br>ACAGTGTCTCTAGAGAGAAGAAGGAGCGCTTCTCCCTGATTCTGGAGT<br>CCGCCAGCACCAACCAGACATCTATGTACCTCTGTGCCAGCAGTTTAT<br>TTGCAACTAATGAAAAACTGTTTTTGGCAGTGGAACCCAGCTCTCTG<br>TCTTG (SEQ ID NO: 48) |

TABLE 4-continued

Amino acid and nucleic acid sequences for Veloci ® TCRs specific for MAGE-A4 (286-294)/HLA-A2

| TCR name Domain name | Domain Sequences Amino Acid Sequence (SEQ ID NO); CDR1, CDR2, and CDR3 sequences are underlined Nucleic Acid Sequence (SEQ ID NO); CDR1, CDR2, and CDR3 sequences are underlined |
|---|---|
| PN41516 Vα | TQLLEQSPQFLSIQEGENLTVYCNSSSVFSSLQWYRQEPGEGPVLLVTVVTGGEVKKLKRLTFQFGDARKDSSLHITAAQPGDTGLYLCAGERDSWGKFQFGAGTQVVVTP (SEQ ID NO: 55) ACCCAGCTGCTGGAGCAGAGCCCTCAGTTTCTAAGCATCCAAGAGGGAGAAAATCTCACTGTGTACTGCAACTCCTCAAGTGTTTTTTCCAGCTTACAATGGTACAGACAGGAGCCTGGGGAAGGTCCTGTCCTCCTGGTGACAGTAGTTACGGGTGGAGAAGTGAAGAAGCTGAAGAGACTAACCTTTCAGTTTGGTGATGCAAGAAAGGACAGTTCTCTCCACATCACTGCGGCCCAGCCTGGTGATACAGGCCTCTACCTCTGTGCAGGAGAGAGGGACAGCTGGGGGAAATTCCAGTTTGGAGCAGGGACCCAGGTTGTGGTCACCCCA (SEQ ID NO: 56) |
| PN41516 Vβ | NAGVTQTPKFRILKIGQSMTLQCAQDMNHNYMYWYRQDPGMGLKLIYYSVGAGITDKGEVPNGYNVSRSTTEYFPLRLELAAPSQTSVYFCASSFWTGGDEKLFFGSGTQLSVL (SEQ ID NO: 63) AATGCTGGTGTCACTCAGACCCCAAAATTCCGCATCCTGAAGATAGGACAGAGCATGACACTGCAGTGTGCCCAGGATATGAACCATAACTACATGTACTGGTATCGACAAGACCCAGGCATGGGGCTGAAGCTGATTTATTATTCAGTTGGTGCTGGTATCACTGATAAAGGAGAAGTCCCGAATGGCTACAACGTCTCCAGATCAACCACAGAGTATTTCCCGCTCAGGCTGGAGTTGGCTGCTCCCTCCCAGACATCTGTGTACTTCTGTGCCAGCAGTTTTTGGACAGGGGGCGATGAAAAACTGTTTTTTGGCAGTGGAACCCAGCTCTCTGTCTTG (SEQ ID NO: 64) |
| PN41518 Vα | AQTVTQSQPEMSVQEAETVTLSCTYDTSESDYYLFWYKQPPSRQMILVIRQEAYKQQNATENRFSVNFQKAAKSFSLKISDSQLGDAAMYFCAYRSAPGNQFYFGTGTSLTVIP (SEQ ID NO: 71) GCTCAGACAGTCACTCAGTCTCAACCAGAGATGTCTGTGCAGGAGGCAGAGACCGTGACCCTGAGCTGCACATATGACACCAGTGAGAGTGATTATTATTTATTCTGGTACAAGCAGCCTCCCAGCAGGCAGATGATTCTCGTTATTCGCCAAGAAGCTTATAAGCAACAGAATGCAACAGAGAATCGTTTCTCTGTGAACTTCCAGAAAGCAGCCAAATCCTTCAGTCTCAAGATCTCAGACTCACAGCTGGGGGATGCCGCGATGTATTTCTGTGCTTATAGGAGCGCGCCCGGTAACCAGTTCTATTTTGGGACAGGGACAAGTTTGACGGTCATTCCA (SEQ ID NO: 72) |
| PN41518 Vβ | DVKVTQSSRYLVKRTGEKVFLECVQDMDHENMFWYRQDPGLGLRLIYFSYDVKMKEKGDIPEGYSVSREKKERFSLILESASTNQTSMYLCASSLWATNEKLFFGSGTQLSVL (SEQ ID NO: 79) GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATTCTGGAGTCCGCCAGCACCAACCAGACATCTATGTACCTCTGTGCCAGCAGTTTATGGGCAACTAATGAAAAACTGTTTTTTGGCAGTGGAACCCAGCTCTCTGTCTTG (SEQ ID NO: 80) |
| PN41520 Vα | AQTVTQSQPEMSVQEAETVTLSCTYDTSESDYYLFWYKQPPSRQMILVIRQEAYKQQNATENRFSVNFQKAAKSFSLKISDSQLGDAAMYFCAYRSARGNQFYFGTGTSLTVIP (SEQ ID NO: 87) GCTCAGACAGTCACTCAGTCTCAACCAGAGATGTCTGTGCAGGAGGCAGAGACCGTGACCCTGAGCTGCACATATGACACCAGTGAGAGTGATTATTATTTATTCTGGTACAAGCAGCCTCCCAGCAGGCAGATGATTCTCGTTATTCGCCAAGAAGCTTATAAGCAACAGAATGCAACAGAGAATCGTTTCTCTGTGAACTTCCAGAAAGCAGCCAAATCCTTCAGTCTCAAGATCTCAGACTCACAGCTGGGGGATGCCGCGATGTATTTCTGTGCTTATAGGAGCGCTCGGGGTAACCAGTTCTATTTTGGGACAGGGACAAGTTTGACGGTCATTCCA (SEQ ID NO: 88) |
| PN41520 Vβ | DVKVTQSSRYLVKRTGEKVFLECVQDMDHENMFWYRQDPGLGLRLIYFSYDVKMKEKGDIPEGYSVSREKKERFSLILESASTNQTSMYLCASSLWGVNSPLHFGNGTRLTVT (SEQ ID NO: 95) GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATTCTGGAGT |

TABLE 4-continued

Amino acid and nucleic acid sequences for Veloci ® TCRs specific for MAGE-A4 (286-294)/HLA-A2

| TCR name Domain name | Domain Sequences Amino Acid Sequence (SEQ ID NO); CDR1, CDR2, and CDR3 sequences are underlined Nucleic Acid Sequence (SEQ ID NO); CDR1, CDR2, and CDR3 sequences are underlined |
|---|---|
| | CCGCCAGCACCAACCAGACATCTATGTACCTCTGTGCCAGCAGTTTATGGGGGGTAAATTCACCCCTCCACTTTGGGAACGGGACCAGGCTCACTGTGACA (SEQ ID NO: 96) |
| PN41523 Vα | AQTVTQSQPEMSVQEAETVTLSCTYDTSESDYYLFWYKQPPSRQMILVIRQEAYKQQNATENRFSVNFQKAAKSFSLKISDSQLGDAAMYFCAYRSAPGNQFYFGTGTSLT VIP (SEQ ID NO: 103) GCTCAGACAGTCACTCAGTCTCAACCAGAGATGTCTGTGCAGGAGGCAGAGACCGTGACCCTGAGCTGCACATATGACACCAGTGAGAGTGATTATTATTTATTCTGGTACAAGCAGCCTCCCAGCAGGCAGATGATTCTCGTTATTCGCCAAGAAGCTTATAAGCAACAGAATGCAACAGAGAATCGTTTCTCTGTGAACTTCCAGAAAGCAGCCAAATCCTTCAGTCTCAAGATCTCAGACTCACAGCTGGGGGATGCCGCGATGTATTTCTGTGCTTATAGGAGCGCGCCCGGTAACCAGTTCTATTTTGGGACAGGGACAAGTTTGACGGTCATTCCA (SEQ ID NO: 104) |
| PN41523 Vβ | DVKVTQSSRYLVKRTGEKVFLECVQDMDHENMFWYRQDPGLGLRLIYFSYDVKMKEKGDIPEGYSVSREKKERFSLILESASTNQTSMYLCASSLWGLNTEAFFGQGTRLTVV (SEQ ID NO: 111) GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATTCTGGAGTCCGCCAGCACCAACCAGACATCTATGTACCTCTGTGCCAGCAGTTTATGGGGGTTGAACACTGAAGCTTTCTTTGGACAAGGCACCAGACTCACAGTTGTA (SEQ ID NO: 112) |
| PN41532 Vα | AQTVTQSQPEMSVQEAETVTLSCTYDTSESDYYLFWYKQPPSRQMILVIRQEAYKQQNATENRFSVNFQKAAKSFSLKISDSQLGDAAMYFCAYRSAEGNQFYFGTGTSLT VIP (SEQ ID NO: 119) GCTCAGACAGTCACTCAGTCTCAACCAGAGATGTCTGTGCAGGAGGCAGAGACCGTGACCCTGAGCTGCACATATGACACCAGTGAGAGTGATTATTATTTATTCTGGTACAAGCAGCCTCCCAGCAGGCAGATGATTCTCGTTATTCGCCAAGAAGCTTATAAGCAACAGAATGCAACAGAGAATCGTTTCTCTGTGAACTTCCAGAAAGCAGCCAAATCCTTCAGTCTCAAGATCTCAGACTCACAGCTGGGGGATGCCGCGATGTATTTCTGTGCTTATAGGAGCGCGGAGGGTAACCAGTTCTATTTTGGGACAGGGACAAGTTTGACGGTCATTCCA (SEQ ID NO: 120) |
| PN41532 Vβ | DVKVTQSSRYLVKRTGEKVFLECVQDMDHENMFWYRQDPGLGLRLIYFSYDVKMKEKGDIPEGYSVSREKKERFSLILESASTNQTSMYLCASSLWGLNTEAFFGQGTRLTVV (SEQ ID NO: 127) GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATTCTGGAGTCCGCCAGCACCAACCAGACATCTATGTACCTCTGTGCCAGCAGTTTATGGGGGTTGAACACTGAAGCTTTCTTTGGACAAGGCACCAGACTCACAGTTGTA (SEQ ID NO: 128) |
| PN41539 Vα | AQKVTQAQTEISVVEKEDVTLDCVYETRDTTYYLFWYKQPPSGELVFLIRRNSFDEQNEISGRYSWNFQKSTSSFNFTITASQVVDSAVYFCALSEGDTGGFKTIFGAGTRLFVKA (SEQ ID NO: 135) GCTCAGAAGGTAACTCAAGCGCAGACTGAAATTTCTGTGGTGGAGAAGGAGGATGTGACCTTGGACTGTGTGTATGAAACCCGTGATACTACTTATTACTTATTCTGGTACAAGCAACCACCAAGTGGAGAATTGGTTTTCCTTATTCGTCGGAACTCTTTTGATGAGCAAAATGAAATAAGTGGTCGGTATTCTTGGAACTTCCAGAAATCCACCAGTTCCTTCAACTTCACCATCACAGCCTCACAAGTCGTGGACTCAGCAGTATACTTCTGTGCTCTGAGTGAGGGGGATACTGGAGGCTTCAAAACTATCTTTGGAGCAGGAACAAGACTATTTGTTAAAGCA (SEQ ID NO: 136) |
| PN41539 Vβ | NAGVTQTPKFRILKIGQSMTLQCAQDMNHNYMYWYRQDPGMGLKLIYYSVGAGITDKGEVPNGYNVSRSTTEYFPLRLELAAPSQTSVYFCASSYFPDRGLGNTIYFGEGSWLTVV (SEQ ID NO: 143) AATGCTGGTGTCACTCAGACCCCAAAATTCCGCATCCTGAAGATAGGACAGAGCATGACACTGCAGTGTGCCCAGGATATGAACCATAACTACATGTACTGGTATCGACAAGACCCAGGCATGGGGCTGAAGCTGATTTATTATTCAGTTGGTGCTGGTATCACTGATAAAGGAGAAGTCCCGAATGGCTA |

TABLE 4-continued

Amino acid and nucleic acid sequences for Veloci ® TCRs specific for MAGE-A4 (286-294)/HLA-A2

| TCR name Domain name | Domain Sequences Amino Acid Sequence (SEQ ID NO); CDR1, CDR2, and CDR3 sequences are underlined Nucleic Acid Sequence (SEQ ID NO); CDR1, CDR2, and CDR3 sequences are underlined |
|---|---|
| | CAACGTCTCCAGATCAACCACAGAGTATTTCCCGCTCAGGCTGGAGTTGGCTGCTCCCTCCCAGACATCTGTGTACTTCTGTGCCAGCAGTTACTTCCCGGACAGGGGGCTTGGAAACACCATATATTTTGGAGAGGGAAGTTGGCTCACTGTTGTA (SEQ ID NO: 144) |
| PN41550 Vα | QKEVEQNSGPLSVPEGAIASLNCTYSDRGSQSFFWYRQYSGKSPELIMSIYSNGDKEDGRFTAQLNKASQYVSLLIRDSQPSDSATYLCAVNLSWGKFQFGAGTQVVVTP (SEQ ID NO: 151)<br>CAGAAGGAGGTGGAGCAGAATTCTGGACCCCTCAGTGTTCCAGAGGGAGCCATTGCCTCTCTCAACTGCACTTACAGTGACCGAGGTTCCCAGTCCTTCTTCTGGTACAGACAATATTCTGGGAAAAGCCCTGAGTTGATAATGTCCATATACTCCAATGGTGACAAAGAAGATGGAAGGTTTACAGCACAGCTCAATAAAGCCAGCCAGTATGTTTCTCTGCTCATCAGAGACTCCCAGCCCAGTGATTCAGCCACCTACCTCTGTGCCGTGAACTTGAGCTGGGGGAAATTCCAGTTTGGAGCAGGGACCCAGGTTGTGGTCACCCCA (SEQ ID NO: 152) |
| PN41550 Vβ | DAGVTQSPTHLIKTRGQQVTLRCSPKSGHDTVSWYQQALGQGPQFIFQYYEEEERQRGNFPDRFSGHQFPNYSSELNVNALLLGDSALYLCASSLDRSTEAFFGQGTRLTVV (SEQ ID NO: 159)<br>GACGCTGGAGTCACCCAAAGTCCCACACACCTGATCAAAACGAGAGGACAGCAAGTGACTCTGAGATGCTCTCCTAAGTCTGGGCATGACACTGTGTCCTGGTACCAACAGGCCCTGGGTCAGGGGCCCCAGTTTATCTTTCAGTATTATGAGGAGGAAGAGAGACAGAGAGGCAACTTCCCTGATCGATTCTCAGGTCACCAGTTCCCTAACTATAGCTCTGAGCTGAATGTGAACGCCTTGTTGCTGGGGGACTCGGCCCTCTATCTCTGTGCCAGCAGCTTGGACAGGAGCACTGAAGCTTTCTTTGGACAAGGCACCAGACTCACAGTTGTA (SEQ ID NO: 160) |
| PN41557 Vα | EDQVTQSPEALRLQEGESSSLNCSYTVSGLRGLFWYRQDPGKGPEFLFTLYSAGEEKEKERLKATLTKKESFLHITAPKPEDSATYLCAVQAVTGGGNKLTFGTGTQLKVEL (SEQ ID NO: 167)<br>GAAGACCAGGTGACGCAGAGTCCCGAGGCCCTGAGACTCCAGGAGGGAGAGAGTAGCAGTCTCAACTGCAGTTACACAGTCAGCGGTTTAAGAGGGCTGTTCTGGTATAGGCAAGATCCTGGGAAAGGCCCTGAATTCCTCTTCACCCTGTATTCAGCTGGGGAAGAAAAGGAGAAAGAAAGGCTAAAAGCCACATTAACAAAGAAGGAAAGCTTTCTGCACATCACAGCCCCTAAACCTGAAGACTCAGCCACTTATCTCTGTGCTGTGCAGGCGGTCACGGGAGGAGGAAACAAACTCACCTTTGGGACAGGCACTCAGCTAAAAGTGGAACTC (SEQ ID NO: 168) |
| PN41557 Vβ | GAVVSQHPSWVICKSGTSVKIECRSLDFQATTMFWYRQFPKQSLMLMATSNEGSKATYEQGVEKDKFLINHASLTLSTLTVTSAHPEDSSFYICSASWDRDYGYTFGSGTRLTVV (SEQ ID NO: 175)<br>GGTGCTGTCGTCTCTCAACATCCGAGCTGGGTTATCTGTAAGAGTGGAACCTCTGTGAAGATCGAGTGCCGTTCCCTGGACTTTCAGGCCACAACTATGTTTTGGTATCGTCAGTTCCCGAAACAGAGTCTCATGCTGATGGCAACTTCCAATGAGGGCTCCAAGGCCACATACGAGCAAGGCGTCGAGAAGGACAAGTTTCTCATCAACCATGCAAGCCTGACCTTGTCCACTCTGACAGTGACCAGTGCCCATCCTGAAGACAGCAGCTTCTACATCTGCAGTGCTAGTTGGGACAGGGACTATGGCTACACCTTCGGTTCGGGGACCAGGTTAACCGTTGTA (SEQ ID NO: 176) |
| PN41559 Vα | AQTVTQSQPEMSVQEAETVTLSCTYDTSESDYYLFWYKQPPSRQMILVIRQEAYKQQNATENRFSVNFQKAAKSFSLKISDSQLGDAAMYFCAYRSATGNQFYFGTGTSLTVIP (SEQ ID NO: 183)<br>GCTCAGACAGTCACTCAGTCTCAACCAGAGATGTCTGTGCAGGAGGCAGAGACCGTGACCCTGAGCTGCACATATGACACCAGTGAGAGTGATTATTATTTATTCTGGTACAAGCAGCCTCCCAGCAGGCAGATGATTCTCGTTATTCGCCAAGAAGCTTATAAGCAACAGAATGCAACAGAGAATCGTTTCTCTGTGAACTTCCAGAAAGCAGCCAAATCCTTCAGTCTCAAGATCTCAGACTCACAGCTGGGGGATGCCGCGATGTATTTCTGTGCTTATAGGAGCGCCACCGGTAACCAGTTCTATTTTGGGACAGGGACAAGTTTGACGGTCATTCCA (SEQ ID NO: 184) |
| PN41559 Vβ | DVKVTQSSRYLVKRTGEKVFLECVQDMDHENMFWYRQDPGLGLRLIYFSYDVKMKEKGDIPEGYSVSREKKERFSLILESASTNQTSMYLCASSLWGWGTEAFFGQGTRLTVV (SEQ ID NO: 191)<br>GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTT |

TABLE 4-continued

Amino acid and nucleic acid sequences for Veloci ® TCRs specific for MAGE-A4 (286-294)/HLA-A2

| TCR name Domain name | Domain Sequences Amino Acid Sequence (SEQ ID NO); CDR1, CDR2, and CDR3 sequences are underlined Nucleic Acid Sequence (SEQ ID NO); CDR1, CDR2, and CDR3 sequences are underlined |
|---|---|
| | CTCATATGATGTTAAAATGAAAGAAAAAGGAGATATTCCTGAGGGGT ACAGTGTCTCTAGAGAGAAGAAGGAGCGCTTCTCCCTGATTCTGGAGT CCGCCAGCACCAACCAGACATCTATGTACCTCTGTGCCAGCAGTTTAT GGGGTTGGGGCACTGAAGCTTTCTTTGGACAAGGCACCAGACTCACAG TTGTA (SEQ ID NO: 192) |
| PN41565 Vα | AQTVTQSQPEMSVQEAETVTLSCTYDTSESDYYLFWYKQPPSRQMILVIR QEAYKQQNATENRFSVNFQKAAKSFSLKISDSQLGDAAMYFCAYRSPTG NQFYFGTGTSLTVIP (SEQ ID NO: 199) GCTCAGACAGTCACTCAGTCTCAACCAGAGATGTCTGTGCAGGAGGCA GAGACCGTGACCCTGAGCTGCACATATGACACCAGTGAGAGTGATTAT TATTTATTCTGGTACAAGCAGCCTCCCAGCAGGCAGATGATTCTCGTT ATTCGCCAAGAAGCTTATAAGCAACAGAATGCAACAGAGAATCGTTT CTCTGTGAACTTCCAGAAAGCAGCCAAATCCTTCAGTCTCAAGATCTC AGACTCACAGCTGGGGGATGCCGCGATGTATTTCTGTGCTTATAGGAG CCCCACCGGTAACCAGTTCTATTTTGGGACAGGGACAAGTTTGACGGT CATTCCA (SEQ ID NO: 200) |
| PN41565 Vβ | DVKVTQSSRYLVKRTGEKVFLECVQDMDHENMFWYRQDPGLGLRLIYF SYDVKMKEKGDIPEGYSVSREKKERFSLILESASTNQTSMYLCASSLWAM NTEAFFGQGTRLTVV (SEQ ID NO: 207) GATGTGAAAGTAACCCAGAGCTCGAGATATCTAGTCAAAAGGACGGG AGAGAAAGTTTTTCTGGAATGTGTCCAGGATATGGACCATGAAAATAT GTTCTGGTATCGACAAGACCCAGGTCTGGGGCTACGGCTGATCTATTT CTCATATGATGTTAAAATGAAAGAAAAAGGAGATATTCCTGAGGGGT ACAGTGTCTCTAGAGAGAAGAAGGAGCGCTTCTCCCTGATTCTGGAGT CCGCCAGCACCAACCAGACATCTATGTACCTCTGTGCCAGCAGTTTAT GGGCAATGAACACTGAAGCTTTCTTTGGACAAGGCACCAGACTCACA GTTGTA (SEQ ID NO: 208) |
| PN41568 Vα | AQTVTQSQPEMSVQEAETVTLSCTYDTSESDYYLFWYKQPPSRQMILVIR QEAYKQQNATENRFSVNFQKAAKSFSLKISDSQLGDAAMYFCAYRSARG NQFYFGTGTSLTVIP (SEQ ID NO: 215) GCTCAGACAGTCACTCAGTCTCAACCAGAGATGTCTGTGCAGGAGGCA GAGACCGTGACCCTGAGCTGCACATATGACACCAGTGAGAGTGATTAT TATTTATTCTGGTACAAGCAGCCTCCCAGCAGGCAGATGATTCTCGTT ATTCGCCAAGAAGCTTATAAGCAACAGAATGCAACAGAGAATCGTTT CTCTGTGAACTTCCAGAAAGCAGCCAAATCCTTCAGTCTCAAGATCTC AGACTCACAGCTGGGGGATGCCGCGATGTATTTCTGTGCTTATAGGAG CGCGCGGGGTAACCAGTTCTATTTTGGGACAGGGACAAGTTTGACGGT CATTCCA (SEQ ID NO: 216) |
| PN41568 Vβ | DVKVTQSSRYLVKRTGEKVFLECVQDMDHENMFWYRQDPGLGLRLIYF SYDVKMKEKGDIPEGYSVSREKKERFSLILESASTNQTSMYLCASSLWGT NEKLFFGSGTQLSVL (SEQ ID NO: 223) GATGTGAAAGTAACCCAGAGCTCGAGATATCTAGTCAAAAGGACGGG AGAGAAAGTTTTTCTGGAATGTGTCCAGGATATGGACCATGAAAATAT GTTCTGGTATCGACAAGACCCAGGTCTGGGGCTACGGCTGATCTATTT CTCATATGATGTTAAAATGAAAGAAAAAGGAGATATTCCTGAGGGGT ACAGTGTCTCTAGAGAGAAGAAGGAGCGCTTCTCCCTGATTCTGGAGT CCGCCAGCACCAACCAGACATCTATGTACCTCTGTGCCAGCAGTTTAT GGGGGACTAATGAAAAACTGTTTTTTGGCAGTGGAACCCAGCTCTCTG TCTTG (SEQ ID NO: 224) |
| PN41573 Vα | AQTVTQSQPEMSVQEAETVTLSCTYDTSESDYYLFWYKQPPSRQMILVIR QEAYKQQNATENRFSVNFQKAAKSFSLKISDSQLGDAAMYFCAYRSATG NQFYFGTGTSLTVIP (SEQ ID NO: 231) GCTCAGACAGTCACTCAGTCTCAACCAGAGATGTCTGTGCAGGAGGCA GAGACCGTGACCCTGAGCTGCACATATGACACCAGTGAGAGTGATTAT TATTTATTCTGGTACAAGCAGCCTCCCAGCAGGCAGATGATTCTCGTT ATTCGCCAAGAAGCTTATAAGCAACAGAATGCAACAGAGAATCGTTT CTCTGTGAACTTCCAGAAAGCAGCCAAATCCTTCAGTCTCAAGATCTC AGACTCACAGCTGGGGGATGCCGCGATGTATTTCTGTGCTTATAGGAG CGCAACCGGTAACCAGTTCTATTTTGGGACAGGGACAAGTTTGACGGT CATTCCA (SEQ ID NO: 232) |
| PN41573 Vβ | DVKVTQSSRYLVKRTGEKVFLECVQDMDHENMFWYRQDPGLGLRLIYF SYDVKMKEKGDIPEGYSVSREKKERFSLILESASTNQTSMYLCASSLWGT NEKLFFGSGTQLSVL (SEQ ID NO: 239) GATGTGAAAGTAACCCAGAGCTCGAGATATCTAGTCAAAAGGACGGG AGAGAAAGTTTTTCTGGAATGTGTCCAGGATATGGACCATGAAAATAT |

TABLE 4-continued

Amino acid and nucleic acid sequences for Veloci ® TCRs specific for MAGE-A4 (286-294)/HLA-A2

| TCR name Domain name | Domain Sequences Amino Acid Sequence (SEQ ID NO); CDR1, CDR2, and CDR3 sequences are underlined Nucleic Acid Sequence (SEQ ID NO); CDR1, CDR2, and CDR3 sequences are underlined |
|---|---|
| | GTTCTGGTATCGACAAGACCCAGGTCTGGGGCTACGGCTGATCTATTT CTCATATGATGTTAAAATGAAAGAAAAAGGAGATATTCCTGAGGGGT ACAGTGTCTCTAGAGAGAAGAAGGAGCGCTTCTCCCTGATTCTGGAGT CCGCCAGCACCAACCAGACATCTATGTACCTCTGTGCCAGCAGTTTGT GGGGAACTAATGAAAAACTGTTTTTTGGCAGTGGAACCCAGCTCTCTG TCTTG (SEQ ID NO: 240) |
| PN41577 Vα | AQTVTQSQPEMSVQEAETVTLSCTYDTSESDYYLFWYKQPPSRQMILVIR QEAYKQQNATENRFSVNFQKAAKSFSLKISDSQLGDAAMYFCAYRSAPG NQFYFGTGTSLTVIP (SEQ ID NO: 247) GCTCAGACAGTCACTCAGTCTCAACCAGAGATGTCTGTGCAGGAGGCA GAGACCGTGACCCTTAGCTGCACATATGACACCAGTGAGAGTGATTAT TATTTATTCTGGTACAAGCAGCCTCCCAGCAGGCAGATGATTCTCGTT ATTCGCCAAGAAGCTTATAAGCAACAGAATGCAACAGAGAATCGTTT CTCTGTGAACTTCCAGAAAGCAGCCAAATCCTTCAGTCTCAAGATCTC AGACTCACAGCTGGGGGATGCCGCGATGTATTTCTGTGCTTATAGGAG CGCGCCCGGTAACCAGTTCTATTTTGGGACAGGGACAAGTTTGACGGT CATTCCA (SEQ ID NO: 248) |
| PN41577 Vβ | DVKVTQSSRYLVKRTGEKVFLECVQDMDHENMFWYRQDPGLGLRLIYF SYDVKMKEKGDIPEGYSVSREKKERFSLILESASTNQTSMYLCASSLWGT NEKLFFGSGTQLSVL (SEQ ID NO: 255) GATGTGAAAGTAACCCAGAGCTCGAGATATCTAGTCAAAAGGACGGG AGAGAAAGTTTTTCTGGAATGTGTCCAGGATATGGACCATGAAAATAT GTTCTGGTATCGACAAGACCCAGGTCTGGGGCTACGGCTGATCTATTT CTCATATGATGTTAAAATGAAAGAAAAAGGAGATATTCCTGAGGGGT ACAGTGTCTCTAGAGAGAAGAAGGAGCGCTTCTCCCTGATTCTGGAGT CCGCCAGCACCAACCAGACATCTATGTACCTCTGTGCCAGCAGTTTAT GGGGGACTAATGAAAAACTGTTTTTTGGCAGTGGAACCCAGCTCTCTG TCTTG (SEQ ID NO: 256) |
| PN41607 Vα | AQTVTQSQPEMSVQEAETVTLSCTYDTSESDYYLFWYKQPPSRQMILVIR QEAYKQQNATENRFSVNFQKAAKSFSLKISDSQLGDAAMYFCAYRSASG NQFYFGTGTSLT VIP (SEQ ID NO: 263) GCTCAGACAGTCACTCAGTCTCAACCAGAGATGTCTGTGCAGGAGGCA GAGACCGTGACCCTGAGCTGCACATATGACACCAGTGAGAGTGATTAT TATTTATTCTGGTACAAGCAGCCTCCCAGCAGGCAGATGATTCTCGTT ATTCGCCAAGAAGCTTATAAGCAACAGAATGCAACAGAGAATCGTTT CTCTGTGAACTTCCAGAAAGCAGCCAAATCCTTCAGTCTCAAGATCTC AGACTCACAGCTGGGGGATGCCGCGATGTATTTCTGTGCTTATAGGAG CGCGTCCGGTAACCAGTTCTATTTTGGGACAGGGACAAGTTTGACGGT CATTCCA (SEQ ID NO: 264) |
| PN41607 Vβ | DVKVTQSSRYLVKRTGEKVFLECVQDMDHENMFWYRQDPGLGLRLIYF SYDVKMKEKGDIPEGYSVSREKKERFSLILESASTNQTSMYLCASSLWGT NEKLFFGSGTQLSVL (SEQ ID NO: 271) GATGTGAAAGTAACCCAGAGCTCGAGATATCTAGTCAAAAGGACGGG AGAGAAAGTTTTTCTGGAATGTGTCCAGGATATGGACCATGAAAATAT GTTCTGGTATCGACAAGACCCAGGTCTGGGGCTACGGCTGATCTATTT CTCATATGATGTTAAAATGAAAGAAAAAGGAGATATTCCTGAGGGGT ACAGTGTCTCTAGAGAGAAGAAGGAGCGCTTCTCCCTGATTCTGGAGT CCGCCAGCACCAACCAGACATCTATGTACCTCTGTGCCAGCAGTTTAT GGGGCACTAATGAAAAACTGTTTTTTGGCAGTGGAACCCAGCTCTCTG TCTTG (SEQ ID NO: 272) |
| PN41608 Vα | AQTVTQSQPEMSVQEAETVTLSCTYDTSESDYYLFWYKQPPSRQMILVIR QEAYKQQNATENRFSVNFQKAAKSFSLKISDSQLGDAAMYFCAYRSAPG NQFYFGTGTSLT VIP (SEQ ID NO: 279) GCTCAGACAGTCACTCAGTCTCAACCAGAGATGTCTGTGCAGGAGGCA GAGACCGTGACCCTGAGCTGCACATATGACACCAGTGAGAGTGATTAT TATTTATTCTGGTACAAGCAGCCTCCCAGCAGGCAGATGATTCTCGTT ATTCGCCAAGAAGCTTATAAGCAACAGAATGCAACAGAGAATCGTTT CTCTGTGAACTTCCAGAAAGCAGCCAAATCCTTCAGTCTCAAGATCTC AGACTCACAGCTGGGGGATGCCGCGATGTATTTCTGTGCTTATAGGAG CGCGCCCGGTAACCAGTTCTATTTTGGGACAGGGACAAGTTTGACGGT CATTCCA (SEQ ID NO: 280) |
| PN41608 Vβ | DVKVTQSSRYLVKRTGEKVFLECVQDMDHENMFWYRQDPGLGLRLIYF SYDVKMKEKGDIPEGYSVSREKKERFSLILESASTNQTSMYLCASSFWGW NTEAFFGQGTRLTVV (SEQ ID NO: 287) GATGTGAAAGTAACCCAGAGCTCGAGATATCTAGTCAAAAGGACGGG |

TABLE 4-continued

Amino acid and nucleic acid sequences for Veloci ® TCRs specific for MAGE-A4 (286-294)/HLA-A2

| TCR name Domain name | Domain Sequences Amino Acid Sequence (SEQ ID NO); CDR1, CDR2, and CDR3 sequences are underlined Nucleic Acid Sequence (SEQ ID NO); CDR1, CDR2, and CDR3 sequences are underlined |
|---|---|
| | AGAGAAAGTTTTTCTGGAATGTGTCCAGGATATGGACCATGAAAATAT GTTCTGGTATCGACAAGACCCAGGTCTGGGGCTACGGCTGATCTATTT CTCATATGATGTTAAAATGAAAGAAAAAGGAGATATTCCTGAGGGGT ACAGTGTCTCTAGAGAGAAGAAGGAGCGCTTCTCCCTGATTCTGGAGT CCGCCAGCACCAACCAGACATCTATGTACCTCTGTGCCAGCAGTTTCT GGGGATGGAACACTGAAGCTTTCTTTGGACAAGGCACCAGACTCACA GTTGTA (SEQ ID NO: 288) |
| PN41613 Vα | AQTVTQSQPEMSVQEAETVTLSCTYDTSESDYYLFWYKQPPSRQMILVIR QEAYKQQNATENRFSVNFQKAAKSFSLKISDSQLGDAAMYFCAYRSATG NQFYFGTGTSLT VIP (SEQ ID NO: 295) GCTCAGACAGTCACTCAGTCTCAACCAGAGATGTCTGTGCAGGAGGCA GAGACCGTGACCCTGAGCTGCACATATGACACCAGTGAGAGTGATTAT TATTTATTCTGGTACAAGCAGCCTCCCAGCAGGCAGATGATTCTCGTT ATTCGCCAAGAAGCTTATAAGCAACAGAATGCAACAGAGAATCGTTT CTCTGTGAACTTCCAGAAAGCAGCCAAATCCTTCAGTCTCAAGATCTC AGACTCACAGCTGGGGGATGCCGCGATGTATTTCTGTGCTTATAGGAG CGCGACCGGTAACCAGTTCTATTTTGGGACAGGGACAAGTTTGACGGT CATTCCA (SEQ ID NO: 296) |
| PN41613 Vβ | EAQVTQNPRYLITVTGKKLTVTCSQNMNHEYMSWYRQDPGLGLRQIYYS MNVEVTDKGDVPEGYKVSRKEKRNFPLILESPSPNQTSLYFCASSLLYSN QPQHFGDGTRLSIL (SEQ ID NO: 303) GAAGCCCAAGTGACCCAGAACCCAAGATACCTCATCACAGTGACTGG AAAGAAGTTAACAGTGACTTGTTCTCAGAATATGAACCATGAGTATAT GTCCTGGTATCGACAAGACCCAGGGCTGGGCTTAAGGCAGATCTACTA TTCAATGAATGTTGAGGTGACTGATAAGGGAGATGTTCCTGAAGGGTA CAAAGTCTCTCGAAAAGAGAAGAGGAATTTCCCCCTGATCCTGGAGTC GCCCAGCCCCAACCAGACCTCTCTGTACTTCTGTGCCAGCAGTTTACT GTATAGCAATCAGCCCCAGCATTTTGGTGATGGGACTCGACTCTCCAT CCTA (SEQ ID NO: 304) |
| PN41617 Vα | AQTVTQSQPEMSVQEAETVTLSCTYDTSESDYYLFWYKQPPSRQMILVIR QEAYKQQNATENRFSVNFQKAAKSFSLKISDSQLGDAAMYFCAYRSASG NQFYFGTGTSLTVIP (SEQ ID NO: 311) GCTCAGACAGTCACTCAGTCTCAACCAGAGATGTCTGTGCAGGAGGCA GAGACCGTGACCCTGAGCTGCACATATGACACCAGTGAGAGTGATTAT TATTTATTCTGGTACAAGCAGCCTCCCAGCAGGCAGATGATTCTCGTT ATTCGCCAAGAAGCTTATAAGCAACAGAATGCAACAGAGAATCGTTT CTCTGTGAACTTCCAGAAAGCAGCCAAATCCTTCAGTCTCAAGATCTC AGACTCACAGCTGGGGGATGCCGCGATGTATTTCTGTGCTTATAGGAG CGCGTCCGGTAACCAGTTCTATTTTGGGACAGGGACAAGTTTGACGGT CATTCCA (SEQ ID NO: 312) |
| PN41617 Vβ | DVKVTQSSRYLVKRTGEKVFLECVQDMDHENMFWYRQDPGLGLRLIYF SYDVKMKEKGDIPEGYSVSREKKERFSLILESASTNQTSMYLCASSLWGM NTEAFFGQGTRLTVV (SEQ ID NO: 319) GATGTGAAAGTAACCCAGAGCTCGAGATATCTAGTCAAAAGGACGGG AGAGAAAGTTTTTCTGGAATGTGTCCAGGATATGGACCATGAAAATAT GTTCTGGTATCGACAAGACCCAGGTCTGGGGCTACGGCTGATCTATTT CTCATATGATGTTAAAATGAAAGAAAAAGGAGATATTCCTGAGGGGT ACAGTGTCTCTAGAGAGAAGAAGGAGCGCTTCTCCCTGATTCTGGAGT CCGCCAGCACCAACCAGACATCTATGTACCTCTGTGCCAGCAGTTTAT GGGGGATGAACACTGAAGCTTTCTTTGGACAAGGCACCAGACTCACA GTTGTA (SEQ ID NO: 320) |
| PN41636 Vα | ILNVEQSPQSLHVQEGDSTNFTCSFPSSNFYALHWYRWETAKSPEALFVM TLNGDEKKKGRISATLNTKEGYSYLYIKGSQPEDSATYLCALNRDDKIIFG KGTRLHILP (SEQ ID NO: 327) ATACTGAACGTGGAACAAAGTCCTCAGTCACTGCATGTTCAGGAGGG AGACAGCACCAATTTCACCTGCAGCTTCCCTTCCAGCAATTTTTATGCC TTACACTGGTACAGATGGGAAACTGCAAAAAGCCCCGAGGCCTTGTTT GTAATGACTTTAAATGGGGATGAAAAGAAGAAAGGACGAATAAGTGC CACTCTTAATACCAAGGAGGGTTACAGCTATTTGTACATCAAAGGATC CCAGCCTGAAGACTCAGCCACATACCTCTGTGCCCTGAACAGAGATGA CAAGATCATCTTTGGAAAAGGGACACGACTTCATATTCTCCCC (SEQ ID NO: 328) |
| PN41636 Vβ | DADVTQTPRNRITKTGKRIMLECSQTKGHDRMYWYRQDPGLGLRLIYYS FDVKDINKGEISDGYSVSRQAQAKFSLSLESAIPNQTALYFCATSDPQRNQ PQHFGDGTRLSIL (SEQ ID NO: 335) |

TABLE 4-continued

Amino acid and nucleic acid sequences for Veloci ® TCRs specific for MAGE-A4 (286-294)/HLA-A2

| TCR name Domain name | Domain Sequences Amino Acid Sequence (SEQ ID NO); CDR1, CDR2, and CDR3 sequences are underlined Nucleic Acid Sequence (SEQ ID NO); CDR1, CDR2, and CDR3 sequences are underlined |
|---|---|
| | GATGCTGATGTTACCCAGACCCCAAGGAATAGGATCACAAAGACAGGAAAGAGGATTATGCTGGAATGTTCTCAGACTAAGGGTCATGATAGAATGTACTGGTATCGACAAGACCCAGGACTGGGCCTACGGTTGATCTATTACTCCTTTGATGTCAAAGATATAAACAAAGGAGAGATCTCTGATGGATACAGTGTCTCTCGACAGGCACAGGCTAAATTCTCCCTGTCCCTAGAGTCTGCCATCCCCAACCAGACAGCTCTTTACTTCTGTGCCACCAGTGATCCTCAGAGAAATCAGCCCCAGCATTTTGGTGATGGGACTCGACTCTCCATCCTA (SEQ ID NO: 336) |
| PN41654 Vα | GESVGLHLPTLSVQEGDNSIINCAYSNSASDYFIWYKQESGKGPQFIIDIRSNMDKRQGQRVTVLLNKTVKHLSLQIAATQPGDSAVYFCAEKRDNYGQNFVFGPGTRLSVLP (SEQ ID NO: 343) GGAGAGAGTGTGGGGCTGCATCTTCCTACCCTGAGTGTCCAGGAGGGTGACAACTCTATTATCAACTGTGCTTATTCAAACAGCGCCTCAGACTACTTCATTTGGTACAAGCAAGAATCTGGAAAAGGTCCTCAATTCATTATAGACATTCGTTCAAATATGGACAAAAGGCAAGGCCAAAGAGTCACCGTTTTATTGAATAAGACAGTGAAACATCTCTCTCTGCAAATTGCAGCTACTCAACCTGGAGACTCAGCTGTCTACTTTTGTGCAGAGAAGAGGGATAACTATGGTCAGAATTTTGTCTTTGGTCCCGGAACCAGATTGTCCGTGCTGCCC (SEQ ID NO: 344) |
| PN41654 Vβ | DVKVTQSSRYLVKRTGEKVFLECVQDMDHENMFWYRQDPGLGLRLIYFSYDVKMKEKGDIPEGYSVSREKKERFSLILESASTNQTSMYLCASSLYSYGYTFGSGTRLTVV (SEQ ID NO: 351) GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATTCTGGAGTCCGCCAGCACCAACCAGACATCTATGTACCTCTGTGCCAGCAGTTTATACAGCTATGGCTACACCTTCGGTTCGGGGACCAGGTTAACCGTTGTA (SEQ ID NO: 352) |
| PN41656 Vα | AQKITQTQPGMFVQEKEAVTLDCTYDTSDPSYGLFWYKQPSSGEMIFLIYQGSYDQQNATEGRYSLNFQKARKSANLVISASQLGDSAMYFCAMRDLTTSGTYKYIFGTGTRLKVLA (SEQ ID NO: 359) GCCCAGAAGATAACTCAAACCCAACCAGGAATGTTCGTGCAGGAAAAGGAGGCTGTGACTCTGGACTGCACATATGACACCAGTGATCCAAGTTATGGTCTATTCTGGTACAAGCAGCCCAGCAGTGGGGAAATGATTTTTCTTATTTATCAGGGGTCTTATGACCAGCAAAATGCAACAGAAGGTCGCTACTCATTGAATTTCCAGAAGGCAAGAAAATCCGCCAACCTTGTCATCTCCGCTTCACAACTGGGGGACTCAGCAATGTACTTCTGTGCAATGAGAGACCTTACTACCTCAGGAACCTACAAATACATCTTTGGAACAGGCACCAGGCTGAAGGTTTTAGCA (SEQ ID NO: 360) |
| PN41656 Vβ | DVKVTQSSRYLVKRTGEKVFLECVQDMDHENMFWYRQDPGLGLRLIYFSYDVKMKEKGDIPEGYSVSREKKERFSLILESASTNQTSMYLCASSFGGWGYGYTFGSGTRLTVV (SEQ ID NO: 367) GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATTCTGGAGTCCGCCAGCACCAACCAGACATCTATGTACCTCTGTGCCAGCAGTTTCGGGGGCTGGGGCTATGGCTACACCTTCGGTTCGGGGACCAGGTTAACCGTTGTA (SEQ ID NO: 368) |
| PN41690 Vα | AQTVTQSQPEMSVQEAETVTLSCTYDTSESDYYLFWYKQPPSRQMILVIRQEAYKQQNATENRFSVNFQKAAKSFSLKISDSQLGDAAMYFCAYRSAIGNQFYFGTGTSLTVIP (SEQ ID NO: 375) GCTCAGACAGTCACTCAGTCTCAACCAGAGATGTCTGTGCAGGAGGCAGAGACCGTGACCCTGAGCTGCACATATGACACCAGTGAGAGTGATTATTATTTATTCTGGTACAAGCAGCCTCCCAGCAGGCAGATGATTCTCGTTATTCGCCAAGAAGCTTATAAGCAACAGAATGCAACAGAGAATCGTTTCTCTGTGAACTTCCAGAAAGCAGCCAAATCCTTCAGTCTCAAGATCTCAGACTCACAGCTGGGGGATGCCGCGATGTATTTCTGTGCTTATAGGAGCGCGATCGGTAACCAGTTCTATTTTGGGACAGGGACAAGTTTGACGGTCATTCCA (SEQ ID NO: 376) |

TABLE 4-continued

Amino acid and nucleic acid sequences for Veloci ® TCRs specific for MAGE-A4 (286-294)/HLA-A2

| TCR name Domain name | Domain Sequences Amino Acid Sequence (SEQ ID NO); CDR1, CDR2, and CDR3 sequences are underlined Nucleic Acid Sequence (SEQ ID NO); CDR1, CDR2, and CDR3 sequences are underlined |
|---|---|
| PN41690 Vβ | DVKVTQSSRYLVKRTGEKVFLECVQDMDHENMFWYRQDPGLGLRLIYFSYDVKMKEKGDIPEGYSVSREKKERFSLILESASTNQTSMYLCASSLWGVNTEAFFGQGTRLTVV (SEQ ID NO: 383) GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATTCTGGAGTCCGCCAGCACCAACCAGACATCTATGTACCTCTGTGCCAGCAGTTTATGGGGTGTGAACACTGAAGCTTTCTTTGGACAAGGCACCAGACTCACAGTTGTA (SEQ ID NO: 384) |
| PN41702 Vα | AQTVTQSQPEMSVQEAETVTLSCTYDTSESDYYLFWYKQPPSRQMILVIRQEAYKQQNATENRFSVNFQKAAKSFSLKISDSQLGDAAMYFCAYRSATGNQFYFGTGTSLTVIP (SEQ ID NO: 391) GCTCAGACAGTCACTCAGTCTCAACCAGAGATGTCTGTGCAGGAGGCAGAGACCGTGACCCTGAGCTGCACATATGACACCAGTGAGAGTGATTATTATTTATTCTGGTACAAGCAGCCTCCCAGCAGGCAGATGATTCTCGTTATTCGCCAAGAAGCTTATAAGCAACAGAATGCAACAGAGAATCGTTTCTCTGTGAACTTCCAGAAAGCAGCCAAATCCTTCAGTCTCAAGATCTCAGACTCACAGCTGGGGGATGCCGCGATGTATTTCTGTGCTTATAGGAGCGCGACCGGTAACCAGTTCTATTTTGGGACAGGGACAAGTTTGACGGTCATTCCA (SEQ ID NO: 392) |
| PN41702 Vβ | DVKVTQSSRYLVKRTGEKVFLECVQDMDHENMFWYRQDPGLGLRLIYFSYDVKMKEKGDIPEGYSVSREKKERFSLILESASTNQTSMYLCASSLWAVNEKLFFGSGTQLSVL (SEQ ID NO: 399) GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATTCTGGAGTCCGCCAGCACCAACCAGACATCTATGTACCTCTGTGCCAGCAGTTTATGGGCCGTTAATGAAAAACTGTTTTTTGGCAGTGGAACCCAGCTCTCTGTCTTG (SEQ ID NO: 400) |
| PN41703 Vα | DAKTTQPPSMDCAEGRAANLPCNHSTISGNEYVYWYRQIHSQGPQYIIHGLKNNETNEMASLIITEDRKSSTLILPHATLRDTAVYYCIVRPGGTYKYIFGTGTRLKVLA (SEQ ID NO: 407) GATGCTAAGACCACCCAGCCACCCTCCATGGATTGCGCTGAAGGAAGAGCTGCAAACCTGCCTTGTAATCACTCTACCATCAGTGGAAATGAGTATGTGTATTGGTATCGACAGATTCACTCCCAGGGGCCACAGTATATCATTCATGGTCTAAAAAACAATGAAACCAATGAAATGGCCTCTCTGATCATCACAGAAGACAGAAAGTCCAGCACCTTGATCCTGCCCCACGCTACGCTGAGAGACACTGCTGTGTACTATTGCATCGTCAGACCGGGGGGAACCTACAAATACATCTTTGGAACAGGCACCAGGCTGAAGGTTTTAGCA (SEQ ID NO: 408) |
| PN41703 Vβ | DVKVTQSSRYLVKRTGEKVFLECVQDMDHENMFWYRQDPGLGLRLIYFSYDVKMKEKGDIPEGYSVSREKKERFSLILESASTNQTSMYLCATGGDNQPQHFGDGTRLSIL (SEQ ID NO: 415) GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATTCTGGAGTCCGCCAGCACCAACCAGACATCTATGTACCTCTGTGCGACCGGGGGTGACAATCAGCCCCAGCATTTTGGTGATGGGACTCGACTCTCCATCCTA (SEQ ID NO: 416) |
| PN41712 Vα | AQTVTQSQPEMSVQEAETVTLSCTYDTSENNYYLFWYKQPPSRQMILVIRQEAYKQQNATENRFSVNFQKAAKSFSLKISDSQLGDTAMYFCALNTGNQFYFGTGTSLTVIP (SEQ ID NO: 423) GCCCAGACAGTCACTCAGTCTCAACCAGAGATGTCTGTGCAGGAGGCAGAGACTGTGACCCTGAGTTGCACATATGACACCAGTGAGAATAATTATTATTTGTTCTGGTACAAGCAGCCTCCCAGCAGGCAGATGATTCTCGTTATTCGCCAAGAAGCTTATAAGCAACAGAATGCAACGGAGAATCGTTT |

TABLE 4-continued

Amino acid and nucleic acid sequences for Veloci ® TCRs specific for MAGE-A4 (286-294)/HLA-A2

| TCR name Domain name | Domain Sequences Amino Acid Sequence (SEQ ID NO); CDR1, CDR2, and CDR3 sequences are underlined Nucleic Acid Sequence (SEQ ID NO); CDR1, CDR2, and CDR3 sequences are underlined |
|---|---|
| | CTCTGTGAACTTCCAGAAAGCAGCCAAATCCTTCAGTCTCAAGATCTC AGACTCACAGCTGGGGGACACTGCGATGTATTTCTGTGCCCTCAACAC CGGTAACCAGTTCTATTTTGGGACAGGGACAAGTTTGACGGTCATTCC A (SEQ ID NO: 424) |
| PN41712 Vβ | GAVVSQHPSWVICKSGTSVKIECRSLDFQATTMFWYRQFPKQSLMLMAT SNEGSKATYEQGVEKDKFLINHASLTLSTLTVTSAHPEDSSFYICSAWDGF YGYTFGSGTRLTVV (SEQ ID NO: 431) GGTGCTGTCGTCTCTCAACATCCGAGCTGGGTTATCTGTAAGAGTGGA ACCTCTGTGAAGATCGAGTGCCGTTCCCTGGACTTTCAGGCCACAACT ATGTTTTGGTATCGTCAGTTCCCGAAACAGAGTCTCATGCTGATGGCA ACTTCCAATGAGGGCTCCAAGGCCACATACGAGCAAGGCGTCGAGAA GGACAAGTTTCTCATCAACCATGCAAGCCTGACCTTGTCCACTCTGAC AGTGACCAGTGCCCATCCTGAAGACAGCAGCTTCTACATCTGCAGTGC CTGGGACGGATTCTATGGCTACACCTTCGGTTCGGGGACCAGGTTAAC CGTTGTA (SEQ ID NO: 432) |
| PN41746 Vα | AQTVTQSQPEMSVQEAETVTLSCTYDTSESDYYLFWYKQPPSRQMILVIR QEAYKQQNATENRFSVNFQKAAKSFSLKISDSQLGDAAMYFCAYRSATG NQFYFGTGTSLTVIP (SEQ ID NO: 439) GCTCAGACAGTCACTCAGTCTCAACCAGAGATGTCTGTGCAGGAGGCA GAGACCGTGACCCTGAGCTGCACATATGACACCAGTGAGAGTGATTAT TATTTATTCTGGTACAAGCAGCCTCCCAGCAGGCAGATGATTCTCGTT ATTCGCCAAGAAGCTTATAAGCAACAGAATGCAACAGAGAATCGTTT CTCTGTGAACTTCCAGAAAGCAGCCAAATCCTTCAGTCTCAAGATCTC AGACTCACAGCTGGGGGATGCCGCGATGTATTTCTGTGCTTATAGGAG CGCGACCGGTAACCAGTTCTATTTTGGGACAGGGACAAGTTTGACGGT CATTCCA (SEQ ID NO: 440) |
| PN41746 Vβ | DVKVTQSSRYLVKRTGEKVFLECVQDMDHENMFWYRQDPGLGLRLIYF SYDVKMKEKGDIPEGYSVSREKKERFSLILESASTNQTSMYLCASSLWGL NTEAFFGQGTRLTVV (SEQ ID NO: 447) GATGTGAAAGTAACCCAGAGCTCGAGATATCTAGTCAAAAGGACGGG AGAGAAAGTTTTTCTGGAATGTGTCCAGGATATGGACCATGAAAATAT GTTCTGGTATCGACAAGACCCAGGTCTGGGGCTACGGCTGATCTATTT CTCATATGATGTTAAAATGAAAGAAAAAGGAGATATTCCTGAGGGGT ACAGTGTCTCTAGAGAGAAGAAGGAGCGCTTCTCCCTGATTCTGGAGT CCGCCAGCACCAACCAGACATCTATGTACCTCTGTGCCAGCAGTTTAT GGGGCTTAAACACTGAAGCTTTCTTTGGACAAGGCACCAGACTCACAG TTGTA (SEQ ID NO: 448) |
| PN41748 Vα | SQELEQSQQSLIVQEGKNLTINCTSSKTLYGLYWYKQKYGEGLIFLMMLQ KGGEEKSHEKITAKLDEKKQQSSLHITASQPSHAGIYLCGADMYSGGGAD GLTFGKGTHLIIQP (SEQ ID NO: 455) AGCCAAGAACTGGAGCAGAGTCAACAGTCCTTGATCGTCCAAGAGGG AAAGAATCTCACCATAAACTGCACGTCATCAAAGACGTTATATGGCTT ATACTGGTATAAGCAAAAGTATGGTGAAGGTCTTATCTTCTTGATGAT GCTACAGAAAGGTGGGGAAGAGAAAAGTCATGAAAAGATAACTGCCA AGTTGGATGAGAAAAAGCAGCAAAGTTCCCTGCATATCACAGCCTCCC AGCCCAGCCATGCAGGCATCTACCTCTGTGGAGCAGACATGTATTCAG GAGGAGGTGCTGACGGACTCACCTTTGGCAAAGGGACTCATCTAATCA TCCAGCCC (SEQ ID NO: 456) |
| PN41748 Vβ | GAVVSQHPSWVICKSGTSVKIECRSLDFQATTMFWYRQFPKQSLMLMAT SNEGSKATYEQGVEKDKFLINHASLTLSTLTVTSAHPEDSSFYICSAWDGF YGYTFGSGTRLTVV (SEQ ID NO: 463) GGTGCTGTCGTCTCTCAACATCCGAGCTGGGTTATCTGTAAGAGTGGA ACCTCTGTGAAGATCGAGTGCCGTTCCCTGGACTTTCAGGCCACAACT ATGTTTTGGTATCGTCAGTTCCCGAAACAGAGTCTCATGCTGATGGCA ACTTCCAATGAGGGCTCCAAGGCCACATACGAGCAAGGCGTCGAGAA GGACAAGTTTCTCATCAACCATGCAAGCCTGACCTTGTCCACTCTGAC AGTGACCAGTGCCCATCCTGAAGACAGCAGCTTCTACATCTGCAGTGC CTGGGACGGATTCTATGGCTACACCTTCGGTTCGGGGACCAGGTTAAC CGTTGTA (SEQ ID NO: 464) |
| PN41805 Vα | AQTVTQSQPEMSVQEAETVTLSCTYDTSENNYYLFWYKQPPSRQMILVIR QEAYKQQNATENRFSVNFQKAAKSFSLKISDSQLGDTAMYFCAFGMYSG GGADGLTFGKGTHLIIQP (SEQ ID NO: 471) GCCCAGACAGTCACTCAGTCTCAACCAGAGATGTCTGTGCAGGAGGC AGAGACTGTGACCCTGAGTTGCACATATGACACCAGTGAGAATAATTA TTATTTGTTCTGGTACAAGCAGCCTCCCAGCAGGCAGATGATTCTCGTT |

TABLE 4-continued

Amino acid and nucleic acid sequences for Veloci ® TCRs specific for MAGE-A4 (286-294)/HLA-A2

| TCR name<br>Domain<br>name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
|---|---|
| | ATTCGCCAAGAAGCTTATAAGCAACAGAATGCAACGGAGAATCGTTT<br>CTCTGTGAACTTCCAGAAAGCAGCCAAATCCTTCAGTCTCAAGATCTC<br>AGACTCACAGCTGGGGGACACTGCGATGTATTTCTGTGCTTTCGGTAT<br>GTATTCAGGAGGAGGTGCTGACGGACTCACCTTTGGCAAAGGGACTC<br>ATCTAATCATCCAGCCC (SEQ ID NO: 472) |
| PN41805<br>Vβ | AAGVIQSPRHLIKEKRETATLKCYPIPRHDTVYWYQQGPGQDPQFLISFYE<br>KMQSDKGSIPDRFSAQQFSDYHSELNMSSLELGDSALYFCASSPTGTGDG<br>YTFGSGTRLTVV (SEQ ID NO: 479)<br>GCTGCTGGAGTCATCCAGTCCCCAAGACATCTGATCAAAGAAAAGAG<br>GGAAACAGCCACTCTGAAATGCTATCCTATCCCTAGACACGACACTGT<br>CTACTGGTACCAGCAGGGTCCAGGTCAGGACCCCCAGTTCCTCATTTC<br>GTTTTATGAAAAGATGCAGAGCGATAAAGGAAGCATCCCTGATCGATT<br>CTCAGCTCAACAGTTCAGTGACTATCATTCTGAACTGAACATGAGCTC<br>CTTGGAGCTGGGGGACTCAGCCCTGTACTTCTGTGCCAGCAGCCCTAC<br>CGGGACAGGGGATGGCTACACCTTCGGTTCGGGGACCAGGTTAACCG<br>TTGTA (SEQ ID NO: 480) |
| PN41820<br>Vα | AQSVTQPGSHVSVSEGALVLLRCNYSSSVPPYLFWYVQYPNQGLQLLLK<br>YTTGATLVKGINGFEAEFKKSETSFHLTKPSAHMSDAAEYFCAVSSGSAR<br>QLTFGSGTQLTVLP (SEQ ID NO: 487)<br>GCCCAGTCGGTGACCCAGCCTGGCAGCCACGTCTCTGTCTCTGAGGGA<br>GCCCTGGTTCTGCTGAGGTGCAACTACTCATCGTCTGTTCCACCATATC<br>TCTTCTGGTATGTGCAATACCCCAACCAAGGACTCCAGCTTCTCCTGA<br>AGTACACAACAGGGGCCACCCTGGTTAAAGGCATCAACGGTTTTGAG<br>GCTGAATTTAAGAAGAGTGAAACCTCCTTCCACCTGACGAAACCCTCA<br>GCCCATATGAGCGACGCGGCTGAGTACTTCTGTGCTGTGAGTTCTGGT<br>TCTGCAAGGCAACTGACCTTTGGATCTGGGACACAATTGACTGTTTTA<br>CCT (SEQ ID NO: 488) |
| PN41820<br>Vβ | DVKVTQS SRYLVKRTGEKVFLECVQDMDHENMFWYRQDPGLGLRLIYF<br>SYDVKMKEKGDIPEGYSVSREKKERFSLILESASTNQTSMYLCASSHDRW<br>DYGYTFGSGTRLTVV (SEQ ID NO: 495)<br>GATGTGAAAGTAACCCAGAGCTCGAGATATCTAGTCAAAAGGACGGG<br>AGAGAAAGTTTTTCTGGAATGTGTCCAGGATATGGACCATGAAAATAT<br>GTTCTGGTATCGACAAGACCCAGGTCTGGGGCTACGGCTGATCTATTT<br>CTCATATGATGTTAAAATGAAAGAAAAAGGAGATATTCCTGAGGGGT<br>ACAGTGTCTCTAGAGAGAAGAAGGAGCGCTTCTCCCTGATTCTGGAGT<br>CCGCCAGCACCAACCAGACATCTATGTACCTCTGTGCCAGCAGTCATG<br>ACAGGTGGGACTATGGCTACACCTTCGGTTCGGGGACCAGGTTAACCG<br>TTGTA (SEQ ID NO: 496) |
| PN41822<br>Vα | AQTVTQSQPEMSVQEAETVTLSCTYDTSESDYYLFWYKQPPSRQMILVIR<br>QEAYKQQNATENRFSVNFQKAAKSFSLKISDSQLGDAAMYFCAYRSATG<br>NQFYFGTGTSLTVIP (SEQ ID NO: 503)<br>GCTCAGACAGTCACTCAGTCTCAACCAGAGATGTCTGTGCAGGAGGCA<br>GAGACCGTGACCCTGAGCTGCACATATGACACCAGTGAGAGTGATTAT<br>TATTTATTCTGGTACAAGCAGCCTCCCAGCAGGCAGATGATTCTCGTT<br>ATTCGCCAAGAAGCTTATAAGCAACAGAATGCAACAGAGAATCGTTT<br>CTCTGTGAACTTCCAGAAAGCAGCCAAATCCTTCAGTCTCAAGATCTC<br>AGACTCACAGCTGGGGGATGCCGCGATGTATTTCTGTGCTTATAGGAG<br>CGCCACCGGTAACCAGTTCTATTTTGGGACAGGGACAAGTTTGACGGT<br>CATTCCA (SEQ ID NO: 504) |
| PN41822<br>Vβ | DVKVTQSSRYLVKRTGEKVFLECVQDMDHENMFWYRQDPGLGLRLIYF<br>SYDVKMKEKGDIPEGYSVSREKKERFSLILESASTNQTSMYLCASSLWAL<br>NTEAFFGQGTRLTVV (SEQ ID NO: 511)<br>GATGTGAAAGTAACCCAGAGCTCGAGATATCTAGTCAAAAGGACGGG<br>AGAGAAAGTTTTTCTGGAATGTGTCCAGGATATGGACCATGAAAATAT<br>GTTCTGGTATCGACAAGACCCAGGTCTGGGGCTACGGCTGATCTATTT<br>CTCATATGATGTTAAAATGAAAGAAAAAGGAGATATTCCTGAGGGGT<br>ACAGTGTCTCTAGAGAGAAGAAGGAGCGCTTCTCCCTGATTCTGGAGT<br>CCGCCAGCACCAACCAGACATCTATGTACCTCTGTGCCAGCAGTTTGT<br>GGGCATTGAACACTGAAGCTTTCTTTGGACAAGGCACCAGACTCACAG<br>TTGTA (SEQ ID NO: 512) |
| PN41829<br>Vα | AQTVTQSQPEMSVQEAETVTLSCTYDTSESDYYLFWYKQPPSRQMILVIR<br>QEAYKQQNATENRFSVNFQKAAKSFSLKISDSQLGDAAMYFCAYRSATG<br>NQFYFGTGTSLTVIP (SEQ ID NO: 519)<br>GCTCAGACAGTCACTCAGTCTCAACCAGAGATGTCTGTGCAGGAGGCA<br>GAGACCGTGACCCTGAGCTGCACATATGACACCAGTGAGAGTGATTAT |

TABLE 4-continued

| Amino acid and nucleic acid sequences for Veloci ® TCRs specific for MAGE-A4 (286-294)/HLA-A2 | |
|---|---|
| TCR name<br>Domain<br>name | Domain Sequences<br>Amino Acid Sequence (SEQ ID NO); CDR1, CDR2, and CDR3 sequences are underlined<br>Nucleic Acid Sequence (SEQ ID NO); CDR1, CDR2, and CDR3 sequences are underlined |
| | TATTTATTCTGGTACAAGCAGCCTCCCAGCAGGCAGATGATTCTCGTT ATTCGCCAAGAAGCTTATAAGCAACAGAATGCAACAGAGAATCGTTT CTCTGTGAACTTCCAGAAAGCAGCCAAATCCTTCAGTCTCAAGATCTC AGACTCACAGCTGGGGGATGCCGCGATGTATTTCTGTGCTTATAGGAG CGCGACCGGTAACCAGTTCTATTTTGGGACAGGGACAAGTTTGACGGT CATTCCA (SEQ ID NO: 520) |
| PN41829<br>Vβ | DVKVTQSSRYLVKRTGEKVFLECVQDMDHENMFWYRQDPGLGLRLIYF SYDVKMKEKGDIPEGYSVSREKKERFSLILESASTNQTSMYLCASSLFALN TEAFFGQGTRLTVV (SEQ ID NO: 527)<br>GATGTGAAAGTAACCCAGAGCTCGAGATATCTAGTCAAAAGGACGGG AGAGAAAGTTTTTCTGGAATGTGTCCAGGATATGGACCATGAAAATAT GTTCTGGTATCGACAAGACCCAGGTCTGGGGCTACGGCTGATCTATTT CTCATATGATGTTAAAATGAAAGAAAAAGGAGATATTCCTGAGGGGT ACAGTGTCTCTAGAGAGAAGAAGGAGCGCTTCTCCCTGATTCTGGAGT CCGCCAGCACCAACCAGACATCTATGTACCTCTGTGCCAGCAGTTTAT TCGCATTGAACACTGAAGCTTTCTTTGGACAAGGCACCAGACTCACAG TTGTA (SEQ ID NO: 528) |
| PN41839<br>Vα | DAKTTQPPSMDCAEGRAANLPCNHSTISGNEYVYWYRQIHSQGPQYIIHG LKNNETNEMASLIITEDRKSSTLILPHATLRDTAVYYCIVYGGSQGNLIFG KGTKLSVKP (SEQ ID NO: 535)<br>GATGCTAAGACCACCCAGCCCCCCTCCATGGATTGCGCTGAAGGAAG AGCTGCAAACCTGCCTTGTAATCACTCTACCATCAGTGGAAATGAGTA TGTGTATTGGTATCGACAGATTCACTCCCAGGGGCCACAGTATATCAT TCATGGTCTAAAAAACAATGAAACCAATGAAATGGCCTCTCTGATCAT CACAGAAGACAGAAAGTCCAGCACCTTGATCCTGCCCCACGCTACGCT GAGAGACACTGCTGTGTACTATTGCATCGTTTATGGAGGAAGCCAAGG AAATCTCATCTTTGGAAAAGGCACTAAACTCTCTGTTAAACCA (SEQ ID NO: 536) |
| PN41839<br>Vβ | DAGVTQSPTHLIKTRGQQVTLRCSPKSGHDTVSWYQQALGQGPQFIFQY YEEEERQRGNFPDRFSGHQFPNYSSELNVNALLLGDSALYLCASSFSRVQ PQHFGDGTRLSIL (SEQ ID NO: 543)<br>GACGCTGGAGTCACCCAAAGTCCCACACACCTGATCAAAACGAGAGG ACAGCAAGTGACTCTGAGATGCTCTCCTAAGTCTGGGCATGACACTGT GTCCTGGTACCAACAGGCCCTGGGTCAGGGGCCCCAGTTTATCTTTCA GTATTATGAGGAGGAAGAGAGACAGAGAGGCAACTTCCCTGATCGAT TCTCAGGTCACCAGTTCCCTAACTATAGCTCTGAGCTGAATGTGAACG CCTTGTTGCTGGGGGACTCGGCCCTCTATCTCTGTGCCAGCAGCTTCAG CAGGGTCCAGCCCCAGCATTTTGGTGATGGGACTCGACTCTCCATCCT A (SEQ ID NO: 544) |
| PN41852<br>Vα | AQTVTQSQPEMSVQEAETVTLSCTYDTSESDYYLFWYKQPPSRQMILVIR QEAYKQQNATENRFSVNFQKAAKSFSLKISDSQLGDAAMYFCAYRSALG NDMRFGAGTRLTVKP (SEQ ID NO: 551)<br>GCTCAGACAGTCACTCAGTCTCAACCAGAGATGTCTGTGCAGGAGGCA GAGACCGTGACCCTGAGCTGCACATATGACACCAGTGAGAGTGATTAT TATTTATTCTGGTACAAGCAGCCTCCCAGCAGGCAGATGATTCTCGTT ATTCGCCAAGAAGCTTATAAGCAACAGAATGCAACAGAGAATCGTTT CTCTGTGAACTTCCAGAAAGCAGCCAAATCCTTCAGTCTCAAGATCTC AGACTCACAGCTGGGGGATGCCGCGATGTATTTCTGTGCTTATAGGAG CGCGTTGGGCAATGACATGCGCTTTGGAGCAGGGACCAGACTGACAG TAAAACCA (SEQ ID NO: 552) |
| PN41852<br>Vβ | DVKVTQSSRYLVKRTGEKVFLECVQDMDHENMFWYRQDPGLGLRLIYF SYDVKMKEKGDIPEGYSVSREKKERFSLILESASTNQTSMYLCASSLWAL NTEAFFGQGTRLTVV (SEQ ID NO: 559)<br>GATGTGAAAGTAACCCAGAGCTCGAGATATCTAGTCAAAAGGACGGG AGAGAAAGTTTTTCTGGAATGTGTCCAGGATATGGACCATGAAAATAT GTTCTGGTATCGACAAGACCCAGGTCTGGGGCTACGGCTGATCTATTT CTCATATGATGTTAAAATGAAAGAAAAAGGAGATATTCCTGAGGGGT ACAGTGTCTCTAGAGAGAAGAAGGAGCGCTTCTCCCTGATTCTGGAGT CCGCCAGCACCAACCAGACATCTATGTACCTCTGTGCCAGCAGTTTAT GGGCACTGAACACTGAAGCTTTCTTTGGACAAGGCACCAGACTCACAG TTGTA (SEQ ID NO: 560) |
| PN41867<br>Vα | AQTVTQSQPEMSVQEAETVTLSCTYDTSENNYYLFWYKQPPSRQMILVIR QEAYKQQNATENRFSVNFQKAAKSFSLKISDSQLGDTAMYFCAFMKTQG GSEKLVFGKGTKLTVNP (SEQ ID NO: 567)<br>GCCCAGACAGTCACTCAGTCTCAACCAGAGATGTCTGTGCAGGAGGC |

TABLE 4-continued

Amino acid and nucleic acid sequences for Veloci ® TCRs specific for MAGE-A4 (286-294)/HLA-A2

| TCR name Domain name | Domain Sequences Amino Acid Sequence (SEQ ID NO); CDR1, CDR2, and CDR3 sequences are underlined Nucleic Acid Sequence (SEQ ID NO); CDR1, CDR2, and CDR3 sequences are underlined |
|---|---|
| | AGAGACTGTGACCCTGAGTTGCACATATGACACCAGTGAGAATAATTATTATTTGTTCTGGTACAAGCAGCCTCCCAGCAGGCAGATGATTCTCGTTATTCGCCAAGAAGCTTATAAGCAACAGAATGCAACGGAGAATCGTTTCTCTGTGAACTTCCAGAAAGCAGCCAAATCCTTCAGTCTCAAGATCTCAGACTCACAGCTGGGGGACACTGCGATGTATTTCTGTGCTTTCATGAAAACTCAGGGCGGATCTGAAAAGCTGGTCTTTGGAAAGGGAACGAAACTGACAGTAAACCCA (SEQ ID NO: 568) |
| PN41867 Vβ | AAGVIQSPRHLIKEKRETATLKCYPIPRHDTVYWYQQGPGQDPQFLISFYEKMQSDKGSIPDRFSAQQFSDYHSELNMSSLELGDSALYFCASSLVGYGYTFGSGTRLTVV (SEQ ID NO: 575) GCTGCTGGAGTCATCCAGTCCCCAAGACATCTGATCAAAGAAAAGAGGGAAACAGCCACTCTGAAATGCTATCCTATCCCTAGACACGACACTGTCTACTGGTACCAGCAGGGTCCAGGTCAGGACCCCCAGTTCCTCATTTCGTTTTATGAAAAGATGCAGAGCGATAAAGGAAGCATCCCTGATCGATTCTCAGCTCAACAGTTCAGTGACTATCATTCTGAACTGAACATGAGCTCCTTGGAGCTGGGGGACTCAGCCCTGTACTTCTGTGCCAGCAGCTTAGTTGGGTATGGCTACACCTTCGGTTCGGGGACCAGGTTAACCGTTGTA (SEQ ID NO: 576) |
| PN41868 Vα | AQTVTQSQPEMSVQEAETVTLSCTYDTSESDYYLFWYKQPPSRQMILVIRQEAYKQQNATENRFSVNFQKAAKSFSLKISDSQLGDAAMYFCAYRSATGNQFYFGTGTSLTVIP (SEQ ID NO: 583) GCTCAGACAGTCACTCAGTCTCAACCAGAGATGTCTGTGCAGGAGGCAGAGACCGTGACCCTGAGCTGCACATATGACACCAGTGAGAGTGATTATTATTTATTCTGGTACAAGCAGCCTCCCAGCAGGCAGATGATTCTCGTTATTCGCCAAGAAGCTTATAAGCAACAGAATGCAACAGAGAATCGTTTCTCTGTGAACTTCCAGAAAGCAGCCAAATCCTTCAGTCTCAAGATCTCAGACTCACAGCTGGGGGATGCCGCGATGTATTTCTGTGCTTATAGGAGCGCAACCGGTAACCAGTTCTATTTTGGGACAGGGACAAGTTTGACGGTCATTCCA (SEQ ID NO: 584) |
| PN41868 Vβ | DVKVTQSSRYLVKRTGEKVFLECVQDMDHENMFWYRQDPGLGLRLIYFSYDVKMKEKGDIPEGYSVSREKKERFSLILESASTNQTSMYLCASSLWGTHEKLFFGSGTQLSVL (SEQ ID NO: 591) GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATTCTGGAGTCCGCCAGCACCAACCAGACATCTATGTACCTCTGTGCCAGCAGTTTATGGGGGACACATGAAAAACTGTTTTTTGGCAGTGGAACCCAGCTCTCTGTCTTG (SEQ ID NO: 592) |
| PN41869 Vα | AQTVTQSQPEMSVQEAETVTLSCTYDTSESDYYLFWYKQPPSRQMILVIRQEAYKQQNATENRFSVNFQKAAKSFSLKISDSQLGDAAMYFCAYRSSTGNQFYFGTGTSLT VIP (SEQ ID NO: 599) GCTCAGACAGTCACTCAGTCTCAACCAGAGATGTCTGTGCAGGAGGCAGAGACCGTGACCCTGAGCTGCACATATGACACCAGTGAGAGTGATTATTATTTATTCTGGTACAAGCAGCCTCCCAGCAGGCAGATGATTCTCGTTATTCGCCAAGAAGCTTATAAGCAACAGAATGCAACAGAGAATCGTTTCTCTGTGAACTTCCAGAAAGCAGCCAAATCCTTCAGTCTCAAGATCTCAGACTCACAGCTGGGGGATGCCGCGATGTATTTCTGTGCTTATAGGAGCTCCACCGGTAACCAGTTCTATTTTGGGACAGGGACAAGTTTGACGGTCATTCCA (SEQ ID NO: 600) |
| PN41869 Vβ | DVKVTQSSRYLVKRTGEKVFLECVQDMDHENMFWYRQDPGLGLRLIYFSYDVKMKEKGDIPEGYSVSREKKERFSLILESASTNQTSMYLCASSLWGTNEKLFFGSGTQLSVL (SEQ ID NO: 607) GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATTCTGGAGTCCGCCAGCACCAACCAGACATCTATGTACCTCTGTGCCAGCAGTTTATGGGGAACTAATGAAAAACTGTTTTTTGGCAGTGGAACCCAGCTCTCTGTCTTG (SEQ ID NO: 608) |

Example 2. Identification of MAGE-A4 Specific T Cell Receptors

Mice humanized for cellular immune system components, Veloci-T® mice (see, e.g., PCT Publication No. WO 2016/164492, the entire contents of which are incorporated herein by reference), were immunized with MAGE-A4 (230-239) peptide (GVYDGREHTV, SEQ ID NO: 612) presented specifically by human HLA-A2, diluted in PBS and mixed with adjuvant, e.g. in equal volume with Complete Freund's Adjuvant (CFA; Chondrex, Inc.). Spleen suspensions from immunized mice were obtained and dissociated. Red blood cells were lysed in ACK lysis buffer (Life Technologies), and splenocytes were suspended in RPMI complete media. Isolated splenocytes are sorted and single T cells that bind MAGE-A4 (230-239) peptide in the context of MHC are isolated by fluorescent-activated cell sorting (FACS). Isolated T cells are single well plated and mixed with TCR alpha and beta variable region-specific PCR primers. cDNAs for each single T cell were synthesized via a reverse transcriptase (RT) reaction. Each resulting RT product was then split and transferred into two corresponding wells for subsequent TCR beta and alpha PCRs. One set of the resulting RT products was first amplified by PCR using a 5' degenerate primer specific for TCR beta variable region leader sequence or a 5' degenerate primer specific for TCR alpha chain variable region leader sequence and a 3' primer specific for TCR constant region, to form an amplicon. The amplicons were then amplified again by PCR using a 5' degenerate primer specific for TCR beta variable region framework 1 or a 5' degenerate primer specific for TCR alpha chain variable region framework 1 and a 3' primer specific for TCR constant region, to generate amplicons for cloning. The TCR beta and alpha derived PCR products were cloned into expression vectors containing beta constant region and alpha constant region, respectively. Expression vectors expressing full-length beta and alpha chain pairs were transfected into CHO cells and tested for binding to a commercial MAGE-A4/HLA tetramer reagent (HLA-A02:01 MAGE-A4 tetramer; MBL International Corporation) or to a commercial MAGE-A8/HLA tetramer reagent (HLA-A02:01 MAGE-A8 tetramer; MBL International Corporation). CHO cells were incubated with an antibody specific for mouse TCR constant region (clone H57-597) (Biolegend, San Diego, CA), and with either a soluble HLA-A2 MAGE-A4 (GVYDGREHTV) (SEQ ID NO: 612) tetramer or a soluble HLA-A2 MAGE-A8 (GLYDGREHSV) (SEQ ID NO: 613). Samples were then analyzed on an LSR-Fortessa X-20 (BD Biosciences, San Jose, CA). To calculate percentage of tetramer positive cells for MAGE-A4 (230-239), antigen positive (Ag+) gates were set based on a negative control TCR that does not bind to the HLA-A2 (GVYDGREHTV) (SEQ ID NO: 612) tetramer. To calculate percentage of tetramer positive cells for MAGE-A8, antigen positive (Ag+) gates were set based on a negative control TCR that does not bind to the HLA-A2 (GLYDGREHSV) (SEQ ID NO: 613), using FlowJo (LLC, Ashland, OR). All Ag+ TCRs had a FlowJo criteria of ≥1% of cells in Ag+ gate with the mean fluorescence intensity (MFI)>250. However, a more stringent cutoff, such as 3%, could be used to separate out Ag+ TCRs that behave better in the binding assay. Ag+ TCRs were determined by Next Generation Sequencing. Table 5 shows the total number of TCRs that express identical TCR alpha and beta nucleotide sequences, the % tetramer in the Ag+ gate (MAGE-A4 (230-239)), the % tetramer in the Ag+ gate (MAGE-A8 (232-241)), and the ratio of the latter two numbers (% tetramer in the Ag+ gate (MAGE-A4 (230-239)) divided by the % tetramer in the Ag+ gate (MAGE-A8 (232-241))). This ratio is an indicator of the specificity of MAGE-A4 (230-239) binding.

TABLE 5

TCR-antigen binding, on-target and off-target

| TCR ID | Total Ag + TCRs (CHOt) | % tetramer in Ag + gate (MAGE-A4) | % tetramer in Ag + gate (MAGE-A8) | MAGE-A4/ MAGE-A8 |
|---|---|---|---|---|
| PN45515 | 1 | 11.50 | 0.00 | 1150.00 |
| PN45593 | 34 | 56.50 | 0.06 | 991.23 |
| PN45539 | 37 | 59.80 | 0.12 | 498.33 |
| PN45545 | 1 | 11.50 | 0.08 | 149.35 |
| PN45584 | 1 | 69.10 | 1.30 | 53.15 |
| PN45581 | 1 | 3.18 | 0.17 | 18.71 |
| PN45428 | 26 | 27.40 | 1.92 | 14.27 |
| PN45418 | 1 | 12.30 | 1.24 | 9.92 |
| PN45446 | 5 | 52.20 | 16.90 | 3.09 |
| PN45489 | 1 | 16.00 | 6.39 | 2.50 |
| PN45460 | 1 | 34.70 | 16.70 | 2.08 |
| PN45494 | 1 | 3.70 | 1.88 | 1.97 |
| PN45590 | 15 | 77.90 | 46.80 | 1.66 |
| PN45557 | 10 | 94.70 | 66.30 | 1.43 |
| PN45546 | 5 | 74.80 | 60.60 | 1.23 |
| PN45481 | 41 | 87.90 | 72.90 | 1.21 |

A detailed list of the beta chain variable CDR1, CDR2, and CDR3 amino acid sequences, and the alpha chain variable domain CDR1, CDR2, and CDR3 amino acid sequences variable of the TCRs that were determined as described above are provided in Table 6, and the corresponding nucleic acid sequences are provided in Table 7. Table 8 provides the amino acid and nucleotide sequences of the beta chain variable and alpha chain variable regions of the TCRs.

Table 9 provides the TCR gene families for the alpha and beta variable and joining regions of the isolated TCRs, and Table 10 provides the amino acid and polynucleic acid sequence identifiers for alpha and beta variable chains and CDRs.

TABLE 6

Amino acid sequences for Veloci-T ® TCRs specific for MAGE-A4 (230-239)/HLA-A2

| TCR No. | TCR ID | Vα CDR1 | SEQ ID NO: | Vα CDR2 | SEQ ID NO: | Vα CDR3 | SEQ ID NO: | Vβ CDR1 | SEQ ID NO: | Vβ CDR2 | SEQ ID NO: | Vβ CDR3 | SEQ ID NO: |
|---|---|---|---|---|---|---|---|---|---|---|---|---|---|
| 39 | PN45515 | TISGNEY | 614 | GLKNN | 615 | IVRPYNAGNNRKL | 616 | MDHEN | 622 | SYDVKM | 623 | ASSFGGGYYGYT | 624 |
| 40 | PN45593 | TSDPSYG | 630 | QGSYDQQ | 631 | AMREGPGNNARL | 632 | MNHEY | 638 | SVGEGT | 639 | ASSYWDRGSPLH | 640 |
| 41 | PN45539 | TISGNEY | 646 | GLKN | 647 | IVRPYNAGNNRKL | 648 | MDHEN | 654 | SYDVKM | 655 | ASSFEGGYYGYT | 656 |
| 42 | PN45545 | TSDPSYG | 662 | QGSYDQQ | 663 | AMRGGGSGGSYIPT | 664 | MDHEN | 670 | SYDVKM | 671 | ASSFTGPYNSPLH | 672 |
| 43 | PN45584 | TSDPSYG | 678 | QGSYDEQ | 679 | AMREGPGSGNTGKLI | 680 | MNHNY | 686 | SVGAGI | 687 | ASSYSEWQNYGYT | 688 |
| 44 | PN45581 | TSDPSYG | 694 | QGSYDQQ | 695 | AMREGPGNNARL | 696 | MNHEY | 702 | SMNVEV | 703 | ASSLWTGGGYT | 704 |
| 45 | PN45428 | VSGLRG | 710 | LYSAGEE | 711 | AVQPLNAGNNRKL | 712 | DFQATT | 718 | SNEGSKA | 719 | SAREWGGTEAF | 720 |
| 46 | PN45418 | VSGLRG | 726 | LYSAGE | 727 | AVQPSYSGAGSYQLT | 728 | MNHEY | 734 | SMNVEV | 735 | ASSPGTGGFSPLH | 736 |
| 47 | PN45446 | VSGLRG | 742 | LYSAGEE | 743 | AVQPSYSGAGSYQLT | 744 | DFQATT | 750 | SNEGSKA | 751 | SAREWRGTEAF | 752 |
| 48 | PN45489 | SVFSS | 758 | VVTGGE | 759 | AEDGGSQGNLI | 760 | MDHEN | 766 | SYDVKM | 767 | ASSLQGRYYGYT | 768 |
| 49 | PN45460 | ATGYPS | 774 | ATKADD | 775 | ALSDTRDDKII | 776 | MNHEY | 782 | SMNVEV | 783 | ASSPGTGGFSPLH | 784 |
| 50 | PN45494 | ATGYPS | 790 | ATKADD | 791 | ALSDTRDDKTI | 792 | MDHEN | 798 | SYDVKM | 799 | ASSLQGRYYGYT | 800 |
| 51 | PN45590 | YGATPY | 806 | YFSGDTL | 807 | AVGAGSARQLT | 808 | SGHDT | 814 | YYEEEE | 815 | ASSFDTEAF | 816 |
| 52 | PN45557 | TSDPSYG | 822 | QGSYDQQ | 823 | AMREGPGSGNTGKLI | 824 | MNHNY | 830 | SVGAGI | 831 | ASSYSEWQNYGYT | 832 |
| 53 | PN45546 | TSESDYY | 838 | QEAYKQQ | 839 | AYRSGAGGTSYGKLT | 840 | SGHKS | 846 | YYEKEE | 847 | ASSIRDTYGYT | 848 |
| 54 | PN45481 | ATGYPS | 854 | ATKADD | 855 | ALSDTRDDKII | 856 | MDHEN | 862 | SYDVKM | 863 | ASSLQGRYYGYT | 864 |

TABLE 7

Nucleic acid CDR sequences for Veloci-T ® TCRs specific for MAGE-A4 (230-239)/HLA-A2

| TCR No. | TCR ID | Vα CDR1 | SEQ ID NO: | Vα CDR2 | SEQ ID NO: | Vα CDR3 | SEQ ID NO: | Vβ CDR1 | SEQ ID NO: | Vβ CDR2 | SEQ ID NO: | Vβ CDR3 | SEQ ID NO: |
|---|---|---|---|---|---|---|---|---|---|---|---|---|---|
| 39 | PN45515 | ACCATCAGTGGAAATGAGTAT | 617 | GGTCTAAAAAACAAT | 618 | ATCGTCAGACCTTATAATGCTGGCAACAACCGTAAGCTG | 619 | ATGGACCATGAAAAT | 625 | TCATATGATGTTAAAATG | 626 | GCCAGCAGTTTTGGGGGGGATACTATGGCTACACC | 627 |
| 40 | PN45593 | ACCAGTGATCCAAGTTATGGT | 633 | CAGGGGTCTTATGACCAGCAA | 634 | GCAATGAGAGAGGGCCCTGGTAACAATGCCAGACTC | 635 | ATGAACCATGAATAC | 641 | TCAGTTGGTGAGGGTACA | 642 | GCCAGCAGTTACTGGGACAGGGGCTCACCCCTCCAC | 643 |
| 41 | PN45539 | ACCATCAGTGGAAATGAGTAT | 649 | GGTCTAAAAAAC | 650 | ATCGTCAGACCTTATAATGCTGGCAACAACCGTAAGCTG | 651 | ATGGACCATGAAAAT | 657 | TCATATGATGTTAAAATG | 658 | GCCAGCAGTTTTGAGGGGGGATACTATGGCTACACC | 659 |
| 42 | PN45545 | ACCAGTGATCCAAGTTATGGT | 665 | CAGGGGTCTTATGACCAGCAA | 666 | GCAATGAGAGGGGGGGGATCAGGAGGAAGCTACATACCTACA | 667 | ATGGACCATGAAAAT | 673 | TCATATGATGTTAAAATG | 674 | GCCAGCAGTTTCACAGGGCCCTATAATTCACCCCTCCAC | 675 |
| 43 | PN45584 | ACCAGTGATCCAAGTTATGGT | 681 | CAGGGGTCTTATGACGAGCAA | 682 | GCAATGAGAGAGGGCCCGGGCTCTGGCAACACAGGCAAACTAATC | 683 | ATGAACCATAACTAC | 689 | TCAGTTGGTGCTGGTATC | 690 | GCCAGCAGTTACTCGGAGTGGCAGAACTATGGCTACACC | 691 |
| 44 | PN45581 | ACCAGTGATCCAAGTTATGGT | 697 | CAGGGGTCTTATGACCAGCAA | 698 | GCAATGAGAGAGGGCCCTGGTAACAATGCCAGACTC | 699 | ATGAACCATGAGTAT | 705 | TCAATGAATGTTGAGGTG | 706 | GCCAGCAGTTTATGGACAGGGGGAGGCTACACC | 707 |
| 45 | PN45428 | GTCAGCGGTTTAAGAGGG | 713 | CTGTATTCAGCTGGGGAA | 714 | GCTGTGCAGCCCCTTAATGCTGGCAACAACCGTAAGCTG | 715 | GACTTTCAGGCCACAACT | 721 | TCCAATGAGGGCTCCAAGGCC | 722 | AGTGCTAGAGAATGGGGTGGCACTGAAGCTTTC | 723 |
| 46 | PN45418 | GTCAGCGGTTTAAGAGGG | 729 | CTGTATTCAGCTGGGGAA | 730 | GCTGTGCAGCCCTCATACTCTGGGGCTGGGAGTTACCAACTCACT | 731 | ATGAACCATGAGTAT | 737 | TCAATGAATGTTGAGGTG | 738 | GCCAGCAGTCCCGGGACAGGGGGATTTTCACCCCTCCAC | 739 |
| 47 | PN45446 | GTCAGCGGTTTAAGAGGG | 745 | CTGTATTCAGCTGGGGAA | 746 | GCTGTGCAGCCCTCATACTCTGGGGCTGGGAGTTACCAACTCACT | 747 | GACTTTCAGGCCACAACT | 753 | TCCAATGAGGGCTCCAAGGCC | 754 | AGTGCTAGAGAGTGGAGGGGCACTGAAGCTTTC | 755 |

TABLE 7-continued

Nucleic acid CDR sequences for Veloci-T ® TCRs specific for MAGE-A4 (230-239)/HLA-A2

| TCR No. | TCR ID | Vα CDR1 | SEQ ID NO: | Vα CDR2 | SEQ ID NO: | Vα CDR3 | SEQ ID NO: | Vβ CDR1 | SEQ ID NO: | Vβ CDR2 | SEQ ID NO: | Vβ CDR3 | SEQ ID NO: |
|---|---|---|---|---|---|---|---|---|---|---|---|---|---|
| 48 | PN45489 | AGTGTTTTTTCCAGC | 761 | GTAGTTACGGGTGGAGAA | 762 | GCAGAAGATGGAGGAAGCCAAGGAAATCTCATC | 763 | ATGGACCATGAAAAT | 769 | TCATATGATGTTAAAATG | 770 | GCCAGCAGTTTACAGGGGAGGTACTATGGCTACACC | 771 |
| 49 | PN45460 | GCCACAGGATACCCTTCC | 777 | GCCACGAAGGCTGATGAC | 778 | GCTCTGAGTGATACCAGAGATGACAAGATCATC | 779 | ATGAACCATGAGTAT | 785 | TCAATGAATGTTGAGGTG | 786 | GCCAGCAGTCCCGGGACAGGGGGATTTTCACCCCTCCAC | 787 |
| 50 | PN45494 | GCCACAGGATACCCTTCC | 793 | GCCACGAAGGCTGATGAC | 794 | GCTCTGAGTGATACCAGAGATGACAAGACCATC | 795 | ATGGACCATGAAAAT | 801 | TCATATGATGTTAAAATG | 802 | GCCAGCAGTTTACAGGGGAGGTACTATGGCTACACC | 803 |
| 51 | PN45590 | TATGGGGCAACACCTTAT | 809 | TACTTTTCAGGAGACACTCTG | 810 | GCTGTGGGTGCTGGTTCTGCAAGGCAACTGACC | 811 | TCTGGGCATGACACT | 817 | TATTATGAGGAGGAAGAG | 818 | GCCAGCAGCTTTGACACTGAAGCTTTC | 819 |
| 52 | PN45557 | ACCAGTGATCCAAGTTATGGT | 825 | CAGGGGTCTTATGACCAGCAA | 826 | GCAATGAGAGAGGGCCCGGGCTCTGGCAACACAGGCAAACTAATC | 827 | ATGAACCATAACTAC | 833 | TCAGTTGGTGCTGGTATC | 834 | GCCAGCAGTTACTCGGAGTGGCAGAACTATGGCTACACC | 835 |
| 53 | PN45546 | ACCAGTGAGAGTGATTATTAT | 841 | CAAGAAGCTTATAAGCAACAG | 842 | GCTTATAGGAGCGGTGCTGGTGGTACTAGCTATGGAAAGCTGACA | 843 | TCTGGGCACAAGAGT | 849 | TATTATGAGAAAGAAGAG | 850 | GCCAGCAGCATCCGGGACACCTATGGCTACACC | 851 |
| 54 | PN45481 | GCCACAGGATACCCTTCC | 857 | GCCACGAAGGCTGATGAC | 858 | GCTCTGAGTGATACCAGAGATGACAAGATCATC | 859 | ATGGACCATGAAAAT | 865 | TCATATGATGTTAAAATG | 866 | GCCAGCAGTTTACAGGGGAGGTACTATGGCTACACC | 867 |

TABLE 8

| Amino acid and nucleic acid sequences for Veloci-T ® TCRs specific for MAGE-A4 (230-239)/HLA-A2 | |
|---|---|
| TCR name<br>Domain<br>name | Domain Sequences<br>Amino Acid Sequence (SEQ ID NO); CDR1, CDR2, and CDR3 sequences are underlined<br>Nucleic Acid Sequence (SEQ ID NO) ; CDR1, CDR2, and CDR3 sequences are underlined |
| PN45515<br>Vα | DAKTTQPPSMDCAEGRAANLPCNHSTISGNEYVYWYRQIHSQGPQYIIHGLKNNETNEMASLIITEDRKSSTLILPHATLRDTAVYYCIVRPYNAGNNRKLIWGLGTSLAVNP (SEQ ID NO: 620)<br>GATGCTAAGACCACCCAGCCCCCCTCCATGGATTGCGCTGAAGGAAGAGCTGCAAACCTGCCTTGTAATCACTCTACCATCAGTGGAAATGAGTATGTGTATTGGTATCGACAGATTCACTCCCAGGGGCCACAGTATATCATTCATGGTCTAAAAAACAATGAAACCAATGAAATGGCCTCTCTGATCATCACAGAAGACAGAAAGTCCAGCACCTTGATCCTGCCCCACGCTACGCTGAGAGACACTGCTGTGTACTATTGCATCGTCAGACCTTATAATGCTGGCAACAACCGTAAGCTGATTTGGGGATTGGGAACAAGCCTGGCAGTAAATCCG (SEQ ID NO: 621) |
| PN45515<br>Vβ | DVKVTQSSRYLVKRTGEKVFLECVQDMDHENMFWYRQDPGLGLRLIYFSYDVKMKEKGDIPEGYSVSREKKERFSLILESASTNQTSMYLCASSFGGGYYGYTFGSGTRLTVV (SEQ ID NO: 628)<br>GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATCCTGGAGTCCGCCAGCACCAACCAGACATCTATGTACCTCTGTGCCAGCAGTTTTGGGGGGGGATACTATGGCTACACCTTCGGTTCGGGGACCAGGCTAACCGTTGTA (SEQ ID NO: 629) |
| PN45593<br>Vα | AQKITQTQPGMFVQEKEAVTLDCTYDTSDPSYGLFWYKQPSSGEMIFLIYQGSYDQQNATEGRYSLNFQKARKSANLVISASQLGDSAMYFCAMREGPGNNARLMFGDGTQLVVKP (SEQ ID NO: 636)<br>GCCCAGAAGATAACTCAAACCCAACCAGGAATGTTCGTGCAGGAAAAGGAGGCTGTGACTCTGGACTGCACATATGACACCAGTGATCCAAGTTATGGTCTATTCTGGTACAAGCAGCCCAGCAGTGGGGAAATGATTTTTCTTATTTATCAGGGGTCTTATGACCAGCAAAATGCAACAGAAGGTCGCTACTCATTGAATTTCCAGAAGGCAAGAAAATCCGCCAACCTTGTCATCTCCGCTTCACAACTGGGGGACTCAGCAATGTACTTCTGTGCAATGAGAGAGGGCCCTGGTAACAATGCCAGACTCATGTTTGGAGATGGAACTCAGCTGGTGGTGAAGCCC (SEQ ID NO: 637) |
| PN45593<br>Vβ | NAGVTQTPKFRVLKTGQSMTLLCAQDMNHEYMYWYRQDPGMGLRLIHYSVGEGTTAKGEVPDGYNVSRLKKQNFLLGLESAAPSQTSVYFCASSYWDRGSPLHFGNGTRLTVT (SEQ ID NO: 644)<br>AATGCTGGTGTCACTCAGACCCCAAAATTCCGGGTCCTGAAGACAGGACAGAGCATGACACTGCTGTGTGCCCAGGATATGAACCATGAATACATGTACTGGTATCGACAAGACCCAGGCATGGGGCTGAGGCTGATTCATTACTCAGTTGGTGAGGGTACAACTGCCAAAGGAGAGGTCCCTGATGGCTACAATGTCTCCAGATTAAAAAAACAGAATTTCCTGCTGGGGTTGGAGTCGGCTGCTCCCTCCCAAACATCTGTGTACTTCTGTGCCAGCAGTTACTGGGACAGGGGCTCACCCCTCCACTTTGGGAACGGGACCAGGCTCACTGTGACA (SEQ ID NO: 645) |
| PN45539<br>Vα | DAKTTQPPSMDCAEGRAANLPCNHSTISGNEYVYWYRQIHSQGPQYIIHGLKNNETNEMASLIITEDRKSSTLILPHATLRDTAVYYCIVRPYNAGNNRKLIWGLGTSLAVNP (SEQ ID NO: 652)<br>GATGCTAAGACCACCCAGCCCCCCTCCATGGATTGCGCTGAAGGAAGAGCTGCAAACCTGCCTTGTAATCACTCTACCATCAGTGGAAATGAGTATGTGTATTGGTATCGACAGATTCACTCCCAGGGGCCACAGTATATCATTCATGGTCTAAAAAACAATGAAACCAATGAAATGGCCTCTCTGATCATCACAGAAGACAGAAAGTCCAGCACCTTGATCCTGCCCCACGCTACGCTGAGAGACACTGCTGTGTACTATTGCATCGTCAGACCTTATAATGCTGGCAACAACCGTAAGCTGATTTGGGGATTGGGAACAAGCCTGGCAGTAAATCCG (SEQ ID NO: 653) |
| PN45539<br>Vβ | DVKVTQSSRYLVKRTGEKVFLECVQDMDHENMFWYRQDPGLGLRLIYFSYDVKMKEKGDIPEGYSVSREKKERFSLILESASTNQTSMYLCASSFEGGYYGYTFGSGTRLTVV (SEQ ID NO: 660)<br>GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATTCTGGAGTCCGCCAGCACCAACCAGACATCTATGTACCTCTGTGCCAGCAGTTTTGAGGGGGGATACTATGGCTACACCTTCGGTTCGGGGACCAGGTTAACCGTTGTA (SEQ ID NO: 661) |

TABLE 8-continued

| Amino acid and nucleic acid sequences for Veloci-T ® TCRs specific for MAGE-A4 (230-239)/HLA-A2 | |
|---|---|
| TCR name<br>Domain<br>name | Domain Sequences<br>Amino Acid Sequence (SEQ ID NO); CDR1, CDR2, and CDR3 sequences are underlined<br>Nucleic Acid Sequence (SEQ ID NO) ; CDR1, CDR2, and CDR3 sequences are underlined |
| PN45545<br>Vα | AQKITQTQPGMFVQEKEAVTLDCTYDTSDPSYGLFWYKQPSSGEMIFLIYQGSYDQQNATEGRYSLNFQKARKSANLVISASQLGDSAMYFCAMRGGGSGGSYIPTFGRGTSLIVHP (SEQ ID NO: 668)<br>GCCCAGAAGATAACTCAAACCCAACCAGGAATGTTCGTGCAGGAAAAGGAGGCTGTGACTCTGGACTGCACATATGACACCAGTGATCCAAGTTATGGTCTATTCTGGTACAAGCAGCCCAGCAGTGGGGAAATGATTTTTCTTATTTATCAGGGGTCTTATGACCAGCAAAATGCAACAGAAGGTCGCTACTCATTGAATTTCCAGAAGGCAAGAAAATCCGCCAACCTTGTCATCTCCGCTTCACAACTGGGGGACTCAGCAATGTACTTCTGTGCAATGAGAGGGGGGGGATCAGGAGGAAGCTACATACCTACATTTGGAAGAGGAACCAGCCTTATTGTTCATCCG (SEQ ID NO: 669) |
| PN45545<br>Vβ | DVKVTQSSRYLVKRTGEKVFLECVQDMDHENMFWYRQDPGLGLRLIYFSYDVKMKEKGDIPEGYSVSREKKERFSLILESASTNQTSMYLCASSFTGPYNSPLHFGNGTRLTVT (SEQ ID NO: 676)<br>GATGTGAAAGTAACCCAGAGCTCGAGATATCTAGTCAAAAGGACGGGAGAGAAAGTTTTTCTGGAATGTGTCCAGGATATGGACCATGAAAATATGTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATTCTGGAGTCCGCCAGCACCAACCAGACATCTATGTACCTCTGTGCCAGCAGTTTCACAGGGCCCTATAATTCACCCCTCCACTTTGGGAACGGGACCAGGCTCACTGTGACA (SEQ ID NO: 677) |
| PN45584<br>Vα | AQKITQTQPGMFVQEKEAVTLDCTYDTSDPSYGLFWYKQPSSGEMIFLIYQGSYDEQNATEGRYSLNFQKARKSANLVISASQLGDSAMYFCAMREGPGSGNTGKLIFGQGTTLQVKP (SEQ ID NO: 684)<br>GCCCAGAAGATAACTCAAACCCAACCAGGAATGTTCGTGCAGGAAAAGGAGGCTGTGACTCTGGACTGCACATATGACACCAGTGATCCAAGTTATGGTCTATTCTGGTACAAGCAGCCCAGCAGTGGGGAAATGATTTTTCTTATTTATCAGGGGTCTTATGACGAGCAAAATGCAACAGAAGGTCGCTACTCATTGAATTTCCAGAAGGCAAGAAAATCCGCCAACCTTGTCATCTCCGCTTCACAACTGGGGGACTCAGCAATGTACTTCTGTGCAATGAGAGAGGGCCCGGGCTCTGGCAACACAGGCAAACTAATCTTTGGGCAAGGGACAACTTTACAAGTAAAACCA (SEQ ID NO: 685) |
| PN45584<br>Vβ | NAGVTQTPKFRILKIGQSMTLQCAQDMNHNYMYWYRQDPGMGLKLIYYSVGAGITDKGEVPNGYNVSRSTTEYFPLRLELAAPSQTSVYFCASSYSEWQNYGYTFGSGTRLTVV (SEQ ID NO: 692)<br>AATGCTGGTGTCACTCAGACCCCAAAATTCCGCATCCTGAAGATAGGACAGAGCATGACACTGCAGTGTGCCCAGGATATGAACCATAACTACATGTACTGGTATCGACAAGACCCAGGCATGGGGCTGAAGCTGATTTATTATTCAGTTGGTGCTGGTATCACTGATAAAGGAGAAGTCCCGAATGGCTACAACGTCTCCAGATCAACCACAGAGTATTTCCCGCTCAGGCTGGAGTTGGCTGCTCCCTCCCAGACATCTGTGTACTTCTGTGCCAGCAGTTACTCGGAGTGGCAGAACTATGGCTACACCTTCGGTTCGGGGACCAGGTTAACCGTTGTA (SEQ ID NO: 693) |
| PN45581<br>Vα | AQKITQTQPGMFVQEKEAVTLDCTYDTSDPSYGLFWYKQPSSGEMIFLIYQGSYDQQNATEGRYSLNFQKARKSANLVISASQLGDSAMYFCAMREGPGNNARLMFGDGTQLVVKP (SEQ ID NO: 700)<br>GCCCAGAAGATAACTCAAACCCAACCAGGAATGTTCGTGCAGGAAAAGGAGGCTGTGACTCTGGACTGCACATATGACACCAGTGATCCAAGTTATGGTCTATTCTGGTACAAGCAGCCCAGCAGTGGGGAAATGATTTTTCTTATTTATCAGGGGTCTTATGACCAGCAAAATGCAACAGAAGGTCGCTACTCATTGAATTTCCAGAAGGCAAGAAAATCCGCCAACCTTGTCATCTCCGCTTCACAACTGGGGGACTCAGCAATGTACTTCTGTGCAATGAGAGAGGGCCCTGGTAACAATGCCAGACTCATGTTTGGAGATGGAACTCAGCTGGTGGTGAAGCCC (SEQ ID NO: 701) |
| PN45581<br>Vβ | EAQVTQTPRYLITVTGKKLTVTCSQNMNHEYMSWYRQDPGLGLRQIYYSMNVEVTDKGDVPEGYKVSRKEKRNFPLILESPSPNQTSLYFCASSLWTGGGYTFGSGTRLTVV (SEQ ID NO: 708)<br>GAAGCCCAAGTGACCCAGACCCCAAGATACCTCATCACAGTGACTGGAAAGAAGTTAACAGTGACTTGTTCTCAGAATATGAACCATGAGTATATGTCCTGGTATCGACAAGACCCAGGGCTGGGCTTAAGGCAGATCTACTATTCAATGAATGTTGAGGTGACTGATAAGGGAGATGTTCCTGAAGGGTA |

TABLE 8-continued

Amino acid and nucleic acid sequences for Veloci-T ® TCRs specific for MAGE-A4 (230-239)/HLA-A2

| TCR name<br>Domain name | Domain Sequences<br>Amino Acid Sequence (SEQ ID NO); CDR1, CDR2, and CDR3 sequences are underlined<br>Nucleic Acid Sequence (SEQ ID NO) ; CDR1, CDR2, and CDR3 sequences are underlined |
|---|---|
| | CAAAGTCTCTCGAAAAGAGAAGAGGAATTTCCCCCTGATCCTGGAGTC GCCCAGCCCCAACCAGACCTCTCTGTACTTCTGTGCCAGCAGTTTATG GACAGGGGGAGGCTACACCTTCGGTTCGGGGACCAGGTTAACCGTTGT A (SEQ ID NO: 709) |
| PN45428<br>Vα | EDQVTQSPEALRLQEGESSSLNCSYTVSGLRGLFWYRQDPGKGPEFLFTL YSAGEEKEKERLKATLTKKESFLHITAPKPEDSATYLCAVQPLNAGNNRK LIWGLGTSLAVNP (SEQ ID NO: 716)<br>GAAGACCAGGTGACGCAGAGTCCCGAGGCCCTGAGACTCCAGGAGGG AGAGAGTAGCAGTCTCAACTGCAGTTACACAGTCAGCGGTTTAAGAG GGCTGTTCTGGTATAGGCAAGATCCTGGGAAAGGCCCTGAATTCCTCT TCACCCTGTATTCAGCTGGGGAAGAAAAGGAGAAAGAAAGGCTAAAA GCCACATTAACAAAGAAGGAAAGCTTTCTGCACATCACAGCCCCTAA ACCTGAAGACTCAGCCACTTATCTCTGTGCTGTGCAGCCCCTTAATGCT GGCAACAACCGTAAGCTGATTTGGGGATTGGGAACAAGCCTGGCAGT AAATCCG (SEQ ID NO: 717) |
| PN45428<br>Vβ | GAVVSQHPSWVICKSGTSVKIECRSLDFQATTMFWYRQFPKQSLMLMAT SNEGSKATYEQGVEKDKFLINHASLTLSTLTVTSAHPEDSSFYICSAREWG GTEAFFGQGTRLTVV (SEQ ID NO: 724)<br>GGTGCTGTCGTCTCTCAACATCCGAGCTGGGTTATCTGTAAGAGTGGA ACCTCTGTGAAGATCGAGTGCCGTTCCCTGGACTTTCAGGCCACAACT ATGTTTTGGTATCGTCAGTTCCCGAAACAGAGTCTCATGCTGATGGCA ACTTCCAATGAGGGCTCCAAGGCCACATACGAGCAAGGCGTCGAGAA GGACAAGTTTCTCATCAACCATGCAAGCCTGACCTTGTCCACTCTGAC AGTGACCAGTGCCCATCCTGAAGACAGCAGCTTCTACATCTGCAGTGC TAGAGAATGGGGTGGCACTGAAGCTTTCTTTGGACAAGGCACCAGACT CACAGTTGTA (SEQ ID NO: 725) |
| PN45418<br>Vα | EDQVTQSPEALRLQEGESSSLNCSYTVSGLRGLFWYRQDPGKGPEFLFTL YSAGEEKEKERLKATLTKKESFLHITAPKPEDSATYLCAVQPSYSGAGSY QLTFGKGTKLSVIP (SEQ ID NO: 732)<br>GAAGACCAGGTGACGCAGAGTCCCGAGGCCCTGAGACTCCAGGAGGG AGAGAGTAGCAGTCTCAACTGCAGTTACACAGTCAGCGGTTTAAGAG GGCTGTTCTGGTATAGGCAAGATCCTGGGAAAGGCCCTGAATTCCTCT TCACCCTGTATTCAGCTGGGGAAGAAAAGGAGAAAGAAAGGCTAAAA GCCACATTAACAAAGAAGGAAAGCTTTCTGCACATCACAGCCCCTAA ACCTGAAGACTCAGCCACTTATCTCTGTGCTGTGCAGCCCTCATACTCT GGGGCTGGGAGTTACCAACTCACTTTCGGGAAGGGGACCAAACTCTC GGTCATACCA (SEQ ID NO: 733) |
| PN45418<br>Vβ | EAQVTQNPRYLITVTGKKLTVTCSQNMNHEYMSWYRQDPGLGLRQIYYS MNVEVTDKGDVPEGYKVSRKEKRNFPLILESPSPNQTSLYFCASSPGTGG FSPLHFGNGTRLTVT (SEQ ID NO: 740)<br>GAAGCCCAAGTGACCCAGAACCCAAGATACCTCATCACAGTGACTGG AAAGAAGTTAACAGTGACTTGTTCTCAGAATATGAACCATGAGTATAT GTCCTGGTATCGACAAGACCCAGGGCTGGGCTTAAGGCAGATCTACTA TTCAATGAATGTTGAGGTGACTGATAAGGGAGATGTTCCTGAAGGGTA CAAAGTCTCTCGAAAAGAGAAGAGGAATTTCCCCCTGATCCTGGAGTC GCCCAGCCCCAACCAGACCTCTCTGTACTTCTGTGCCAGCAGTCCCGG GACAGGGGGATTTTCACCCCTCCACTTTGGGAACGGGACCAGGCTCAC TGTGACA (SEQ ID NO: 741) |
| PN45446<br>Vα | EDQVTQSPEALRLQEGESSSLNCSYTVSGLRGLFWYRQDPGKGPEFLFTL YSAGEEKEKERLKATLTKKESFLHITAPKPEDSATYLCAVQPSYSGAGSY QLTFGKGTKLSVIP (SEQ ID NO: 748)<br>GAAGACCAGGTGACGCAGAGTCCCGAGGCCCTGAGACTCCAGGAGGG AGAGAGTAGCAGTCTCAACTGCAGTTACACAGTCAGCGGTTTAAGAG GGCTGTTCTGGTATAGGCAAGATCCTGGGAAAGGCCCTGAATTCCTCT TCACCCTGTATTCAGCTGGGGAAGAAAAGGAGAAAGAAAGGCTAAAA GCCACATTAACAAAGAAGGAAAGCTTTCTGCACATCACAGCCCCTAA ACCTGAAGACTCAGCCACTTATCTCTGTGCTGTGCAGCCCTCATACTCT GGGGCTGGGAGTTACCAACTCACTTTCGGGAAGGGGACCAAACTCTC GGTCATACCA (SEQ ID NO: 749) |
| PN45446<br>Vβ | GAVVSQHPSWVICKSGTSVKIECRSLDFQATTMFWYRQFPKQSLMLMAT SNEGSKATYEQGVEKDKFLINHASLTLSTLTVTSAHPEDSSFYICSAREWR GTEAFFGQGTRLTVV (SEQ ID NO: 756)<br>GGTGCTGTCGTCTCTCAACATCCGAGCTGGGTTATCTGTAAGAGTGGA ACCTCTGTGAAGATCGAGTGCCGTTCCCTGGACTTTCAGGCCACAACT ATGTTTTGGTATCGTCAGTTCCCGAAACAGAGTCTCATGCTGATGGCA |

TABLE 8-continued

Amino acid and nucleic acid sequences for Veloci-T ® TCRs specific for MAGE-A4 (230-239)/HLA-A2

| TCR name<br>Domain<br>name | Domain Sequences<br>Amino Acid Sequence (SEQ ID NO); CDR1, CDR2, and CDR3 sequences are underlined<br>Nucleic Acid Sequence (SEQ ID NO) ; CDR1, CDR2, and CDR3 sequences are underlined |
|---|---|
| | ACTTCCAATGAGGGCTCCAAGGCCACATACGAGCAAGGCGTCGAGAA<br>GGACAAGTTTCTCATCAACCATGCAAGCCTGACCTTGTCCACTCTGAC<br>AGTGACCAGTGCCCATCCTGAAGACAGCAGCTTCTACATCTGCAGTGC<br>TAGAGAGTGGAGGGGCACTGAAGCTTTCTTTGGACAAGGCACCAGAC<br>TCACAGTTGTA (SEQ ID NO: 757) |
| PN45489<br>Vα | TQLLEQSPQFLSIQEGENLTVYCNSSSVFSSLQWYRQEPGEGPVLLVTVVT<br>GGEVKKLKRLTFQFGDARKDSSLHITAAQPGDTGLYLCAEDGGSQGNLIF<br>GKGTKLSVKP (SEQ ID NO: 764)<br>ACCCAGCTGCTGGAGCAGAGTCCTCAGTTTCTAAGCATCCAAGAGGGA<br>GAAAATCTCACTGTGTACTGCAACTCCTCAAGTGTTTTTTCCAGCTTAC<br>AATGGTACAGACAGGAGCCTGGGGAAGGTCCTGTCCTCCTGGTGACA<br>GTAGTTACGGGTGGAGAAGTGAAGAAGCTGAAGAGACTAACCTTTCA<br>GTTTGGTGATGCAAGAAAGGACAGTTCTCTCCACATCACTGCGGCCCA<br>GCCTGGTGATACAGGCCTCTACCTCTGTGCAGAAGATGGAGGAAGCC<br>AAGGAAATCTCATCTTTGGAAAAGGCACTAAACTCTCTGTTAAACCA<br>(SEQ ID NO: 765) |
| PN45489<br>Vβ | DVKVTQTSRYLVKRTGEKVFLECVQDMDHENMFWYRQDPGLGLRLIYF<br>SYDVKMKEKGDIPEGYSVSREKKERFSLILESASTNQTSMYLCASSLQGR<br>YYGYTFGSGTRLTVV (SEQ ID NO: 772)<br>GATGTGAAAGTAACCCAGACCTCGAGATATCTAGTCAAAAGGACGGG<br>AGAGAAAGTTTTTCTGGAATGTGTCCAGGATATGGACCATGAAAATAT<br>GTTCTGGTATCGACAAGACCCAGGTCTGGGGCTACGGCTGATCTATTT<br>CTCATATGATGTTAAAATGAAAGAAAAAGGAGATATTCCTGAGGGGT<br>ACAGTGTCTCTAGAGAGAAGAAGGAGCGCTTCTCCCTGATTCTGGAGT<br>CCGCCAGCACCAACCAGACATCTATGTACCTCTGTGCCAGCAGTTTAC<br>AGGGGAGGTACTATGGCTACACCTTCGGTTCGGGGACCAGGTTAACCG<br>TTGTA (SEQ ID NO: 773) |
| PN45460<br>Vα | GNSVTQMEGPVTLSEEAFLTINCTYTATGYPSLFWYVQYPGEGLQLLLKA<br>TKADDKGSNKGFEATYRKETTSFHLEKGSVQVSDSAVYFCALSDTRDDK<br>IIFGKGTRLHILP (SEQ ID NO: 780)<br>GGAAATTCAGTGACCCAGATGGAAGGGCCAGTGACTCTCTCAGAAGA<br>GGCCTTCCTGACTATAAACTGCACGTACACAGCCACAGGATACCCTTC<br>CCTTTTCTGGTATGTCCAATATCCTGGAGAAGGTCTACAGCTCCTCCTG<br>AAAGCCACGAAGGCTGATGACAAGGGAAGCAACAAAGGTTTTGAAGC<br>CACATACCGTAAAGAAACCACTTCTTTCCACTTGGAGAAAGGCTCAGT<br>TCAAGTGTCAGACTCAGCGGTGTACTTCTGTGCTCTGAGTGATACCAG<br>AGATGACAAGATCATCTTTGGAAAAGGGACACGACTTCATATTCTCCC<br>C (SEQ ID NO: 788) |
| PN45460<br>Vβ | EAQVTQSPRYLITVTGKKLTVTCSQNMNHEYMSWYRQDPGLGLRQIYYS<br>MNVEVTDKGDVPEGYKVSRKEKRNFPLILESPSPNQTSLYFCASSPGTGG<br>FSPLHFGNGTRLTVT (SEQ ID NO: 781)<br>GAAGCCCAAGTGACCCAGAGCCCAAGATACCTCATCACAGTGACTGG<br>AAAGAAGTTAACAGTGACTTGTTCTCAGAATATGAACCATGAGTATAT<br>GTCCTGGTATCGACAAGACCCAGGGCTGGGCTTAAGGCAGATCTACTA<br>TTCAATGAATGTTGAGGTGACTGATAAGGGAGATGTTCCTGAAGGGTA<br>CAAAGTCTCTCGAAAAGAGAAGAGGAATTTCCCCCTGATCCTGGAGTC<br>GCCCAGCCCCAACCAGACCTCTCTGTACTTCTGTGCCAGCAGTCCCGG<br>GACAGGGGGATTTTCACCCCTCCACTTTGGGAACGGGACCAGGCTCAC<br>TGTGACA (SEQ ID NO: 789) |
| PN45494<br>Vα | GNSVTQIEGPVTLSEEAFLTINCTYTATGYPSLFWYVQYPGEGLQLLLKAT<br>KADDKGSNKGFEATYRKETTSFHLEKGSVQVSDSAVYFCALSDTRDDKT<br>IFGKGTRLHILP (SEQ ID NO: 796)<br>GGAAATTCAGTGACCCAGATTGAAGGGCCAGTGACTCTCTCAGAAGA<br>GGCCTTCCTGACTATAAACTGCACGTACACAGCCACAGGATACCCTTC<br>CCTTTTCTGGTATGTCCAATATCCTGGAGAAGGTCTACAGCTCCTCCTG<br>AAAGCCACGAAGGCTGATGACAAGGGAAGCAACAAAGGTTTTGAAGC<br>CACATACCGTAAAGAAACCACTTCTTTCCACTTGGAGAAAGGCTCAGT<br>TCAAGTGTCAGACTCAGCGGTGTACTTCTGTGCTCTGAGTGATACCAG<br>AGATGACAAGACCATCTTTGGAAAAGGGACACGACTTCATATTCTCCC<br>C (SEQ ID NO: 804) |
| PN45494<br>Vβ | DVKVTQSSRYLVKRTGEKVFLECVQDMDHENMFWYRQDPGLGLRLIYF<br>SYDVKMKEKGDIPEGYSVSREKKERFSLILESASTNQTSMYLCASSLQGR<br>YYGYTFGSGTRLTVV (SEQ ID NO: 797)<br>GATGTGAAAGTAACCCAGAGTTCGAGATATCTAGTCAAAAGGACGGG<br>AGAGAAAGTTTTTCTGGAATGTGTCCAGGATATGGACCATGAAAATAT |

TABLE 8-continued

| TCR name Domain name | Domain Sequences Amino Acid Sequence (SEQ ID NO); CDR1, CDR2, and CDR3 sequences are underlined Nucleic Acid Sequence (SEQ ID NO) ; CDR1, CDR2, and CDR3 sequences are underlined |
|---|---|
| | GTTCTGGTATCGACAAGACCCAGGTCTGGGGCTACGGCTGATCTATTTCTCATATGATGTTAAAATGAAAGAAAAAGGAGATATTCCTGAGGGGTACAGTGTCTCTAGAGAGAAGAAGGAGCGCTTCTCCCTGATTCTGGAGTCCGCCAGCACCAACCAGACATCTATGTACCTCTGTGCCAGCAGTTTACAGGGGAGGTACTATGGCTACACCTTCGGTTCGGGGACCAGGTTAACCGTTGTA (SEQ ID NO: 805) |
| PN45590 Vα | AQSVTQPDIHITVSEGASLELRCNYSYGATPYLFWYVQSPGQGLQLLLKYFSGDTLVQGIKGFEAEFKRSQSSFNLRKPSVHWSDAAEYFCAVGAGSARQLTFGSGTQLTVLP (SEQ ID NO: 812) GCCCAGTCAGTGACCCAGCCTGACATCCACATCACTGTCTCTGAAGGAGCCTCACTGGAGTTGAGATGTAACTATTCCTATGGGGCAACACCTTATCTCTTCTGGTATGTCCAGTCCCCCGGCCAAGGCCTCCAGCTGCTCCTGAAGTACTTTTCAGGAGACACTCTGGTTCAAGGCATTAAAGGCTTTGAGGCTGAATTTAAGAGGAGTCAATCTTCCTTCAATCTGAGGAAACCCTCTGTGCATTGGAGTGATGCTGCTGAGTACTTCTGTGCTGTGGGTGCTGGTTCTGCAAGGCAACTGACCTTTGGATCTGGGACACAATTGACTGTTTTACCT (SEQ ID NO: 820) |
| PN45590 Vβ | DAGVTQSPTHLIKTRGQQVTLRCSPKSGHDTVSWYQQALGQGPQFIFQYYEEEERQRGNFPDRFSGHQFPNYSSELNVNALLLGDSALYLCASSFDTEAFFGQGTRLTVV (SEQ ID NO: 813) GACGCTGGAGTCACCCAAAGTCCCACACACCTGATCAAAACGAGAGGACAGCAAGTGACTCTGAGATGCTCTCCTAAGTCTGGGCATGACACTGTGTCCTGGTACCAACAGGCCCTGGGTCAGGGGCCCCAGTTTATCTTTCAGTATTATGAGGAGGAAGAGAGACAGAGAGGCAACTTCCCTGATCGATTCTCAGGTCACCAGTTCCCTAACTATAGCTCTGAGCTGAATGTGAACGCCTTGTTGCTGGGGGACTCGGCCCTCTATCTCTGTGCCAGCAGCTTTGACACTGAAGCTTTCTTTGGACAAGGCACCAGACTCACAGTTGTA (SEQ ID NO: 821) |
| PN45557 Vα | AQKITQTQPGMFVQEKEAVTLDCTYDTSDPSYGLFWYKQPSSGEMIFLIYQGSYDQQNATEGRYSLNFQKARKSANLVISASQLGDSAMYFCAMREGPGSGNTGKLIFGQGTTLQVKP (SEQ ID NO: 828) GCCCAGAAGATAACTCAAACCCAACCAGGAATGTTCGTGCAGGAAAAGGAGGCTGTGACTCTGGACTGCACATATGACACCAGTGATCCAAGTTATGGTCTATTCTGGTACAAGCAGCCCAGCAGTGGGGAAATGATTTTTCTTATTTATCAGGGGTCTTATGACCAGCAAAATGCAACAGAAGGTCGCTACTCATTGAATTTCCAGAAGGCAAGAAAATCCGCCAACCTTGTCATCTCCGCTTCACAACTGGGGGACTCAGCAATGTACTTCTGTGCAATGAGAGAGGGCCCGGGCTCTGGCAACACAGGCAAACTAATCTTTGGGCAAGGGACAACTTTACAAGTAAAACCA (SEQ ID NO: 836) |
| PN45557 Vβ | NAGVTQTPKFRILKIGQSMTLQCAQDMNHNYMYWYRQDPGMGLKLIYYSVGAGITDKGEVPNGYNVSRSTTEYFPLRLELAAPSQTSVYFCASSYSEWQNYGYTFGSGTRLTVV (SEQ ID NO: 829) AATGCTGGTGTCACTCAGACCCCAAAATTCCGCATCCTGAAGATAGGACAGAGCATGACACTGCAGTGTGCCCAGGATATGAACCATAACTACATGTACTGGTATCGACAAGACCCAGGCATGGGGCTGAAGCTGATTTATTATTCAGTTGGTGCTGGTATCACTGATAAAGGAGAAGTCCCGAATGGCTACAACGTCTCCAGATCAACCACAGAGTATTTCCCGCTCAGGCTGGAGTTGGCTGCTCCCTCCCAGACATCTGTGTACTTCTGTGCCAGCAGTTACTCGGAGTGGCAGAACTATGGCTACACCTTCGGTTCGGGGACCAGGTTAACCGTTGTA (SEQ ID NO: 837) |
| PN45546 Vα | AQTVTQSQPEMSVQEAETVTLSCTYDTSESDYYLFWYKQPPSRQMILVIRQEAYKQQNATENRFSVNFQKAAKSFSLKISDSQLGDAAMYFCAYRSGAGGTSYGKLTFGQGTILTVHP (SEQ ID NO: 844) GCTCAGACAGTCACTCAGTCTCAACCAGAGATGTCTGTGCAGGAGGCAGAGACCGTGACCCTGAGCTGCACATATGACACCAGTGAGAGTGATTATTATTTATTCTGGTACAAGCAGCCTCCCAGCAGGCAGATGATTCTCGTTATTCGCCAAGAAGCTTATAAGCAACAGAATGCAACAGAGAATCGTTTCTCTGTGAACTTCCAGAAAGCAGCCAAATCCTTCAGTCTCAAGATCTCAGACTCACAGCTGGGGGATGCCGCGATGTATTTCTGTGCTTATAGGAGCGGTGCTGGTGGTACTAGCTATGGAAAGCTGACATTTGGACAAGGGACCATCTTGACTGTCCATCCA (SEQ ID NO: 852) |
| PN45546 Vβ | DAGVTQSPTHLIKTRGQQVTLRCSPISGHKSVSWYQQVLGQGPQFIFQYYEKEERGRGNFPDRFSARQFPNYSSELNVNALLLGDSALYLCASSIRDTYGYTFGSGTRLTVV (SEQ ID NO: 845) GACGCTGGAGTCACCCAAAGTCCCACACACCTGATCAAAACGAGAGG |

TABLE 8-continued

| TCR name Domain name | Domain Sequences Amino Acid Sequence (SEQ ID NO); CDR1, CDR2, and CDR3 sequences are underlined Nucleic Acid Sequence (SEQ ID NO) ; CDR1, CDR2, and CDR3 sequences are underlined |
|---|---|
| | ACAGCAAGTGACTCTGAGATGCTCTCCTATCTCTGGGCACAAGAGTGT GTCCTGGTACCAACAGGTCCTGGGTCAGGGGCCCCAGTTTATCTTTCA GTATTATGAGAAAGAAGAGAGAGGAAGAGGAAACTTCCCTGATCGAT TCTCAGCTCGCCAGTTCCCTAACTATAGCTCTGAGCTGAATGTGAACG CCTTGTTGCTGGGGGACTCGGCCCTGTATCTCTGTGCCAGCAGCATCC GGGACACCTATGGCTACACCTTCGGTTCGGGGACCAGGTTAACCGTTG TA (SEQ ID NO: 853) |
| PN45481 Vα | GNSVTQMEGPVTLSEEAFLTINCTYTATGYPSLFWYVQYPGEGLQLLLKA TKADDKGSNKGFEATYRKETTSFHLEKGSVQVSDSAVYFCALSDTRDDK IIFGKGTRLHILP (SEQ ID NO: 860) GGAAATTCAGTGACCCAGATGGAAGGGCCAGTGACTCTCTCAGAAGA GGCCTTCCTGACTATAAACTGCACGTACACAGCCACAGGATACCCTTC CCTTTTCTGGTATGTCCAATATCCTGGAGAAGGTCTACAGCTCCTCCTG AAAGCCACGAAGGCTGATGACAAGGGAAGCAACAAAGGTTTTGAAGC CACATACCGTAAAGAAACCACTTCTTTCCACTTGGAGAAAGGCTCAGT TCAAGTGTCAGACTCAGCGGTGTACTTCTGTGCTCTGAGTGATACCAG AGATGACAAGATCATCTTTGGAAAAGGGACACGACTTCATATTCTCCC C (SEQ ID NO: 868) |
| PN45481 Vβ | DVKVTQSSRYLVKRTGEKVFLECVQDMDHENMFWYRQDPGLGLRLIYF SYDVKMKEKGDIPEGYSVSREKKERFSLILESASTNQTSMYLCASSLQGR YYGYTFGSGTRLTVV (SEQ ID NO: 861) GATGTGAAAGTAACCCAGAGCTCGAGATATCTAGTCAAAAGGACGGG AGAGAAAGTTTTTCTGGAATGTGTCCAGGATATGGACCATGAAAATAT GTTCTGGTATCGACAAGACCCAGGTCTGGGGCTACGGCTGATCTATTT CTCATATGATGTTAAAATGAAAGAAAAAGGAGATATTCCTGAGGGGT ACAGTGTCTCTAGAGAGAAGAAGGAGCGCTTCTCCCTGATTCTGGAGT CCGCCAGCACCAACCAGACATCTATGTACCTCTGTGCCAGCAGTTTAC AGGGGAGGTACTATGGCTACACCTTCGGTTCGGGGACCAGGTTAACCG TTGTA (SEQ ID NO: 869) |

Amino acid and nucleic acid sequences for Veloci-T ® TCRs specific for MAGE-A4 (230-239)/HLA-A2

TABLE 9

Variable (V) and joining (J) region gene families for the α and β chains of Veloci-T ® TCRs specific for MAGE-A4 (230-239)/HLA-A2

| TCR ID | V β | J β | V α | J α |
|---|---|---|---|---|
| PN45515 | 28 | 1-2 | 26-1 | 38 |
| PN45593 | 6-2 | 1-6 | 14/DV4 | 31 |
| PN45539 | 28 | 1-2 | 26-1 | 38 |
| PN45545 | 28 | 1-6 | 14/DV4 | 6 |
| PN45584 | 6-6 | 1-2 | 14/DV4 | 37 |
| PN45581 | 27 | 1-2 | 14/DV4 | 31 |
| PN45428 | 20-1 | 1-1 | 20 | 38 |
| PN45418 | 27 | 1-6 | 20 | 28 |

TABLE 9-continued

Variable (V) and joining (J) region gene families for the α and β chains of Veloci-T ® TCRs specific for MAGE-A4 (230-239)/HLA-A2

| TCR ID | V β | J β | V α | J α |
|---|---|---|---|---|
| PN45446 | 20-1 | 1-1 | 20 | 28 |
| PN45489 | 28 | 1-2 | 27 | 42 |
| PN45460 | 27 | 1-6 | 9-2 | 30 |
| PN45494 | 28 | 1-2 | 9-2 | 30 |
| PN45590 | 5-6 | 1-1 | 8-3 | 22 |
| PN45557 | 6-6 | 1-2 | 14/DV4 | 37 |
| PN45546 | 5-5 | 1-2 | 38-2/DV8 | 52 |
| PN45481 | 28 | 1-2 | 9-2 | 30 |

TABLE 10

Amino acid and polynucleic acid sequence identifiers for TCR alpha and beta variable chains and CDRs

| | Amino Acid Sequences | | | | | | | | Polynucleic Acid Sequences | | | | | | | |
|---|---|---|---|---|---|---|---|---|---|---|---|---|---|---|---|---|
| | | α CDRs | | | | β CDRs | | | | α CDRs | | | | β CDRs | | |
| TCR ID | Vα | CDR1 | CDR2 | CDR3 | Vβ | CDR1 | CDR2 | CDR3 | Vα | CDR1 | CDR2 | CDR3 | Vβ | CDR1 | CDR2 | CDR3 |
| | SEQ ID NO: | | | | | | | | SEQ ID NO: | | | | | | | |
| PN45515 | 620 | 614 | 615 | 616 | 628 | 622 | 623 | 624 | 621 | 617 | 618 | 619 | 629 | 625 | 626 | 627 |
| PN45593 | 636 | 630 | 631 | 632 | 644 | 638 | 639 | 640 | 637 | 633 | 634 | 635 | 645 | 641 | 642 | 643 |
| PN45539 | 652 | 646 | 647 | 648 | 660 | 654 | 655 | 656 | 653 | 649 | 650 | 651 | 661 | 657 | 658 | 659 |
| PN45545 | 668 | 662 | 663 | 664 | 676 | 670 | 671 | 672 | 669 | 665 | 666 | 667 | 677 | 673 | 674 | 675 |
| PN45584 | 684 | 678 | 679 | 680 | 692 | 686 | 687 | 688 | 685 | 681 | 682 | 683 | 693 | 689 | 690 | 691 |
| PN45581 | 700 | 694 | 695 | 696 | 708 | 702 | 703 | 704 | 701 | 697 | 698 | 699 | 709 | 705 | 706 | 707 |
| PN45428 | 716 | 710 | 711 | 712 | 724 | 718 | 719 | 720 | 717 | 713 | 714 | 715 | 725 | 721 | 722 | 723 |

TABLE 10-continued

| Amino acid and polynucleic acid sequence identifiers for TCR alpha and beta variable chains and CDRs | | | | | | | | | | | | | | | | |
|---|---|---|---|---|---|---|---|---|---|---|---|---|---|---|---|---|
| | Amino Acid Sequences | | | | | | | | Polynucleic Acid Sequences | | | | | | | |
| | | α CDRs | | | | β CDRs | | | | α CDRs | | | | β CDRs | | |
| TCR ID | Vα | CDR1 | CDR2 | CDR3 | Vβ SEQ ID NO: | CDR1 | CDR2 | CDR3 | Vα | CDR1 | CDR2 | CDR3 | Vβ SEQ ID NO: | CDR1 | CDR2 | CDR3 |
| PN45418 | 732 | 726 | 727 | 728 | 740 | 734 | 735 | 736 | 733 | 729 | 730 | 731 | 741 | 737 | 738 | 739 |
| PN45446 | 748 | 742 | 743 | 744 | 756 | 750 | 751 | 752 | 749 | 745 | 746 | 747 | 757 | 753 | 754 | 755 |
| PN45489 | 764 | 758 | 759 | 760 | 772 | 766 | 767 | 768 | 765 | 761 | 762 | 763 | 773 | 769 | 770 | 771 |
| PN45460 | 780 | 774 | 775 | 776 | 788 | 782 | 783 | 784 | 781 | 777 | 778 | 779 | 789 | 785 | 786 | 787 |
| PN45494 | 796 | 790 | 791 | 792 | 804 | 798 | 799 | 800 | 797 | 793 | 794 | 795 | 805 | 801 | 802 | 803 |
| PN45590 | 812 | 806 | 807 | 808 | 820 | 814 | 815 | 816 | 813 | 809 | 810 | 811 | 821 | 817 | 818 | 819 |
| PN45557 | 828 | 822 | 823 | 824 | 836 | 830 | 831 | 832 | 829 | 825 | 826 | 827 | 837 | 833 | 834 | 835 |
| PN45546 | 844 | 838 | 839 | 840 | 852 | 846 | 847 | 848 | 845 | 841 | 842 | 843 | 853 | 849 | 850 | 851 |
| PN45481 | 860 | 854 | 855 | 856 | 868 | 862 | 863 | 864 | 861 | 857 | 858 | 859 | 869 | 865 | 866 | 867 |

Example 3. Cytotoxicity of MAGE-A4 TCRs Against A375 Melanoma Cells

This example describes the ability of certain Mage-A4 TCRs of the invention to selectively kill A375 melanoma cells.

Methods

T Cell Manipulation

Pan T cells were purified by negative selection from human peripheral blood monocyte cells (PBMCs) using the EasySep Human T cell isolation kit (StemCell Technologies 17951), then cryopreserved. On experiment day 0, T cells were thawed and plated at $1\times10^6$ cells/ml in media (CTS OpTmizer media [Life Technologies A1048501] supplemented with 10 mg/ml gentamicin, 4 mM L-glutamine) containing 200 U/ml human IL-2 and anti-CD3/anti-CD28 activation beads at a 1:1 bead:cell ratio (Life Technologies 111.32D). On day 3, activation beads were removed, and $5\times10^6$ cells were transfected with 20 mg Cas9 protein (Life Technologies A36499) complexed with sgRNAs targeting the TRAC and TRBC loci using the Nucleofector IIb device and Human T cell Nucleofection Kit (Lonza VVPA-1002). After nucleofection, cells were transduced with adeno-associated virus (AAV) vectors engineered to target TCRa and TCRb expression cassettes to the human TRAC locus. Every 2-3 days, cells were re-plated in fresh supplemented media to about $1\times10^6$ cells/ml. At various points after TCR construct transduction, cells were stained with antibodies against surface markers and peptide-MHC tetramer reagents, then analyzed by flow cytometry to quantitate transduction efficiency.

Cytotoxicity Assay

Antigen-specific, cytotoxic T cell function was assessed by calcein release assay. Target tumor cells were labeled in the presence of 8 mM Calcein AM dye (Life Technologies C1430) for 30 minutes at 37° C., then washed with media. $1\times10^4$ target cells were plated per assay well in a 96-well plate, along with varying dilutions of transduced T cells or untransduced (UTD) controls. After two hours, released fluorescence dye was measured in culture supernatants. Spontaneous release (SR) was measured in wells containing labeled target cells but no T cells, and maximum release (MR) was measured in wells with labeled target cells in the presence of 0.5% Triton X-100. Percent specific cytoxicity was determined as 100×(test release−SR)/(MR−SR).

Results

Primary human T cells were engineered to express MAGE-A4 specific TCRs against two HLA-A2 restricted peptides (MAGE-A4 286-294 (KVLEHVVRV; SEQ ID NO: 609) and MAGE-A4 230-239 (GVYDGREHTV; SEQ ID NO: 294)), or an irrelevant HLA-A2 restricted peptide derived from a viral protein (HPV). As depicted in FIG. 1, flow cytometry analysis using peptide MHC tetramer reagents confirmed expression and expected antigen specificity of transduced TCRs.

To validate cytotoxic activity of the TCRs, engineered T cells were tested for their ability to direct cytolytic function against MAGE-A4 expressing tumor cells in a Calcein AM dye release assay, which was performed in duplicate (FIG. 2A, FIG. 2B, FIG. 3A, FIG. 3B). These assays confirmed that the MAGE-A4 specific TCRs (against both the MAGE-A4 286-294 and the MAGE-A4 230-239 peptides), but not the TCR against the irrelevant HLA-A2 restricted peptide, mediated killing of A375 melanoma cells in a dose dependent manner.

Example 4. MAGE-A4 (286-294) TCRs in Jurkat Cell TCR Signaling Bioassays

This example describes the ability of selected Mage-A4 TCRs of the invention to activate TCR signaling in Jurkat cells Method Jurkat Cell Line Generation A Jurkat cell line lacking endogenous TCRα and TCRβ expression was generated by knockout of those genes, and then engineered to allow single-copy Cre recombinase-mediated insertion of transgenic TCR constructs. An AP1 response element-driven luciferase reporter was then incorporated into this parental bioassay line. TCR bioassay lines were generated by Cre mediated insertion of customized TCRα/β expression constructs.

TCR Activation Bioassay

Jurkat bioassay lines expressing TCR constructs were FACS sorted to homogeneity, then tested in peptide-MHC stimulation assays. 293T cells (HLA-A2*01) were plated in assay wells with varying dilutions of antigenic (MAGE-A4 286-294 (KVLE)) or irrelevant (MAGE-A4 230-239 (GVY)) peptide. After 2 hours of incubation, engineered Jurkat cells were added to wells at a 3:1 Jurkat:293T cell ratio and incubated a further 5 hours. Luciferase reporter activity was determined by measuring luminescence output in assay cells.

Results

Figure 4:
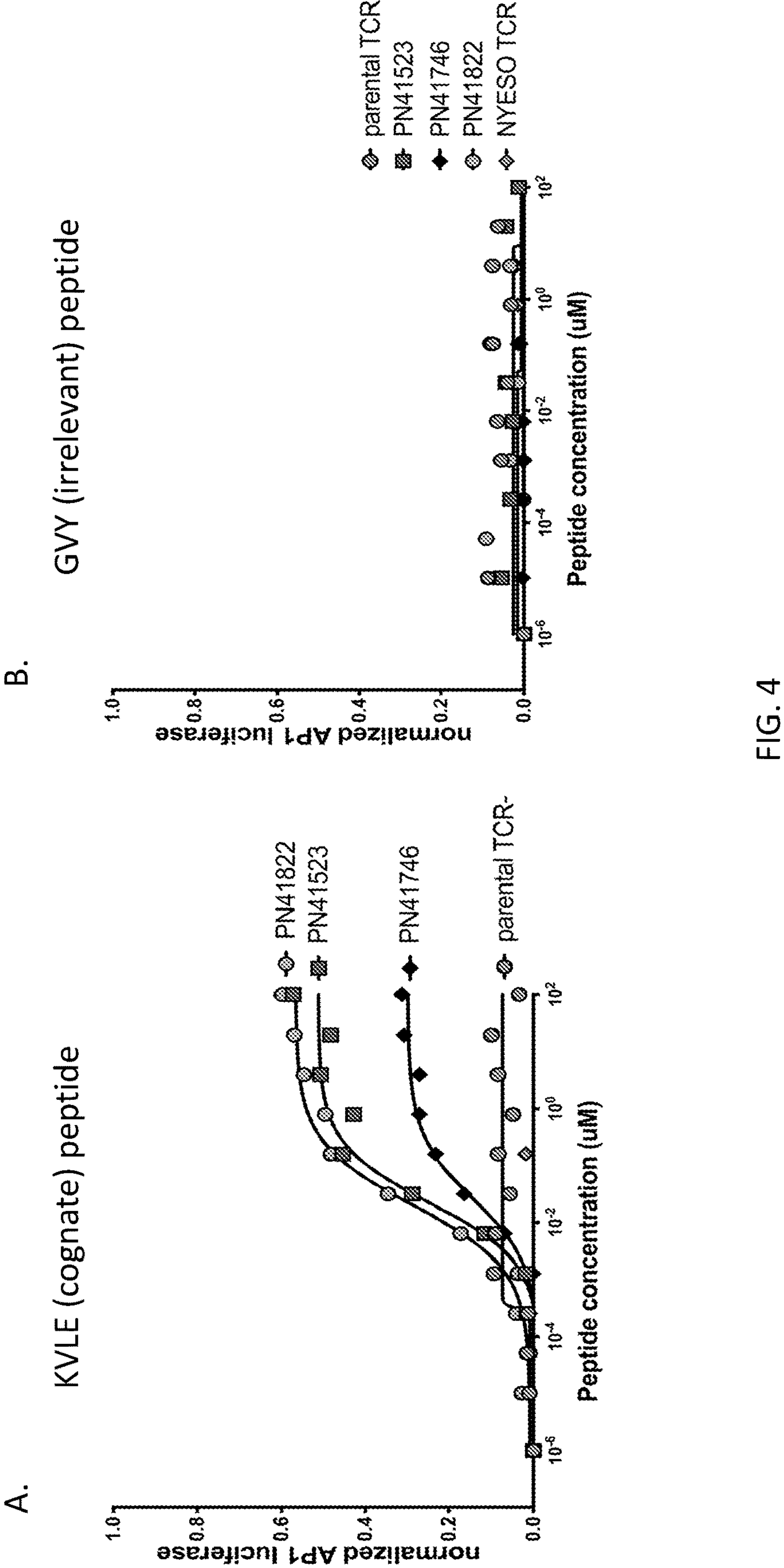
FIG. 4 depicts TCR signaling measured by activation of AP1-RE-luciferase reporter activation.

Jurkat bioassay lines with an AP1 response element-driven luciferase transgene and engineered to express MAGE-A4 specific TCRs, or a TCR against an irrelevant antigen (NY-ESO-1), were tested in peptide stimulation assays. As depicted in FIG. 4A and FIG. 4B, TCRs specific for HLA-A2*01-restricted MAGE-A4 (286-294 (KVLE)) were reactive only to the cognate (KVLE) peptide, but not to an irrelevant MAGE-A4 (230-239 (GVY)) peptide. Parental TCR-negative (TCR−) cells and cells expressing irrelevant TCR (to NY ESO) showed no reactivity. In addition, FIG. 4A and FIG. 4B demonstrate that the AP1 reporter activation induced by the MAGE-A4 specific TCRs was dose-dependent.

Example 5. Specific Activity of MAGE-A4 (230-239) TCRs in T Cells

This example describes the ability of selected Mage-A4 TCRs of the invention to activate TCR signaling in T cells.

Figure 5:
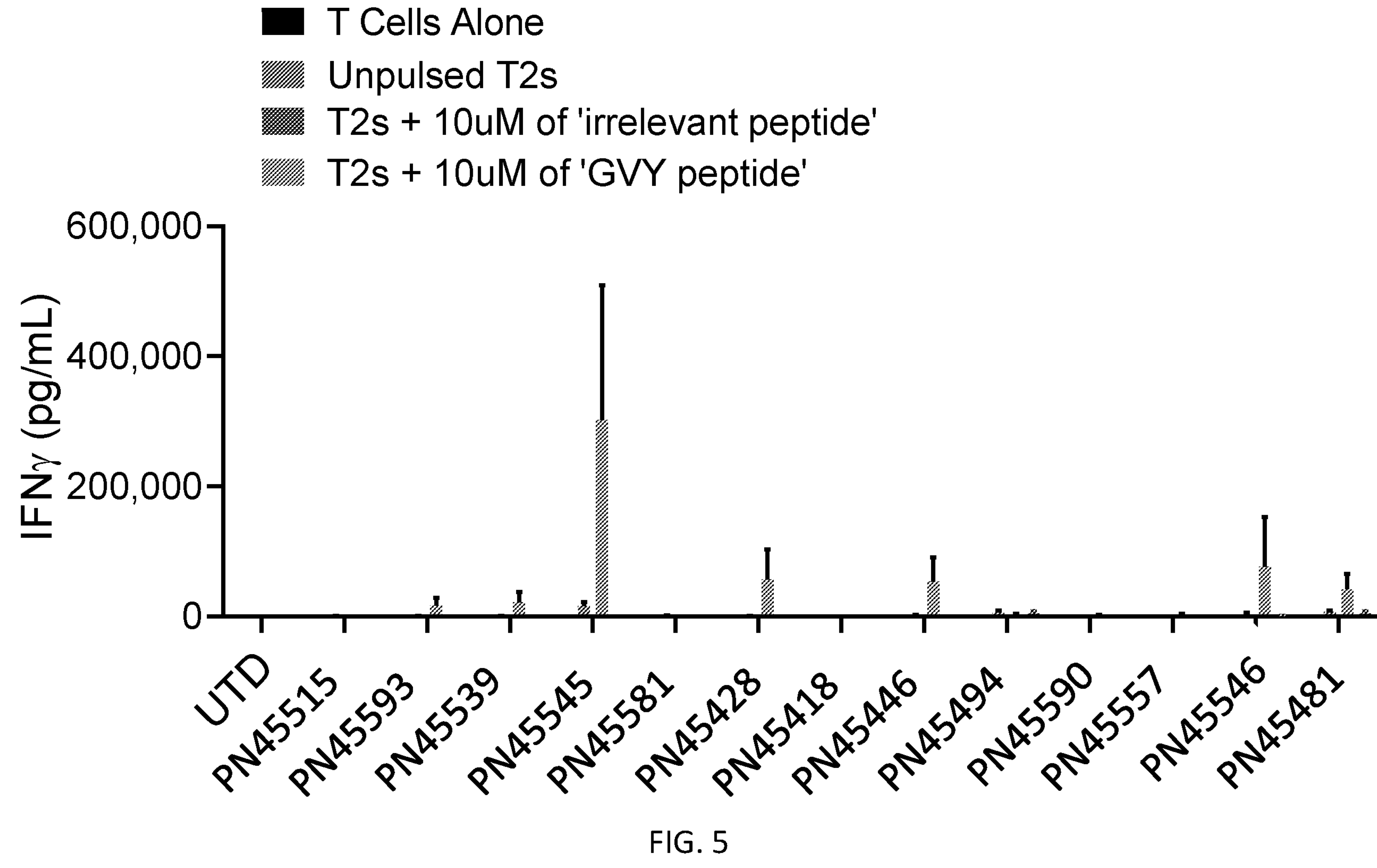
FIG. 5 depicts the average interferon gamma signal+/− standard error of the mean (SEM) of n=3 donors, and shows that MAGE-A4 (230-239)-specific TCRs of the present disclosure exhibit specific activity against T2 cells pulsed with the MAGE-A4 (230-239) peptide.

Human peripheral blood mononuclear cells (PBMCs) (n=3 donors) were activated, transduced with a lentiviral vector encoding TCRs binding to HLA-A2 restricted MAGE-A4 (230-239 (GVY)), and expanded in vitro for 10 days before freezing. After thawing, T cells containing the aforementioned TCRs were cultured at a 1:1 ratio with T2 cells pulsed with the MAGE-A4 230-239 peptide. Reactivity was measured as interferon gamma release 24 hours after co-culture. T cells alone were used as control for antigen-independent interferon gamma release. T cells cultured with unpulsed T2 cells or T2 cells pulsed with an irrelevant peptide were used as a control for specificity. FIG. 5 depicts the average interferon gamma signal+/−standard error of the mean (SEM) of n=3 donors, and shows that MAGE-A4 (230-239)-specific TCRs of the present disclosure exhibit specific activity against T2 cells pulsed with the MAGE-A4 (230-239) peptide.

Figure 6:
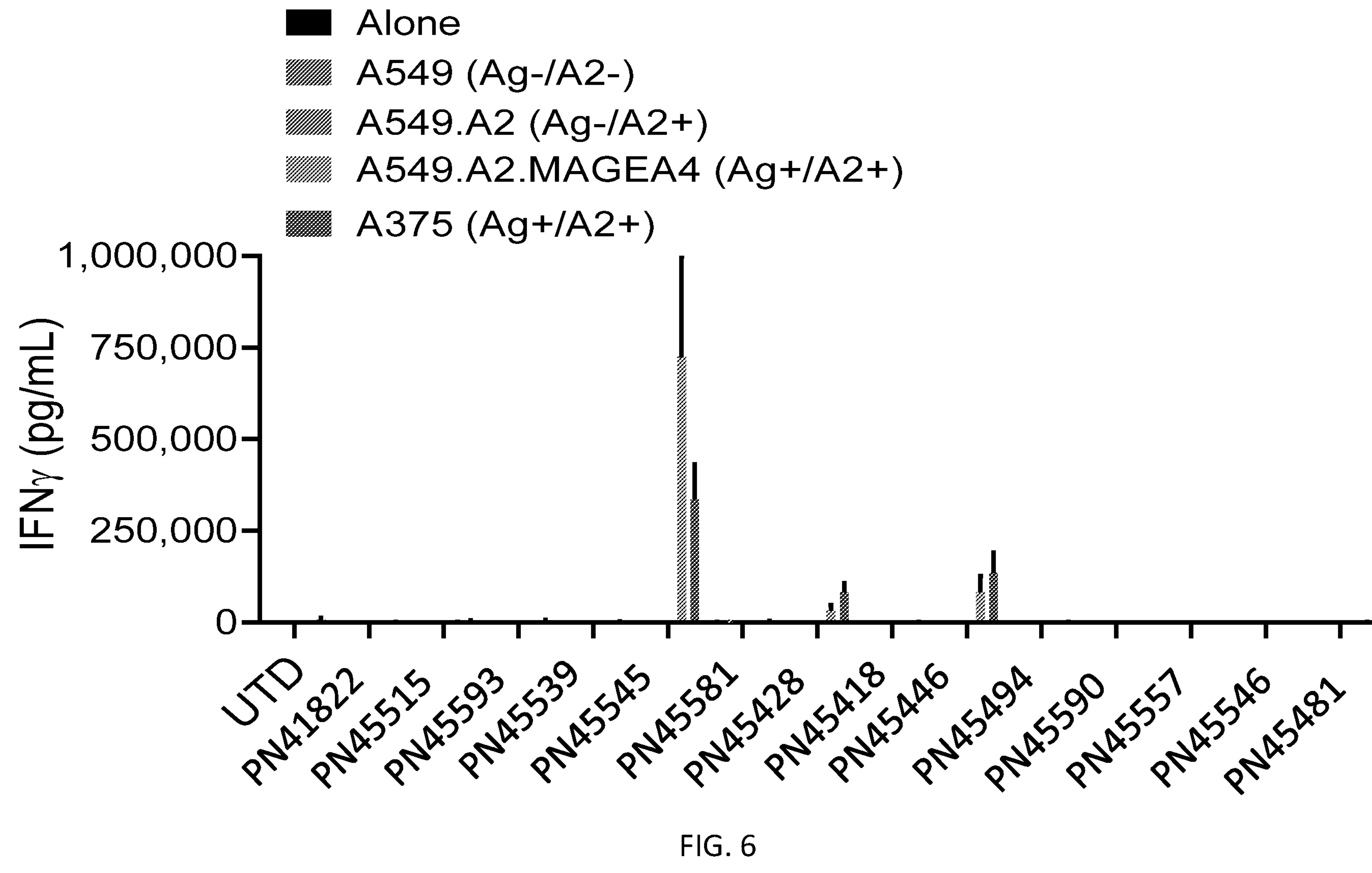
FIG. 6 depicts the average interferon gamma signal+/− standard error of the mean (SEM) of n=3 donors, and shows that MAGE-A4 (230-239)-specific TCRs of the present disclosure exhibit specific activity against tumor cells expressing HLA-A2 and MAGE-A4.
Figure 7:
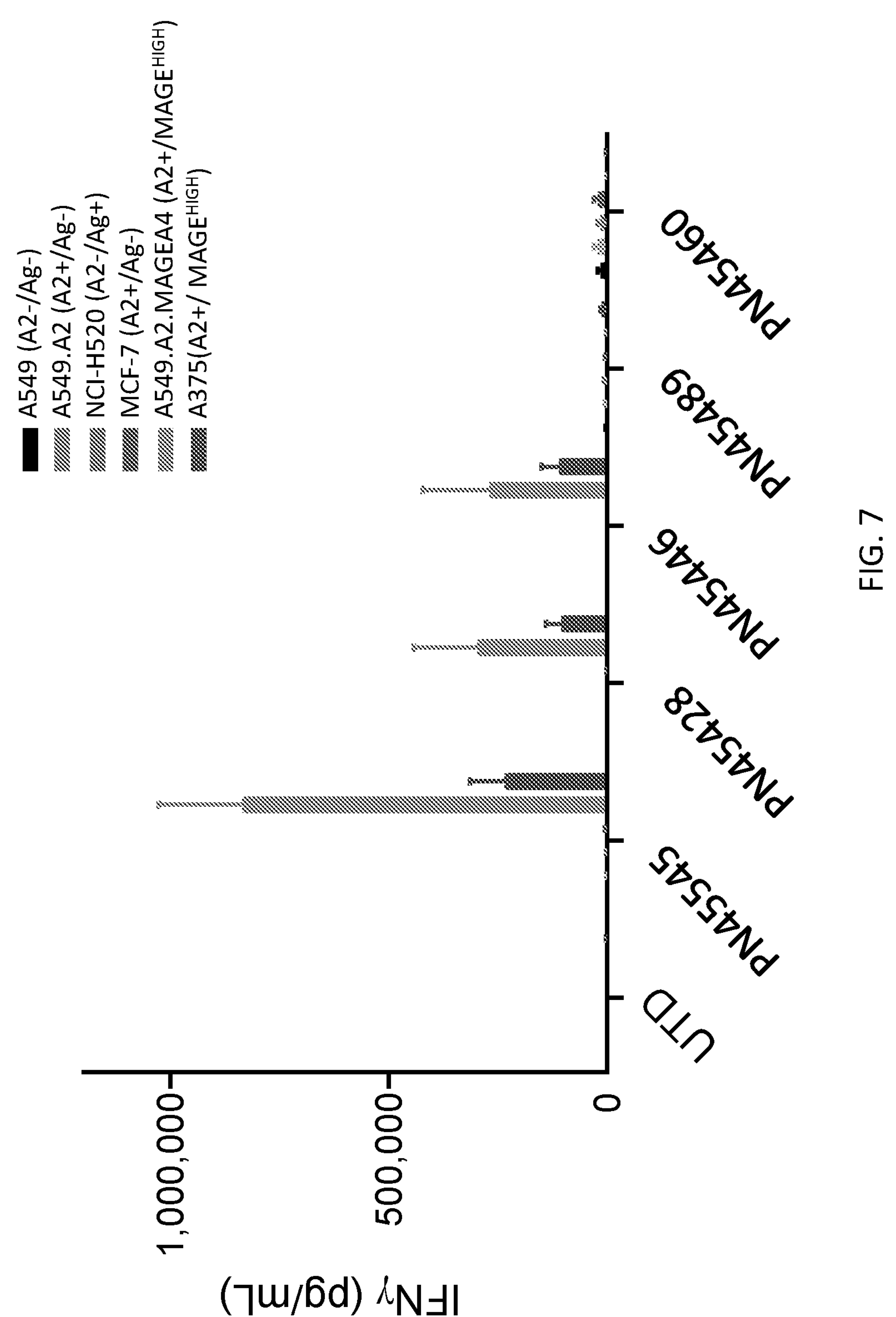
FIG. 7 depicts the average interferon gamma signal+/− standard error of the mean (SEM) of n=3 donors, and shows that MAGE-A4 (230-239)-specific TCRs of the present disclosure exhibit specific activity against tumor cells expressing HLA-A2 and MAGE-A4.
Figure 8:
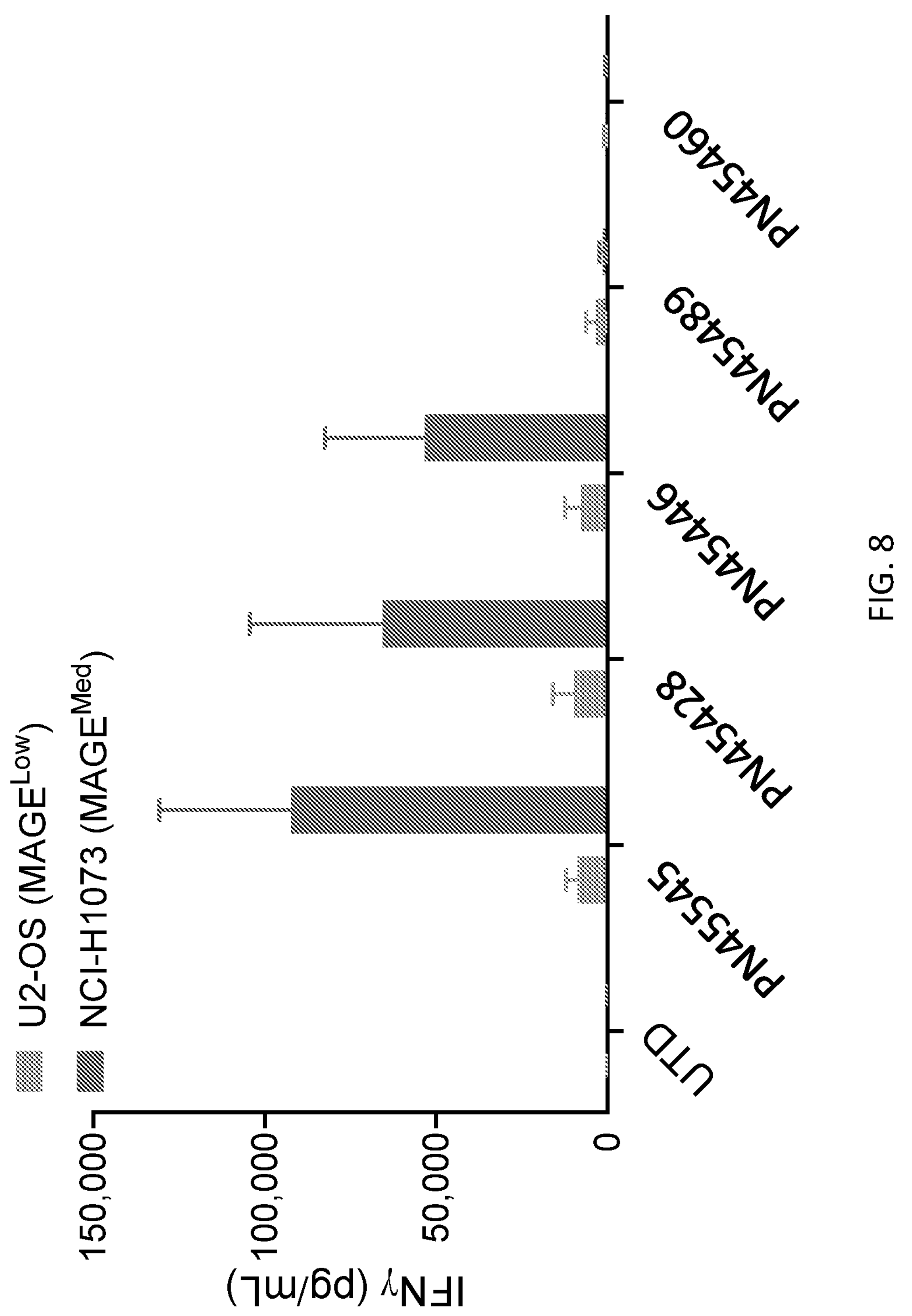
FIG. 8 depicts the average interferon gamma signal+/− standard error of the mean (SEM) of n=3 donors, and shows that MAGE-A4 (230-239)-specific TCRs of the present disclosure exhibit specific activity against HLA-A2-expressing tumor cells expressing even just low or medium endogenous levels of MAGE-A4.

To test activity against tumor cells expressing MAGE-A4, human PBMCs (n=3 donors) were activated, transduced with a lentiviral vector encoding MAGE-A4 (230-239) TCRs, and expanded in vitro for 10 days before freezing. After thawing, MAGE-A4 (230-239) TCR T cells were cultured at a 5:1 ratio with tumor cells expressing engineered levels of HLA-A2 and MAGE-A4 (A549.A2.MAGEA4 cells) or endogenous levels of HLA-A2 and MAGE-A4 (A375 cells). Reactivity was measured as interferon gamma release 24 hours after co-culture. T cells alone were used as control for antigen-independent interferon gamma release. T cells cultured with unmodified A549 cells (which are MAGE-A4 negative and HLA-A2 negative) or A549 cells modified to express HLA-A2 (A549.A2) were used as a control for specificity. FIG. 6 depicts the average interferon gamma signal+/−standard error of the mean (SEM) of n=3 donors, and shows that MAGE-A4 (230-239)-specific TCRs of the present disclosure exhibit specific activity against tumor cells expressing HLA-A2 and MAGE-A4. In a separate assay, the T cells were co-cultured with A549 cells, A549.A2 cells, NCI-H520 (HLA-A2 negative/MAGE-A4 positive) cells, and MCF-7 (HLA-A2 positive/MAGE-A4 negative) cells to provide further controls for specificity to the HLA-A2/MAGE-A4 complex. FIG. 7 depicts the average interferon gamma signal+/−standard error of the mean (SEM) of n=3 donors, and shows that MAGE-A4 (230-239)-specific TCRs of the present disclosure exhibit specific activity against tumor cells expressing HLA-A2 and MAGE-A4. In a further assay, the MAGE-A4 (230-239) TCR-expressing T cells were cultured at 5:1 ratio with tumor cells expressing low or medium endogenous levels of MAGE-A4 (U2-OS and NCI-H1703, respectively). Reactivity was measured as IFNg release 24 hours after co-culture. FIG. 8 depicts the average interferon gamma signal+/−standard error of the mean (SEM) of n=3 donors, and shows that MAGE-A4 (230-239)-specific TCRs of the present disclosure exhibit specific activity against HLA-A2-expressing tumor cells expressing even just low or medium endogenous levels of MAGE-A4.

EQUIVALENTS

Those skilled in the art will recognize or be able to ascertain, using no more than routine experimentation, many equivalents to the specific embodiments of the invention described herein, such equivalents are intended to be encompassed by the following claims. The contents of all references, patents and published patent applications cited throughout this application are incorporated herein by reference.

We claim:

1. A T cell receptor (TCR) that binds specifically to an HLA-A2 presented cancer testis antigen melanoma-associated antigen 4 (MAGE-A4) peptide, wherein:

the TCR comprises a TCR alpha chain and a TCR beta chain, and wherein the TCR alpha chain comprises an alpha chain variable domain comprising a complementarity determining region (CDR) 1, a CDR2, and a CDR3, wherein the TCR alpha chain variable domain CDR1, CDR2, and CDR3 comprise the amino acid sequences of SEQ ID NOs: 662, 663, and 664, respectively, and wherein the TCR beta chain comprises a beta chain variable domain comprising a CDR1, a CDR2, and a CDR3, wherein the TCR beta chain variable domain CDR1, CDR2, and CDR3 comprise the amino acid sequences of SEQ ID NOs: 670, 671, and 672, respectively.

2. A pharmaceutical composition comprising the TCR of claim 1 and a pharmaceutically acceptable carrier or diluent.

3. A method of treating a subject having a MAGE-A4-associated cancer, comprising administering to the subject a therapeutically effective amount of the TCR as set forth in claim 1, or the pharmaceutical composition of claim 2, thereby treating the subject.

4. The TCR of claim 1, wherein the TCR alpha chain variable domain comprises the amino acid sequence of SEQ ID NO: 668.

5. The TCR of claim 1, wherein the TCR beta chain variable domain comprises the amino acid sequence of SEQ ID NO: 676.

6. The TCR of claim 1, wherein the TCR comprises the TCR alpha chain variable domain/TCR beta chain variable domain amino acid sequence pair of SEQ ID NO: 668/676.

7. The TCR of claim 1, further comprising a detectable moiety.

8. The method of claim 3, wherein the MAGE-A4-associated cancer is a liposarcoma, a neuroblastoma, a myeloma, a melanoma, a metastatic melanoma, a synovial sarcoma, a bladder cancer, an esophageal cancer, an esophageal squamous cell carcinoma, a hepatocellular cancer, a head and neck cancer, a non-small cell lung cancer, an ovarian cancer, an ovarian epithelial cancer, a prostate cancer, a breast cancer, an astrocytic tumor, a glioblastoma multiforme, an anaplastic astrocytoma, a brain tumor, a fallopian tube cancer, primary peritoneal cavity cancer, advanced solid tumors, soft tissue sarcoma, a sarcoma, a myelodysplastic syndrome, an acute myeloid leukemia, a Hodgkin lymphoma, a non-Hodgkin lymphoma, a Hodgkin disease, a multiple myeloma, metastatic solid tumors, a colorectal carcinoma, a stomach cancer, a gastric cancer, a rhabdomyosarcoma, a myxoid round cell liposarcoma, or a recurrent non-small cell lung cancer.

9. The method of claim 3, wherein the TCR or the pharmaceutical composition is administered to the subject in combination with a second therapeutic agent.

10. The method of claim 3, wherein the TCR or the pharmaceutical composition is administered to the subject in combination with an immunostimulatory and/or immunosupportive therapy.

11. The method of claim 3, wherein the TCR or the pharmaceutical composition is administered to the subject in combination with a PD-1 inhibitor.

12. The method of claim 3, wherein the TCR or the pharmaceutical composition is administered to the subject in combination with a cancer vaccine.

13. The method of claim 3, wherein the TCR or the pharmaceutical composition is administered to the subject in combination with radiation therapy.

14. The method of claim 3, wherein the administering is parenteral administration.

15. The method of claim 3, wherein the TCR or the pharmaceutical composition is administered subcutaneously, intravenously, intradermally, intraperitoneally, orally, intramuscularly or intracranially to the subject.

* * * * *